(12) United States Patent
Kellinger et al.

(10) Patent No.: US 12,091,657 B2
(45) Date of Patent: Sep. 17, 2024

(54) REVERSE TRANSCRIPTASE FOR NUCLEIC ACID SEQUENCING

(71) Applicant: ELEMENT BIOSCIENCES, INC., San Diego, CA (US)

(72) Inventors: Matthew Kellinger, San Diego, CA (US); Molly He, San Diego, CA (US); Tyler Lopez, San Diego, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 825 days.

(21) Appl. No.: 17/120,030

(22) Filed: Dec. 11, 2020

(65) Prior Publication Data

US 2021/0139884 A1    May 13, 2021

Related U.S. Application Data

(63) Continuation of application No. PCT/US2019/036631, filed on Jun. 11, 2019.

(60) Provisional application No. 62/684,115, filed on Jun. 12, 2018.

(51) Int. Cl.
| | | |
|---|---|---|
| *C12N 15/10* | (2006.01) | |
| *C12N 9/12* | (2006.01) | |
| *C12P 21/00* | (2006.01) | |
| *C12Q 1/6874* | (2018.01) | |

(52) U.S. Cl.
CPC ......... *C12N 15/102* (2013.01); *C12N 9/1276* (2013.01); *C12N 15/1068* (2013.01); *C12Q 1/6874* (2013.01); *C12Y 207/07049* (2013.01); *C12N 2310/321* (2013.01); *C12P 21/00* (2013.01)

(58) Field of Classification Search
CPC .................................................... C12N 9/1276
See application file for complete search history.

(56) References Cited

U.S. PATENT DOCUMENTS

| | | |
|---|---|---|
| 8,399,196 B2 | 3/2013 | Hoser |
| 10,233,490 B2 | 3/2019 | Stapleton et al. |
| 10,704,094 B1 | 7/2020 | Arslan et al. |
| 10,768,173 B1 | 9/2020 | Arslan et al. |
| 10,876,148 B2 | 12/2020 | Zhou et al. |
| 10,954,496 B2 | 3/2021 | Kamtekar et al. |
| 10,982,280 B2 | 4/2021 | Arslan et al. |
| 11,053,540 B1 | 7/2021 | Chen et al. |
| 11,060,138 B1 | 7/2021 | Chen et al. |
| 11,198,121 B1 | 12/2021 | Guo et al. |
| 11,200,446 B1 | 12/2021 | Zhou et al. |
| 11,220,707 B1 | 1/2022 | Arslan et al. |
| 11,236,388 B1 | 2/2022 | Arslan et al. |
| 11,261,489 B2 | 3/2022 | Chen et al. |
| 11,287,422 B2 | 3/2022 | Previte et al. |
| 11,339,433 B2 | 5/2022 | Chen et al. |
| 11,427,855 B1 | 8/2022 | Arslan et al. |
| 11,535,892 B1 | 12/2022 | Arslan et al. |
| 11,781,185 B2 | 10/2023 | Arslan et al. |
| 11,795,504 B2 | 10/2023 | Chen et al. |
| 2004/0152072 A1 | 8/2004 | Gerard |
| 2014/0286907 A1 | 9/2014 | Sarkis et al. |
| 2016/0357173 A1 | 12/2016 | Foschini et al. |
| 2020/0149095 A1 | 5/2020 | Arslan et al. |
| 2020/0179921 A1 | 6/2020 | Arslan et al. |
| 2020/0182866 A1 | 6/2020 | Arslan et al. |
| 2020/0347443 A1 | 11/2020 | Arslan et al. |
| 2020/0370113 A1 | 11/2020 | Kellinger et al. |
| 2021/0040534 A1 | 2/2021 | Zhou et al. |
| 2021/0072234 A1 | 3/2021 | Arslan et al. |
| 2021/0121882 A1 | 4/2021 | Guo et al. |
| 2021/0123098 A1 | 4/2021 | Previte et al. |
| 2021/0123911 A1 | 4/2021 | Arslan et al. |
| 2021/0139981 A1 | 5/2021 | Arslan et al. |
| 2021/0223161 A1 | 7/2021 | Chen et al. |
| 2021/0247389 A1 | 8/2021 | Arslan et al. |
| 2021/0269793 A1 | 9/2021 | Kellinger et al. |
| 2021/0318295 A1 | 10/2021 | Arslan et al. |
| 2021/0332416 A1 | 10/2021 | Chen et al. |
| 2021/0332430 A1 | 10/2021 | Arslan et al. |
| 2021/0333211 A1 | 10/2021 | Chen et al. |
| 2021/0373000 A1 | 12/2021 | Arslan et al. |

(Continued)

FOREIGN PATENT DOCUMENTS

| | | |
|---|---|---|
| WO | WO-2014171898 A2 | 10/2014 |
| WO | WO-2018045109 A1 | 3/2018 |
| WO | WO-2019033062 A2 | 2/2019 |

(Continued)

OTHER PUBLICATIONS

Arezi, et al. Novel mutations in Moloney Murine Leukemia Virus reverse transcriptase increase thermostability through tighter binding to template-primer. Nucleic Acids Res. Feb. 2009;37(2):473-81. doi: 10.1093/nar/gkn952. Epub Dec. 4, 2008.

(Continued)

*Primary Examiner* — Suzanne M Noakes
(74) *Attorney, Agent, or Firm* — WILSON SONSINI GOODRICH & ROSATI

(57) ABSTRACT

Provided herein are compositions and methods for the incorporation of unnatural nucleotides using mutant polymerases, such as reverse transcriptases. Further provided herein are methods of detection and sequencing of polynucleotide sequences. In some aspects, the compositions and methods are used enhance the efficiency and speed of detecting nucleotide bases. The methods and compositions described herein may further reduce time, cost, or scale of devices for next generation sequencing platforms.

17 Claims, 8 Drawing Sheets

Specification includes a Sequence Listing.

(56) References Cited

U.S. PATENT DOCUMENTS

2021/0387184 A1 12/2021 Guo et al.

FOREIGN PATENT DOCUMENTS

| WO | WO-2019241305 A1 | 12/2019 |
|---|---|---|
| WO | WO-2020102594 A1 | 5/2020 |
| WO | WO-2020102766 A2 | 5/2020 |
| WO | WO-2020118255 A1 | 6/2020 |
| WO | WO-2020223695 A1 | 11/2020 |
| WO | WO-2020242901 A1 | 12/2020 |
| WO | WO-2020243017 A1 | 12/2020 |
| WO | WO-2021061841 A1 | 4/2021 |
| WO | WO-2021146597 A1 | 7/2021 |
| WO | WO-2021236792 A1 | 11/2021 |
| WO | WO-2021252671 A2 | 12/2021 |
| WO | WO-2022026891 A1 | 2/2022 |
| WO | WO-2022094332 A1 | 5/2022 |
| WO | WO-2022266470 A1 | 12/2022 |
| WO | WO-2023004014 A1 | 1/2023 |
| WO | WO-2022266462 A3 | 5/2023 |
| WO | WO-2023107719 A2 | 6/2023 |
| WO | WO-2023196924 A2 | 10/2023 |
| WO | WO-2023205707 A2 | 10/2023 |

OTHER PUBLICATIONS

Telesnitsky et al.: RNase H domain mutations affect the interaction between Moloney murine leukemia virus reverse transcriptase and its primer-template. Proc Natl Acad Sci USA 90(4):1276-1280 doi:10.1073/pnas.90.4.1276 (1993).

PCT/US2019/036631 International Preliminary Report on Patentability dated Dec. 15, 2020.

PCT/US2019/036631 International Search Report and Written Opinion dated Nov. 8, 2019.

Ren et al., Azide and trans-cyclooctene dUTPs: incorporation into DNA probes and fluorescent click-labelling. Analyst 140(8): 2671-2678 (2015).

Ren et al., Efficient enzymatic synthesis and dual-colour fluorescent labelling of DNA probes using long chain azido-dUTP and BCN dyes. Nucleic Acids Res 44(8):e79 (2016).

1   LNIEDEHRLH ETSKEPDVSL GSTWLSDFPQ AWAETGGMGL AVRQAPLIIP LKATSTPVSI

61  KQypMSQEAR LGIKPHIQRL LDQGILVPCQ SPWNTPLlPV KKPGTNDYRP VqdlrEVnkR

121 VEDIHPTVPN PYNLLSGLPP SHQWYTVLDL KDAFFCLRLH PTSQPLFAFE WRDPEMGISG

181 QLTWTRLPQg FKNSPTLFDE ALHRDLADFR IQHPDLILLQ YVDDLLLAAT SELDCQQGTR

241 ALLQTLGNLG YRASAKKAQI CQKQVKYLGY LLKEGQRWLT EARKETVMGQ PTPKTPRQLR

301 EFLGTAGFCR LWIPGFAEMA APLYPLTKTG TLFNWGPDQQ KAYQEIKQAL LTAPALGLPD

361 LTKPFELFVD EKQGYAKGVL TQKLGPWRRP VAYLSKKLDP VAAGWPPCLR MVAAIAVLTK

421 DAGKLTMGQP LVILAPHAVE ALVKQPPDRW LSNARMTHYQ ALLLDTDRVQ FGPVVALNPA

481 TLLPLPEEGL QHNCLDILAE AHGTRPDLTD QPLPDADHTW YTDGSSLLQE GQRKAGAAVT

541 TETEVIWAKA LPAGTSAQRA ELIALTQALK MAEGKKLNVY TDSRYAFATA HIHGEIYRRR

601 GLLTSEGKEI RNKDEILALL KALFLPKRLS IIHCPGHQKG HSAEARGNRM ADQAARKAAI

661 TETPDTSTLL I

FIG. 3

```
SEQ_ID_NO_1    1    MLNIEDEHRLHETSKEPDVSLgSTWLSDFPQAWAETGGMGLAVRQAPLIIPLATSTPVSIKQYMSQEARLGIKP     76
SEQ_ID_NO_2    1    M----------------------STWLSDFPQAWAETGGMGLAVRQAPLIIPLATSTPVSIKQYMSQEARLGIKP     55
SEQ_ID_NO_3    1    ----------------------------------------PISPIETVPVKLPGMDGPKVKWPLTEEKIKALVE     36
SEQ_ID_NO_4    1    ----------------------------------------TVALHLAIPLKWPNHTPVWIDWPLPEGKLVALTQ     36
SEQ_ID_NO_17   1    [11]TLNIEDEHRLHETSKEPDVSLgSTWLSDFPQAWAETGGMGLAVRQAPLIIPLATSTPVSIKQYMSQKARLGIKP  87
SEQ_ID_NO_18   1    TLQLEEEYRLFEPESTQKQEM-DIWLKNFPQAWAETGGMGTAHCQAPVLIQLKATATPISIRQYMPHEAYQGIKP     75

SEQ_ID_NO_1    77   HIQRLLDQGILVPC--QSPWTPLLPVKPGTNDYRPVQDLREVKKRVED---IHPTVNPYNLSGLPPSHQWYTVLDL   151
SEQ_ID_NO_2    56   HIQRLLDQGILVPC--QSPWTPLLPVKPGTNDYRPVQDLREVKKRVED---IHPTVNPYNLSGLPPSHQWYTVLDL   130
SEQ_ID_NO_3    37   ICTEMEKEKISKIgpENPYNTPVFAIKKDSTKWRKLVFRELKRTQDfweVQLGIHPAGKKKKS-----VTVLDV    111
SEQ_ID_NO_4    37   LVEKELQLHIEPSl--SCWNTPVFVIRA-SGSYPLLHDLRAVAKLVPfgaVQQGAPVLSALPRGWP-----LMVLDL   108
SEQ_ID_NO_17   88   HIQRLLDQGILVPC--QSPWTPLLPVKPGTNDYRPVQDLREVKKRVED---IHPTVNPYNLSGLPPSHQWYTVLDL   162
SEQ_ID_NO_18   76   HIRRMLDQGILKPC--QSPWTPLLPVKPGTEDYRPVQDLREVKKRVED---IHPTVNPYNLSTLPPSHPWYTVLDL   150

*****                                   *
SEQ_ID_NO_1    152  KDAFTCLRHPTSQPLFAFEWRDPEMGISG-QLTWTRLPQGFKNSPTLFDEALHRDLADFRIQHPDLILLQIVDDLLAA   230
SEQ_ID_NO_2    131  KDAFTCLRHPTSQPLFAFEWRDPEMGISG-QLTWTRLPQGFKNSPTLFDEALHRDLADFRIQHPDLILLQIVDDLLAA   209
SEQ_ID_NO_3    112  GDAYSVPDEDFRKYTAFTIPSINNETPGiRYQYNVLPQGWKGSPAIFQSSMTKILEPFKQNPDIVIYQMDDLYVGS    191
SEQ_ID_NO_4    109  KDCFSSIPLAEQDREAFAFTLPSVNNQAPArRFQWKVLPQGMTCSPTICQLIVGQILEPLRLKHPSLRMLHMDLLLAA   188
SEQ_ID_NO_17   163  KDAFTCLRHPTSQPLFAFEWRDPEMGISG-QLTWTRLPQGFKNSPTLFDEALHRDLADFRIQHPDLILLQIVDDLLAA   241
SEQ_ID_NO_18   151  KDAFTCLRHSESQLLFAFEWRDPEIGLSG-QLTWTRLPQGFKNSPTLFDEALHSDLADFRVRYPALVLLQIVDDLLAA   229

SEQ_ID_NO_1    231  TSELDC-QQGTRALLQTIGNLGYRASAKAQICQKQVKYLGYLLKEGQRWLTEARKETVMGQPTPKTPRQLREFLCTAGF   309
SEQ_ID_NO_2    210  TSELDC-QQGTRALLQTIGNLGYRASAKAQICQKQVKYLGYLLKEGQRWLTEARKETVMGQPTPKTPRQLREFLCTAGF   288
SEQ_ID_NO_3    192  DLEIGQhRTKIEELRQHLRWGLTTPDKHQK-EPPFLWMCYELHPD----KWTVQPIVLPEKDSWTVNDIQKLVKLNW    266
SEQ_ID_NO_4    189  SSHDGL-EAAGEEVISTIERAGFTISPDKVQR-EPGVQYLGYKLGS-----TYVAPVGLVAEPRIATLWDVQKLVSLQW   261
SEQ_ID_NO_17   242  TSELDC-QQGTRALLQTIGNLGYRASAKAQICQKQVKYLGYLLKEGQRWLTEARKETVMGQPTPKTPRQLRRFLCTAGF   320
SEQ_ID_NO_18   230  ATRTEC-LEGTKALLETIGNKGYRASAKAQICLQEVTYLGYSIKDGQRWLTKARKEAILSIPVPKNSRQVREFLCTAGY   308

SEQ_ID_NO_1    310  CRLWIPGF-AEMAAPLYPLTK---TGTLFNWGPDQQKAY-QEIKQALLTAPALGLPDLTKPFELFVDEKQGYAKVLTQK   384
SEQ_ID_NO_2    289  CRLWIPGF-AEMAAPLYPLTK---TGTLFNWGPDQQKAY-QEIKQALLTAPALGLPDLTKPFELFVDEKQGYAKVLTQK   363
SEQ_ID_NO_3    267  ASQIYPGIkVRQLCKLLRGTKaltEVIPLTEEAELELAE-REILKEPVHG-VY--YDPSKDL---IAEIQKCGQWTYQ   340
SEQ_ID_NO_4    262  LRPAL-GIpPRLMGPFYEQLRgsdPNEAREWNLDMKMAW-REIVQLSTTA-ALERNDPALPLEGAVARCEQGAIGVLGQG  338
SEQ_ID_NO_17   321  CRLFIPGF-AEMAAPLYPLTK---TGTLFNWGPDQQKAY-QEIKQALLTAPALGLPDLTKPFELFVDEKQGYAKVLTQK   395
SEQ_ID_NO_18   309  CRLWIPGF-AELAAPLYPLTR---PGTLFQWGTEQQLAF-EDKKALLSSPALGLPDITKPFELFIDENSGFAKVLVQK   383
```

FIG. 4A

```
SEQ_ID_NO_1   385 LGPWRRPVAYLSKKLDPVA-AGWPPCLRMVAAIAVLTKDAGKLTMGQPLVILAPHAVEALVKQPDRWLSNARMTHY--Q 461
SEQ_ID_NO_2   364 LGPWRRPVAYLSKKLDPVA-AGWPPCLRMVAAIAVLTKDAGKLTMGQPLVILAPHAVEALVKQPDRWLSNARMTHY--Q 440
SEQ_ID_NO_3   341 IYQEPFKNLKTGKYARMRG-AHTNDVKQLTEAVQKITTESIVIWGKT----------PKFKLIQKETWETWWTEYwqA 408
SEQ_ID_NO_4   339 LSTHPRPCLWLFSTQPTKAfTAWLEVLTLL--ITKLRASAVRTFGKEVDILLLPACFREDLPLEGILLALRGFAGK--- 413
SEQ_ID_NO_17  396 LGPWRRPVAYLSKKLDPVA-AGWPPCLRMVAAIAVLTKDAGKLTMGQPLVIGAPHAVEALVKQPDRWLSKARMTHY--Q 472
SEQ_ID_NO_18  384 LGPWRRPVAYLSKKLDTVA-SGWPPCLRMVAAIAILVKDAGKLTLGQPLTILTSHPVEALVRQPNKWLSNARMTHY--Q 460

SEQ_ID_NO_1   462 ALLLDTDRVQFGPVVALNPATLLPLPEEGLQHNCLDILAEAH-GTRPDLTDQPLPDADHTWYTDGSSLLQEGQRKAGAAV 540
SEQ_ID_NO_2   441 ALLLDTDRVQFGPVVALNPATLLPLPEEGLQHNCLDILAEAH-GTRPDLTDQPLPDADHTWYTDGSSLLQEGQRKAGAAV 519
SEQ_ID_NO_3   409 TWIPENEFVNTPPLVKL----------------------WYQLEKEPIVGA--ETP-------------------- 440
SEQ_ID_NO_4   414 ---------IRSSDTPSI--------------FDIARPLHvSLKVRVTDHEVPGP--TVFTDASSSTHKG-----VVV 461
SEQ_ID_NO_17  473 ALLLDTDRVQFGPVVALNPATLLPLPEEGLQHNCLDILAEAH-GTRPDLTDQPLPDADHTWYTNGSSLLQEGQRKAGAAV 551
SEQ_ID_NO_18  461 AMLLDAERVHFGPTVSLNPATLLPLPSGGNHHDCLQILAETH-GTRPDLTDQPLPDADLTWYTDGSSFIRNGEREAGAAV 539

SEQ_ID_NO_1   541 TTETEVIWAKALP-AGTSAQRAELIALTQALKMAEGKKLNVYTDSRYAFATAHIHGEIYRRRGLLTSEGKEIKNKDEILA 619
SEQ_ID_NO_2   520 TTETEVIWAKALP-AGTSAQRAELIALTQALKMAEGKKLNVYTDSRYAFATAHIHGEIYRRRGLLTSEGKEIKNKDEILA 598
SEQ_ID_NO_3       ---------------------------------------------------------------------------
SEQ_ID_NO_4   462 WREGPRWEIKEIAdLGASVQQLEARAVAMALLLWPTTPTNVVTDSAFV-------AKMLLKMG---QEGVPSTAAAFILE 531
SEQ_ID_NO_17  552 TTETEVIWAKALP-AGTSAQRAELIALTQALKMAEGKKLNVYTDSRYAFATAHIHGEIYRRRGLLTSEGKEIKNKDEILA 630
SEQ_ID_NO_18  540 TTESEVIWAAPLP-PGTSAQRAELIALTQALKMAEGKKLTVYTDSRYAFATTHVHGEIYRRRGLLTSEGKEIKNKNEILA 618

SEQ_ID_NO_1   620 LLKALFLPKRLSIIHCPGHQKGHSAEARGNRMADQAARKAAIT--ETPDTSTLLI           672
SEQ_ID_NO_2   599 LLKALFLPKRLSIIHCPGHQKGHSAEARGNRMADQAARKAAIT--ETPDTSTLLI           651
SEQ_ID_NO_3       ---------------------------------------------------------
SEQ_ID_NO_4   532 DALSQ-RSAMAAVLHVRSHSEVPGFFTEGNDVADSQATFQAYPlrEAKDLHTALH[273]       858
SEQ_ID_NO_17  631 LLKALFLPKRLSIIHCPGHQKGHSAEARGNRMADQAARKAAIT--ET--------           675
SEQ_ID_NO_18  619 LLEALFLPKRLSIIHCPGHQKGDSPQAKGNRLADDTAKKAA-T--ETHSSLTVL-           669
```

FIG. 4B

SEQUENCE LISTING

<160> NUMBER OF SEQ ID NOS: 317

<210> SEQ ID NO 1
<211> LENGTH: 672
<212> TYPE: PRT
<213> ORGANISM: Moloney murine leukemia virus

<400> SEQUENCE: 1

```
Met Leu Asn Ile Glu Asp Glu His Arg Leu His Glu Thr Ser Lys Glu
1               5                   10                  15

Pro Asp Val Ser Leu Gly Ser Thr Trp Leu Ser Asp Phe Pro Gln Ala
            20                  25                  30

Trp Ala Glu Thr Gly Gly Met Gly Leu Ala Val Arg Gln Ala Pro Leu
        35                  40                  45

Ile Ile Pro Leu Lys Ala Thr Ser Thr Pro Val Ser Ile Lys Gln Tyr
    50                  55                  60

Pro Met Ser Gln Glu Ala Arg Leu Gly Ile Lys Pro His Ile Gln Arg
65                  70                  75                  80

Leu Leu Asp Gln Gly Ile Leu Val Pro Cys Gln Ser Pro Trp Asn Thr
                85                  90                  95

Pro Leu Leu Pro Val Lys Lys Pro Gly Thr Asn Asp Tyr Arg Pro Val
            100                 105                 110

Gln Asp Leu Arg Glu Val Asn Lys Arg Val Glu Asp Ile His Pro Thr
        115                 120                 125
```

```
Val Pro Asn Pro Tyr Asn Leu Leu Ser Gly Leu Pro Pro Ser His Gln
130                 135                 140

Trp Tyr Thr Val Leu Asp Leu Lys Asp Ala Phe Phe Cys Leu Arg Leu
145                 150                 155                 160

His Pro Thr Ser Gln Pro Leu Phe Ala Phe Glu Trp Arg Asp Pro Glu
                165                 170                 175

Met Gly Ile Ser Gly Gln Leu Thr Trp Thr Arg Leu Pro Gln Gly Phe
            180                 185                 190

Lys Asn Ser Pro Thr Leu Phe Asp Glu Ala Leu His Arg Asp Leu Ala
        195                 200                 205

Asp Phe Arg Ile Gln His Pro Asp Leu Ile Leu Leu Gln Tyr Val Asp
    210                 215                 220

Asp Leu Leu Leu Ala Ala Thr Ser Glu Leu Asp Cys Gln Gln Gly Thr
225                 230                 235                 240

Arg Ala Leu Leu Gln Thr Leu Gly Asn Leu Gly Tyr Arg Ala Ser Ala
                245                 250                 255

Lys Lys Ala Gln Ile Cys Gln Lys Gln Val Lys Tyr Leu Gly Tyr Leu
            260                 265                 270

Leu Lys Glu Gly Gln Arg Trp Leu Thr Glu Ala Arg Lys Glu Thr Val
        275                 280                 285

Met Gly Gln Pro Thr Pro Lys Thr Pro Arg Gln Leu Arg Glu Phe Leu
    290                 295                 300

Gly Thr Ala Gly Phe Cys Arg Leu Trp Ile Pro Gly Phe Ala Glu Met
305                 310                 315                 320

Ala Ala Pro Leu Tyr Pro Leu Thr Lys Thr Gly Thr Leu Phe Asn Trp
                325                 330                 335

Gly Pro Asp Gln Gln Lys Ala Tyr Gln Glu Ile Lys Gln Ala Leu Leu
            340                 345                 350

Thr Ala Pro Ala Leu Gly Leu Pro Asp Leu Thr Lys Pro Phe Glu Leu
        355                 360                 365

Phe Val Asp Glu Lys Gln Gly Tyr Ala Lys Gly Val Leu Thr Gln Lys
    370                 375                 380

Leu Gly Pro Trp Arg Arg Pro Val Ala Tyr Leu Ser Lys Lys Leu Asp
385                 390                 395                 400

Pro Val Ala Ala Gly Trp Pro Pro Cys Leu Arg Met Val Ala Ala Ile
                405                 410                 415

Ala Val Leu Thr Lys Asp Ala Gly Lys Leu Thr Met Gly Gln Pro Leu
            420                 425                 430

Val Ile Leu Ala Pro His Ala Val Glu Ala Leu Val Lys Gln Pro Pro
        435                 440                 445

Asp Arg Trp Leu Ser Asn Ala Arg Met Thr His Tyr Gln Ala Leu Leu
    450                 455                 460

Leu Asp Thr Asp Arg Val Gln Phe Gly Pro Val Val Ala Leu Asn Pro
465                 470                 475                 480

Ala Thr Leu Leu Pro Leu Pro Glu Glu Gly Leu Gln His Asn Cys Leu
                485                 490                 495

Asp Ile Leu Ala Glu Ala His Gly Thr Arg Pro Asp Leu Thr Asp Gln
            500                 505                 510

Pro Leu Pro Asp Ala Asp His Thr Trp Tyr Thr Asp Gly Ser Ser Leu
        515                 520                 525

Leu Gln Glu Gly Gln Arg Lys Ala Gly Ala Ala Val Thr Thr Glu Thr
    530                 535                 540

Glu Val Ile Trp Ala Lys Ala Leu Pro Ala Gly Thr Ser Ala Gln Arg
```

```
545                 550                 555                 560
Ala Glu Leu Ile Ala Leu Thr Gln Ala Leu Lys Met Ala Gly Lys
                565                 570                 575

Lys Leu Asn Val Tyr Thr Asp Ser Arg Tyr Ala Phe Ala Thr Ala His
                580                 585                 590

Ile His Gly Glu Ile Tyr Arg Arg Gly Leu Leu Thr Ser Glu Gly
                595                 600                 605

Lys Glu Ile Lys Asn Lys Asp Glu Ile Leu Ala Leu Lys Ala Leu
            610                 615                 620

Phe Leu Pro Lys Arg Leu Ser Ile Ile His Cys Pro Gly His Gln Lys
625                 630                 635                 640

Gly His Ser Ala Glu Ala Arg Gly Asn Arg Met Ala Asp Gln Ala Ala
                645                 650                 655

Arg Lys Ala Ala Ile Thr Glu Thr Pro Asp Thr Ser Thr Leu Leu Ile
                660                 665                 670

<210> SEQ ID NO 2
<211> LENGTH: 651
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ser Thr Trp Leu Ser Asp Phe Pro Gln Ala Trp Ala Glu Thr Gly
1               5                   10                  15

Gly Met Gly Leu Ala Val Arg Gln Ala Pro Leu Ile Ile Pro Leu Lys
                20                  25                  30

Ala Thr Ser Thr Pro Val Ser Ile Lys Gln Tyr Pro Met Ser Gln Glu
            35                  40                  45

Ala Arg Leu Gly Ile Lys Pro His Ile Gln Arg Leu Leu Asp Gln Gly
        50                  55                  60

Ile Leu Val Pro Cys Gln Ser Pro Trp Asn Thr Pro Leu Leu Pro Val
65                  70                  75                  80

Lys Lys Pro Gly Thr Asn Asp Tyr Arg Pro Val Gln Asp Leu Arg Glu
                85                  90                  95

Val Asn Lys Arg Val Glu Asp Ile His Pro Thr Val Pro Asn Pro Tyr
                100                 105                 110

Asn Leu Leu Ser Gly Leu Pro Pro Ser His Gln Trp Tyr Thr Val Leu
            115                 120                 125

Asp Leu Lys Asp Ala Phe Phe Cys Leu Arg Leu His Pro Thr Ser Gln
        130                 135                 140

Pro Leu Phe Ala Phe Glu Trp Arg Asp Pro Glu Met Gly Ile Ser Gly
145                 150                 155                 160

Gln Leu Thr Trp Thr Arg Leu Pro Gln Gly Phe Lys Asn Ser Pro Thr
                165                 170                 175

Leu Phe Asp Glu Ala Leu His Arg Asp Leu Ala Asp Phe Arg Ile Gln
                180                 185                 190

His Pro Asp Leu Ile Leu Leu Gln Tyr Val Asp Asp Leu Leu Leu Ala
            195                 200                 205

Ala Thr Ser Glu Leu Asp Cys Gln Gln Gly Thr Arg Ala Leu Leu Gln
        210                 215                 220

Thr Leu Gly Asn Leu Gly Tyr Arg Ala Ser Ala Lys Lys Ala Gln Ile
225                 230                 235                 240
```

```
Cys Gln Lys Gln Val Lys Tyr Leu Gly Tyr Leu Leu Lys Glu Gly Gln
                245                 250                 255

Arg Trp Leu Thr Glu Ala Arg Lys Glu Thr Val Met Gly Gln Pro Thr
            260                 265                 270

Pro Lys Thr Pro Arg Gln Leu Arg Glu Phe Leu Gly Thr Ala Gly Phe
        275                 280                 285

Cys Arg Leu Trp Ile Pro Gly Phe Ala Glu Met Ala Ala Pro Leu Tyr
    290                 295                 300

Pro Leu Thr Lys Thr Gly Thr Leu Phe Asn Trp Gly Pro Asp Gln Gln
305                 310                 315                 320

Lys Ala Tyr Gln Glu Ile Lys Gln Ala Leu Leu Thr Ala Pro Ala Leu
                325                 330                 335

Gly Leu Pro Asp Leu Thr Lys Pro Phe Glu Leu Phe Val Asp Glu Lys
            340                 345                 350

Gln Gly Tyr Ala Lys Gly Val Leu Thr Gln Lys Leu Gly Pro Trp Arg
        355                 360                 365

Arg Pro Val Ala Tyr Leu Ser Lys Lys Leu Asp Pro Val Ala Ala Gly
    370                 375                 380

Trp Pro Pro Cys Leu Arg Met Val Ala Ile Ala Val Leu Thr Lys
385                 390                 395                 400

Asp Ala Gly Lys Leu Thr Met Gly Gln Pro Leu Val Ile Leu Ala Pro
                405                 410                 415

His Ala Val Glu Ala Leu Val Lys Gln Pro Pro Asp Arg Trp Leu Ser
            420                 425                 430

Asn Ala Arg Met Thr His Tyr Gln Ala Leu Leu Leu Asp Thr Asp Arg
        435                 440                 445

Val Gln Phe Gly Pro Val Val Ala Leu Asn Pro Ala Thr Leu Leu Pro
    450                 455                 460

Leu Pro Glu Glu Gly Leu Gln His Asn Cys Leu Asp Ile Leu Ala Glu
465                 470                 475                 480

Ala His Gly Thr Arg Pro Asp Leu Thr Asp Gln Pro Leu Pro Asp Ala
                485                 490                 495

Asp His Thr Trp Tyr Thr Asp Gly Ser Ser Leu Leu Gln Glu Gly Gln
            500                 505                 510

Arg Lys Ala Gly Ala Ala Val Thr Thr Glu Thr Glu Val Ile Trp Ala
        515                 520                 525

Lys Ala Leu Pro Ala Gly Thr Ser Ala Gln Arg Ala Glu Leu Ile Ala
    530                 535                 540

Leu Thr Gln Ala Leu Lys Met Ala Glu Gly Lys Lys Leu Asn Val Tyr
545                 550                 555                 560

Thr Asp Ser Arg Tyr Ala Phe Ala Thr Ala His Ile His Gly Glu Ile
                565                 570                 575

Tyr Arg Arg Arg Gly Leu Leu Thr Ser Glu Gly Lys Glu Ile Lys Asn
            580                 585                 590

Lys Asp Glu Ile Leu Ala Leu Leu Lys Ala Leu Phe Leu Pro Lys Arg
        595                 600                 605

Leu Ser Ile Ile His Cys Pro Gly His Gln Lys Gly His Ser Ala Glu
610                 615                 620

Ala Arg Gly Asn Arg Met Ala Asp Gln Ala Ala Arg Lys Ala Ala Ile
625                 630                 635                 640

Thr Glu Thr Pro Asp Thr Ser Thr Leu Leu Ile
                645                 650
```

```
<210> SEQ ID NO 3
<211> LENGTH: 440
<212> TYPE: PRT
<213> ORGANISM: Human immunodeficiency virus

<400> SEQUENCE: 3

Pro Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
            20                  25                  30

Ala Leu Val Glu Ile Cys Thr Glu Met Glu Lys Glu Gly Lys Ile Ser
        35                  40                  45

Lys Ile Gly Pro Glu Asn Pro Tyr Asn Thr Pro Val Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Ala Gly Leu Lys Lys Lys Ser Val Thr Val Leu Asp Val Gly
            100                 105                 110

Asp Ala Tyr Phe Ser Val Pro Leu Asp Glu Asp Phe Arg Lys Tyr Thr
        115                 120                 125

Ala Phe Thr Ile Pro Ser Ile Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
            180                 185                 190

Leu Glu Ile Gly Gln His Arg Thr Lys Ile Glu Glu Leu Arg Gln His
        195                 200                 205

Leu Leu Arg Trp Gly Leu Thr Thr Pro Asp Lys Lys His Gln Lys Glu
    210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Gln Lys Leu Val Gly Lys Leu Asn Trp Ala Ser Gln Ile Tyr Pro
            260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
    290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
            340                 345                 350

Lys Tyr Ala Arg Met Arg Gly Ala His Thr Asn Asp Val Lys Gln Leu
        355                 360                 365

Thr Glu Ala Val Gln Lys Ile Thr Thr Glu Ser Ile Val Ile Trp Gly
    370                 375                 380
```

```
Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
                420                 425                 430

Pro Ile Val Gly Ala Glu Thr Phe
        435                 440

<210> SEQ ID NO 4
<211> LENGTH: 858
<212> TYPE: PRT
<213> ORGANISM: Avian myeoblastosis virus

<400> SEQUENCE: 4

Thr Val Ala Leu His Leu Ala Ile Pro Leu Lys Trp Lys Pro Asn His
1               5                   10                  15

Thr Pro Val Trp Ile Asp Gln Trp Pro Leu Pro Glu Gly Lys Leu Val
                20                  25                  30

Ala Leu Thr Gln Leu Val Glu Lys Glu Leu Gln Leu Gly His Ile Glu
                35                  40                  45

Pro Ser Leu Ser Cys Trp Asn Thr Pro Val Phe Val Ile Arg Lys Ala
        50                  55                  60

Ser Gly Ser Tyr Arg Leu Leu His Asp Leu Arg Ala Val Asn Ala Lys
65                  70                  75                  80

Leu Val Pro Phe Gly Ala Val Gln Gln Gly Ala Pro Val Leu Ser Ala
                85                  90                  95

Leu Pro Arg Gly Trp Pro Leu Met Val Leu Asp Leu Lys Asp Cys Phe
                100                 105                 110

Phe Ser Ile Pro Leu Ala Glu Gln Asp Arg Glu Ala Phe Ala Phe Thr
                115                 120                 125

Leu Pro Ser Val Asn Asn Gln Ala Pro Ala Arg Arg Phe Gln Trp Lys
        130                 135                 140

Val Leu Pro Gln Gly Met Thr Cys Ser Pro Thr Ile Cys Gln Leu Ile
145                 150                 155                 160

Val Gly Gln Ile Leu Glu Pro Leu Arg Leu Lys His Pro Ser Leu Arg
                165                 170                 175

Met Leu His Tyr Met Asp Asp Leu Leu Leu Ala Ala Ser Ser His Asp
                180                 185                 190

Gly Leu Glu Ala Ala Gly Glu Glu Val Ile Ser Thr Leu Glu Arg Ala
                195                 200                 205

Gly Phe Thr Ile Ser Pro Asp Lys Val Gln Arg Glu Pro Gly Val Gln
        210                 215                 220

Tyr Leu Gly Tyr Lys Leu Gly Ser Thr Tyr Val Ala Pro Val Gly Leu
225                 230                 235                 240

Val Ala Glu Pro Arg Ile Ala Thr Leu Trp Asp Val Gln Lys Leu Val
                245                 250                 255

Gly Ser Leu Gln Trp Leu Arg Pro Ala Leu Gly Ile Pro Pro Arg Leu
                260                 265                 270

Met Gly Pro Phe Tyr Glu Gln Leu Arg Gly Ser Asp Pro Asn Glu Ala
                275                 280                 285

Arg Glu Trp Asn Leu Asp Met Lys Met Ala Trp Arg Glu Ile Val Gln
        290                 295                 300

Leu Ser Thr Thr Ala Ala Leu Glu Arg Trp Asp Pro Ala Leu Pro Leu
305                 310                 315                 320
```

```
Glu Gly Ala Val Ala Arg Cys Glu Gln Gly Ala Ile Gly Val Leu Gly
                325                 330                 335

Gln Gly Leu Ser Thr His Pro Arg Pro Cys Leu Trp Leu Phe Ser Thr
                340                 345                 350

Gln Pro Thr Lys Ala Phe Thr Ala Trp Leu Glu Val Leu Thr Leu Leu
                355                 360                 365

Ile Thr Lys Leu Arg Ala Ser Ala Val Arg Thr Phe Gly Lys Glu Val
                370                 375                 380

Asp Ile Leu Leu Leu Pro Ala Cys Phe Arg Glu Asp Leu Pro Leu Pro
385                 390                 395                 400

Glu Gly Ile Leu Leu Ala Leu Arg Gly Phe Ala Gly Lys Ile Arg Ser
                405                 410                 415

Ser Asp Thr Pro Ser Ile Phe Asp Ile Ala Arg Pro Leu His Val Ser
                420                 425                 430

Leu Lys Val Arg Val Thr Asp His Pro Val Pro Gly Pro Thr Val Phe
                435                 440                 445

Thr Asp Ala Ser Ser Ser Thr His Lys Gly Val Val Val Trp Arg Glu
                450                 455                 460

Gly Pro Arg Trp Glu Ile Lys Glu Ile Ala Asp Leu Gly Ala Ser Val
465                 470                 475                 480

Gln Gln Leu Glu Ala Arg Ala Val Ala Met Ala Leu Leu Leu Trp Pro
                485                 490                 495

Thr Thr Pro Thr Asn Val Val Thr Asp Ser Ala Phe Val Ala Lys Met
                500                 505                 510

Leu Leu Lys Met Gly Gln Glu Gly Val Pro Ser Thr Ala Ala Ala Phe
                515                 520                 525

Ile Leu Glu Asp Ala Leu Ser Gln Arg Ser Ala Met Ala Ala Val Leu
                530                 535                 540

His Val Arg Ser His Ser Glu Val Pro Gly Phe Phe Thr Glu Gly Asn
545                 550                 555                 560

Asp Val Ala Asp Ser Gln Ala Thr Phe Gln Ala Tyr Pro Leu Arg Glu
                565                 570                 575

Ala Lys Asp Leu His Thr Ala Leu His Ile Gly Pro Arg Ala Leu Ser
                580                 585                 590

Lys Ala Cys Asn Ile Ser Met Gln Gln Ala Arg Glu Val Val Gln Thr
                595                 600                 605

Cys Pro His Cys Asn Ser Ala Pro Ala Leu Glu Ala Gly Val Asn Pro
                610                 615                 620

Arg Gly Leu Gly Pro Leu Gln Ile Trp Gln Thr Asp Phe Thr Leu Glu
625                 630                 635                 640

Pro Arg Met Ala Pro Arg Ser Trp Leu Ala Val Thr Val Asp Thr Ala
                645                 650                 655

Ser Ser Ala Ile Val Val Thr Gln His Gly Arg Val Thr Ser Val Ala
                660                 665                 670

Ala Gln His His Trp Ala Thr Ala Ile Ala Val Leu Gly Arg Pro Lys
                675                 680                 685

Ala Ile Lys Thr Asp Asn Gly Ser Cys Phe Thr Ser Lys Ser Thr Arg
                690                 695                 700

Glu Trp Leu Ala Arg Trp Gly Ile Ala His Thr Thr Gly Ile Pro Gly
705                 710                 715                 720

Asn Ser Gln Gly Gln Ala Met Val Glu Arg Ala Asn Arg Leu Leu Lys
                725                 730                 735
```

```
Asp Lys Ile Arg Val Leu Ala Glu Gly Asp Gly Phe Met Lys Arg Ile
            740                 745                 750

Pro Thr Ser Lys Gln Gly Glu Leu Leu Ala Lys Ala Met Tyr Ala Leu
        755                 760                 765

Asn His Phe Glu Arg Gly Glu Asn Thr Lys Thr Pro Ile Gln Lys His
    770                 775                 780

Trp Arg Pro Thr Val Leu Thr Glu Gly Pro Pro Val Lys Ile Arg Ile
785                 790                 795                 800

Glu Thr Gly Glu Trp Glu Lys Gly Trp Asn Val Leu Val Trp Gly Arg
                805                 810                 815

Gly Tyr Ala Ala Val Lys Asn Arg Asp Thr Asp Lys Val Ile Trp Val
            820                 825                 830

Pro Ser Arg Lys Val Lys Pro Asp Ile Ala Gln Lys Asp Glu Val Thr
        835                 840                 845

Lys Lys Asp Glu Ala Ser Pro Leu Phe Ala
    850                 855

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Tyr Thr Val Leu Asp Leu Arg Asp Ala Phe Phe Cys Leu Arg Leu
1               5                   10                  15

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Leu Asp Leu Cys Asp Ala Phe Phe
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Val Leu Asp Leu Ser Asp Ala Phe Phe
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Asp Leu Leu Asp Ala Phe Phe
1               5
```

<210> SEQ ID NO 9
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Val Leu Asp Leu Lys Tyr Ala Phe Phe Cys Leu Arg Leu
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Lys Asp Tyr Phe Phe Cys
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Leu Lys Asp Ala Ala Phe Cys Leu
1               5

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Leu Asp Leu Lys Asp Ala Phe Asn Cys Leu Arg Leu His Pro
1               5                   10                  15

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Leu Pro Ala Gly Phe Lys
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Leu Pro Ser Gly Phe Lys Asn
1               5

<210> SEQ ID NO 15
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Pro Val Ser Ile Lys Gln Tyr Pro Met Ser Gln Glu Ala Arg Leu Gly
1               5                   10                  15

Ile Lys Pro His Ile Gln Arg Leu Leu Asp Gln Gly Ile Leu Val Pro
            20                  25                  30

Cys Gln Ser Pro Trp Asn Thr Pro Leu Leu Pro Val Lys Lys Pro Gly
        35                  40                  45

Thr Asn Asp Tyr Arg Pro Val Gln Asp Leu Arg Glu Val Asn Lys Arg
    50                  55                  60

Val Glu Asp Ile His Pro Thr Val Pro Asn Pro Tyr Asn Leu Leu Ser
65                  70                  75                  80

Gly Leu Pro Pro Ser His Gln Trp Tyr Thr Val Leu Asp Leu Lys Asp
                85                  90                  95

Ala Phe Phe Cys Leu Arg Leu His Pro Thr Ser Gln Pro Leu Phe Ala
            100                 105                 110

Phe Glu Trp Arg Asp Pro Glu Met Gly Ile Ser Gly Gln Leu Thr Trp
        115                 120                 125

Thr Arg Leu Pro Gln Gly Phe Lys Asn Ser Pro Thr Leu Phe Asp Glu
    130                 135                 140

Ala Leu His Arg Asp Leu Ala Asp Phe Arg Ile Gln His Pro Asp Leu
145                 150                 155                 160

Ile Leu Leu Gln Tyr Val Asp Asp Leu Leu Leu Ala Ala Thr Ser Glu
                165                 170                 175

Leu Asp Cys Gln Gln Gly Thr Arg Ala Leu Leu Gln Thr Leu Gly Asn
            180                 185                 190

Leu Gly Tyr Arg Ala Ser Ala Lys Lys Ala Gln Ile Cys Gln Lys Gln
        195                 200                 205

Val Lys Tyr Leu Gly Tyr Leu Leu
    210                 215

<210> SEQ ID NO 16
<211> LENGTH: 141
<212> TYPE: PRT
<213> ORGANISM: Moloney murine leukemia virus

<400> SEQUENCE: 16

Thr Trp Tyr Thr Asp Gly Ser Ser Leu Leu Gln Glu Gly Gln Arg Lys
1               5                   10                  15

Ala Gly Ala Ala Val Thr Thr Glu Thr Glu Val Ile Trp Ala Lys Ala
            20                  25                  30

Leu Pro Ala Gly Thr Ser Ala Gln Arg Ala Glu Leu Ile Ala Leu Thr
        35                  40                  45

Gln Ala Leu Lys Met Ala Glu Gly Lys Lys Leu Asn Val Tyr Thr Asp
    50                  55                  60

```
Ser Arg Tyr Ala Phe Ala Thr Ala His Ile His Gly Glu Ile Tyr Arg
 65                  70                  75                  80

Arg Arg Gly Leu Leu Thr Ser Glu Gly Lys Glu Ile Lys Asn Lys Asp
                 85                  90                  95

Glu Ile Leu Ala Leu Leu Lys Ala Leu Phe Leu Pro Lys Arg Leu Ser
            100                 105                 110

Ile Ile His Cys Pro Gly His Gln Lys Gly His Ser Ala Glu Ala Arg
        115                 120                 125

Gly Asn Arg Met Ala Asp Gln Ala Ala Arg Lys Ala Ala
    130                 135                 140

<210> SEQ ID NO 17
<211> LENGTH: 675
<212> TYPE: PRT
<213> ORGANISM: Tumebacillus flagellatus

<400> SEQUENCE: 17

Ser Ser Gly Leu Val Pro Arg Gly Ser His Met Thr Leu Asn Ile Glu
  1               5                  10                  15

Asp Glu His Arg Leu His Glu Thr Ser Lys Glu Pro Asp Val Ser Leu
             20                  25                  30

Gly Ser Thr Trp Leu Ser Asp Phe Pro Gln Ala Trp Ala Glu Thr Gly
         35                  40                  45

Gly Met Gly Leu Ala Val Arg Gln Ala Pro Leu Ile Ile Pro Leu Lys
 50                  55                  60

Ala Thr Ser Thr Pro Val Ser Ile Lys Gln Tyr Pro Met Ser Gln Lys
 65                  70                  75                  80

Ala Arg Leu Gly Ile Lys Pro His Ile Gln Arg Leu Leu Asp Gln Gly
                 85                  90                  95

Ile Leu Val Pro Cys Gln Ser Pro Trp Asn Thr Pro Leu Leu Pro Val
            100                 105                 110

Lys Lys Pro Gly Thr Asn Asp Tyr Arg Pro Val Gln Asp Leu Arg Glu
        115                 120                 125

Val Asn Lys Arg Val Glu Asp Ile His Pro Thr Val Pro Asn Pro Tyr
    130                 135                 140

Asn Leu Leu Ser Gly Leu Pro Pro Ser His Gln Trp Tyr Thr Val Leu
145                 150                 155                 160

Asp Leu Lys Asp Ala Phe Phe Cys Leu Arg Leu His Pro Thr Ser Gln
                165                 170                 175

Pro Leu Phe Ala Phe Glu Trp Arg Asp Pro Glu Met Gly Ile Ser Gly
            180                 185                 190

Gln Leu Thr Trp Thr Arg Leu Pro Gln Gly Phe Lys Asn Ser Pro Thr
        195                 200                 205

Leu Phe Asp Glu Ala Leu His Arg Asp Leu Ala Asp Phe Arg Ile Gln
    210                 215                 220

His Pro Asp Leu Ile Leu Leu Gln Tyr Val Asp Asp Leu Leu Leu Ala
225                 230                 235                 240

Ala Thr Ser Glu Leu Asp Cys Gln Gln Gly Thr Arg Ala Leu Leu Gln
                245                 250                 255

Thr Leu Gly Asn Leu Gly Tyr Arg Ala Ser Ala Lys Lys Ala Gln Ile
            260                 265                 270

Cys Gln Lys Gln Val Lys Tyr Leu Gly Tyr Leu Leu Lys Glu Gly Gln
        275                 280                 285

Arg Trp Leu Thr Glu Ala Arg Lys Glu Thr Val Met Gly Gln Pro Thr
    290                 295                 300
```

```
Pro Lys Thr Pro Arg Gln Leu Arg Arg Phe Leu Gly Thr Ala Gly Phe
305                 310                 315                 320

Cys Arg Leu Phe Ile Pro Gly Phe Ala Glu Met Ala Ala Pro Leu Tyr
            325                 330                 335

Pro Leu Thr Lys Thr Gly Thr Leu Phe Asn Trp Gly Pro Asp Gln Gln
        340                 345                 350

Lys Ala Tyr Gln Glu Ile Lys Gln Ala Leu Leu Thr Ala Pro Ala Leu
            355                 360                 365

Gly Leu Pro Asp Leu Thr Lys Pro Phe Glu Leu Phe Val Asp Glu Lys
        370                 375                 380

Gln Gly Tyr Ala Lys Gly Val Leu Thr Gln Lys Leu Gly Pro Trp Arg
385                 390                 395                 400

Arg Pro Val Ala Tyr Leu Ser Lys Lys Leu Asp Pro Val Ala Ala Gly
            405                 410                 415

Trp Pro Pro Cys Leu Arg Met Val Ala Ile Ala Val Leu Thr Lys
            420                 425                 430

Asp Ala Gly Lys Leu Thr Met Gly Gln Pro Leu Val Ile Gly Ala Pro
        435                 440                 445

His Ala Val Glu Ala Leu Val Lys Gln Pro Pro Asp Arg Trp Leu Ser
450                 455                 460

Lys Ala Arg Met Thr His Tyr Gln Ala Leu Leu Leu Asp Thr Asp Arg
465                 470                 475                 480

Val Gln Phe Gly Pro Val Val Ala Leu Asn Pro Ala Thr Leu Leu Pro
            485                 490                 495

Leu Pro Glu Glu Gly Leu Gln His Asn Cys Leu Asp Ile Leu Ala Glu
        500                 505                 510

Ala His Gly Thr Arg Pro Asp Leu Thr Asp Gln Pro Leu Pro Asp Ala
        515                 520                 525

Asp His Thr Trp Tyr Thr Asn Gly Ser Ser Leu Leu Gln Glu Gly Gln
        530                 535                 540

Arg Lys Ala Gly Ala Ala Val Thr Thr Glu Thr Glu Val Ile Trp Ala
545                 550                 555                 560

Lys Ala Leu Pro Ala Gly Thr Ser Ala Gln Arg Ala Glu Leu Ile Ala
            565                 570                 575

Leu Thr Gln Ala Leu Lys Met Ala Glu Gly Lys Lys Leu Asn Val Tyr
        580                 585                 590

Thr Asp Ser Arg Tyr Ala Phe Ala Thr Ala His Ile His Gly Glu Ile
        595                 600                 605

Tyr Arg Arg Arg Gly Leu Leu Thr Ser Glu Gly Lys Glu Ile Lys Asn
        610                 615                 620

Lys Asp Glu Ile Leu Ala Leu Leu Lys Ala Leu Phe Leu Pro Lys Arg
625                 630                 635                 640

Leu Ser Ile Ile His Cys Pro Gly His Gln Lys Gly His Ser Ala Glu
                645                 650                 655

Ala Arg Gly Asn Arg Met Ala Asp Gln Ala Ala Arg Lys Ala Ala Ile
            660                 665                 670

Thr Glu Thr
        675

<210> SEQ ID NO 18
<211> LENGTH: 669
<212> TYPE: PRT
<213> ORGANISM: Feline leukemia virus
```

```
<400> SEQUENCE: 18

Thr Leu Gln Leu Glu Glu Tyr Arg Leu Phe Glu Pro Glu Ser Thr
1               5                   10                  15

Gln Lys Gln Glu Met Asp Ile Trp Leu Lys Asn Phe Pro Gln Ala Trp
            20                  25                  30

Ala Glu Thr Gly Gly Met Gly Thr Ala His Cys Gln Ala Pro Val Leu
        35                  40                  45

Ile Gln Leu Lys Ala Thr Ala Thr Pro Ile Ser Ile Arg Gln Tyr Pro
    50                  55                  60

Met Pro His Glu Ala Tyr Gln Gly Ile Lys Pro His Ile Arg Arg Met
65                  70                  75                  80

Leu Asp Gln Gly Ile Leu Lys Pro Cys Gln Ser Pro Trp Asn Thr Pro
                85                  90                  95

Leu Leu Pro Val Lys Lys Pro Gly Thr Glu Asp Tyr Arg Pro Val Gln
            100                 105                 110

Asp Leu Arg Glu Val Asn Lys Arg Val Glu Asp Ile His Pro Thr Val
        115                 120                 125

Pro Asn Pro Tyr Asn Leu Leu Ser Thr Leu Pro Pro Ser His Pro Trp
    130                 135                 140

Tyr Thr Val Leu Asp Leu Lys Asp Ala Phe Phe Cys Leu Arg Leu His
145                 150                 155                 160

Ser Glu Ser Gln Leu Leu Phe Ala Phe Glu Trp Arg Asp Pro Glu Ile
                165                 170                 175

Gly Leu Ser Gly Gln Leu Thr Trp Thr Arg Leu Pro Gln Gly Phe Lys
            180                 185                 190

Asn Ser Pro Thr Leu Phe Asp Glu Ala Leu His Ser Asp Leu Ala Asp
        195                 200                 205

Phe Arg Val Arg Tyr Pro Ala Leu Val Leu Leu Gln Tyr Val Asp Asp
    210                 215                 220

Leu Leu Leu Ala Ala Thr Arg Thr Glu Cys Leu Glu Gly Thr Lys
225                 230                 235                 240

Ala Leu Leu Glu Thr Leu Gly Asn Lys Gly Tyr Arg Ala Ser Ala Lys
                245                 250                 255

Lys Ala Gln Ile Cys Leu Gln Glu Val Thr Tyr Leu Gly Tyr Ser Leu
            260                 265                 270

Lys Asp Gly Gln Arg Trp Leu Thr Lys Ala Arg Lys Glu Ala Ile Leu
        275                 280                 285

Ser Ile Pro Val Pro Lys Asn Ser Arg Gln Val Arg Glu Phe Leu Gly
    290                 295                 300

Thr Ala Gly Tyr Cys Arg Leu Trp Ile Pro Gly Phe Ala Glu Leu Ala
305                 310                 315                 320

Ala Pro Leu Tyr Pro Leu Thr Arg Pro Gly Thr Leu Phe Gln Trp Gly
                325                 330                 335

Thr Glu Gln Gln Leu Ala Phe Glu Asp Ile Lys Lys Ala Leu Leu Ser
            340                 345                 350

Ser Pro Ala Leu Gly Leu Pro Asp Ile Thr Lys Pro Phe Glu Leu Phe
        355                 360                 365

Ile Asp Glu Asn Ser Gly Phe Ala Lys Gly Val Leu Val Gln Lys Leu
    370                 375                 380

Gly Pro Trp Lys Arg Pro Val Ala Tyr Leu Ser Lys Lys Leu Asp Thr
385                 390                 395                 400

Val Ala Ser Gly Trp Pro Pro Cys Leu Arg Met Val Ala Ala Ile Ala
                405                 410                 415
```

-continued

```
Ile Leu Val Lys Asp Ala Gly Lys Leu Thr Leu Gly Gln Pro Leu Thr
            420                 425                 430

Ile Leu Thr Ser His Pro Val Glu Ala Leu Val Arg Gln Pro Pro Asn
            435                 440                 445

Lys Trp Leu Ser Asn Ala Arg Met Thr His Tyr Gln Ala Met Leu Leu
450                 455                 460

Asp Ala Glu Arg Val His Phe Gly Pro Thr Val Ser Leu Asn Pro Ala
465                 470                 475                 480

Thr Leu Leu Pro Leu Pro Ser Gly Gly Asn His His Asp Cys Leu Gln
                485                 490                 495

Ile Leu Ala Glu Thr His Gly Thr Arg Pro Asp Leu Thr Asp Gln Pro
            500                 505                 510

Leu Pro Asp Ala Asp Leu Thr Trp Tyr Thr Asp Gly Ser Ser Phe Ile
            515                 520                 525

Arg Asn Gly Glu Arg Glu Ala Gly Ala Ala Val Thr Thr Glu Ser Glu
            530                 535                 540

Val Ile Trp Ala Ala Pro Leu Pro Pro Gly Thr Ser Ala Gln Arg Ala
545                 550                 555                 560

Glu Leu Ile Ala Leu Thr Gln Ala Leu Lys Met Ala Glu Gly Lys Lys
                565                 570                 575

Leu Thr Val Tyr Thr Asp Ser Arg Tyr Ala Phe Ala Thr Thr His Val
            580                 585                 590

His Gly Glu Ile Tyr Arg Arg Arg Gly Leu Leu Thr Ser Glu Gly Lys
            595                 600                 605

Glu Ile Lys Asn Lys Asn Glu Ile Leu Ala Leu Leu Glu Ala Leu Phe
610                 615                 620

Leu Pro Lys Arg Leu Ser Ile Ile His Cys Pro Gly His Gln Lys Gly
625                 630                 635                 640

Asp Ser Pro Gln Ala Lys Gly Asn Arg Leu Ala Asp Asp Thr Ala Lys
                645                 650                 655

Lys Ala Ala Thr Glu Thr His Ser Ser Leu Thr Val Leu
            660                 665
```

<210> SEQ ID NO 19
<211> LENGTH: 650
<212> TYPE: PRT
<213> ORGANISM: Moloney murine leukemia virus
<400> SEQUENCE: 19

```
Met Thr Trp Leu Ser Asp Phe Pro Gln Ala Trp Ala Glu Thr Gly Gly
1               5                   10                  15

Met Gly Leu Ala Val Arg Gln Ala Pro Leu Ile Ile Pro Leu Lys Ala
            20                  25                  30

Thr Ser Thr Pro Val Ser Ile Lys Gln Tyr Pro Met Ser Gln Glu Ala
            35                  40                  45

Arg Leu Gly Ile Lys Pro His Ile Gln Arg Leu Leu Asp Gln Gly Ile
            50                  55                  60

Leu Val Pro Cys Gln Ser Pro Trp Asn Thr Pro Leu Leu Pro Val Lys
65                  70                  75                  80

Lys Pro Gly Thr Asn Asp Tyr Arg Pro Val Gln Asp Leu Arg Glu Val
                85                  90                  95

Asn Lys Arg Val Glu Asp Ile His Pro Thr Val Pro Asn Pro Tyr Asn
            100                 105                 110

Leu Leu Ser Gly Leu Pro Pro Ser His Gln Trp Tyr Thr Val Leu Asp
```

```
                115                 120                 125
Leu Lys Asp Ala Phe Phe Cys Leu Arg Leu His Pro Thr Ser Gln Pro
    130                 135                 140
Leu Phe Ala Phe Glu Trp Arg Asp Pro Glu Met Gly Ile Ser Gly Gln
145                 150                 155                 160
Leu Thr Trp Thr Arg Leu Pro Gln Gly Phe Lys Asn Ser Pro Thr Leu
                165                 170                 175
Phe Asp Glu Ala Leu His Arg Asp Leu Ala Asp Phe Arg Ile Gln His
                180                 185                 190
Pro Asp Leu Ile Leu Leu Gln Tyr Val Asp Asp Leu Leu Leu Ala Ala
                195                 200                 205
Thr Ser Glu Leu Asp Cys Gln Gln Gly Thr Arg Ala Leu Leu Gln Thr
    210                 215                 220
Leu Gly Asn Leu Gly Tyr Arg Ala Ser Ala Lys Lys Ala Gln Ile Cys
225                 230                 235                 240
Gln Lys Gln Val Lys Tyr Leu Gly Tyr Leu Leu Lys Glu Gly Gln Arg
                245                 250                 255
Trp Leu Thr Glu Ala Arg Lys Glu Thr Val Met Gly Gln Pro Thr Pro
    260                 265                 270
Lys Thr Pro Arg Gln Leu Arg Glu Phe Leu Gly Thr Ala Gly Phe Cys
            275                 280                 285
Arg Leu Trp Ile Pro Gly Phe Ala Glu Met Ala Ala Pro Leu Tyr Pro
    290                 295                 300
Leu Thr Lys Thr Gly Thr Leu Phe Asn Trp Gly Pro Asp Gln Gln Lys
305                 310                 315                 320
Ala Tyr Gln Glu Ile Lys Gln Ala Leu Leu Thr Ala Pro Ala Leu Gly
                325                 330                 335
Leu Pro Asp Leu Thr Lys Pro Phe Glu Leu Phe Val Asp Glu Lys Gln
                340                 345                 350
Gly Tyr Ala Lys Gly Val Leu Thr Gln Lys Leu Gly Pro Trp Arg Arg
                355                 360                 365
Pro Val Ala Tyr Leu Ser Lys Lys Leu Asp Pro Val Ala Ala Gly Trp
    370                 375                 380
Pro Pro Cys Leu Arg Met Val Ala Ala Ile Ala Val Leu Thr Lys Asp
385                 390                 395                 400
Ala Gly Lys Leu Thr Met Gly Gln Pro Leu Val Ile Lys Ala Pro His
                405                 410                 415
Ala Val Glu Ala Leu Val Lys Gln Pro Pro Asp Arg Trp Leu Ser Asn
                420                 425                 430
Ala Arg Met Thr His Tyr Gln Ala Leu Leu Leu Asp Thr Asp Arg Val
            435                 440                 445
Gln Phe Gly Pro Val Val Ala Leu Asn Pro Ala Thr Leu Leu Pro Leu
    450                 455                 460
Pro Glu Glu Gly Leu Gln His Asn Cys Leu Asp Ile Leu Ala Glu Ala
465                 470                 475                 480
His Gly Thr Arg Pro Asp Leu Thr Asp Gln Pro Leu Pro Asp Ala Asp
                485                 490                 495
His Thr Trp Tyr Thr Asp Gly Ser Ser Leu Leu Gln Glu Gly Gln Arg
                500                 505                 510
Lys Ala Gly Ala Ala Val Thr Thr Glu Thr Glu Val Ile Trp Ala Lys
            515                 520                 525
Ala Leu Pro Ala Gly Thr Ser Ala Gln Arg Ala Ala Leu Ile Ala Leu
    530                 535                 540
```

```
Thr Gln Ala Leu Lys Met Ala Glu Gly Lys Lys Leu Asn Val Tyr Thr
545                 550                 555                 560

Ala Ser Arg Tyr Ala Phe Ala Thr Ala His Ile His Gly Glu Ile Tyr
                565                 570                 575

Arg Arg Arg Gly Leu Leu Thr Ser Glu Gly Lys Glu Ile Lys Asn Lys
            580                 585                 590

Asp Glu Ile Leu Ala Leu Leu Lys Ala Leu Phe Leu Pro Lys Arg Leu
                595                 600                 605

Ser Ile Ile His Cys Pro Gly His Gln Lys Gly His Ser Ala Glu Ala
            610                 615                 620

Arg Gly Asn Arg Met Ala Asp Gln Ala Ala Arg Lys Ala Ala Ile Thr
625                 630                 635                 640

Glu Thr Pro Asp Thr Ser Thr Leu Leu Ile
                645                 650

<210> SEQ ID NO 20
<211> LENGTH: 441
<212> TYPE: PRT
<213> ORGANISM: Xenotropic murine leukemia virus-related virus

<400> SEQUENCE: 20

Asp Phe Pro Gln Ala Trp Ala Glu Thr Gly Gly Met Gly Leu Ala Val
1               5                   10                  15

Arg Gln Ala Pro Leu Ile Ile Pro Leu Lys Ala Thr Ser Thr Pro Val
                20                  25                  30

Ser Ile Lys Gln Tyr Pro Met Ser Gln Glu Ala Arg Leu Gly Ile Lys
            35                  40                  45

Pro His Ile Gln Arg Leu Leu Asp Gln Gly Ile Leu Val Pro Cys Gln
        50                  55                  60

Ser Pro Trp Asn Thr Pro Leu Leu Pro Val Lys Lys Asp Tyr Arg Pro
65              70                  75                  80

Val Gln Asp Leu Arg Glu Val Asn Lys Arg Val Glu Asp Ile His Pro
                85                  90                  95

Thr Val Pro Asn Pro Tyr Asn Leu Leu Ser Gly Leu Pro Pro Ser His
            100                 105                 110

Gln Trp Tyr Thr Val Leu Asp Leu Lys Asp Ala Phe Phe Cys Leu Arg
        115                 120                 125

Leu His Pro Thr Ser Gln Pro Leu Phe Ala Phe Glu Trp Arg Asp Gln
        130                 135                 140

Leu Thr Trp Thr Arg Leu Pro Gln Gly Phe Lys Asn Ser Pro Thr Leu
145                 150                 155                 160

Phe Asp Glu Ala Leu His Arg Asp Leu Ala Asp Phe Arg Ile Gln His
                165                 170                 175

Pro Asp Leu Ile Leu Leu Gln Tyr Val Asp Asp Leu Leu Leu Ala Ala
            180                 185                 190

Thr Ser Glu Gln Asp Cys Gln Arg Gly Thr Arg Ala Leu Leu Gln Thr
        195                 200                 205

Leu Gly Asn Leu Gly Tyr Arg Ala Ser Ala Lys Lys Ala Gln Ile Cys
    210                 215                 220

Gln Lys Gln Val Lys Tyr Leu Gly Tyr Leu Leu Lys Glu Gly Gln Arg
225                 230                 235                 240

Trp Leu Thr Glu Ala Arg Lys Glu Thr Val Met Gly Gln Pro Thr Pro
                245                 250                 255

Lys Thr Pro Arg Gln Leu Arg Glu Phe Leu Gly Thr Ala Gly Phe Cys
```

```
                260                 265                 270
Arg Leu Trp Ile Pro Gly Phe Ala Glu Met Ala Ala Pro Leu Tyr Pro
            275                 280                 285

Leu Thr Lys Thr Leu Phe Asn Trp Gly Pro Asp Gln Gln Lys Ala Tyr
        290                 295                 300

Gln Glu Ile Lys Gln Ala Leu Leu Thr Ala Pro Ala Leu Gly Leu Pro
305                 310                 315                 320

Asp Leu Thr Lys Pro Phe Glu Leu Phe Val Asp Glu Lys Gln Gly Tyr
                325                 330                 335

Ala Lys Gly Val Leu Thr Gln Lys Leu Gly Pro Trp Arg Arg Pro Val
            340                 345                 350

Ala Tyr Leu Ser Lys Lys Leu Asp Pro Val Ala Ala Gly Trp Pro Pro
        355                 360                 365

Cys Leu Arg Met Val Ala Ile Ala Val Leu Thr Lys Asp Ala Gly
        370                 375                 380

Lys Leu Thr Met Gly Gln Pro Leu Val Ile Leu Ala Pro His Ala Val
385                 390                 395                 400

Glu Ala Leu Val Lys Gln Pro Ala Arg Met Thr His Tyr Gln Ala
                405                 410                 415

Met Leu Leu Asp Thr Asp Arg Val Gln Phe Gly Pro Val Val Ala Leu
            420                 425                 430

Asn Pro Ala Thr Leu Pro Leu Pro
        435                 440

<210> SEQ ID NO 21
<211> LENGTH: 453
<212> TYPE: PRT
<213> ORGANISM: Unknown
<220> FEATURE:
<223> OTHER INFORMATION: Description of Unknown:
      4mh8 sequence

<400> SEQUENCE: 21

Thr Trp Leu Ser Asp Phe Pro Gln Ala Trp Ala Glu Thr Gly Gly Met
1               5                   10                  15

Gly Leu Ala Val Arg Gln Ala Pro Leu Ile Ile Pro Leu Lys Ala Thr
            20                  25                  30

Ser Thr Pro Val Ser Ile Lys Gln Tyr Pro Met Ser Gln Glu Ala Arg
        35                  40                  45

Leu Gly Ile Lys Pro His Ile Gln Arg Leu Leu Asp Gln Gly Ile Leu
    50                  55                  60

Val Pro Cys Gln Ser Pro Trp Asn Thr Pro Leu Leu Pro Val Lys Thr
65                  70                  75                  80

Asn Asp Tyr Arg Pro Val Gln Asp Leu Arg Glu Val Asn Lys Arg Val
                85                  90                  95

Glu Asp Ile His Pro Thr Val Pro Asn Pro Tyr Asn Leu Leu Ser Gly
            100                 105                 110

Leu Pro Pro Ser His Gln Trp Tyr Thr Val Leu Asp Leu Lys Asp Ala
        115                 120                 125

Phe Phe Cys Leu Arg Leu His Pro Thr Ser Gln Pro Leu Phe Ala Phe
    130                 135                 140

Glu Trp Arg Asp Pro Glu Met Gly Ile Ser Gly Gln Leu Thr Trp Thr
145                 150                 155                 160

Arg Leu Pro Gln Gly Phe Lys Asn Ser Pro Thr Leu Phe Asp Glu Ala
                165                 170                 175
```

```
Leu His Arg Asp Leu Ala Asp Phe Arg Ile Gln His Pro Asp Leu Ile
            180                 185                 190

Leu Leu Gln Tyr Val Asp Asp Leu Leu Ala Ala Thr Ser Glu Leu
        195                 200                 205

Asp Cys Gln Gln Gly Thr Arg Ala Leu Leu Gln Thr Leu Gly Asn Leu
    210                 215                 220

Gly Tyr Arg Ala Ser Ala Lys Lys Ala Gln Ile Cys Gln Lys Gln Val
225                 230                 235                 240

Lys Tyr Leu Gly Tyr Leu Leu Lys Glu Gly Gln Arg Trp Leu Thr Glu
                245                 250                 255

Ala Arg Lys Glu Thr Val Met Gly Gln Pro Thr Pro Lys Thr Pro Arg
            260                 265                 270

Gln Leu Arg Glu Phe Leu Gly Thr Ala Gly Phe Cys Arg Leu Trp Ile
        275                 280                 285

Pro Gly Phe Ala Glu Met Ala Ala Pro Leu Tyr Pro Leu Thr Lys Thr
    290                 295                 300

Leu Phe Asn Trp Gly Pro Asp Gln Gln Lys Ala Tyr Gln Glu Ile Lys
305                 310                 315                 320

Gln Ala Leu Leu Thr Ala Pro Ala Leu Gly Leu Pro Asp Leu Thr Lys
                325                 330                 335

Pro Phe Glu Leu Phe Val Asp Glu Lys Gln Gly Tyr Ala Lys Gly Val
            340                 345                 350

Leu Thr Gln Lys Leu Gly Pro Trp Arg Arg Pro Val Ala Tyr Leu Ser
        355                 360                 365

Lys Lys Leu Asp Pro Val Ala Ala Gly Trp Pro Pro Cys Leu Arg Met
    370                 375                 380

Val Ala Ile Ala Val Leu Thr Lys Asp Ala Gly Lys Leu Thr Met
385                 390                 395                 400

Gly Gln Pro Leu Val Ile Lys Ala Pro His Ala Val Glu Ala Leu Val
                405                 410                 415

Lys Gln Pro Pro Ala Arg Met Thr His Tyr Gln Ala Leu Leu Leu Asp
            420                 425                 430

Thr Asp Arg Val Gln Phe Gly Pro Val Val Ala Leu Asn Pro Ala Thr
        435                 440                 445

Leu Leu Pro Leu Pro
    450

<210> SEQ ID NO 22
<211> LENGTH: 935
<212> TYPE: PRT
<213> ORGANISM: Feline immunodeficiency virus

<400> SEQUENCE: 22

Gln Ile Lys Gln Trp Pro Leu Thr Asn Glu Lys Ile Glu Ala Leu Thr
1               5                   10                  15

Glu Ile Val Glu Arg Leu Glu Arg Glu Gly Lys Val Lys Arg Ala Asp
            20                  25                  30

Pro Asn Asn Pro Trp Asn Thr Pro Val Phe Ala Ile Lys Lys Lys Ser
        35                  40                  45

Gly Lys Trp Arg Met Leu Ile Asp Phe Arg Glu Leu Asn Lys Leu Thr
    50                  55                  60

Glu Lys Gly Ala Gln Leu Gly Leu Pro His Pro Ala Gly Leu Gln Ile
65                  70                  75                  80

Lys Lys Gln Val Thr Val Leu Asp Ile Gly Asp Ala Tyr Phe Thr Ile
                85                  90                  95
```

```
Pro Leu Asp Pro Asp Tyr Ala Pro Tyr Thr Ala Phe Thr Leu Pro Arg
            100                 105                 110

Lys Asn Asn Ala Gly Pro Gly Arg Arg Phe Val Trp Cys Ser Leu Pro
            115                 120                 125

Gln Gly Trp Ile Leu Ser Pro Leu Ile Tyr Gln Ser Thr Leu Asp Asn
            130                 135                 140

Ile Ile Gln Pro Phe Ile Arg Gln Asn Pro Gln Leu Asp Ile Tyr Gln
145                 150                 155                 160

Tyr Met Asp Asp Ile Tyr Ile Gly Ser Asn Leu Ser Lys Lys Glu His
                165                 170                 175

Lys Glu Lys Val Glu Glu Leu Arg Lys Leu Leu Leu Trp Trp Gly Phe
            180                 185                 190

Glu Thr Pro Glu Asp Lys Leu Gln Glu Glu Pro Pro Tyr Thr Trp Met
            195                 200                 205

Gly Tyr Glu Leu His Pro Leu Thr Trp Thr Ile Gln Gln Lys Gln Leu
210                 215                 220

Asp Ile Pro Glu Gln Pro Thr Leu Asn Glu Leu Gln Lys Leu Ala Gly
225                 230                 235                 240

Lys Ile Asn Trp Ala Ser Gln Ala Ile Pro Asp Leu Ser Ile Lys Ala
                245                 250                 255

Leu Thr Asn Met Met Arg Gly Asn Gln Asn Leu Asn Ser Thr Arg Gln
            260                 265                 270

Trp Thr Lys Glu Ala Arg Leu Glu Val Gln Lys Ala Lys Lys Ala Ile
            275                 280                 285

Glu Glu Gln Val Gln Leu Gly Tyr Tyr Asp Pro Ser Lys Glu Leu Tyr
            290                 295                 300

Ala Lys Leu Ser Leu Val Gly Pro His Gln Ile Ser Tyr Gln Val Tyr
305                 310                 315                 320

Gln Lys Asp Pro Glu Lys Ile Leu Trp Tyr Gly Lys Met Ser Arg Gln
                325                 330                 335

Lys Lys Lys Ala Glu Asn Thr Cys Asp Ile Ala Leu Arg Ala Cys Tyr
            340                 345                 350

Lys Ile Arg Glu Glu Ser Ile Ile Arg Ile Gly Lys Glu Pro Arg Tyr
            355                 360                 365

Glu Ile Pro Thr Ser Arg Glu Ala Trp Glu Ser Asn Leu Ile Asn Ser
            370                 375                 380

Pro Tyr Leu Lys Ala Pro Pro Glu Val Glu Tyr Ile His Ala Ala
385                 390                 395                 400

Leu Asn Ile Lys Arg Ala Leu Ser Met Ile Lys Asp Ala Pro Ile Pro
                405                 410                 415

Gly Ala Glu Thr Trp Tyr Ile Asp Gly Gly Arg Lys Leu Gly Lys Ala
            420                 425                 430

Ala Lys Ala Ala Tyr Trp Thr Asp Thr Gly Lys Trp Gln Val Met Glu
            435                 440                 445

Leu Glu Gly Ser Asn Gln Lys Ala Glu Ile Gln Ala Leu Leu Leu Ala
            450                 455                 460

Leu Lys Ala Gly Ser Glu Glu Met Asn Ile Ile Thr Asp Ser Gln Tyr
465                 470                 475                 480

Val Ile Asn Ile Ile Leu Gln Gln Pro Asp Met Met Glu Gly Ile Trp
                485                 490                 495

Gln Glu Val Leu Glu Glu Leu Glu Lys Lys Thr Ala Ile Phe Ile Asp
            500                 505                 510
```

```
Trp Val Pro Gly His Lys Gly Ile Pro Gly Asn Glu Glu Val Asp Lys
            515                 520                 525

Leu Cys Ser Asp Lys Ile Pro Val Val Lys Val Lys Met Lys Asp Pro
        530                 535                 540

Asn Lys Gly Pro Gln Ile Lys Gln Trp Pro Leu Thr Asn Glu Lys Ile
545                 550                 555                 560

Glu Ala Leu Thr Glu Ile Val Glu Arg Leu Glu Arg Glu Gly Lys Val
                565                 570                 575

Lys Arg Ala Asp Pro Asn Asn Pro Trp Asn Thr Pro Val Phe Ala Ile
            580                 585                 590

Lys Lys Lys Ser Gly Lys Trp Arg Met Leu Ile Asp Phe Arg Glu Leu
        595                 600                 605

Asn Lys Leu Thr Glu Lys Leu Gly Leu Pro His Pro Ala Gly Leu Gln
    610                 615                 620

Ile Lys Lys Gln Val Thr Val Leu Asp Ile Gly Asp Ala Tyr Phe Thr
625                 630                 635                 640

Ile Pro Leu Asp Pro Asp Tyr Ala Pro Tyr Thr Ala Phe Thr Leu Pro
                645                 650                 655

Arg Lys Asn Asn Ala Gly Pro Gly Arg Arg Phe Val Trp Cys Ser Leu
            660                 665                 670

Pro Gln Gly Trp Ile Leu Ser Pro Leu Ile Tyr Gln Ser Thr Leu Asp
        675                 680                 685

Asn Ile Ile Gln Pro Phe Ile Arg Gln Asn Pro Gln Leu Asp Ile Tyr
    690                 695                 700

Gln Tyr Met Asp Asp Ile Tyr Ile Gly Ser Asn Leu Ser Lys Lys Glu
705                 710                 715                 720

His Lys Glu Lys Val Glu Glu Leu Arg Lys Leu Leu Leu Trp Pro Glu
                725                 730                 735

Asp Lys Leu Gln Glu Glu Thr Trp Thr Ile Gln Gln Lys Gln Leu Asp
            740                 745                 750

Ile Pro Glu Gln Pro Thr Leu Asn Glu Leu Gln Lys Leu Ala Gly Lys
        755                 760                 765

Ile Asn Trp Ala Ser Gln Ala Ile Pro Asp Leu Ser Ile Lys Ala Leu
    770                 775                 780

Thr Asn Met Met Arg Gly Asn Gln Asn Leu Asn Ser Thr Arg Gln Trp
785                 790                 795                 800

Thr Lys Glu Ala Arg Leu Glu Val Gln Lys Ala Lys Lys Ala Ile Glu
                805                 810                 815

Glu Gln Val Gln Leu Gly Tyr Tyr Asp Pro Ser Lys Glu Leu Tyr Ala
            820                 825                 830

Lys Leu Ser Leu Val Gly Pro His Gln Ile Ser Tyr Gln Val Tyr Gln
        835                 840                 845

Lys Asp Pro Glu Lys Ile Leu Trp Tyr Gly Lys Met Ser Arg Gln Lys
    850                 855                 860

Lys Lys Ala Glu Asn Thr Cys Asp Ile Ala Leu Arg Ala Cys Tyr Lys
865                 870                 875                 880

Ile Arg Glu Glu Ser Ile Ile Arg Ile Gly Lys Glu Pro Arg Tyr Glu
                885                 890                 895

Ile Pro Thr Ser Arg Glu Ala Trp Glu Ser Asn Leu Ile Asn Ser Pro
            900                 905                 910

Tyr Leu Lys Ala Pro Pro Glu Val Glu Tyr Ile His Ala Ala Leu
        915                 920                 925

Asn Ile Lys Arg Ala Leu Ser
```

930                 935

<210> SEQ ID NO 23
<211> LENGTH: 940
<212> TYPE: PRT
<213> ORGANISM: Human immunodeficiency virus 2

<400> SEQUENCE: 23

Ala Lys Val Glu Pro Ile Lys Ile Met Leu Lys Pro Gly Lys Asp Gly
1               5                   10                  15

Pro Lys Leu Arg Gln Trp Pro Leu Thr Lys Glu Lys Ile Glu Ala Leu
            20                  25                  30

Lys Glu Ile Cys Glu Lys Met Glu Lys Glu Gly Gln Leu Glu Glu Ala
        35                  40                  45

Pro Pro Thr Asn Pro Tyr Asn Thr Pro Thr Phe Ala Ile Lys Lys Lys
    50                  55                  60

Asp Arg Met Leu Ile Asp Phe Arg Glu Leu Asn Lys Val Thr Gln Asp
65                  70                  75                  80

Phe Thr Glu Ile Gln Leu Gly Ile Pro His Pro Ala Gly Leu Ala Lys
                85                  90                  95

Lys Arg Arg Ile Thr Val Leu Asp Val Gly Asp Ala Tyr Phe Ser Ile
            100                 105                 110

Pro Leu His Glu Asp Phe Arg Pro Tyr Thr Ala Phe Thr Leu Lys Arg
        115                 120                 125

Tyr Ile Tyr Lys Val Leu Pro Gln Gly Trp Lys Gly Ser Pro Ala Ile
    130                 135                 140

Phe Gln His Thr Met Arg Gln Val Leu Glu Pro Phe Arg Lys Ala Asn
145                 150                 155                 160

Lys Asp Val Ile Ile Gln Tyr Met Asp Asp Ile Leu Ile Ala Ser
                165                 170                 175

Asp Arg Thr Asp Leu Glu His Asp Arg Val Val Leu Gln Leu Lys Glu
            180                 185                 190

Leu Leu Asn Gly Leu Gly Phe Ser Thr Pro Asp Glu Lys Phe Gln Lys
        195                 200                 205

Asp Pro Pro Tyr His Trp Met Gly Tyr Glu Leu Trp Pro Thr Lys Trp
    210                 215                 220

Lys Leu Gln Lys Ile Gln Leu Pro Gln Lys Glu Ile Trp Thr Val Asn
225                 230                 235                 240

Asp Ile Gln Lys Leu Val Gly Val Leu Asn Trp Ala Ala Gln Leu Tyr
                245                 250                 255

Pro Gly Ile Lys Thr Lys His Leu Cys Arg Leu Ile Ser Gly Lys Met
            260                 265                 270

Thr Leu Thr Glu Glu Val Gln Trp Thr Glu Leu Ala Glu Ala Glu Leu
        275                 280                 285

Glu Glu Asn Arg Ile Ile Leu Ser Gln Glu Gln Glu Gly His Tyr Tyr
    290                 295                 300

Gln Glu Glu Lys Glu Leu Glu Ala Thr Val Gln Lys Asp Gln Asp Asn
305                 310                 315                 320

Gln Trp Thr Tyr Lys Ile His Gln Glu Glu Lys Ile Leu Lys Val Gly
                325                 330                 335

Lys Tyr Ala Lys Val Thr His Thr Asn Gly Ile Arg Leu Leu Ala Gln
            340                 345                 350

Val Val Gln Lys Ile Gly Lys Glu Ala Leu Val Ile Trp Gly Arg Ile
        355                 360                 365

```
Pro Lys Phe His Leu Pro Val Glu Arg Glu Ile Trp Glu Gln Trp Trp
    370                 375                 380

Asp Asn Tyr Trp Gln Val Thr Trp Ile Pro Asp Trp Asp Phe Val Ser
385                 390                 395                 400

Thr Pro Pro Leu Val Arg Leu Ala Phe Asn Leu Val Gly Asp Pro Ile
                405                 410                 415

Pro Gly Ala Glu Thr Phe Tyr Thr Asp Gly Ser Cys Asn Arg Gln Ser
            420                 425                 430

Lys Glu Gly Lys Ala Gly Tyr Val Thr Asp Arg Gly Lys Asp Lys Val
            435                 440                 445

Lys Lys Leu Glu Gln Thr Thr Asn Gln Gln Ala Glu Leu Glu Ala Phe
450                 455                 460

Ala Met Ala Leu Thr Asp Ser Gly Pro Lys Val Asn Ile Ile Val Asp
465                 470                 475                 480

Ser Gln Tyr Val Met Gly Ile Val Ala Ser Gln Pro Thr Glu Ser Glu
                485                 490                 495

Ser Lys Ile Val Asn Gln Ile Ile Glu Glu Met Ile Lys Lys Glu Ala
                500                 505                 510

Ile Tyr Val Ala Trp Val Pro Ala His Lys Gly Ile Gly Gly Asn Gln
            515                 520                 525

Glu Val Asp His Leu Val Ser Gln Gly Ile Glu Pro Ile Lys Ile Met
530                 535                 540

Leu Lys Pro Gly Lys Asp Gly Pro Lys Leu Arg Gln Trp Pro Leu Thr
545                 550                 555                 560

Lys Glu Lys Ile Glu Ala Leu Lys Glu Ile Cys Glu Lys Met Glu Lys
                565                 570                 575

Glu Gly Gln Leu Glu Glu Ala Pro Pro Thr Asn Pro Tyr Asn Thr Pro
            580                 585                 590

Thr Phe Ala Ile Lys Asn Lys Trp Arg Met Leu Ile Asp Phe Arg Glu
            595                 600                 605

Leu Asn Lys Val Thr Gln Asp Phe Thr Glu Ile Gln Pro His Pro Ala
    610                 615                 620

Gly Leu Ala Lys Lys Arg Arg Ile Thr Val Leu Asp Val Gly Asp Ala
625                 630                 635                 640

Tyr Phe Ser Ile Pro Leu His Glu Asp Phe Arg Pro Tyr Thr Ala Phe
                645                 650                 655

Thr Leu Pro Ser Val Asn Asn Ala Glu Pro Gly Lys Arg Tyr Ile Tyr
            660                 665                 670

Lys Val Leu Pro Gln Gly Trp Lys Gly Ser Pro Ala Ile Phe Gln His
            675                 680                 685

Thr Met Arg Gln Val Leu Glu Pro Phe Arg Lys Ala Asn Lys Asp Val
690                 695                 700

Ile Ile Ile Gln Tyr Met Asp Asp Ile Leu Ile Ala Ser Asp Arg Thr
705                 710                 715                 720

Asp Leu Glu His Asp Arg Val Val Leu Gln Leu Lys Glu Leu Leu Asn
                725                 730                 735

Gly Trp Met Gly Tyr Glu Leu Trp Pro Thr Lys Trp Lys Leu Gln Lys
            740                 745                 750

Ile Gln Leu Pro Gln Lys Glu Ile Trp Thr Val Asn Asp Ile Gln Lys
    755                 760                 765

Leu Val Gly Val Leu Asn Trp Ala Ala Gln Leu Tyr Pro Gly Ile Lys
    770                 775                 780

Thr Lys His Leu Cys Arg Leu Ile Ser Gly Lys Met Thr Leu Thr Glu
```

```
                785                 790                 795                 800
Glu Val Gln Trp Thr Glu Leu Ala Glu Ala Glu Leu Glu Asn Arg
                    805                 810                 815

Ile Ile Leu Ser Gln Glu Gln Glu Gly His Tyr Tyr Gln Glu Lys
                    820                 825                 830

Glu Leu Glu Ala Thr Val Gln Asp Gln Asp Asn Gln Trp Thr Tyr
                    835                 840                 845

Lys Ile His Gln Glu Lys Ile Leu Lys Val Gly Lys Tyr Ala Lys
850                 855                 860

Val Lys Asn Thr His Thr Asn Gly Ile Arg Leu Leu Ala Gln Val Val
865                 870                 875                 880

Gln Lys Ile Gly Lys Glu Ala Leu Val Ile Trp Gly Arg Ile Pro Lys
                    885                 890                 895

Phe His Leu Pro Val Glu Arg Glu Ile Trp Glu Gln Trp Trp Asp Asn
                    900                 905                 910

Tyr Trp Gln Val Thr Trp Ile Pro Asp Trp Asp Phe Val Ser Thr Pro
                    915                 920                 925

Pro Leu Val Arg Leu Ala Phe Asn Leu Val Gly Asp
                    930                 935                 940

<210> SEQ ID NO 24
<211> LENGTH: 560
<212> TYPE: PRT
<213> ORGANISM: Unknown
<220> FEATURE:
<223> OTHER INFORMATION: Description of Unknown:
      Seq3SS sequence

<400> SEQUENCE: 24

Pro Ile Ser Pro Ile Ala Pro Val Pro Val Lys Leu Lys Pro Gly Met
1               5                   10                  15

Asp Gly Pro Lys Val Lys Gln Trp Pro Leu Ser Lys Glu Lys Ile Glu
                20                  25                  30

Ala Leu Thr Ala Ile Cys Gln Glu Met Glu Gln Glu Gly Lys Ile Ser
            35                  40                  45

Arg Ile Gly Pro Glu Asn Pro Tyr Asn Thr Pro Ile Phe Ala Ile Lys
    50                  55                  60

Lys Lys Asp Ser Thr Lys Trp Arg Lys Leu Val Asp Phe Arg Glu Leu
65                  70                  75                  80

Asn Lys Arg Thr Gln Asp Phe Trp Glu Val Gln Leu Gly Ile Pro His
                85                  90                  95

Pro Gly Gly Leu Lys Gln Lys Arg Ser Val Thr Val Leu Asp Val Gly
                100                 105                 110

Asp Ala Tyr Phe Ser Cys Pro Leu Asp Pro Asp Phe Arg Lys Tyr Thr
            115                 120                 125

Ala Phe Thr Ile Pro Ser Val Asn Asn Glu Thr Pro Gly Ile Arg Tyr
    130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Asp Pro Phe Arg Lys Asp Asn Pro
                165                 170                 175

Glu Leu Glu Ile Cys Gln Tyr Met Asp Asp Leu Tyr Val Gly Ser Asp
                180                 185                 190

Leu Pro Leu Ala Glu His Arg Lys Arg Val Glu Leu Leu Arg Glu His
            195                 200                 205
```

-continued

Leu Tyr Gln Trp Gly Phe Thr Thr Pro Asp Lys Lys His Gln Lys Glu
    210                 215                 220

Pro Pro Phe Met Trp Met Gly Tyr Glu Leu His Pro Asp Lys Trp Thr
225                 230                 235                 240

Val Gln Pro Ile Lys Leu Pro Asn Lys Asp Val Trp Thr Val Asn Asp
            245                 250                 255

Ile Gln Lys Leu Ile Gly Lys Leu Asn Trp Ala Ser Gln Ile Tyr Gln
        260                 265                 270

Gly Ile Arg Val Arg Glu Leu Cys Lys Leu Ile Arg Gly Thr Lys Ser
    275                 280                 285

Leu Thr Glu Val Val Pro Leu Ser Lys Glu Ala Glu Met Glu Leu Glu
290                 295                 300

Glu Asn Arg Glu Lys Leu Lys Glu Pro Met His Gly Val Tyr Tyr Gln
305                 310                 315                 320

Pro Asp Lys Asp Leu Trp Val Asn Ile Gln Lys Gly Glu Gly Gln
            325                 330                 335

Trp Thr Tyr Gln Ile Tyr Gln Asp Glu His Lys Asn Leu Lys Thr Gly
        340                 345                 350

Lys Tyr Thr Arg Gln Arg Gly Ala His Thr Asn Asp Ile Arg Gln Leu
    355                 360                 365

Ala Glu Val Ile Gln Lys Val Ser Gln Glu Ser Ile Val Ile Trp Gly
370                 375                 380

Lys Leu Pro Lys Phe Lys Leu Pro Val Thr Arg Glu Thr Trp Glu Thr
385                 390                 395                 400

Trp Trp Ala Asp Tyr Trp Gln Ala Thr Trp Ile Pro Glu Trp Asp Tyr
            405                 410                 415

Val Ser Thr Pro Pro Leu Ile Lys Leu Trp Tyr Arg Leu Glu Ser Glu
        420                 425                 430

Pro Ile Met Gly Ala Glu Thr Tyr Tyr Val Asp Gly Ala Ala Asn Arg
    435                 440                 445

Asp Thr Lys Leu Gly Lys Ala Gly Tyr Val Thr Glu Gln Gly Lys Gln
450                 455                 460

Lys Ile Ile Lys Leu Asn Glu Thr Thr Asn Gln Lys Ala Glu Leu Met
465                 470                 475                 480

Ala Val Leu Leu Ala Leu Gln Asp Ser Lys Glu Lys Val Asn Ile Val
            485                 490                 495

Thr Asp Ser Gln Tyr Val Leu Gly Ile Ile Ser Ser Gln Pro Thr Gln
        500                 505                 510

Ser Glu Ser Pro Ile Val Gln Gln Ile Ile Glu Glu Leu Thr Lys Lys
    515                 520                 525

Glu Gln Val Tyr Leu Thr Trp Val Pro Ala His Lys Gly Ile Gly Gly
530                 535                 540

Asn Glu Lys Ile Asp Lys Leu Val Ser Lys Asp Ile Arg Arg Val Leu
545                 550                 555                 560

<210> SEQ ID NO 25
<211> LENGTH: 968
<212> TYPE: PRT
<213> ORGANISM: Human immunodeficiency virus 1

<400> SEQUENCE: 25

Met Val Pro Ile Ser Pro Ile Glu Thr Val Pro Val Lys Leu Lys Pro
1               5                   10                  15

Gly Met Asp Gly Pro Lys Val Lys Gln Trp Pro Leu Thr Glu Glu Lys
            20                  25                  30

```
Ile Lys Ala Leu Val Glu Ile Cys Thr Glu Met Glu Lys Glu Gly Lys
            35                  40                  45

Ile Ser Lys Ile Gly Pro Glu Asn Pro Tyr Asn Thr Pro Val Phe Ala
        50                  55                  60

Ile Lys Lys Lys Asp Ser Thr Lys Trp Arg Lys Leu Val Asp Phe Arg
 65                  70                  75                  80

Glu Leu Asn Lys Arg Thr Gln Asp Phe Trp Glu Val Gln Leu Gly Ile
                85                  90                  95

Pro His Pro Ala Gly Leu Lys Lys Lys Ser Val Thr Val Leu Asp
                100                 105                 110

Val Gly Asp Ala Tyr Phe Ser Val Pro Leu Asp Glu Asp Phe Arg Lys
            115                 120                 125

Tyr Thr Ala Phe Thr Ile Pro Ser Ile Asn Asn Glu Thr Pro Gly Ile
        130                 135                 140

Arg Tyr Gln Tyr Asn Val Leu Pro Gln Gly Trp Lys Gly Ser Pro Ala
145                 150                 155                 160

Ile Phe Gln Ser Ser Met Thr Lys Ile Leu Glu Pro Phe Lys Lys Gln
                165                 170                 175

Asn Pro Asp Ile Val Ile Tyr Gln Tyr Met Asp Asp Leu Tyr Val Gly
            180                 185                 190

Ser Asp Leu Glu Ile Gly Gln His Arg Thr Lys Ile Glu Glu Leu Arg
        195                 200                 205

Gln His Leu Leu Arg Trp Gly Leu Thr Thr Pro Asp Lys Lys His Gln
    210                 215                 220

Lys Glu Pro Pro Phe Leu Trp Met Gly Tyr Glu Leu His Pro Asp Lys
225                 230                 235                 240

Trp Thr Val Gln Pro Ile Val Leu Pro Glu Lys Asp Ser Trp Thr Val
                245                 250                 255

Asn Asp Ile Cys Lys Leu Val Gly Lys Leu Asn Trp Ala Ser Gln Ile
            260                 265                 270

Tyr Pro Gly Ile Lys Val Arg Gln Leu Ser Lys Leu Leu Arg Gly Thr
        275                 280                 285

Lys Ala Leu Thr Glu Val Ile Pro Leu Thr Glu Glu Ala Glu Leu Glu
    290                 295                 300

Leu Ala Glu Asn Arg Glu Ile Leu Lys Glu Pro Val His Gly Val Tyr
305                 310                 315                 320

Tyr Asp Pro Ser Lys Asp Leu Ile Ala Glu Ile Gln Lys Gln Gly Gln
                325                 330                 335

Gly Gln Trp Thr Tyr Gln Ile Tyr Gln Glu Pro Phe Lys Asn Leu Lys
            340                 345                 350

Thr Gly Lys Tyr Ala Arg Met Arg Gly Ala His Thr Asn Asp Val Lys
        355                 360                 365

Gln Leu Thr Glu Ala Val Gln Lys Ile Thr Thr Glu Ser Ile Val Ile
    370                 375                 380

Trp Gly Lys Thr Pro Lys Phe Lys Leu Pro Ile Gln Lys Glu Thr Trp
385                 390                 395                 400

Glu Thr Trp Trp Thr Glu Tyr Trp Gln Ala Thr Trp Ile Pro Glu Trp
                405                 410                 415

Glu Phe Val Asn Thr Pro Pro Leu Val Lys Leu Trp Tyr Gln Leu Glu
            420                 425                 430

Lys Glu Pro Ile Val Gly Ala Glu Thr Phe Tyr Val Asp Gly Ala Ala
        435                 440                 445
```

```
Asn Arg Glu Thr Lys Leu Gly Lys Ala Gly Tyr Val Thr Asn Lys Gly
    450                 455                 460

Arg Gln Lys Val Val Pro Leu Thr Asn Thr Thr Asn Gln Lys Thr Glu
465                 470                 475                 480

Leu Gln Ala Ile Tyr Leu Ala Leu Gln Asp Ser Gly Leu Glu Val Asn
                485                 490                 495

Ile Val Thr Asn Ser Gln Tyr Ala Leu Gly Ile Ile Gln Ala Gln Pro
            500                 505                 510

Asp Lys Ser Glu Ser Glu Leu Val Asn Gln Ile Ile Glu Gln Leu Ile
                515                 520                 525

Lys Lys Glu Lys Val Tyr Leu Ala Trp Val Pro Ala His Lys Gly Ile
530                 535                 540

Gly Gly Asn Glu Gln Val Asp Lys Leu Val Ser Ala Pro Ile Glu Thr
545                 550                 555                 560

Val Pro Val Lys Leu Lys Pro Gly Met Asp Gly Pro Lys Val Lys Gln
                565                 570                 575

Trp Pro Leu Thr Glu Glu Lys Ile Lys Ala Leu Val Glu Ile Cys Thr
            580                 585                 590

Glu Met Glu Lys Glu Gly Lys Ile Ser Lys Ile Gly Pro Glu Asn Pro
            595                 600                 605

Tyr Asn Thr Pro Val Phe Ala Ile Lys Lys Lys Asp Ser Thr Lys Trp
    610                 615                 620

Arg Lys Leu Val Asp Phe Arg Glu Leu Asn Lys Arg Thr Gln Asp Phe
625                 630                 635                 640

Trp Glu Val Gln Leu Gly Ile Pro His Pro Ala Gly Leu Lys Lys Lys
                645                 650                 655

Lys Ser Val Thr Val Leu Asp Val Gly Asp Ala Tyr Phe Ser Val Pro
            660                 665                 670

Leu Asp Glu Asp Phe Arg Lys Tyr Thr Ala Phe Thr Ile Pro Ser Ile
        675                 680                 685

Asn Asn Glu Thr Pro Gly Ile Arg Tyr Gln Tyr Asn Val Leu Pro Gln
    690                 695                 700

Gly Trp Lys Gly Ser Pro Ala Ile Phe Gln Ser Ser Met Thr Lys Ile
705                 710                 715                 720

Leu Glu Pro Phe Lys Lys Gln Asn Pro Asp Ile Val Ile Tyr Gln Tyr
                725                 730                 735

Met Asp Asp Leu Tyr Val Gly Ser Asp Leu Glu Ile Gly Gln His Arg
            740                 745                 750

Thr Lys Ile Glu Glu Leu Arg Gln His Leu Leu Arg Trp Gly Leu Thr
            755                 760                 765

Thr Pro Gly Tyr Glu Leu His Pro Asp Lys Trp Thr Val Gln Pro Ile
    770                 775                 780

Val Leu Pro Glu Lys Asp Ser Trp Thr Val Asn Asp Ile Gln Lys Leu
785                 790                 795                 800

Val Gly Lys Leu Asn Trp Ala Ser Gln Ile Tyr Pro Gly Ile Lys Val
                805                 810                 815

Arg Gln Leu Ser Lys Leu Leu Arg Gly Thr Lys Ala Leu Thr Glu Val
            820                 825                 830

Ile Pro Leu Thr Glu Glu Ala Glu Leu Glu Leu Ala Glu Asn Arg Glu
            835                 840                 845

Ile Leu Lys Glu Pro Val His Gly Val Tyr Tyr Asp Pro Ser Lys Asp
    850                 855                 860

Leu Ile Ala Glu Ile Gln Lys Gln Gly Gln Gly Gln Trp Thr Tyr Gln
```

```
                865                 870                 875                 880
Ile Tyr Gln Glu Pro Phe Lys Asn Leu Lys Thr Gly Lys Tyr Ala Arg
                    885                 890                 895

Met Arg Gly Ala His Thr Asn Asp Val Lys Gln Leu Thr Glu Ala Val
                900                 905                 910

Gln Lys Ile Thr Thr Glu Ser Ile Val Ile Trp Gly Lys Thr Pro Lys
            915                 920                 925

Phe Lys Leu Pro Ile Gln Lys Glu Thr Trp Glu Thr Trp Trp Thr Glu
        930                 935                 940

Tyr Trp Gln Ala Thr Trp Ile Pro Glu Trp Glu Phe Val Asn Thr Pro
945                 950                 955                 960

Pro Leu Val Lys Leu Trp Tyr Gln
                965

<210> SEQ ID NO 26
<211> LENGTH: 5
<212> TYPE: PRT
<213> ORGANISM: Moloney murine leukemia virus

<400> SEQUENCE: 26

Lys Asp Ala Phe Phe
1               5

<210> SEQ ID NO 27
<211> LENGTH: 5
<212> TYPE: PRT
<213> ORGANISM: Moloney murine leukemia virus

<400> SEQUENCE: 27

Lys Asp Ala Phe Phe
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Lys Asp Ala Phe Phe
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Asp Ala Phe Phe
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 30

Lys Asp Ala Phe Asn
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Asp Ala Phe Asn
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Asp Ala Phe Asn
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Lys Asp Ala Ala Phe
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Lys Asp Ala Ala Phe
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Lys Asp Ala Ala Phe
1               5

<210> SEQ ID NO 36
<211> LENGTH: 5
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 36

Lys Asp Ala Ala Asn
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Lys Asp Ala Ala Asn
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Asp Ala Ala Asn
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Lys Asp Tyr Phe Phe
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Lys Asp Tyr Phe Phe
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Lys Asp Tyr Phe Phe
1               5
```

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Lys Asp Tyr Phe Asn
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Lys Asp Tyr Phe Asn
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Asp Tyr Phe Asn
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Asp Tyr Ala Phe
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Lys Asp Tyr Ala Phe
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 47

Lys Asp Tyr Ala Phe
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Asp Tyr Ala Asn
1               5

<210> SEQ ID NO 49
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Lys Asp Tyr Ala Asn
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Lys Asp Tyr Ala Asn
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Lys Tyr Ala Phe Phe
1               5

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Lys Tyr Ala Phe Phe
1               5

<210> SEQ ID NO 53
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Lys Tyr Ala Phe Phe
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Lys Tyr Ala Phe Asn
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Tyr Ala Phe Asn
1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Tyr Ala Phe Asn
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Tyr Ala Ala Phe
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Tyr Ala Ala Phe
```

```
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Tyr Ala Ala Phe
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Lys Tyr Ala Ala Asn
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Tyr Ala Ala Asn
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Tyr Ala Ala Asn
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Tyr Tyr Phe Phe
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 64

Lys Tyr Tyr Phe Phe
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Lys Tyr Tyr Phe Phe
1               5

<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Lys Tyr Tyr Phe Asn
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Lys Tyr Tyr Phe Asn
1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Tyr Tyr Phe Asn
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Tyr Tyr Ala Phe
1               5

<210> SEQ ID NO 70

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Tyr Tyr Ala Phe
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Tyr Tyr Ala Phe
1               5

<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Tyr Tyr Ala Asn
1               5

<210> SEQ ID NO 73
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Tyr Tyr Ala Asn
1               5

<210> SEQ ID NO 74
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Lys Tyr Tyr Ala Asn
1               5

<210> SEQ ID NO 75
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75
```

-continued

Arg Asp Ala Phe Phe
1               5

<210> SEQ ID NO 76
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Arg Asp Ala Phe Phe
1               5

<210> SEQ ID NO 77
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Arg Asp Ala Phe Phe
1               5

<210> SEQ ID NO 78
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Asp Ala Phe Asn
1               5

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Asp Ala Phe Asn
1               5

<210> SEQ ID NO 80
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Arg Asp Ala Phe Asn
1               5

<210> SEQ ID NO 81
<211> LENGTH: 5
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 81

Arg Asp Ala Ala Phe
1               5

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Arg Asp Ala Ala Phe
1               5

<210> SEQ ID NO 83
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Arg Asp Ala Ala Phe
1               5

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

Arg Asp Ala Ala Asn
1               5

<210> SEQ ID NO 85
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 85

Arg Asp Ala Ala Asn
1               5

<210> SEQ ID NO 86
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 86

Arg Asp Ala Ala Asn
1               5

```
<210> SEQ ID NO 87
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Asp Tyr Phe Phe
1               5

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Asp Tyr Phe Phe
1               5

<210> SEQ ID NO 89
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Asp Tyr Phe Phe
1               5

<210> SEQ ID NO 90
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Arg Asp Tyr Phe Asn
1               5

<210> SEQ ID NO 91
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Asp Tyr Phe Asn
1               5

<210> SEQ ID NO 92
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92
```

-continued

Arg Asp Tyr Phe Asn
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Asp Tyr Ala Phe
1               5

<210> SEQ ID NO 94
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Asp Tyr Ala Phe
1               5

<210> SEQ ID NO 95
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Asp Tyr Ala Phe
1               5

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Asp Tyr Ala Asn
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Asp Tyr Ala Asn
1               5

<210> SEQ ID NO 98
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 98

Arg Asp Tyr Ala Asn
1               5

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Tyr Ala Phe Phe
1               5

<210> SEQ ID NO 100
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Tyr Ala Phe Phe
1               5

<210> SEQ ID NO 101
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Tyr Ala Phe Phe
1               5

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Tyr Ala Phe Asn
1               5

<210> SEQ ID NO 103
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Tyr Ala Phe Asn
1               5
```

<210> SEQ ID NO 104
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Tyr Ala Phe Asn
1               5

<210> SEQ ID NO 105
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Tyr Ala Ala Phe
1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Tyr Ala Ala Phe
1               5

<210> SEQ ID NO 107
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Tyr Ala Ala Phe
1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Tyr Ala Ala Asn
1               5

<210> SEQ ID NO 109
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 109

Arg Tyr Ala Ala Asn
1               5

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Tyr Ala Ala Asn
1               5

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Tyr Tyr Phe Phe
1               5

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Tyr Tyr Phe Phe
1               5

<210> SEQ ID NO 113
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Tyr Tyr Phe Phe
1               5

<210> SEQ ID NO 114
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Tyr Tyr Phe Asn
1               5

<210> SEQ ID NO 115
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 115

Arg Tyr Tyr Phe Asn
1               5

<210> SEQ ID NO 116
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Tyr Tyr Phe Asn
1               5

<210> SEQ ID NO 117
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Tyr Tyr Ala Phe
1               5

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Tyr Tyr Ala Phe
1               5

<210> SEQ ID NO 119
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Arg Tyr Tyr Ala Phe
1               5

<210> SEQ ID NO 120
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Tyr Tyr Ala Asn
1               5
```

```
<210> SEQ ID NO 121
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Tyr Tyr Ala Asn
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Tyr Tyr Ala Asn
1               5

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Cys Asp Ala Phe Phe
1               5

<210> SEQ ID NO 124
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Cys Asp Ala Phe Phe
1               5

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Cys Asp Ala Phe Phe
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 126

Cys Asp Ala Phe Asn
1               5

<210> SEQ ID NO 127
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Cys Asp Ala Phe Asn
1               5

<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Cys Asp Ala Phe Asn
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Cys Asp Ala Ala Phe
1               5

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Cys Asp Ala Ala Phe
1               5

<210> SEQ ID NO 131
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Cys Asp Ala Ala Phe
1               5

<210> SEQ ID NO 132
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Cys Asp Ala Ala Asn
1               5

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Cys Asp Ala Ala Asn
1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Cys Asp Ala Ala Asn
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Cys Asp Tyr Phe Phe
1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Cys Asp Tyr Phe Phe
1               5

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Cys Asp Tyr Phe Phe
```

1               5

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Cys Asp Tyr Phe Asn
1               5

<210> SEQ ID NO 139
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Cys Asp Tyr Phe Asn
1               5

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Cys Asp Tyr Phe Asn
1               5

<210> SEQ ID NO 141
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Cys Asp Tyr Ala Phe
1               5

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Cys Asp Tyr Ala Phe
1               5

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic

```
                       peptide

<400> SEQUENCE: 143

Cys Asp Tyr Ala Phe
1               5

<210> SEQ ID NO 144
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Cys Asp Tyr Ala Asn
1               5

<210> SEQ ID NO 145
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Cys Asp Tyr Ala Asn
1               5

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Cys Asp Tyr Ala Asn
1               5

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Cys Tyr Ala Phe Phe
1               5

<210> SEQ ID NO 148
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Cys Tyr Ala Phe Phe
1               5

<210> SEQ ID NO 149
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Cys Tyr Ala Phe Phe
1               5

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Cys Tyr Ala Phe Asn
1               5

<210> SEQ ID NO 151
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Cys Tyr Ala Phe Asn
1               5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Cys Tyr Ala Phe Asn
1               5

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Cys Tyr Ala Ala Phe
1               5

<210> SEQ ID NO 154
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154
```

```
Cys Tyr Ala Ala Phe
1               5

<210> SEQ ID NO 155
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Cys Tyr Ala Ala Phe
1               5

<210> SEQ ID NO 156
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Cys Tyr Ala Ala Asn
1               5

<210> SEQ ID NO 157
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Cys Tyr Ala Ala Asn
1               5

<210> SEQ ID NO 158
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Cys Tyr Ala Ala Asn
1               5

<210> SEQ ID NO 159
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Cys Tyr Tyr Phe Phe
1               5

<210> SEQ ID NO 160
<211> LENGTH: 5
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 160

Cys Tyr Tyr Phe Phe
1               5

<210> SEQ ID NO 161
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Tyr Tyr Phe Phe
1               5

<210> SEQ ID NO 162
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Cys Tyr Tyr Phe Asn
1               5

<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Tyr Tyr Phe Asn
1               5

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Cys Tyr Tyr Phe Asn
1               5

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Cys Tyr Tyr Ala Phe
1               5

```
<210> SEQ ID NO 166
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Cys Tyr Tyr Ala Phe
1               5

<210> SEQ ID NO 167
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Cys Tyr Tyr Ala Phe
1               5

<210> SEQ ID NO 168
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Cys Tyr Tyr Ala Asn
1               5

<210> SEQ ID NO 169
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Cys Tyr Tyr Ala Asn
1               5

<210> SEQ ID NO 170
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Cys Tyr Tyr Ala Asn
1               5

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171
```

```
Ser Asp Ala Phe Phe
1               5

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ser Asp Ala Phe Phe
1               5

<210> SEQ ID NO 173
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ser Asp Ala Phe Phe
1               5

<210> SEQ ID NO 174
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Asp Ala Phe Asn
1               5

<210> SEQ ID NO 175
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Asp Ala Phe Asn
1               5

<210> SEQ ID NO 176
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ser Asp Ala Phe Asn
1               5

<210> SEQ ID NO 177
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 177

Ser Asp Ala Ala Phe
1               5

<210> SEQ ID NO 178
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Ser Asp Ala Ala Phe
1               5

<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ser Asp Ala Ala Phe
1               5

<210> SEQ ID NO 180
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ser Asp Ala Ala Asn
1               5

<210> SEQ ID NO 181
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ser Asp Ala Ala Asn
1               5

<210> SEQ ID NO 182
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Asp Ala Ala Asn
1               5
```

<210> SEQ ID NO 183
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ser Asp Tyr Phe Phe
1               5

<210> SEQ ID NO 184
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Asp Tyr Phe Phe
1               5

<210> SEQ ID NO 185
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Ser Asp Tyr Phe Phe
1               5

<210> SEQ ID NO 186
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Ser Asp Tyr Phe Asn
1               5

<210> SEQ ID NO 187
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Asp Tyr Phe Asn
1               5

<210> SEQ ID NO 188
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 188

Ser Asp Tyr Phe Asn
1               5

<210> SEQ ID NO 189
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ser Asp Tyr Ala Phe
1               5

<210> SEQ ID NO 190
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ser Asp Tyr Ala Phe
1               5

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Ser Asp Tyr Ala Phe
1               5

<210> SEQ ID NO 192
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Ser Asp Tyr Ala Asn
1               5

<210> SEQ ID NO 193
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ser Asp Tyr Ala Asn
1               5

<210> SEQ ID NO 194
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 194

Ser Asp Tyr Ala Asn
1               5

<210> SEQ ID NO 195
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ser Tyr Ala Phe Phe
1               5

<210> SEQ ID NO 196
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Ser Tyr Ala Phe Phe
1               5

<210> SEQ ID NO 197
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ser Tyr Ala Phe Phe
1               5

<210> SEQ ID NO 198
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ser Tyr Ala Phe Asn
1               5

<210> SEQ ID NO 199
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Ser Tyr Ala Phe Asn
1               5
```

<210> SEQ ID NO 200
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Ser Tyr Ala Phe Asn
1               5

<210> SEQ ID NO 201
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ser Tyr Ala Ala Phe
1               5

<210> SEQ ID NO 202
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ser Tyr Ala Ala Phe
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Ser Tyr Ala Ala Phe
1               5

<210> SEQ ID NO 204
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Ser Tyr Ala Ala Asn
1               5

<210> SEQ ID NO 205
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ser Tyr Ala Ala Asn
1               5

<210> SEQ ID NO 206
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Ser Tyr Ala Ala Asn
1               5

<210> SEQ ID NO 207
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ser Tyr Tyr Phe Phe
1               5

<210> SEQ ID NO 208
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Ser Tyr Tyr Phe Phe
1               5

<210> SEQ ID NO 209
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Tyr Tyr Phe Phe
1               5

<210> SEQ ID NO 210
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Ser Tyr Tyr Phe Asn
1               5

<210> SEQ ID NO 211
<211> LENGTH: 5

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Ser Tyr Tyr Phe Asn
1               5

<210> SEQ ID NO 212
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ser Tyr Tyr Phe Asn
1               5

<210> SEQ ID NO 213
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ser Tyr Tyr Ala Phe
1               5

<210> SEQ ID NO 214
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Ser Tyr Tyr Ala Phe
1               5

<210> SEQ ID NO 215
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Ser Tyr Tyr Ala Phe
1               5

<210> SEQ ID NO 216
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Tyr Tyr Ala Asn
```

```
1               5

<210> SEQ ID NO 217
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ser Tyr Tyr Ala Asn
1               5

<210> SEQ ID NO 218
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Ser Tyr Tyr Ala Asn
1               5

<210> SEQ ID NO 219
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Thr Asp Ala Phe Phe
1               5

<210> SEQ ID NO 220
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Thr Asp Ala Phe Phe
1               5

<210> SEQ ID NO 221
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Thr Asp Ala Phe Phe
1               5

<210> SEQ ID NO 222
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 222

Thr Asp Ala Phe Asn
1               5

<210> SEQ ID NO 223
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Thr Asp Ala Phe Asn
1               5

<210> SEQ ID NO 224
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Thr Asp Ala Phe Asn
1               5

<210> SEQ ID NO 225
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Thr Asp Ala Ala Phe
1               5

<210> SEQ ID NO 226
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Thr Asp Ala Ala Phe
1               5

<210> SEQ ID NO 227
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Thr Asp Ala Ala Phe
1               5

<210> SEQ ID NO 228

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Thr Asp Ala Ala Asn
1               5

<210> SEQ ID NO 229
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Thr Asp Ala Ala Asn
1               5

<210> SEQ ID NO 230
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Thr Asp Ala Ala Asn
1               5

<210> SEQ ID NO 231
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Thr Asp Tyr Phe Phe
1               5

<210> SEQ ID NO 232
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Thr Asp Tyr Phe Phe
1               5

<210> SEQ ID NO 233
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233
```

```
Thr Asp Tyr Phe Phe
1               5

<210> SEQ ID NO 234
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Thr Asp Tyr Phe Asn
1               5

<210> SEQ ID NO 235
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Thr Asp Tyr Phe Asn
1               5

<210> SEQ ID NO 236
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Thr Asp Tyr Phe Asn
1               5

<210> SEQ ID NO 237
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Thr Asp Tyr Ala Phe
1               5

<210> SEQ ID NO 238
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Thr Asp Tyr Ala Phe
1               5

<210> SEQ ID NO 239
<211> LENGTH: 5
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 239

Thr Asp Tyr Ala Phe
1               5

<210> SEQ ID NO 240
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 240

Thr Asp Tyr Ala Asn
1               5

<210> SEQ ID NO 241
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 241

Thr Asp Tyr Ala Asn
1               5

<210> SEQ ID NO 242
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 242

Thr Asp Tyr Ala Asn
1               5

<210> SEQ ID NO 243
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 243

Thr Tyr Ala Phe Phe
1               5

<210> SEQ ID NO 244
<211> LENGTH: 5
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 244

Thr Tyr Ala Phe Phe
1               5

```
<210> SEQ ID NO 245
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Thr Tyr Ala Phe Phe
1               5

<210> SEQ ID NO 246
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Thr Tyr Ala Phe Asn
1               5

<210> SEQ ID NO 247
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Thr Tyr Ala Phe Asn
1               5

<210> SEQ ID NO 248
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Thr Tyr Ala Phe Asn
1               5

<210> SEQ ID NO 249
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Thr Tyr Ala Ala Phe
1               5

<210> SEQ ID NO 250
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250
```

-continued

```
Thr Tyr Ala Ala Phe
1               5

<210> SEQ ID NO 251
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Thr Tyr Ala Ala Phe
1               5

<210> SEQ ID NO 252
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Thr Tyr Ala Ala Asn
1               5

<210> SEQ ID NO 253
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Thr Tyr Ala Ala Asn
1               5

<210> SEQ ID NO 254
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Thr Tyr Ala Ala Asn
1               5

<210> SEQ ID NO 255
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Thr Tyr Tyr Phe Phe
1               5

<210> SEQ ID NO 256
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 256

Thr Tyr Tyr Phe Phe
1               5

<210> SEQ ID NO 257
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Thr Tyr Tyr Phe Phe
1               5

<210> SEQ ID NO 258
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Thr Tyr Tyr Phe Asn
1               5

<210> SEQ ID NO 259
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Thr Tyr Tyr Phe Asn
1               5

<210> SEQ ID NO 260
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Thr Tyr Tyr Phe Asn
1               5

<210> SEQ ID NO 261
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Thr Tyr Tyr Ala Phe
1               5
```

```
<210> SEQ ID NO 262
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Thr Tyr Tyr Ala Phe
1               5

<210> SEQ ID NO 263
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Thr Tyr Tyr Ala Phe
1               5

<210> SEQ ID NO 264
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Thr Tyr Tyr Ala Asn
1               5

<210> SEQ ID NO 265
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Thr Tyr Tyr Ala Asn
1               5

<210> SEQ ID NO 266
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Thr Tyr Tyr Ala Asn
1               5

<210> SEQ ID NO 267
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 267

Leu Asp Ala Phe Phe
1               5

<210> SEQ ID NO 268
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Leu Asp Ala Phe Phe
1               5

<210> SEQ ID NO 269
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Leu Asp Ala Phe Phe
1               5

<210> SEQ ID NO 270
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Leu Asp Ala Phe Asn
1               5

<210> SEQ ID NO 271
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Leu Asp Ala Phe Asn
1               5

<210> SEQ ID NO 272
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Leu Asp Ala Phe Asn
1               5

<210> SEQ ID NO 273
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 273

Leu Asp Ala Ala Phe
1               5

<210> SEQ ID NO 274
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Leu Asp Ala Ala Phe
1               5

<210> SEQ ID NO 275
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Leu Asp Ala Ala Phe
1               5

<210> SEQ ID NO 276
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Leu Asp Ala Ala Asn
1               5

<210> SEQ ID NO 277
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Leu Asp Ala Ala Asn
1               5

<210> SEQ ID NO 278
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Leu Asp Ala Ala Asn
1               5
```

```
<210> SEQ ID NO 279
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Leu Asp Tyr Phe Phe
1               5

<210> SEQ ID NO 280
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Leu Asp Tyr Phe Phe
1               5

<210> SEQ ID NO 281
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Leu Asp Tyr Phe Phe
1               5

<210> SEQ ID NO 282
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Leu Asp Tyr Phe Asn
1               5

<210> SEQ ID NO 283
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Leu Asp Tyr Phe Asn
1               5

<210> SEQ ID NO 284
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 284

Leu Asp Tyr Phe Asn
1               5

<210> SEQ ID NO 285
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Leu Asp Tyr Ala Phe
1               5

<210> SEQ ID NO 286
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Leu Asp Tyr Ala Phe
1               5

<210> SEQ ID NO 287
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Leu Asp Tyr Ala Phe
1               5

<210> SEQ ID NO 288
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Leu Asp Tyr Ala Asn
1               5

<210> SEQ ID NO 289
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Leu Asp Tyr Ala Asn
1               5

<210> SEQ ID NO 290
<211> LENGTH: 5
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Leu Asp Tyr Ala Asn
1               5

<210> SEQ ID NO 291
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Leu Tyr Ala Phe Phe
1               5

<210> SEQ ID NO 292
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Leu Tyr Ala Phe Phe
1               5

<210> SEQ ID NO 293
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Leu Tyr Ala Phe Phe
1               5

<210> SEQ ID NO 294
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Leu Tyr Ala Phe Asn
1               5

<210> SEQ ID NO 295
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Leu Tyr Ala Phe Asn
```

```
1               5

<210> SEQ ID NO 296
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Leu Tyr Ala Phe Asn
1               5

<210> SEQ ID NO 297
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Leu Tyr Ala Ala Phe
1               5

<210> SEQ ID NO 298
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Leu Tyr Ala Ala Phe
1               5

<210> SEQ ID NO 299
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Leu Tyr Ala Ala Phe
1               5

<210> SEQ ID NO 300
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Leu Tyr Ala Ala Asn
1               5

<210> SEQ ID NO 301
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 301

Leu Tyr Ala Ala Asn
1               5

<210> SEQ ID NO 302
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Leu Tyr Ala Ala Asn
1               5

<210> SEQ ID NO 303
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Leu Tyr Tyr Phe Phe
1               5

<210> SEQ ID NO 304
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Leu Tyr Tyr Phe Phe
1               5

<210> SEQ ID NO 305
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Leu Tyr Tyr Phe Phe
1               5

<210> SEQ ID NO 306
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Leu Tyr Tyr Phe Asn
1               5

<210> SEQ ID NO 307

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Leu Tyr Tyr Phe Asn
1               5

<210> SEQ ID NO 308
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Leu Tyr Tyr Phe Asn
1               5

<210> SEQ ID NO 309
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Leu Tyr Tyr Ala Phe
1               5

<210> SEQ ID NO 310
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Leu Tyr Tyr Ala Phe
1               5

<210> SEQ ID NO 311
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Leu Tyr Tyr Ala Phe
1               5

<210> SEQ ID NO 312
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312
```

```
Leu Tyr Tyr Ala Asn
1               5

<210> SEQ ID NO 313
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Leu Tyr Tyr Ala Asn
1               5

<210> SEQ ID NO 314
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Leu Tyr Tyr Ala Asn
1               5

<210> SEQ ID NO 315
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 315

His His His His His His
1               5

<210> SEQ ID NO 316
<211> LENGTH: 671
<212> TYPE: PRT
<213> ORGANISM: Moloney murine leukemia virus

<400> SEQUENCE: 316

Leu Asn Ile Glu Asp Glu His Arg Leu His Glu Thr Ser Lys Glu Pro
1               5                   10                  15

Asp Val Ser Leu Gly Ser Thr Trp Leu Ser Asp Phe Pro Gln Ala Trp
                20                  25                  30

Ala Glu Thr Gly Gly Met Gly Leu Ala Val Arg Gln Ala Pro Leu Ile
            35                  40                  45

Ile Pro Leu Lys Ala Thr Ser Thr Pro Val Ser Ile Lys Gln Tyr Pro
        50                  55                  60

Met Ser Gln Glu Ala Arg Leu Gly Ile Lys Pro His Ile Gln Arg Leu
65                  70                  75                  80

Leu Asp Gln Gly Ile Leu Val Pro Cys Gln Ser Pro Trp Asn Thr Pro
                85                  90                  95

Leu Leu Pro Val Lys Lys Pro Gly Thr Asn Asp Tyr Arg Pro Val Gln
                100                 105                 110

Asp Leu Arg Glu Val Asn Lys Arg Val Glu Asp Ile His Pro Thr Val
            115                 120                 125

Pro Asn Pro Tyr Asn Leu Leu Ser Gly Leu Pro Pro Ser His Gln Trp
        130                 135                 140
```

```
Tyr Thr Val Leu Asp Leu Lys Asp Ala Phe Phe Cys Leu Arg Leu His
145                 150                 155                 160

Pro Thr Ser Gln Pro Leu Phe Ala Phe Glu Trp Arg Asp Pro Glu Met
                165                 170                 175

Gly Ile Ser Gly Gln Leu Thr Trp Thr Arg Leu Pro Gln Gly Phe Lys
            180                 185                 190

Asn Ser Pro Thr Leu Phe Asp Glu Ala Leu His Arg Asp Leu Ala Asp
        195                 200                 205

Phe Arg Ile Gln His Pro Asp Leu Ile Leu Leu Gln Tyr Val Asp Asp
    210                 215                 220

Leu Leu Leu Ala Ala Thr Ser Glu Leu Asp Cys Gln Gln Gly Thr Arg
225                 230                 235                 240

Ala Leu Leu Gln Thr Leu Gly Asn Leu Gly Tyr Arg Ala Ser Ala Lys
                245                 250                 255

Lys Ala Gln Ile Cys Gln Lys Gln Val Lys Tyr Leu Gly Tyr Leu Leu
                260                 265                 270

Lys Glu Gly Gln Arg Trp Leu Thr Glu Ala Arg Lys Glu Thr Val Met
            275                 280                 285

Gly Gln Pro Thr Pro Lys Thr Pro Arg Gln Leu Arg Glu Phe Leu Gly
        290                 295                 300

Thr Ala Gly Phe Cys Arg Leu Trp Ile Pro Gly Phe Ala Glu Met Ala
305                 310                 315                 320

Ala Pro Leu Tyr Pro Leu Thr Lys Thr Gly Thr Leu Phe Asn Trp Gly
                325                 330                 335

Pro Asp Gln Gln Lys Ala Tyr Gln Glu Ile Lys Gln Ala Leu Leu Thr
                340                 345                 350

Ala Pro Ala Leu Gly Leu Pro Asp Leu Thr Lys Pro Phe Glu Leu Phe
            355                 360                 365

Val Asp Glu Lys Gln Gly Tyr Ala Lys Gly Val Leu Thr Gln Lys Leu
        370                 375                 380

Gly Pro Trp Arg Arg Pro Val Ala Tyr Leu Ser Lys Lys Leu Asp Pro
385                 390                 395                 400

Val Ala Ala Gly Trp Pro Pro Cys Leu Arg Met Val Ala Ala Ile Ala
                405                 410                 415

Val Leu Thr Lys Asp Ala Gly Lys Leu Thr Met Gly Gln Pro Leu Val
                420                 425                 430

Ile Leu Ala Pro His Ala Val Glu Ala Leu Val Lys Gln Pro Pro Asp
            435                 440                 445

Arg Trp Leu Ser Asn Ala Arg Met Thr His Tyr Gln Ala Leu Leu Leu
            450                 455                 460

Asp Thr Asp Arg Val Gln Phe Gly Pro Val Val Ala Leu Asn Pro Ala
465                 470                 475                 480

Thr Leu Leu Pro Leu Pro Glu Glu Gly Leu Gln His Asn Cys Leu Asp
                485                 490                 495

Ile Leu Ala Glu Ala His Gly Thr Arg Pro Asp Leu Thr Asp Gln Pro
            500                 505                 510

Leu Pro Asp Ala Asp His Thr Trp Tyr Thr Asp Gly Ser Ser Leu Leu
        515                 520                 525

Gln Glu Gly Gln Arg Lys Ala Gly Ala Ala Val Thr Thr Glu Thr Glu
        530                 535                 540

Val Ile Trp Ala Lys Ala Leu Pro Ala Gly Thr Ser Ala Gln Arg Ala
545                 550                 555                 560
```

```
Glu Leu Ile Ala Leu Thr Gln Ala Leu Lys Met Ala Glu Gly Lys Lys
                565                 570                 575

Leu Asn Val Tyr Thr Asp Ser Arg Tyr Ala Phe Ala Thr Ala His Ile
            580                 585                 590

His Gly Glu Ile Tyr Arg Arg Gly Leu Leu Thr Ser Glu Gly Lys
        595                 600                 605

Glu Ile Lys Asn Lys Asp Glu Ile Leu Ala Leu Leu Lys Ala Leu Phe
    610                 615                 620

Leu Pro Lys Arg Leu Ser Ile Ile His Cys Pro Gly His Gln Lys Gly
625                 630                 635                 640

His Ser Ala Glu Ala Arg Gly Asn Arg Met Ala Asp Gln Ala Ala Arg
                645                 650                 655

Lys Ala Ala Ile Thr Glu Thr Pro Asp Thr Ser Thr Leu Leu Ile
                660                 665                 670

<210> SEQ ID NO 317
<211> LENGTH: 671
<212> TYPE: PRT
<213> ORGANISM: Moloney murine leukemia virus

<400> SEQUENCE: 317

Leu Asn Ile Glu Asp Glu His Arg Leu His Glu Thr Ser Lys Glu Pro
1               5                   10                  15

Asp Val Ser Leu Gly Ser Thr Trp Leu Ser Asp Phe Pro Gln Ala Trp
            20                  25                  30

Ala Glu Thr Gly Gly Met Gly Leu Ala Val Arg Gln Ala Pro Leu Ile
        35                  40                  45

Ile Pro Leu Lys Ala Thr Ser Thr Pro Val Ser Ile Lys Gln Tyr Pro
    50                  55                  60

Met Ser Gln Glu Ala Arg Leu Gly Ile Lys Pro His Ile Gln Arg Leu
65                  70                  75                  80

Leu Asp Gln Gly Ile Leu Val Pro Cys Gln Ser Pro Trp Asn Thr Pro
                85                  90                  95

Leu Leu Pro Val Lys Lys Pro Gly Thr Asn Asp Tyr Arg Pro Val Gln
            100                 105                 110

Asp Leu Arg Glu Val Asn Lys Arg Val Glu Asp Ile His Pro Thr Val
        115                 120                 125

Pro Asn Pro Tyr Asn Leu Leu Ser Gly Leu Pro Pro Ser His Gln Trp
    130                 135                 140

Tyr Thr Val Leu Asp Leu Lys Asp Ala Phe Phe Cys Leu Arg Leu His
145                 150                 155                 160

Pro Thr Ser Gln Pro Leu Phe Ala Phe Glu Trp Arg Asp Pro Glu Met
                165                 170                 175

Gly Ile Ser Gly Gln Leu Thr Trp Thr Arg Leu Pro Gln Gly Phe Lys
            180                 185                 190

Asn Ser Pro Thr Leu Phe Asp Glu Ala Leu His Arg Asp Leu Ala Asp
        195                 200                 205

Phe Arg Ile Gln His Pro Asp Leu Ile Leu Leu Gln Tyr Val Asp Asp
    210                 215                 220

Leu Leu Leu Ala Ala Thr Ser Glu Leu Asp Cys Gln Gln Gly Thr Arg
225                 230                 235                 240

Ala Leu Leu Gln Thr Leu Gly Asn Leu Gly Tyr Arg Ala Ser Ala Lys
                245                 250                 255

Lys Ala Gln Ile Cys Gln Lys Gln Val Lys Tyr Leu Gly Tyr Leu Leu
            260                 265                 270
```

```
Lys Glu Gly Gln Arg Trp Leu Thr Glu Ala Arg Lys Glu Thr Val Met
            275                 280                 285

Gly Gln Pro Thr Pro Lys Thr Pro Arg Gln Leu Arg Glu Phe Leu Gly
        290                 295                 300

Thr Ala Gly Phe Cys Arg Leu Trp Ile Pro Gly Phe Ala Glu Met Ala
305                 310                 315                 320

Ala Pro Leu Tyr Pro Leu Thr Lys Thr Gly Thr Leu Phe Asn Trp Gly
                325                 330                 335

Pro Asp Gln Gln Lys Ala Tyr Gln Glu Ile Lys Gln Ala Leu Leu Thr
            340                 345                 350

Ala Pro Ala Leu Gly Leu Pro Asp Leu Thr Lys Pro Phe Glu Leu Phe
        355                 360                 365

Val Asp Glu Lys Gln Gly Tyr Ala Lys Gly Val Leu Thr Gln Lys Leu
    370                 375                 380

Gly Pro Trp Arg Arg Pro Val Ala Tyr Leu Ser Lys Lys Leu Asp Pro
385                 390                 395                 400

Val Ala Ala Gly Trp Pro Pro Cys Leu Arg Met Val Ala Ala Ile Ala
                405                 410                 415

Val Leu Thr Lys Asp Ala Gly Lys Leu Thr Met Gly Gln Pro Leu Val
            420                 425                 430

Ile Leu Ala Pro His Ala Val Glu Ala Leu Val Lys Gln Pro Pro Asp
        435                 440                 445

Arg Trp Leu Ser Asn Ala Arg Met Thr His Tyr Gln Ala Leu Leu Leu
    450                 455                 460

Asp Thr Asp Arg Val Gln Phe Gly Pro Val Val Ala Leu Asn Pro Ala
465                 470                 475                 480

Thr Leu Leu Pro Leu Pro Glu Glu Gly Leu Gln His Asn Cys Leu Asp
                485                 490                 495

Ile Leu Ala Glu Ala His Gly Thr Arg Pro Asp Leu Thr Asp Gln Pro
            500                 505                 510

Leu Pro Asp Ala Asp His Thr Trp Tyr Thr Asp Gly Ser Ser Leu Leu
        515                 520                 525

Gln Glu Gly Gln Arg Lys Ala Gly Ala Ala Val Thr Thr Glu Thr Glu
    530                 535                 540

Val Ile Trp Ala Lys Ala Leu Pro Ala Gly Thr Ser Ala Gln Arg Ala
545                 550                 555                 560

Glu Leu Ile Ala Leu Thr Gln Ala Leu Lys Met Ala Glu Gly Lys Lys
                565                 570                 575

Leu Asn Val Tyr Thr Asp Ser Arg Tyr Ala Phe Ala Thr Ala His Ile
            580                 585                 590

His Gly Glu Ile Tyr Arg Arg Arg Gly Leu Leu Thr Ser Glu Gly Lys
        595                 600                 605

Glu Ile Lys Asn Lys Asp Glu Ile Leu Ala Leu Leu Lys Ala Leu Phe
    610                 615                 620

Leu Pro Lys Arg Leu Ser Ile Ile His Cys Pro Gly His Gln Lys Gly
625                 630                 635                 640

His Ser Ala Glu Ala Arg Gly Asn Arg Met Ala Asp Gln Ala Ala Arg
                645                 650                 655

Lys Ala Ala Ile Thr Glu Thr Pro Asp Thr Ser Thr Leu Leu Ile
            660                 665                 670
```

REVERSE TRANSCRIPTASE FOR NUCLEIC ACID SEQUENCING

CROSS-REFERENCE

This application is a continuation application of International Application No. PCT/US2019/036631, filed Jun. 11, 2019, which claims the benefit of U.S. Provisional Application No. 62/684,115, filed Jun. 12, 2018, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 19, 2024, is named 52933-714_301SL and is 151,086 bytes in size.

BACKGROUND OF THE INVENTION

Next-generation sequencing (NGS) techniques have become a powerful tool for acquiring sequencing data used in molecular biology techniques, taxonomy, agriscience, medical diagnostics, and the development of new therapies. For example, sequencing-by-synthesis (SBS) methods are used to extend a growing polynucleotide chain with a polymerase, while analyzing the identity of matching complementary nucleotides that are incorporated. However, additional methods to increase the sensitivity, accuracy, scalability, and cost efficiency of these methods is needed.

SUMMARY OF THE INVENTION

Provided herein are methods, compositions, and systems that facilitate the addition of 3' modified nucleotides into a nucleotide chain. Provided herein are polypeptides comprising mutations that differ from wild-type polypeptides, such as at positions in a retrotranscriptase-like domain. Provided herein are polypeptides having at least 85% identity to SEQ ID NO: 2, and differing from SEQ ID NO: 2 at at least one of positions K152, D153, A154, F155, F156, and Q190 relative to SEQ ID NO: 1. Also provided herein are polypeptides wherein the polypeptide has at least 90% identity to SEQ ID NO: 2. Also provided herein are polypeptides wherein the polypeptide has at least 95% identity to SEQ ID NO: 2. Also provided herein are polypeptides wherein the polypeptide comprises a mutation at at least two of positions K152, D153, A154, F155, F156, and Q190. Also provided herein are polypeptides wherein the polypeptide comprises a mutation at at least three of positions K152, D153, A154, F155, F156, and Q190. Also provided herein are polypeptides wherein the polypeptide comprises a mutation at at least four of positions K152, D153, A154, F155, F156, and Q190. Also provided herein are polypeptides wherein the polypeptide comprises a mutation at at least five of positions K152, D153, A154, F155, F156, and Q190. Also provided herein are polypeptides wherein the polypeptide comprises a mutation at position K152. Also provided herein are polypeptides wherein the polypeptide comprises a substitution at K152. Also provided herein are polypeptides wherein the mutation is K152R. Also provided herein are polypeptides wherein the mutation is K152C. Also provided herein are polypeptides wherein the mutation is K152T. Also provided herein are polypeptides wherein the mutation is K152L. Also provided herein are polypeptides wherein the polypeptide comprises a mutation at position D153. Also provided herein are polypeptides wherein the polypeptide comprises a substitution at D153. Also provided herein are polypeptides wherein the mutation is D153Y. Also provided herein are polypeptides wherein the polypeptide comprises a mutation at position A154. Also provided herein are polypeptides wherein the polypeptide comprises a substitution at A154. Also provided herein are polypeptides wherein the mutation is A154Y. Also provided herein are polypeptides wherein the polypeptide comprises a mutation at position F155. Also provided herein are polypeptides wherein the polypeptide comprises a substitution at F155. Also provided herein are polypeptides wherein the mutation is F155A. Also provided herein are polypeptides wherein the polypeptide comprises a mutation at position F156. Also provided herein are polypeptides wherein the polypeptide comprises a substitution at F156. Also provided herein are polypeptides wherein the mutation is F156N. Also provided herein are polypeptides wherein the polypeptide comprises a mutation at position Q190. Also provided herein are polypeptides wherein the polypeptide comprises a substitution at Q190. Also provided herein are polypeptides wherein the mutation is Q190A or Q190S.

Provided herein are mutant nucleic acid polymerases, wherein the nucleic acid polymerase exhibits increased incorporation of 3' methylazido nucleotide relative to a nearest related wild-type sequence. Also provided herein are mutant nucleic acid polymerases wherein the nucleic acid polymerase sequence differs from a nearest related wild-type sequence by at least one position in an RT domain. Also provided herein are mutant nucleic acid polymerases wherein the nucleic acid polymerase exhibits at least 30% higher incorporation of 3' methylazido-dUTP relative to a nearest wild type sequence under conditions comprising contacting a polynucleotide template with the nucleic acid polymerase and 10 uM 3' methylazido-dUTP for 20 minutes. Also provided herein are mutant nucleic acid polymerases wherein the nucleic acid polymerase exhibits at least 20% higher incorporation of 3' methylazido-dUTP relative to a nearest wild type sequence under conditions comprising contacting a polynucleotide template with the nucleic acid polymerase and 10 uM 3' methylazido-dUTP for 20 minutes. Also provided herein are nucleic acid polymerases wherein the nucleic acid polymerase is a reverse transcriptase family polymerase, or comprises a reverse transcriptase domain. Also provided herein are nucleic acid polymerases wherein the nucleic acid polymerase comprises a sequence that has at least 85% identity to SEQ ID NO: 2. Also provided herein are nucleic acid polymerases wherein the nucleic acid polymerase comprises a sequence that has at least 90% identity to SEQ ID NO: 2.

Provided herein are nucleic acid polymerases exhibiting increased kcat for incorporation of 3' methylazido-dUTP relative to a nearest related wild-type sequence.

Provided herein are nucleic acid polymerases exhibiting decreased Km of 3' methylazido-dUTP relative to a nearest related wild-type sequence.

Provided herein are nucleic acid polymerases exhibiting increased kcat/Km of 3' methylazido-dUTP relative to a nearest related wild-type sequence.

Provided herein are polypeptides comprising a fragment comprising the sequence of SEQ ID NO: 4, wherein the fragment further comprises an adjacent N-terminal aspartic acid, adjacent C-terminal arginine, or a combination thereof.

Provided herein are polypeptides comprising a fragment comprising the sequence of SEQ ID NO: 5, wherein the fragment further comprises an adjacent N-terminal glutamine, adjacent C-terminal histidine, or a combination thereof.

Provided herein are polypeptides comprising a fragment comprising the sequence of SEQ ID NO: 6, wherein the fragment further comprises an adjacent N-terminal valine, adjacent C-terminal cysteine, or a combination thereof.

Provided herein are polypeptides comprising a fragment comprising the sequence of SEQ ID NO: 7, wherein the fragment further comprises an adjacent N-terminal threonine, adjacent C-terminal cysteine, or a combination thereof.

Provided herein are polypeptides comprising a fragment comprising the sequence of SEQ ID NO: 8, wherein the fragment further comprises an adjacent N-terminal threonine, adjacent C-terminal cysteine, or a combination thereof.

Provided herein are polypeptides comprising a fragment comprising the sequence of SEQ ID NO: 9, wherein the fragment further comprises an adjacent N-terminal aspartic acid, adjacent C-terminal leucine, or a combination thereof.

Provided herein are polypeptides comprising a fragment comprising the sequence of SEQ ID NO: 10, wherein the fragment further comprises an adjacent N-terminal aspartic acid, adjacent C-terminal arginine, or a combination thereof.

Provided herein are polypeptides comprising a fragment comprising the sequence of SEQ ID NO: 11, wherein the fragment further comprises an adjacent N-terminal threonine, adjacent C-terminal threonine, or a combination thereof.

Provided herein are polypeptides comprising a fragment comprising the sequence of SEQ ID NO: 12, wherein the fragment further comprises an adjacent N-terminal threonine, adjacent C-terminal asparagine, or a combination thereof.

Provided herein are polypeptides comprising a fragment comprising the sequence of SEQ ID NO: 13, wherein the fragment further comprises an adjacent N-terminal threonine, adjacent C-terminal asparagine, or a combination thereof.

Provided herein are polypeptides comprising a fragment comprising the sequence of SEQ ID NO: 14, wherein the fragment further comprises an adjacent N-terminal threonine, adjacent C-terminal serine, or a combination thereof.

Provided herein are polypeptides comprising a reverse transcriptase domain, wherein the polypeptide comprises at least one mutation in an RNA/DNA binding site relative to a nearest related wild-type sequence. Also provided herein are polypeptides wherein the polypeptide comprises a sequence with at least 85% identity to any one of SEQ ID NOs: 1-4, 17, or 18. Also provided herein are polypeptides wherein the polypeptide comprises a sequence with at least 90% identity to any one of SEQ ID NOs: 1-4, 17, or 18.

Provided herein are polypeptides comprising a reverse transcriptase domain, wherein the polypeptide further comprises at least one mutation in a nucleotide binding site relative to a nearest related wild-type sequence. Also provided herein are polypeptides wherein the polypeptide comprises a sequence with at least 85% identity to any one of SEQ ID NOs: 1-4, 17, or 18. Also provided herein are polypeptides wherein the polypeptide comprises a sequence with at least 90% identity to any one of SEQ ID NOs: 1-4, 17, or 18.

Provided herein are polypeptides comprising a reverse transcriptase domain, wherein the polypeptide further comprises at least one of K152C, K152T, K152L, D153Y, A154Y, F155A, F156N, and Q190A, or Q190S as identified with reference to the residues of FIG. 4. Also provided herein are polypeptides wherein the polypeptide comprises a sequence with at least 85% identity to any one of SEQ ID NOs: 1-4, 17, or 18. Also provided herein are polypeptides wherein the polypeptide comprises a sequence with at least 90% identity to any one of SEQ ID NOs: 1-4, 17, or 18.

Provided herein are methods of incorporating a nucleotide analogue into a polynucleotide primer comprising contacting the nucleotide analogue to a polymerase described herein. Also provided herein are methods wherein the nucleotide analogue comprises a 3' OH blocking group. Also provided herein are methods wherein the 3' OH blocking group comprises at least one of an azido, aminoxy, nitro, and a disulfide radical. Also provided herein are methods wherein the nucleotide analogue comprises a modified base. Also provided herein are methods wherein the modified base comprises a detectable moiety. Also provided herein are methods wherein the detectable moiety comprises a fluorescent label.

Provided herein are methods of polynucleotide extension, comprising incorporating a nucleotide analogue into a polynucleotide primer using a nucleic acid polymerase, wherein the nucleic acid polymerase exhibits an increased incorporation of 3' methylazido-dUTP relative to a nearest related wild-type sequence. Also provided herein are methods wherein the nucleic acid polymerase is a reverse transcriptase. Also provided herein are methods wherein the nucleic acid polymerase exhibits at least 10% higher incorporation of 3' methylazido-dUTP relative to a nearest related wild-type sequence under conditions comprising contacting the nucleic acid polymerase with a polynucleotide primer and 10 uM 3' methylazido-dUTP for 20 minutes. Also provided herein are methods wherein the nucleic acid polymerase exhibits at least 30% higher incorporation of 3' methylazido-dUTP relative to a nearest related wild-type sequence under conditions comprising contacting the nucleic acid polymerase with a polynucleotide primer and 10 uM 3' methylazido-dUTP for 20 minutes. Also provided herein are methods wherein the nucleic acid polymerase exhibits at least 50% higher incorporation of 3' methylazido-dUTP relative to a nearest related wild-type sequence under conditions comprising contacting the nucleic acid polymerase with a polynucleotide primer and 10 uM 3' methylazido-dUTP for 20 minutes. Also provided herein are methods wherein the nucleic acid polymerase exhibits at least 30% higher incorporation of 3' methylazido-dUTP relative to SEQ ID NO: 2 under conditions comprising contacting the nucleic acid polymerase with a polynucleotide primer and 10 uM 3' methylazido-dUTP for 20 minutes.

Provided herein are methods of polynucleotide extension, comprising incorporating a nucleotide analogue into a polynucleotide primer using a nucleic acid polymerase, wherein the nucleic acid polymerase exhibits a decreased Km for 3' methylazido-dUTP relative to the nearest related wild-type sequence. Also provided herein are methods wherein the nucleic acid polymerase having at least 90% identity to SEQ ID NO:2 and a mutation at at least one of positions K152, D153, A154, F155, F156, and Q190. Also provided herein are methods wherein the polypeptide comprises a mutation at at least two of positions K152, D153, A154, F155, F156, and Q190. Also provided herein are methods wherein the polypeptide comprises a mutation at at least three of positions K152, D153, A154, F155, F156, and Q190. Also provided herein are methods wherein the polypeptide comprises a mutation at at least four of positions K152, D153, A154, F155, F156, and Q190. Also provided herein are methods wherein the polypeptide comprises a mutation at at least five of positions K152, D153, A154, F155, F156, and Q190. Also provided herein are methods wherein the polypeptide comprises a mutation at position K152. Also provided herein are methods wherein the polypeptide comprises a substitution at K152. Also provided herein are methods wherein the mutation is K152R. Also provided herein are methods wherein the mutation is K152C. Also provided herein are methods wherein the mutation is K152T. Also provided herein are methods wherein the mutation is K152L. Also provided herein are methods wherein the polypeptide comprises a mutation at position D153. Also provided herein are methods wherein the polypeptide comprises a substitution at D153. Also provided herein are methods wherein the mutation is D153Y. Also provided herein are methods wherein the polypeptide comprises a mutation at position A154. Also provided herein are methods wherein the polypeptide comprises a substitution at A154. Also provided herein are methods wherein the mutation is A154Y. Also provided herein are methods wherein the polypeptide comprises a mutation at position F155. Also provided herein are methods wherein the polypeptide comprises a substitution at F155. Also provided herein are methods wherein the mutation is F155A. Also provided herein are methods wherein the polypeptide comprises a mutation at position F156. Also provided herein are methods wherein the polypeptide comprises a substitution at F156. Also provided herein are methods wherein the mutation is F156N. Also provided herein are methods wherein the polypeptide comprises a mutation at position Q190. Also provided herein are methods wherein the polypeptide comprises a substitution at Q190. Also provided herein are methods wherein the mutation is Q190A or Q190S. Also provided herein are methods wherein incorporating further comprises contact with a polynucleotide template.

Provided herein are methods of polynucleotide extension, comprising incorporating a nucleotide analogue into a polynucleotide primer using a nucleic acid polymerase, wherein the nucleic acid polymerase exhibits an increased kcat for incorporation of 3' methylazido-dfUTP relative to the nearest related wild-type sequence. Also provided herein are methods wherein the nucleic acid polymerase having at least 90% identity to SEQ ID NO:2 and a mutation at at least one of positions K152, D153, A154, F155, F156, and Q190. Also provided herein are methods wherein the polypeptide comprises a mutation at at least two of positions K152, D153, A154, F155, F156, and Q190. Also provided herein are methods wherein the polypeptide comprises a mutation at at least three of positions K152, D153, A154, F155, F156, and Q190. Also provided herein are methods wherein the polypeptide comprises a mutation at at least four of positions K152, D153, A154, F155, F156, and Q190. Also provided herein are methods wherein the polypeptide comprises a mutation at at least five of positions K152, D153, A154, F155, F156, and Q190. Also provided herein are methods wherein the polypeptide comprises a mutation at position K152. Also provided herein are methods wherein the polypeptide comprises a substitution at K152. Also provided herein are methods wherein the mutation is K152R. Also provided herein are methods wherein the mutation is K152C. Also provided herein are methods wherein the mutation is K152T. Also provided herein are methods wherein the mutation is K152L. Also provided herein are methods wherein the polypeptide comprises a mutation at position D153. Also provided herein are methods wherein the polypeptide comprises a substitution at D153. Also provided herein are methods wherein the mutation is D153Y. Also provided herein are methods wherein the polypeptide comprises a mutation at position A154. Also provided herein are methods wherein the polypeptide comprises a substitution at A154. Also provided herein are methods wherein the mutation is A154Y. Also provided herein are methods wherein the polypeptide comprises a mutation at position F155. Also provided herein are methods wherein the polypeptide comprises a substitution at F155. Also provided herein are methods wherein the mutation is F155A. Also provided herein are methods wherein the polypeptide comprises a mutation at position F156. Also provided herein are methods wherein the polypeptide comprises a substitution at F156. Also provided herein are methods wherein the mutation is F156N. Also provided herein are methods wherein the polypeptide comprises a mutation at position Q190. Also provided herein are methods wherein the polypeptide comprises a substitution at Q190. Also provided herein are methods wherein the mutation is Q190A or Q190S. Also provided herein are methods wherein incorporating further comprises contact with a polynucleotide template.

Provided herein are methods of polynucleotide extension, comprising incorporating a nucleotide analogue into a polynucleotide primer using a nucleic acid polymerase, wherein the nucleic acid polymerase exhibits an increased kcat/Km for incorporation of 3' methylazido-dfUTP relative to the nearest related wild-type sequence. Also provided herein are methods wherein the nucleic acid polymerase having at least 90% identity to SEQ ID NO:2 and a mutation at at least one of positions K152, D153, A154, F155, F156, and Q190. Also provided herein are methods wherein the polypeptide comprises a mutation at at least two of positions K152, D153, A154, F155, F156, and Q190. Also provided herein are methods wherein the polypeptide comprises a mutation at at least three of positions K152, D153, A154, F155, F156, and Q190. Also provided herein are methods wherein the polypeptide comprises a mutation at at least four of positions K152, D153, A154, F155, F156, and Q190. Also provided herein are methods wherein the polypeptide comprises a mutation at at least five of positions K152, D153, A154, F155, F156, and Q190. Also provided herein are methods wherein the polypeptide comprises a mutation at position K152. Also provided herein are methods wherein the polypeptide comprises a substitution at K152. Also provided herein are methods wherein the mutation is K152R. Also provided herein are methods wherein the mutation is K152C. Also provided herein are methods wherein the mutation is K152T. Also provided herein are methods wherein the mutation is K152L. Also provided herein are methods wherein the polypeptide comprises a mutation at position D153. Also provided herein are methods wherein the polypeptide comprises a substitution at D153. Also provided herein are methods wherein the mutation is D153Y. Also provided herein are methods wherein the polypeptide comprises a mutation at position A154. Also provided herein are methods wherein the polypeptide comprises a substitution at A154. Also provided herein are methods wherein the mutation is A154Y. Also provided herein are methods wherein the polypeptide comprises a mutation at position F155. Also provided herein are methods wherein the polypeptide comprises a substitution at F155. Also provided herein are methods wherein the mutation is F155A. Also provided herein are methods wherein the polypeptide comprises a mutation at position F156. Also provided herein are methods wherein the polypeptide comprises a substitution at F156. Also provided herein are methods wherein the mutation is F156N. Also provided herein are methods wherein the polypeptide comprises a mutation at position Q190. Also provided herein are methods wherein the polypeptide comprises a substitution at Q190. Also provided herein are methods wherein the mutation is Q190A or Q190S. Also provided herein are methods wherein incorporating further comprises contact with a polynucleotide template.

Provided herein are methods of sequencing a nucleic acid comprising: contacting the polypeptide of described herein with a nucleotide analogue, a template polynucleotide, and a polynucleotide primer; incorporating the nucleotide analogue into the polynucleotide primer; and detecting the incorporation of the nucleotide analogue.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The invention has other advantages and features which will be more readily apparent from the following detailed description of the invention and the appended claims, when taken in conjunction with the accompanying drawings, in which:

FIG. 3 illustrates an annotated MMLV sequence (SEQ ID NO: 317).

FIG. 4A illustrates an annotated sequence alignment of SEQ ID NOs: 1-4, 17, and 18 for residues 1-384 of SEQ ID NO:1.

FIG. 4B illustrates an annotated sequence alignment of SEQ ID NOs: 1-4, 17, and 18 for residues 385-672 of SEQ ID NO: 1.

DETAILED DESCRIPTION OF THE INVENTION

Figure 1:
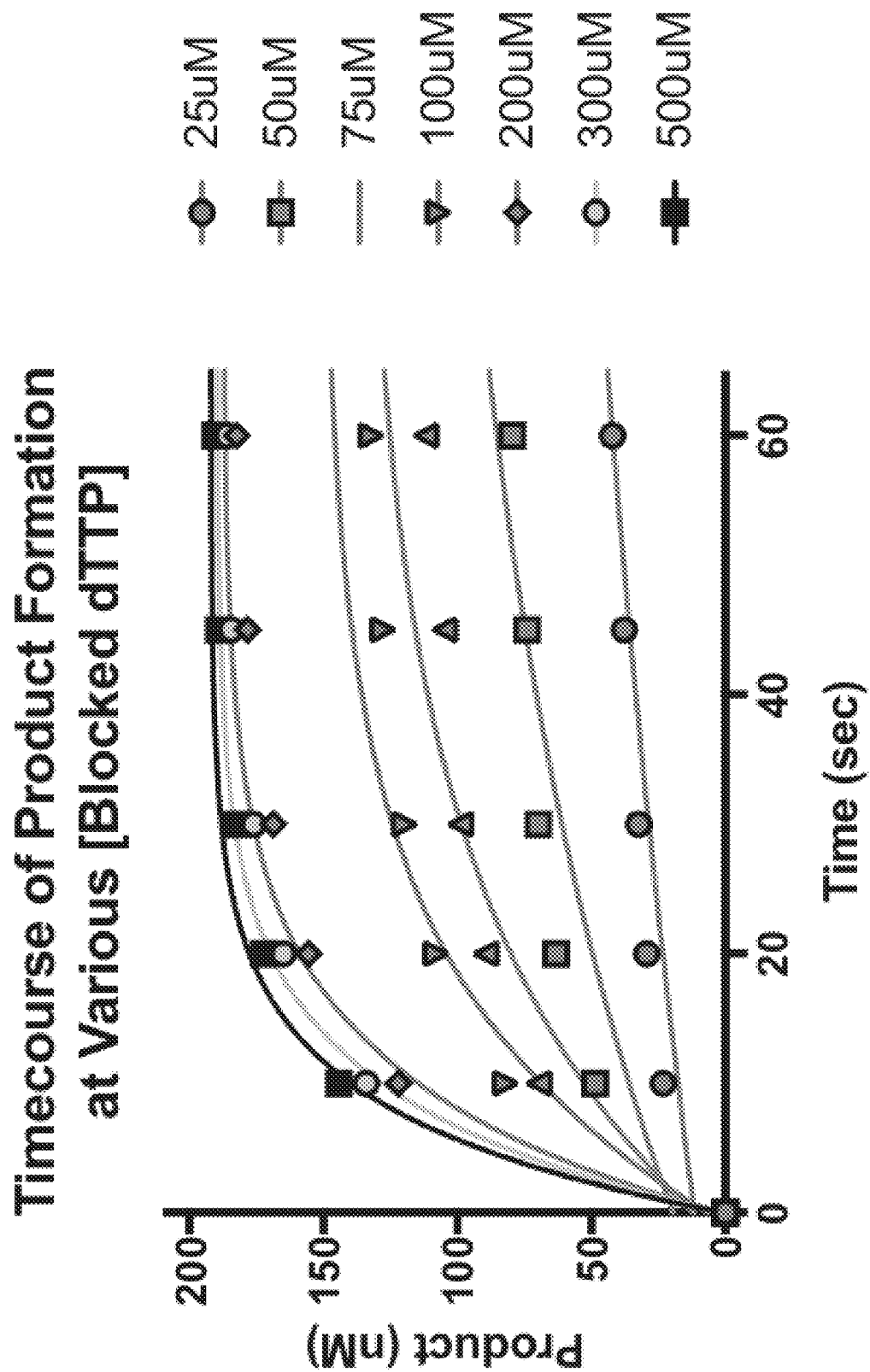
FIG. 1 illustrates a plot of polynucleotide extension rates obtained by contacting wild-type or mutated reverse transcriptase MMLV and 3'methylazido dUTP.

Provided herein are compositions and methods for the incorporation of modified nucleotides into a nucleic acid chain. Polymerases variously comprise DNA polymerases, RNA polymerases, template-independent polymerases, reverse transcriptases, or other enzyme capable of nucleotide extension. Reverse transcriptases are RNA/DNA-dependent DNA polymerases that have been shown to tolerate certain types of nucleotide modifications, such as modifications to the 3' position of the sugar. This property makes reverse transcriptases a desirable protein engineering target to further enhance reversible terminator (removable chemical groups which prevent nucleic acid extension) incorporation for applications such as sequencing. Further provided herein are methods of sequencing employing mutant polymerases that incorporate modified nucleotides.

Polypeptide Engineering

Provided herein are compositions and methods comprising mutant polypeptides relating to enzymes exhibiting increased incorporation of 3' modified nucleotides. Mutations in the polymerases described herein variously comprise one or more changes to amino acid residues present in the polypeptide. Additions, substitutions, or deletions are all examples of mutations that are used to generate mutant polypeptides. Substitutions in some instances comprise the exchange of one amino acid for an alternative amino acid, and such alternative amino acids differ from the original amino acid with regard to size, shape, conformation, or chemical structure. Mutations in some instances are conservative or non-conservative. Conservative mutations comprise the substitution of an amino acid with an amino acid that possesses similar chemical properties. Additions often comprise the insertion of one or more amino acids at the N-terminal, C-terminal, or internal positions of the polypeptide. In some cases, additions comprise fusion polypeptides, wherein one or more additional polypeptides is connected to the polypeptide. Such additional polypeptides in some instances comprise domains with additional activity, or sequences with additional function (e.g., improve expression, aid purification, improve solubility, attach to a solid support, or other function). Often a polypeptide described herein comprises one or more non-amino acid groups. Fusion polypeptides optionally comprise an amino acid or other chemical linker that connects the one or more proteins. Any number of mutations is introduced into a polypeptide or portion of a polypeptide described herein, such as 1, 2, 3, 4, 5, 6, 7, 8, 9, 10, 20, 50, or more than 50 mutations.

In some cases, entire domains (portions of the polypeptide with a defined function) are added, deleted or substituted with domains from other polypeptides. Exemplary domains include DNA/RNA binding domains, nucleotide binding domains, nuclease domains, subcellular localization domains such as nuclear localization domains, or other domain. In some instances, one or more mutations are present in a catalytic site or binding domain. For example, a polypeptide comprises a reverse transcriptase-like binding domain comprising SEQ ID NO:14 or a functional equivalent thereof. A domain in some cases comprises a DNA/RNA binding site, for example comprising residues at positions 63, 64, 97, 112-115, 118, 119, and 190 of SEQ ID NO: 14. Such sites are optionally found in analogous positions after alignment of other sequences to SEQ ID NO: 14. In other instances, a domain comprises an RNase (ribonuclease) domain comprising residues at SEQ ID NO: 15, or functional equivalent thereof. In some cases, a polypeptide comprises an active site. The active site of a polypeptide often comprises residues 149-154, 190, 191, 221, 223, 224, 168, and 169 of SEQ ID NO: 14. Such sites are often found at analogous positions in other domains (identified by aligning the two or more sequences for comparison), and polypeptides that comprise such domains are consistent with methods and compositions described herein.

Wild type sequences are often starting points for protein or enzyme engineering to generate mutant polypeptides. In some embodiments, a polypeptide differs from a wild-type sequence (naturally occurring) by at least one amino acid. Often a polypeptide differs by at least one amino acid from the nearest wild-type polypeptide. In some embodiments, a polypeptide differs from a wild-type sequence (naturally occurring) by at least two amino acids. In some embodiments, a polypeptide differs from a wild-type sequence (naturally occurring) by at least three, four, five, or at least six amino acids. Often, a wild type sequence is the closest wild type sequence, identified by aligning the polypeptide comprising at least one mutation with a wild type sequences.

Polypeptides described herein include but are not limited to polypeptides possessing enzymatic activity, such as polymerase activity, and are often described as families. Often, polymerases are DNA polymerases, RNA polymerases, template-independent polymerases, reverse transcriptases, or other enzyme capable of nucleotide extension. Many reverse transcriptases are known in the art, and such enzymes in some instances are mutated to generate the compositions described herein. Members of the reverse transcriptase family are often defined in terms of polymerase activity, active site structure, domain homology/function, or sequence homology to other known reverse transcriptase family members. For example, reverse transcriptases include but are not limited to HIVRT, MMLV, AVN or other member of the reverse transcriptase family. In some instances, SEQ ID Nos.: 1, 2, 3, 4, 17, and 18 are members of the reverse transcriptase family. Wild-type reverse transcriptases are obtained from any number of origins, such as eukaryotic, prokaryotic, or viral origins.

Further provided herein are polypeptides comprising a sequence that has at least 85% identity with SEQ ID NO: 1 or 2 and at least one mutation at K152, D153, A154, F155, F156, Q190 (SEQ ID NO: 1 numbering). In some cases, a polypeptide described herein comprises a sequence that has at least 70%, 75%, 80%, 85%, 90%, 95%, or at least 97% identity with SEQ ID NO: 1 or 2 and at least one mutation at K152, D153, A154, F155, F156, Q190 (SEQ ID NO: 1 numbering). Often a polypeptide described herein will comprise at least one mutation not found in the wild type polypeptide. A polypeptide that has at least 70%, 75%, 80%, 85%, 90%, 95%, or at least 97% identity with SEQ ID NOs: 1, 2, 3, 17, or 18 and having at least one mutation at a position analogous to K152, D153, A154, F155, F156, Q190 is further described herein.

Exemplary amino acid sequences corresponding to the compositions and methods described herein are shown in Table 1.

TABLE 1

| SEQ ID NO | Name | Amino Acid Sequence |
|---|---|---|
| 1 | MMLV (Murine Moloney Reverse Transcriptase) | MLNIEDEHRLHETSKEPDVSLGSTWLSDFPQAWAETGG MGLAVRQAPLIIPLKATSTPVSIKQYPMSQEARLGIKPHIQ RLLDQGILVPCQSPWNTPLLPVKKPGTNDYRPVQDLREV NKRVEDIHPTVPNPYNLLSGLPPSHQWYTVLDLKDAFFC LRLHPTSQPLFAFEWRDPEMGISGQLTWTRLPQGFKNSP TLFDEALHRDLADFRIQHPDLILLQYVDDLLLAATSELDC QQGTRALLQTLGNLGYRASAKKAQICQKQVKYLGYLLK EGQRWLTEARKETVMGQPTPKTPRQLREFLGTAGFCRL WIPGFAEMAAPLYPLTKTGTLFNWGPDQQKAYQEIKQA LLTAPALGLPDLTKPFELFVDEKQGYAKGVLTQKLGPW |

TABLE 1-continued

| SEQ ID NO | Name | Amino Acid Sequence |
|---|---|---|
| | | RRPVAYLSKKLDPVAAGWPPCLRMVAAIAVLTKDAGKL<br>TMGQPLVILAPHAVEALVKQPPDRWLSNARMTHYQALL<br>LDTDRVQFGPVVALNPATLLPLPEEGLQHNCLDILAEAH<br>GTRPDLTDQPLPDADHTWYTDGSSLLQEGQRKAGAAVT<br>TETEVIWAKALPAGTSAQRAELIALTQALKMAEGKKLN<br>VYTDSRYAFATAHIHGEIYRRRGLLTSEGKEIKNKDEILA<br>LLKALFLPKRLSIIHCPGHQKGHSAEARGNRMADQAARK<br>AAITETPDTSTLLI (SEQ ID NO: 1) |
| 2 | MMLV-ΔN23 | MSTWLSDFPQAWAETGGMGLAVRQAPLIIPLKATSTPVSIKQYPMSQ<br>EARLGIKPHIQRLLDQGILVPCQSPWNTPLLPVKKPGTNDYRPVQDL<br>REVNKRVEDIHPTVPNPYNLLSGLPPSHQWYTVLDLKDAFFCLRLHP<br>TSQPLFAFEWRDPEMGISGQLTWTRLPQGFKNSPTLFDEALHRDLAD<br>FRIQHPDLILLQYVDDLLLAATSELDCQQGTRALLQTLGNLGYRASA<br>KKAQICQKQVKYLGYLLKEGQRWLTEARKETVMGQPTPKTPRQLR<br>EFLGTAGFCRLWIPGFAEMAAPLYPLTKTGTLFNWGPDQQKAYQEI<br>KQALLTAPALGLPDLTKPFELFVDEKQGYAKGVLTQKLGPWRRPVA<br>YLSKKLDPVAAGWPPCLRMVAAIAVLTKDAGKLTMGQPLVILAPHA<br>VEALVKQPPDRWLSNARMTHYQALLLDTDRVQFGPVVALNPATLLP<br>LPEEGLQHNCLDILAEAHGTRPDLTDQPLPDADHTWYTDGSSLLQEG<br>QRKAGAAVTTETEVIWAKALPAGTSAQRAELIALTQALKMAEGKKL<br>NVYTDSRYAFATAHIHGEIYRRRGLLTSEGKEIKNKDEILALLKALFL<br>PKRLSIIHCPGHQKGHSAEARGNRMADQAARKAAITETPDTSTLLI<br>(SEQ ID NO: 2) |
| 3 | HIVRT<br>(HIV Reverse<br>Transcriptase) | PISPIETVPVKLKPGMDGPKVKQWPLTEEKIKALVEICIEMEKEGKIS<br>KIGPENPYNTPVFAIKKKDSTKWRKLVDFRELNKRTQDFWEVQLGIP<br>HPAGLKKKKSVTVLDVGDAYFSVPLDEDFRKYTAFTIPSINNETPGIR<br>YQYNVLPQGWKGSPAIFQSSMTKILEPFRKQNPDIVIYQYMDDLYVG<br>SDLEIGQHRTKIEELRQHLLRWGLTTPDKKHQKEPPFLWMGYELHPD<br>KWTVQPIVLPEKDSWTVNDIQKLVGKLNWASQTYPGIKVRQLCKLL<br>RGTKALTEVIPLTEEAELELAENREILKEPVHGVYYDPSKDLIAEIQK<br>QGQGQWTYQIYQEPFKNLKTGKYARMRGAITINDVKQLIEAVQKIT<br>TESIVIWGKTPKFKLPIQKETWETWWTEYWQATWIPEWEFVNTPPLV<br>KLWYQLEKEPIVGAETF (SEQ ID NO: 3) |
| 4 | AMVRT<br>(Avian<br>Myeoblastosis<br>Virus Reverse<br>Transcriptase) | TVALHLAIPLKWKPNHTPVWIDQWPLPEGKLVALTQLV<br>EKELQLGHIEPSLSCWNTPVFVIRKASGSYRLLHDLRAV<br>NAKLVPFGAVQQGAPVLSALPRGWPLMVLDLKDCFFSIP<br>LAEQDREAFAFTLPSVNNQAPARRFQWKVLPQGMTCSP<br>TICQLIVGQILEPLRLKHPSLRMLHYMDDLLLAASSHDGL<br>EAAGEEVISTLERAGFTISPDKVQREPGVQYLGYKLGSTY<br>VAPVGLVAEPRIATLWDVQKLVGSLQWLRPALGIPPRL<br>MGPFYEQLRGSDPNEAREWNLDMKMAWREIVQLSTTA<br>ALERWDPALPLEGAVARCEQGAIGVLGQGLSTHPRPCL<br>WLFSTQPTKAFTAWLEVLTLLITKLRASAVRTFGKEVDIL<br>LLPACFREDLPLPEGILLALRGFAGKIRSSDTPSIFDIARPL<br>HVSLKVRVTDHPVPGPTVFTDASSSTHKGVVVWREGPR<br>WEIKEIADLGASVQQLEARAVAMALLLWPTTPTNVVTD<br>SAFVAKMLLKMGQEGVPSTAAAFILEDALSQRSAMAAV<br>LHVRSHSEVPGFFTEGNDVADSQATFQAYPLREAKDLHT<br>ALHIGPRALSKACNISMQQAREVVQTCPHCNSAPALEAG<br>VNPRGLGPLQIWQTDFTLEPRMAPRSWLAVTVDTASSAI<br>VVTQHGRVTSVAAQHHWATAIAVLGRPKAIKTDNGSCF<br>TSKSTREWLARWGIAHTTGIPGNSQGQAMVERANRLLK<br>DKIRVLAEGDGFMKRIPTSKQGELLAKAMYALNHFERG<br>ENTKTPIQKHWRPTVLTEGPPVKIRIETGEWEKGWNVLV<br>WGRGYAAVKNRDTDKVIWVPSRKVKPDIAQKDEVTKK<br>DEASPLFA (SEQ ID NO: 4) |
| 5 | MMLV-K152R | WYTVLDLRDAFFCLRL (SEQ ID NO: 5) |
| 6 | MMLV-K152C | LDLCDAFF (SEQ ID NO: 6) |
| 7 | MMLV-K152S | VLDLSDAFF (SEQ ID NO: 7) |
| 8 | MMLV-K152L | VLDLLDAFF (SEQ ID NO: 8) |
| 9 | MMLV-D153Y | TVLDLKYAFFCLRL (SEQ ID NO: 9) |
| 10 | MMLV-A154Y | LKDYFFC (SEQ ID NO: 10) |
| 11 | MMLV-F155A | LKDAAFCL (SEQ ID NO: 11) |
| 12 | MMLV-F156N | VLDLKDAFNCLRLHP (SEQ ID NO: 12) |
| 13 | MMLV-Q190A | RLPAGFK (SEQ ID NO: 13) |

TABLE 1-continued

| SEQ ID NO | Name | Amino Acid Sequence |
|---|---|---|
| 14 | MMLV-Q190S | RLPSGFKN (SEQ ID NO: 14) |
| 15 | MMLV-ZFREV | PVSIKQYPMSQEARLGIKPHIQRLLDQGILVPCQSPWNTPLLPVKKPG TNDYRPVQDLREVNKRVEDIHPTVPNPYNLLSGLPPSHQWYTVLDL KDAFFCLRLHPTSQPLFAFEWRDPEMGISGQLTWTRLPQGFKNSPTL FDEALHRDLADFRIQHPDLILLQYVDDLLLAATSELDCQQGTRALLQ TLGNLGYRASAKKAQICQKQVKYLGYLL (SEQ ID NO: 15) |
| 16 | MMLV-RNase_HI_RT_Bel | TWYTDGSSLLQEGQRKAGAAVTTETEVIWAKALPAGTSAQRAELIA LTQALKMAEGKKLNVYTDSRYAFATAHIHGEIYRRRGLLTSEGKEIK NKDEILALLKALFLPKRLSIIHCPGHQKGHSAEARGNRMADQAARKA A (SEQ ID NO: 16) |
| 17 | TFRT (*Tumebacillus flagellates*_RT) | SSGLVPRGSHMTLNIEDEHRLHETSKEPDVSLGSTWLSDFPQAWAET GGMGLAVRQAPLIIPLKATSTPVSIKQYPMSQKARLGIKPHIQRLLDQ GILVPCQSPWNTPLLPVKKPGTNDYRPVQDLREVNKRVEDIHPTVPN PYNLLSGLPPSHQWYTVLDLKDAFFCLRLHPTSQPLFAFEWRDPEMG ISGQLTWTRLPQGFKNSPTLFDEALHRDLADFRIQHPDLILLQYVDDL LLAATSELDCQQGTRALLQTLGNLGYRASAKKAQICQKQVKYLGYL LKEGQRWLTEARKETVMGQPTPKTPRQLRRFLGTAGFCRLFIPGFAE MAAPLYPLTKTGTLFNWGPDQQKAYQEIKQALLTAPALGLPDLTKP FELFVDEKQGYAKGVLTQKLGPWRRPVAYLSKKLDPVAAGWPPCL RMVAAIAVLTKDAGKLTMGQPLVIGAPHAVEALVKQPPDRWLSKA RMTHYQALLLDTDRVQFGPVVALNPATLLPLPEEGLQHNCLDILAEA HGTRPDLTDQPLPDADHTWYTNGSSLLQEGQRKAGAAVTTETEVIW AKALPAGTSAQRAELIALTQALKMAEGKKLNVYTDSRYAFATAHIH GEIYRRRGLLTSEGKEIKNKDEILALLKALFLPKRLSIIHCPGHQKGHS AEARGNRMADQAARKAAITET (SEQ ID NO: 17) |
| 18 | FLV (feline leukemia virus) | TLQLEEEYRLFEPESTQKQEMDIWLKNFPQAWAETGGMGTAHCQAP VLIQLKATATPISIRQYPMPHEAYQGIKPHIRRMLDQGILKPCQSPWN TPLLPVKKPGTEDYRPVQDLREVNKRVEDIHPTVPNPYNLLSTLPPSH PWYTVLDLKDAFFCLRLHSESQLLFAFEWRDPEIGLSGQLTWTRLPQ GFKNSPTLFDEALHSDLADFRVRYPALVLLQYVDDLLLAAATRTECL EGTKALLETLGNKGYRASAKKAQICLQEVTYLGYSLKDGQRWLTK ARKEAILSIPVPKNSRQVREFLGTAGYCRLWIPGFAELAAPLYPLTRP GTLFQWGTEQQLAFEDIKKALLSSPALGLPDITKPFELFIDENSGFAK GVLVQKLGPWKRPVAYLSKKLDTVASGWPPCLRMVAAIAILVKDA GKLTLGQPLTILTSHPVEALVRQPPNKWLSNARMTHYQAMLLDAER VHFGPTVSLNPATLLPLPSGGNHHDCLQILAETHGTRPDLTDQPLPDA DLTWYTDGSSFIRNGEREAGAAVTTESEVIWAAPLPPGTSAQRAELI ALTQALKMAEGKKLTVYTDSRYAFATTHVHGEIYRRRGLLTSEGKEI KNKNEILALLEALFLPKRLSIIHCPGHQKGDSPQAKGNRLADDTAKK AATETHSSLTVL (SEQ ID NO: 18) |
| 19 | MMLV | MTWLSDFPQAWAETGGMGLAVRQAPLIIPLKATSTPVSIKQYPMSQE ARLGIKPHIQRLLDQGILVPCQSPWNTPLLPVKKPGTNDYRPVQDLR EVNKRVEDIHPTVPNPYNLLSGLPPSHQWYTVLDLKDAFFCLRLHPT SQPLFAFEWRDPEMGISGQLTWTRLPQGFKNSPTLFDEALHRDLADF RIQHPDLILLQYVDDLLLAATSELDCQQGTRALLQTLGNLGYRASAK KAQICQKQVKYLGYLLKEGQRWLTEARKETVMGQPTPKTPRQLREF LGTAGFCRLWIPGFAEMAAPLYPLTKTGTLFNWGPDQQKAYQEIKQ ALLTAPALGLPDLTKPFELFVDEKQGYAKGVLTQKLGPWRRPVAYL SKKLDPVAAGWPPCLRMVAAIAVLTKDAGKLTMGQPLVIKAPHAV EALVKQPPDRWLSNARMTHYQALLLDTDRVQFGPVVALNPATLLPL PEEGLQHNCLDILAEAHGTRPDLTDQPLPDADHTWYTDGSSLLQEG QRKAGAAVTTETEVIWAKALPAGTSAQRAALIALTQALKMAEGKKL NVYTASRYAFATAHIHGEIYRRRGLLTSEGKEIKNKDEILALLKALFL PKRLSIIHCPGHQKGHSAEARGNRMADQAARKAAITETPDTSTLLI (SEQ ID NO: 19) |
| 20 | XMRV (Xenotropic murine leukemia virus-related virus) | DFPQAWAETGGMGLAVRQAPLIIPLKATSTPVSIKQYPMSQEARLGI KPHIQRLLDQGILVPCQSPWNTPLLPVKKPGTDYRPVQDLREVNKRV EDIHPTVPNPYNLLSGLPPSHQWYTVLDLKDAFFCLRLHPTSQPLFAFEW RDQLTWTRLPQGFKNSPTLFDEALHRDLADFRIQHPDLILLQYVDDL LLAATSEQDCQRGTRALLQTLGNLGYRASAKKAQICQKQVKYLGYL LKEGQRWLTEARKETVMGQPTPKTPRQLREFLGTAGFCRLWIPGFA EMAAPLYPLTKTLFNWGPDQQKAYQEIKQALLTAPALGLPDLTKPFE LFVDEKQGYAKGVLTQKLGPWRRPVAYLSKKLDPVAAGWPPCLRM VAAIAVLTKDAGKLTMGQPLVILAPHAVEALVKQPPARMTHYQAM LLDTDRVQFGPVVALNPATLLPLP (SEQ ID NO: 20) |
| 21 | 4mh8 | TWLSDFPQAWAETGGMGLAVRQAPLIIPLKATSTPVSIKQYPMSQEA RLGIKPHIQRLLDQGILVPCQSPWNTPLLPVKTNDYRPVQDLREVNK RVEDIHPTVPNPYNLLSGLPPSHQWYTVLDLKDAFFCLRLHPTSQPLF AFEWRDPEMGISGQLTWTRLPQGFKNSPTLFDEALHRDLADFRIQHP |

TABLE 1-continued

| SEQ ID NO | Name | Amino Acid Sequence |
|---|---|---|
| | | DLILLQYVDDLLLAATSELDCQQGTRALLQTLGNLGYRASAKKAQIC QKQVKYLGYLLKEGQRWLTEARKETVMGQPTPKTPRQLREFLGTA GFCRLWIPGFAEMAAPLYPLTKTLFNWGPDQQKAYQEIKQALLTAP ALGLPDLTKPFELFVDEKQGYAKGVLTQKLGPWRRPVAYLSKKLDP VAAGWPPCLRMVAAIAVLTKDAGKLTMGQPLVIKAPHAVEALVKQ PPARMTHYQALLLDTDRVQFGPVVALNPATLLPLP (SEQ ID NO: 21) |
| 22 | FIV (feline immunodeficiency virus) | QIKQWPLTNEKIEALTEIVERLEREGKVKRADPNNPWNTPVFAIKKK SGKWRMLIDFRELNKLIEKGAQLGLPHPAGLQIKKQVTVLDIGDAY FTIPLDPDYAPYTAFTLPRKNNAGPGRRFVWCSLPQGWILSPLIYQST LDNIIQPFIRQNPQLDIYQYMDDIYIGSNLSKKEHKEKVEELRKLLLW WGFETPEDKLQEEPPYTWMGYELHPLTWTIQQKQLDIPEQPTLNELQ KLAGKINWASQAIPDLSIKALTNMMRGNQNLNSTRQWTKEARLEVQ KAKKAIEEQVQLGYYDPSKELYAKLSLVGPHQISYQVYQKDPEKIL WYGKMSRQKKKAENTCDIALRACYKIREESIIRIGKEPRYEIPTSREA WESNLINSPYLKAPPPEVEYIHAALNIKRALSMIKDAPIPGAETWYID GGRKLGKAAKAAYWTDTGKWQVMELEGSNQKAEIQALLLALKAG SEEMNIITDSQYVINIILQQPDMMEGIWQEVLEELEKKTAIFIDWVPG HKGIPGNEEVDKLCSDKIPVVKVKMKDPNKGPQIKQWPLTNEKIEAL TEIVERLEREGKVKRADPNNPWNTPVFAIKKKSGKWRMLIDFRELN KLIEKLGLPHPAGLQIKKQVTVLDIGDAYFTIPLDPDYAPYTAFTLPR KNNAGPGRRFVWCSLPQGWILSPLIYQSTLDNIIQPFIRQNPQLDIYQY MDDIYIGSNLSKKEHKEKVEELRKLLLWPEDKLQEETWTIQQKQLDI PEQPTLNELQKLAGKINWASQAIPDLSIKALTNMMRGNQNLNSTRQ WTKEARLEVQKAKKAIEEQVQLGYYDPSKELYAKLSLVGPHQISYQ VYQKDPEKILWYGKMSRQKKKAENTCDIALRACYKIREESIIRIGKEP RYEIPTSREAWESNLINSPYLKAPPPEVEYIHAALNIKRALS (SEQ ID NO: 22) |
| 23 | HIV2 | AKVEPIKIMLKPGKDGPKLRQWPLTKEKIEALKEICEKMEKEGQLEE APPTNPYNTPTFAIKKKDRMLIDFRELNKVTQDFTEIQLGIPHPAGLA KKRRITVLDVGDAYFSIPLHEDFRPYTAFTLKRYIYKVLPQGWKGSP AIFQHTMRQVLEPFRKANKDVIIIQYMDDILIASDRTDLEHDRVVLQL KELLNGLGFSTPDEKFQKDPPYHWMGYELWPTKWLQKIQLPQKEI WTVNDIQKLVGVLNWAAQLYPGIKTKHLCRLISGKMTLTEEVQWTE LAEAELEENRIILSQEQEGHYYQEEKELEATVQKDQDNQWTYKIHQE EKILKVGKYAKVTHTNGIRLLAQVVQKIGKEALVIWGRIPKFHLPVE REIWEQWWDNYWQVTWIPDWDFVSTPPLVRLAFNLVGDPIPGAETF YTDGSCNRQSKEGKAGYVTDRGKDKVKKLEQTTNQQAELEAFAMA LTDSGPKVNIIVDSQYVMGIVASQPIESESKIVNQIIEEMIKKEAIYVA WVPAHKGIGGNQEVDHLVSQGIEPIKIMLKPGKDGPKLRQWPLTKE KIEALKEICEKMEKEGQLEEAPPTNPYNTPTFAIKNKWRMLIDFRELN KVTQDFTEIQPHPAGLAKKRRITVLDVGDAYFSIPLHEDFRPYTAFTL PSVNNAEPGKRYIYKVLPQGWKGSPAIFQHTMRQVLEPFRKANKDVI IIQYMDDILIASDRTDLEHDRVVLQLKELLNGWMGYELWPTKWKLQ KIQLPQKEIWTVNDIQKLVGVLNWAAQLYPGIKTKHLCRLISGKMTL IEEVQWIELAEAELEENRIILSQEQEGHYYQEEKELEATVQKDQDNQ WTYKIHQEEKILKVGKYAKVKNTHTNGIRLLAQVVQKIGKEALVIW GRIPKFHLPVEREIWEQWWDNYWQVTWIPDWDFVSTPPLVRLAFNL VGD (SEQ ID NO: 23) |
| 24 | HIV Type O Reverse Transcriptase | PISPIAPVPVKLKPGMDGPKVKQWPLSKEKIEALTAICQEMEQEGKIS RIGPENPYNTPIFAIKKKDSTKWRKLVDFRELNKRTQDFWEVQLGIP HPGGLKQKRSVTVLDVGDAYFSCPLDPDFRKYTAFTIPSVNNETPGIR YQYNVLPQGWKGSPAIFQSSMTKILDPFRKDNPELEICQYMDDLYVG SDLPLAEHRKRVELLREHLYQWGFTTPDKKHQKEPPFMWMGYELH PDKWTVQPIKLPNKDVWTVNDIQKLIGKLNWASQIYQGIRVRELCKL IRGTKSLIEVVPLSKEAEMELEENREKLKEPMHGVYYQPDKDLWVN IQKQGEGQWTYQIYQDEHKNLKTGKYTRQRGAFFINDIRQLAEVIQK VSQESIVIWGKLPKFKLPVTRETWETWWADYWQATWIPEWDYVST PPLIKLWYRLESEPIMGAETYYVDGAANRDTKLGKAGYVTEQGKQK IIKLNETTNQKAELMAVLLALQDSKEKVNIVTDSQYVLGIISSQPTQS ESPIVQQIIEELTKKEQVYLTWVPAHKGIGGNEKIDKLVSKDIRRVL (SEQ ID NO: 24) |
| 25 | HIV1 | MVPISPIETVPVKLKPGMDGPKVKQWPLIEEKIKALVEICIEMEKEG KISKIGPENPYNTPVFAIKKKDSTKWRKLVDFRELNKRTQDFWEVQL GIPHPAGLKKKKSVTVLDVGDAYFSVPLDEDFRKYTAFTIPSINNETP GIRYQYNVLPQGWKGSPAIFQSSMTKILEPFKKQNPDIVIYQYMDDL YVGSDLEIGQHRTKIEELRQHLLRWGLTTPDKKHQKEPPFLWMGYE LHPDKWTVQPIVLPEKDSWTVNDICKLVGKLNWASQIYPGIKVRQLS KLLRGTKALIEVIPLTEEAELELAENREIKEPVHGVYYDPSKDLIAEI QKQGQGQWTYQIYQEPFKNLKTGKYARMRGAHTNDVKQLTEAVQ KITTESIVIWGKTPKFKLPIQKETWETWWIEYWQATWIPEWEFVNTP PLVKLWYQLEKEPIVGAETFYVDGAANRETKLGKAGYVTNKGRQK VVPLTNTTNQKIELQATYLALQDSGLEVNIVTNSQYALGIIQAQPDKS ESELVNQIIEQLIKKEKVYLAWVPAHKGIGGNEQVDKLVSAPIETVPV |

TABLE 1-continued

| SEQ ID NO Name | Amino Acid Sequence |
|---|---|
| | KLKPGMDGPKVKQWPLIEEKIKALVEICIEMEKEGKISKIGPENPYN
TPVFAIKKKDSTKWRKLVDFRELNKRTQDFWEVQLGIPHPAGLKKK
KSVTVLDVGDAYFSVPLDEDFRKYTAFTIPSINNETPGIRYQYNVLPQ
GWKGSPAIFQSSMTKILEPFKKQNPDIVIYQYMDDLYVGSDLEIGQH
RTKIEELRQHLLRWGLTTPGYELHPDKWTVQPIVLPEKDSWTVNDIQ
KLVGKLNWASQIYPGIKVRQLSKLLRGTKALTEVIPLTEEAELELAEN
REILKEPVHGVYYDPSKDLIAEIQKQGQGQWTYQIYQEPFKNLKTGK
YARMRGAHTNDVKQLTEAVQKITTESIVIWGKTPKFKLPIQKETWET
WWIEYWQATWIPEWEFVNTPPLVKLWYQ (SEQ ID NO: 25) |

Further described herein are segments, or portions of a larger polypeptide. Optionally, segments have catalytic activity such as nucleic acid extension activity, particularly in the context of a reverse transcriptase domain or polymerase domain as described herein. Described herein are polypeptides comprising any one of the segments of SEQ ID NOs:4-16, and at least one additional residue at the N or C terminus (+1 residue). In some instances both the N and C terminus has at least an additional residue, two, three four five, six seven, eight, nine, ten 11, 12, 13, 14, 15, 16, 17, 18, 19, 20, 21, 22, 23, 24, 25, 26, 27, 28, 29, 30, 35, 40, 45, 50, 60, 70, 80, 90, 100, or more than 100 additional residues. For example, described herein are polypeptides comprising SEQ ID NO: 4(+1 residue), such as an adjacent N-terminal aspartic acid, an adjacent C-terminal arginine, or a combination thereof, or additional residues such as residues identified through an alignment of SEQ ID NO:4 to SEQ ID NO:1, accounting for a single mutated residue or other residues contributed to a polypeptide comprising the SEQ ID NO. Described herein are polypeptides comprising SEQ ID NO: 5(+1 residue), such as an adjacent N-terminal glutamine, an adjacent C-terminal histidine, or a combination thereof, or additional residues such as residues identified through an alignment of SEQ ID NO:5 to SEQ ID NO: 1, accounting for a single mutated residue, or other residues contributed to a polypeptide comprising the SEQ ID NO. Described herein are polypeptides comprising SEQ ID NO: 6(+1 residue), such as an adjacent N-terminal valine, an adjacent C-terminal cysteine, or a combination thereof, or additional residues such as residues identified through an alignment of SEQ ID NO:6 to SEQ ID NO:1, accounting for a single mutated residue, or other residues contributed to a polypeptide comprising the SEQ ID NO. Described herein are polypeptides comprising SEQ ID NO: 7(+1 residue), such as an adjacent N-terminal threonine, an adjacent C-terminal cysteine, or a combination thereof, or additional residues such as residues identified through an alignment of SEQ ID NO:7 to SEQ ID NO:1, accounting for a single mutated residue, or other residues contributed to a polypeptide comprising the SEQ ID NO. Described herein are polypeptides comprising SEQ ID NO: 8(+1 residue), such as an adjacent N-terminal threonine, an adjacent C-terminal cysteine, or a combination thereof, or additional residues such as residues identified through an alignment of SEQ ID NO:8 to SEQ ID NO:1, accounting for a single mutated residue, or other residues contributed to a polypeptide comprising the SEQ ID NO. Described herein are polypeptides comprising SEQ ID NO: 9(+1 residue), such as an adjacent N-terminal aspartic acid, an adjacent C-terminal leucine, or a combination thereof, or additional residues such as residues identified through an alignment of SEQ ID NO:9 to SEQ ID NO:1, accounting for a single mutated residue, or other residues contributed to a polypeptide comprising the SEQ ID NO. Described herein are polypeptides comprising SEQ ID NO: 10(+1 residue), such as an adjacent N-terminal aspartic acid, an adjacent C-terminal arginine, or a combination thereof, or additional residues such as residues identified through an alignment of SEQ ID NO: 10 to SEQ ID NO: 1, accounting for a single mutated residue, or other residues contributed to a polypeptide comprising the SEQ ID NO. Described herein are polypeptides comprising SEQ ID NO: 11(+1 residue), such as an adjacent N-terminal threonine, an adjacent C-terminal threonine, or a combination thereof, or additional residues such as residues identified through an alignment of SEQ ID NO:11 to SEQ ID NO:1, accounting for a single mutated residue, or other residues contributed to a polypeptide comprising the SEQ ID NO. Described herein are polypeptides comprising SEQ ID NO: 12(+1 residue), such as an adjacent N-terminal threonine, an adjacent C-terminal asparagine, or a combination thereof, or additional residues such as residues identified through an alignment of SEQ ID NO: 12 to SEQ ID NO:1, accounting for a single mutated residue, or other residues contributed to a polypeptide comprising the SEQ ID NO. Described herein are polypeptides comprising SEQ ID NO: 13(+1 residue), such as an adjacent N-terminal threonine, an adjacent C-terminal asparagine, or a combination thereof, or additional residues such as residues identified through an alignment of SEQ ID NO:13 to SEQ ID NO:1, accounting for a single mutated residue, or other residues contributed to a polypeptide comprising the SEQ ID NO. Described herein are polypeptides comprising SEQ ID NO: 14(+1 residue), such as an adjacent N-terminal threonine, an adjacent C-terminal serine, or a combination thereof, or additional residues such as residues identified through an alignment of SEQ ID NO: 14 to SEQ ID NO:1, accounting for a single mutated residue, or other residues contributed to a polypeptide comprising the SEQ ID NO.

Exemplary polypeptide mutants described herein are shown in Table 2. In some instances, a polypeptide described herein has a sequence that has at least 85% identity to SEQ ID NO: 1 or 2, and that further exhibits at least one of the mutations shown in Table 2. In some cases, a polypeptide described herein has a sequence that has at least 70%, 75%, 80%, 85%, 90%, 91%, 92%, 93%, 94%, 95%, 96%, 97%, 98%, 99%, or greater than 99% identity to SEQ ID NO: 1 or 2, and that further exhibits at least one of the mutations shown in Table 2. Some polypeptides described herein has a sequence exhibiting substantial identity, such as at least 70%, 75%, 80%, 85%, 90%, 91%, 92%, 93%, 94%, 95%, 96%, 97%, 98%, 99%, or greater than 99% identity to a polypeptide of SEQ ID NO: 1, 2, 3, 4, 17, or 18 and exhibits at least one of the mutations shown in Table 2. Additional polypeptides contemplated and disclosed herein comprise a reverse transcriptase domain having at least one mutation at a position analogous to at least one of the positions in Table 2, up to and including all of the positions indicated in Table 2, in some cases to come to polypeptides having one or more of the mutations indicated in Table 2 at a homologous position.

TABLE 2

| | Position relative to SEQ ID NO: 1 | | | | | | |
|---|---|---|---|---|---|---|---|
| # | K152 | D153 | A154 | F155 | F156 | Q190 | Mutations relative to SEQ ID NO: 1 |
| — | K | D | A | F | F | Q | Wildtype |
| 1 | K | D | A | F | F | A | Q190A |
| 2 | K | D | A | F | F | S | Q190S |
| 3 | K | D | A | F | N | Q | F156N |
| 4 | K | D | A | F | N | A | F156N; Q190A |
| 5 | K | D | A | F | N | S | F156N; Q190S |
| 6 | K | D | A | A | F | Q | F155A |
| 7 | K | D | A | A | F | A | F155A; Q190A |
| 8 | K | D | A | A | F | S | F155A; Q190S |
| 9 | K | D | A | A | N | Q | F155A; F156N |
| 10 | K | D | A | A | N | A | F155A; F156N; Q190A |
| 11 | K | D | A | A | N | S | F155A; F156N; Q190S |
| 12 | K | D | Y | F | F | Q | A154Y |
| 13 | K | D | Y | F | F | A | A154Y; Q190A |
| 14 | K | D | Y | F | F | S | A154Y; Q190S |
| 15 | K | D | Y | F | N | Q | A154Y; F156N |
| 16 | K | D | Y | F | N | A | A154Y; F156N; Q190A |
| 17 | K | D | Y | F | N | S | A154Y; F156N; Q190S |
| 18 | K | D | Y | A | F | Q | A154Y; F155A |
| 19 | K | D | Y | A | F | A | A154Y; F155A; Q190A |
| 20 | K | D | Y | A | F | S | A154Y; F155A; Q190S |
| 21 | K | D | Y | A | N | Q | A154Y; F155A; F156N |
| 22 | K | D | Y | A | N | A | A154Y; F155A; F156N; Q190A |
| 23 | K | D | Y | A | N | S | A154Y; F155A; F156N; Q190S |
| 24 | K | Y | A | F | F | Q | D153Y |
| 25 | K | Y | A | F | F | A | D153Y; Q190A |
| 26 | K | Y | A | F | F | S | D153Y; Q190S |
| 27 | K | Y | A | F | N | Q | D153Y; F156N |
| 28 | K | Y | A | F | N | A | D153Y; F156N; Q190A |
| 29 | K | Y | A | F | N | S | D153Y; F156N; Q190S |
| 30 | K | Y | A | A | F | Q | D153Y; F155A |
| 31 | K | Y | A | A | F | A | D153Y; F155A; Q190A |
| 32 | K | Y | A | A | F | S | D153Y; F155A; Q190S |
| 33 | K | Y | A | A | N | Q | D153Y; F155A; F156N |
| 34 | K | Y | A | A | N | A | D153Y; F155A; F156N; Q190A |
| 35 | K | Y | A | A | N | S | D153Y; F155A; F156N; Q190S |
| 36 | K | Y | Y | F | F | Q | D153Y; A154Y |
| 37 | K | Y | Y | F | F | A | D153Y; A154Y; Q190A |
| 38 | K | Y | Y | F | F | S | D153Y; A154Y; Q190S |
| 39 | K | Y | Y | F | N | Q | D153Y; A154Y; F156N |
| 40 | K | Y | Y | F | N | A | D153Y; A154Y; F156N; Q190A |
| 41 | K | Y | Y | F | N | S | D153Y; A154Y; F156N; Q190S |
| 42 | K | Y | Y | A | F | Q | D153Y; A154Y; F155A |
| 43 | K | Y | Y | A | F | A | D153Y; A154Y; F155A; Q190A |
| 44 | K | Y | Y | A | F | S | D153Y; A154Y; F155A; Q190S |
| 45 | K | Y | Y | A | N | Q | D153Y; A154Y; F155A; F156N |
| 46 | K | Y | Y | A | N | A | D153Y; A154Y; F155A; F156N; Q190A |
| 47 | K | Y | Y | A | N | S | D153Y; A154Y; F155A; F156N; Q190S |
| 48 | R | D | A | F | F | Q | K152R |
| 49 | R | D | A | F | F | A | K152R; Q190A |
| 50 | R | D | A | F | F | S | K152R; Q190S |
| 51 | R | D | A | F | N | Q | K152R; F156N |
| 52 | R | D | A | F | N | A | K152R; F156N; Q190A |
| 53 | R | D | A | F | N | S | K152R; F156N; Q190S |
| 54 | R | D | A | A | F | Q | K152R; F155A |
| 55 | R | D | A | A | F | A | K152R; F155A; Q190A |
| 56 | R | D | A | A | F | S | K152R; F155A; Q190S |
| 57 | R | D | A | A | N | Q | K152R; F155A; F156N |
| 58 | R | D | A | A | N | A | K152R; F155A; F156N; Q190A |
| 59 | R | D | A | A | N | S | K152R; F155A; F156N; Q190S |
| 60 | R | D | Y | F | F | Q | K152R; A154Y |
| 61 | R | D | Y | F | F | A | K152R; A154Y; Q190A |
| 62 | R | D | Y | F | F | S | K152R; A154Y; Q190S |
| 63 | R | D | Y | F | N | Q | K152R; A154Y; F156N |
| 64 | R | D | Y | F | N | A | K152R; A154Y; F156N; Q190A |
| 65 | R | D | Y | F | N | S | K152R; A154Y; F156N; Q190S |
| 66 | R | D | Y | A | F | Q | K152R; A154Y; F155A |
| 67 | R | D | Y | A | F | A | K152R; A154Y; F155A; Q190A |
| 68 | R | D | Y | A | F | S | K152R; A154Y; F155A; Q190S |
| 69 | R | D | Y | A | N | Q | K152R; A154Y; F155A; F156N |

TABLE 2-continued

Position relative to SEQ ID NO: 1

| # | K152 | D153 | A154 | F155 | F156 | Q190 | Mutations relative to SEQ ID NO: 1 |
|---|------|------|------|------|------|------|-----------------------------------|
| 70 | R | D | Y | A | N | A | K152R; A154Y; F155A; F156N; Q190A |
| 71 | R | D | Y | A | N | S | K152R; A154Y; F155A; F156N; Q190S |
| 72 | R | Y | A | F | F | Q | K152R; D153Y |
| 73 | R | Y | A | F | F | A | K152R; D153Y; Q190A |
| 74 | R | Y | A | F | F | S | K152R; D153Y; Q190S |
| 75 | R | Y | A | F | N | Q | K152R; D153Y; F156N |
| 76 | R | Y | A | F | N | A | K152R; D153Y; F156N; Q190A |
| 77 | R | Y | A | F | N | S | K152R; D153Y; F156N; Q190S |
| 78 | R | Y | A | A | F | Q | K152R; D153Y; F155A |
| 79 | R | Y | A | A | F | A | K152R; D153Y; F155A; Q190A |
| 80 | R | Y | A | A | F | S | K152R; D153Y; F155A; Q190S |
| 81 | R | Y | A | A | N | Q | K152R; D153Y; F155A; F156N |
| 82 | R | Y | A | A | N | A | K152R; D153Y; F155A; F156N; Q190A |
| 83 | R | Y | A | A | N | S | K152R; D153Y; F155A; F156N; Q190S |
| 84 | R | Y | Y | F | F | Q | K152R; D153Y; A154Y |
| 85 | R | Y | Y | F | F | A | K152R; D153Y; A154Y; Q190A |
| 86 | R | Y | Y | F | F | S | K152R; D153Y; A154Y; Q190S |
| 87 | R | Y | Y | F | N | Q | K152R; D153Y; A154Y; F156N |
| 88 | R | Y | Y | F | N | A | K152R; D153Y; A154Y; F156N; Q190A |
| 89 | R | Y | Y | F | N | S | K152R; D153Y; A154Y; F156N; Q190S |
| 90 | R | Y | Y | A | F | Q | K152R; D153Y; A154Y; F155A |
| 91 | R | Y | Y | A | F | A | K152R; D153Y; A154Y; F155A; Q190A |
| 92 | R | Y | Y | A | F | S | K152R; D153Y; A154Y; F155A; Q190S |
| 93 | R | Y | Y | A | N | Q | K152R; D153Y; A154Y; F155A; F156N |
| 94 | R | Y | Y | A | N | A | K152R; D153Y; A154Y; F155A; F156N; Q190A |
| 95 | R | Y | Y | A | N | S | K152R; D153Y; A154Y; F155A; F156N; Q190S |
| 96 | C | D | A | F | F | Q | K152C |
| 97 | C | D | A | F | F | A | K152C; Q190A |
| 98 | C | D | A | F | F | S | K152C; Q190S |
| 99 | C | D | A | F | N | Q | K152C; F156N |
| 100 | C | D | A | F | N | A | K152C; F156N; Q190A |
| 101 | C | D | A | F | N | S | K152C; F156N; Q190S |
| 102 | C | D | A | A | F | Q | K152C; F155A |
| 103 | C | D | A | A | F | A | K152C; F155A; Q190A |
| 104 | C | D | A | A | F | S | K152C; F155A; Q190S |
| 105 | C | D | A | A | N | Q | K152C; F155A; F156N |
| 106 | C | D | A | A | N | A | K152C; F155A; F156N; Q190A |
| 107 | C | D | A | A | N | S | K152C; F155A; F156N; Q190S |
| 108 | C | D | Y | F | F | Q | K152C; A154Y |
| 109 | C | D | Y | F | F | A | K152C; A154Y; Q190A |
| 110 | C | D | Y | F | F | S | K152C; A154Y; Q190S |
| 111 | C | D | Y | F | N | Q | K152C; A154Y; F156N |
| 112 | C | D | Y | F | N | A | K152C; A154Y; F156N; Q190A |
| 113 | C | D | Y | F | N | S | K152C; A154Y; F156N; Q190S |
| 114 | C | D | Y | A | F | Q | K152C; A154Y; F155A |
| 115 | C | D | Y | A | F | A | K152C; A154Y; F155A; Q190A |
| 116 | C | D | Y | A | F | S | K152C; A154Y; F155A; Q190S |
| 117 | C | D | Y | A | N | Q | K152C; A154Y; F155A; F156N |
| 118 | C | D | Y | A | N | A | K152C; A154Y; F155A; F156N; Q190A |
| 119 | C | D | Y | A | N | S | K152C; A154Y; F155A; F156N; Q190S |
| 120 | C | Y | A | F | F | Q | K152C; D153Y |
| 121 | C | Y | A | F | F | A | K152C; D153Y; Q190A |
| 122 | C | Y | A | F | F | S | K152C; D153Y; Q190S |
| 123 | C | Y | A | F | N | Q | K152C; D153Y; F156N |
| 124 | C | Y | A | F | N | A | K152C; D153Y; F156N; Q190A |
| 125 | C | Y | A | F | N | S | K152C; D153Y; F156N; Q190S |
| 126 | C | Y | A | A | F | Q | K152C; D153Y; F155A |
| 127 | C | Y | A | A | F | A | K152C; D153Y; F155A; Q190A |
| 128 | C | Y | A | A | F | S | K152C; D153Y; F155A; Q190S |
| 129 | C | Y | A | A | N | Q | K152C; D153Y; F155A; F156N |
| 130 | C | Y | A | A | N | A | K152C; D153Y; F155A; F156N; Q190A |
| 131 | C | Y | A | A | N | S | K152C; D153Y; F155A; F156N; Q190S |
| 132 | C | Y | Y | F | F | Q | K152C; D153Y; A154Y |
| 133 | C | Y | Y | F | F | A | K152C; D153Y; A154Y; Q190A |
| 134 | C | Y | Y | F | F | S | K152C; D153Y; A154Y; Q190S |
| 135 | C | Y | Y | F | N | Q | K152C; D153Y; A154Y; F156N |
| 136 | C | Y | Y | F | N | A | K152C; D153Y; A154Y; F156N; Q190A |
| 137 | C | Y | Y | F | N | S | K152C; D153Y; A154Y; F156N; Q190S |
| 138 | C | Y | Y | A | F | Q | K152C; D153Y; A154Y; F155A |
| 139 | C | Y | Y | A | F | A | K152C; D153Y; A154Y; F155A; Q190A |
| 140 | C | Y | Y | A | F | S | K152C; D153Y; A154Y; F155A; Q190S |
| 141 | C | Y | Y | A | N | Q | K152C; D153Y; A154Y; F155A; F156N |
| 142 | C | Y | Y | A | N | A | K152C; D153Y; A154Y; F155A; F156N; Q190A |
| 143 | C | Y | Y | A | N | S | K152C; D153Y; A154Y; F155A; F156N; Q190S |
| 144 | S | D | A | F | F | Q | K152S |
| 145 | S | D | A | F | F | A | K152S; Q190A |

TABLE 2-continued

| | Position relative to SEQ ID NO: 1 | | | | | |
|---|---|---|---|---|---|---|
| # | K152 | D153 | A154 | F155 | F156 | Q190 | Mutations relative to SEQ ID NO: 1 |
| 146 | S | D | A | F | F | S | K152S; Q190S |
| 147 | S | D | A | F | N | Q | K152S; F156N |
| 148 | S | D | A | F | N | A | K152S; F156N; Q190A |
| 149 | S | D | A | F | N | S | K152S; F156N; Q190S |
| 150 | S | D | A | A | F | Q | K152S; F155A |
| 151 | S | D | A | A | F | A | K152S; F155A; Q190A |
| 152 | S | D | A | A | F | S | K152S; F155A; Q190S |
| 153 | S | D | A | A | N | Q | K152S; F155A; F156N |
| 154 | S | D | A | A | N | A | K152S; F155A; F156N; Q190A |
| 155 | S | D | A | A | N | S | K152S; F155A; F156N; Q190S |
| 156 | S | D | Y | F | F | Q | K152S; A154Y |
| 157 | S | D | Y | F | F | A | K152S; A154Y; Q190A |
| 158 | S | D | Y | F | F | S | K152S; A154Y; Q190S |
| 159 | S | D | Y | F | N | Q | K152S; A154Y; F156N |
| 160 | S | D | Y | F | N | A | K152S; A154Y; F156N; Q190A |
| 161 | S | D | Y | F | N | S | K152S; A154Y; F156N; Q190S |
| 162 | S | D | Y | A | F | Q | K152S; A154Y; F155A |
| 163 | S | D | Y | A | F | A | K152S; A154Y; F155A; Q190A |
| 164 | S | D | Y | A | F | S | K152S; A154Y; F155A; Q190S |
| 165 | S | D | Y | A | N | Q | K152S; A154Y; F155A; F156N |
| 166 | S | D | Y | A | N | A | K152S; A154Y; F155A; F156N; Q190A |
| 167 | S | D | Y | A | N | S | K152S; A154Y; F155A; F156N; Q190S |
| 168 | S | Y | A | F | F | Q | K152S; D153Y |
| 169 | S | Y | A | F | F | A | K152S; D153Y; Q190A |
| 170 | S | Y | A | F | F | S | K152S; D153Y; Q190S |
| 171 | S | Y | A | F | N | Q | K152S; D153Y; F156N |
| 172 | S | Y | A | F | N | A | K152S; D153Y; F156N; Q190A |
| 173 | S | Y | A | F | N | S | K152S; D153Y; F156N; Q190S |
| 174 | S | Y | A | A | F | Q | K152S; D153Y; F155A |
| 175 | S | Y | A | A | F | A | K152S; D153Y; F155A; Q190A |
| 176 | S | Y | A | A | F | S | K152S; D153Y; F155A; Q190S |
| 177 | S | Y | A | A | N | Q | K152S; D153Y; F155A; F156N |
| 178 | S | Y | A | A | N | A | K152S; D153Y; F155A; F156N; Q190A |
| 179 | S | Y | A | A | N | S | K152S; D153Y; F155A; F156N; Q190S |
| 180 | S | Y | Y | F | F | Q | K152S; D153Y; A154Y |
| 181 | S | Y | Y | F | F | A | K152S; D153Y; A154Y; Q190A |
| 182 | S | Y | Y | F | F | S | K152S; D153Y; A154Y; Q190S |
| 183 | S | Y | Y | F | N | Q | K152S; D153Y; A154Y; F156N |
| 184 | S | Y | Y | F | N | A | K152S; D153Y; A154Y; F156N; Q190A |
| 185 | S | Y | Y | F | N | S | K152S; D153Y; A154Y; F156N; Q190S |
| 186 | S | Y | Y | A | F | Q | K152S; D153Y; A154Y; F155A |
| 187 | S | Y | Y | A | F | A | K152S; D153Y; A154Y; F155A; Q190A |
| 188 | S | Y | Y | A | F | S | K152S; D153Y; A154Y; F155A; Q190S |
| 189 | S | Y | Y | A | N | Q | K152S; D153Y; A154Y; F155A; F156N |
| 190 | S | Y | Y | A | N | A | K152S; D153Y; A154Y; F155A; F156N; Q190A |
| 191 | S | Y | Y | A | N | S | K152S; D153Y; A154Y; F155A; F156N; Q190S |
| 192 | T | D | A | F | F | Q | K152T |
| 193 | T | D | A | F | F | A | K152T; Q190A |
| 194 | T | D | A | F | F | S | K152T; Q190S |
| 195 | T | D | A | F | N | Q | K152T; F156N |
| 196 | T | D | A | F | N | A | K152T; F156N; Q190A |
| 197 | T | D | A | F | N | S | K152T; F156N; Q190S |
| 198 | T | D | A | A | F | Q | K152T; F155A |
| 199 | T | D | A | A | F | A | K152T; F155A; Q190A |
| 200 | T | D | A | A | F | S | K152T; F155A; Q190S |
| 201 | T | D | A | A | N | Q | K152T; F155A; F156N |
| 202 | T | D | A | A | N | A | K152T; F155A; F156N; Q190A |
| 203 | T | D | A | A | N | S | K152T; F155A; F156N; Q190S |
| 204 | T | D | Y | F | F | Q | K152T; A154Y |
| 205 | T | D | Y | F | F | A | K152T; A154Y; Q190A |
| 206 | T | D | Y | F | F | S | K152T; A154Y; Q190S |
| 207 | T | D | Y | F | N | Q | K152T; A154Y; F156N |
| 208 | T | D | Y | F | N | A | K152T; A154Y; F156N; Q190A |
| 209 | T | D | Y | F | N | S | K152T; A154Y; F156N; Q190S |
| 210 | T | D | Y | A | F | Q | K152T; A154Y; F155A |
| 211 | T | D | Y | A | F | A | K152T; A154Y; F155A; Q190A |
| 212 | T | D | Y | A | F | S | K152T; A154Y; F155A; Q190S |
| 213 | T | D | Y | A | N | Q | K152T; A154Y; F155A; F156N |
| 214 | T | D | Y | A | N | A | K152T; A154Y; F155A; F156N; Q190A |
| 215 | T | D | Y | A | N | S | K152T; A154Y; F155A; F156N; Q190S |
| 216 | T | Y | A | F | F | Q | K152T; D153Y |
| 217 | T | Y | A | F | F | A | K152T; D153Y; Q190A |
| 218 | T | Y | A | F | F | S | K152T; D153Y; Q190S |
| 219 | T | Y | A | F | N | Q | K152T; D153Y; F156N |
| 220 | T | Y | A | F | N | A | K152T; D153Y; F156N; Q190A |
| 221 | T | Y | A | F | N | S | K152T; D153Y; F156N; Q190S |

TABLE 2-continued

| # | K152 | D153 | A154 | F155 | F156 | Q190 | Mutations relative to SEQ ID NO: 1 |
|---|------|------|------|------|------|------|-----------------------------------|
| 222 | T | Y | A | A | F | Q | K152T; D153Y; F155A |
| 223 | T | Y | A | A | F | A | K152T; D153Y; F155A; Q190A |
| 224 | T | Y | A | A | F | S | K152T; D153Y; F155A; Q190S |
| 225 | T | Y | A | A | N | Q | K152T; D153Y; F155A; F156N |
| 226 | T | Y | A | A | N | A | K152T; D153Y; F155A; F156N; Q190A |
| 227 | T | Y | A | A | N | S | K152T; D153Y; F155A; F156N; Q190S |
| 228 | T | Y | Y | F | F | Q | K152T; D153Y; A154Y |
| 229 | T | Y | Y | F | F | A | K152T; D153Y; A154Y; Q190A |
| 230 | T | Y | Y | F | F | S | K152T; D153Y; A154Y; Q190S |
| 231 | T | Y | Y | F | N | Q | K152T; D153Y; A154Y; F156N |
| 232 | T | Y | Y | F | N | A | K152T; D153Y; A154Y; F156N; Q190A |
| 233 | T | Y | Y | F | N | S | K152T; D153Y; A154Y; F156N; Q190S |
| 234 | T | Y | Y | A | F | Q | K152T; D153Y; A154Y; F155A |
| 235 | T | Y | Y | A | F | A | K152T; D153Y; A154Y; F155A; Q190A |
| 236 | T | Y | Y | A | F | S | K152T; D153Y; A154Y; F155A; Q190S |
| 237 | T | Y | Y | A | N | Q | K152T; D153Y; A154Y; F155A; F156N |
| 238 | T | Y | Y | A | N | A | K152T; D153Y; A154Y; F155A; F156N; Q190A |
| 239 | T | Y | Y | A | N | S | K152T; D153Y; A154Y; F155A; F156N; Q190S |
| 240 | L | D | A | F | F | Q | K152L |
| 241 | L | D | A | F | F | A | K152L; Q190A |
| 242 | L | D | A | F | F | S | K152L; Q190S |
| 243 | L | D | A | F | N | Q | K152L; F156N |
| 244 | L | D | A | F | N | A | K152L; F156N; Q190A |
| 245 | L | D | A | F | N | S | K152L; F156N; Q190S |
| 246 | L | D | A | A | F | Q | K152L; F155A |
| 247 | L | D | A | A | F | A | K152L; F155A; Q190A |
| 248 | L | D | A | A | F | S | K152L; F155A; Q190S |
| 249 | L | D | A | A | N | Q | K152L; F155A; F156N |
| 250 | L | D | A | A | N | A | K152L; F155A; F156N; Q190A |
| 251 | L | D | A | A | N | S | K152L; F155A; F156N; Q190S |
| 252 | L | D | Y | F | F | Q | K152L; A154Y |
| 253 | L | D | Y | F | F | A | K152L; A154Y; Q190A |
| 254 | L | D | Y | F | F | S | K152L; A154Y; Q190S |
| 255 | L | D | Y | F | N | Q | K152L; A154Y; F156N |
| 256 | L | D | Y | F | N | A | K152L; A154Y; F156N; Q190A |
| 257 | L | D | Y | F | N | S | K152L; A154Y; F156N; Q190S |
| 258 | L | D | Y | A | F | Q | K152L; A154Y; F155A |
| 259 | L | D | Y | A | F | A | K152L; A154Y; F155A; Q190A |
| 260 | L | D | Y | A | F | S | K152L; A154Y; F155A; Q190S |
| 261 | L | D | Y | A | N | Q | K152L; A154Y; F155A; F156N |
| 262 | L | D | Y | A | N | A | K152L; A154Y; F155A; F156N; Q190A |
| 263 | L | D | Y | A | N | S | K152L; A154Y; F155A; F156N; Q190S |
| 264 | L | Y | A | F | F | Q | K152L; D153Y |
| 265 | L | Y | A | F | F | A | K152L; D153Y; Q190A |
| 266 | L | Y | A | F | F | S | K152L; D153Y; Q190S |
| 267 | L | Y | A | F | N | Q | K152L; D153Y; F156N |
| 268 | L | Y | A | F | N | A | K152L; D153Y; F156N; Q190A |
| 269 | L | Y | A | F | N | S | K152L; D153Y; F156N; Q190S |
| 270 | L | Y | A | A | F | Q | K152L; D153Y; F155A |
| 271 | L | Y | A | A | F | A | K152L; D153Y; F155A; Q190A |
| 272 | L | Y | A | A | F | S | K152L; D153Y; F155A; Q190S |
| 273 | L | Y | A | A | N | Q | K152L; D153Y; F155A; F156N |
| 274 | L | Y | A | A | N | A | K152L; D153Y; F155A; F156N; Q190A |
| 275 | L | Y | A | A | N | S | K152L; D153Y; F155A; F156N; Q190S |
| 276 | L | Y | Y | F | F | Q | K152L; D153Y; A154Y |
| 277 | L | Y | Y | F | F | A | K152L; D153Y; A154Y; Q190A |
| 278 | L | Y | Y | F | F | S | K152L; D153Y; A154Y; Q190S |
| 279 | L | Y | Y | F | N | Q | K152L; D153Y; A154Y; F156N |
| 280 | L | Y | Y | F | N | A | K152L; D153Y; A154Y; F156N; Q190A |
| 281 | L | Y | Y | F | N | S | K152L; D153Y; A154Y; F156N; Q190S |
| 282 | L | Y | Y | A | F | Q | K152L; D153Y; A154Y; F155A |
| 283 | L | Y | Y | A | F | A | K152L; D153Y; A154Y; F155A; Q190A |
| 284 | L | Y | Y | A | F | S | K152L; D153Y; A154Y; F155A; Q190S |
| 285 | L | Y | Y | A | N | Q | K152L; D153Y; A154Y; F155A; F156N |
| 286 | L | Y | Y | A | N | A | K152L; D153Y; A154Y; F155A; F156N; Q190A |
| 287 | L | Y | Y | A | N | S | K152L; D153Y; A154Y; F155A; F156N; Q190S |

Provided herein are compositions and methods for the incorporation of modified nucleotides into a nucleic acid chain. Polymerases variously comprise DNA polymerases, RNA polymerases, template-independent polymerases, reverse transcriptases, or other enzymes capable of nucleotide extension. Reverse transcriptases are RNA/DNA-dependent DNA polymerases that have been shown to tolerate certain types of nucleotide modifications, such as modifications to the 3' position of the sugar. This property makes reverse transcriptases a desirable protein engineering target to further enhance reversible terminator (removable chemical groups which prevent nucleic acid extension) incorporation for applications such as sequencing. Further provided herein are methods of sequencing employing mutant polymerases that incorporate modified nucleotides. Further, the use of engineered reverse transcriptases allows the incorporation of mutations that enhance the thermostability of the enzyme or the ability of the enzyme to function at higher temperatures. Thermostable reverse transcriptases may be useful in isothermal sequencing or elongation techniques. Isothermal techniques include SDA, LAMP, SMAP, ICAN, SMART. In these techniques, the elongation reaction proceeds at a constant temperature, for example using strand displacement reactions. Amplification can be completed in a single step, by incubating the mixture of samples, primers, DNA polymerase with strand displacement activity, and substrates at a constant temperature. This reduces the number of steps required, eliminating thermal ramping steps and reducing the total cycle time for each sequencing or elongation cycle, while simultaneously decreasing the reaction time required for each cycle. Reverse transcriptases which may be used according to the methods and compositions of the present disclosure include viral, bacterial, and eukaryotic reverse transcriptases and homologs and orthologs thereof. Exemplary reverse transcriptases include but are not limited to Murine Moloney Leukemia Virus (MMLV) reverse transcriptase and engineered and/or truncated variants thereof; xenotropic murine leukemia virus (XMLV) reverse transcriptase and engineered and/or truncated variants thereof; HIV-1 reverse transcriptase and engineered and/or truncated variants thereof; HIV Type M reverse transcriptase and engineered and/or truncated variants thereof; HIV Type O reverse transcriptase and engineered and/or truncated variants thereof; HIV-2 reverse transcriptase and engineered and/or truncated variants thereof; Feline immunodeficiency Virus (FIV) reverse transcriptase and engineered and/or truncated variants thereof, and Sunscript® reverse transcriptase and engineered and/or truncated variants thereof. Other reverse transcriptases and homologous or orthologous polymerases are known in the art and are expressly contemplated within this disclosure. Provided herein are compositions and methods comprising mutant polypeptides which have enhanced thermostability. In some case, such mutant polypeptides possess polymerase activity (e.g., mutant nucleic acid polymerase). Thermostability in some instances includes increased Tm, resistance to degradation, and/or the ability to maintain functional activity (e.g., incorporation of nucleotides) at elevated temperatures relative to a nearest wild-type enzyme, such as a wild-type enzyme comprising a nearest wild-type enzyme sequence. Mutant polymerases in some cases comprise Tm that are increased about 1, 2, 5, 10, 15, 20, 25, or about 30 degrees C. relative to a nearest wild-type enzyme. Mutant polypeptides in some instances comprise a Tm that are increased at least 1, 2, 5, 10, 15, 20, 25, or at least 30 degrees C. relative to a nearest wild-type enzyme. Mutant polymerases often comprise a Tm value that are increased at least 1-10, 5-15, 4-20, 2-10, 4-15, 20-30, 10-60, or 25-35 degrees C. relative to a nearest wild-type enzyme. Polymerase activity, in some instances, comprises $k_{cat}$, $k_{cat}/K_m$, or yields of incorporated nucleotides for a given time period. In some cases, mutant polymerases functioning at an elevated temperature maintain at least 99%, 98%, 95%, 90%, 85%, or at least 80% of the optimal activity of a nearest wild-type enzyme functioning at a lower temperature. For example, mutant polymerases functioning at about 37 degrees C. maintain at least 99%, 98%, 95%, 90%, 85%, or at least 80% of the optimal activity of a nearest wild-type enzyme. In some instances, mutant polymerases functioning at about 42 degrees C. maintain at least 99%, 98%, 95%, 90%, 85%, or at least 80% of the optimal activity of a nearest wild-type enzyme. In some instances, mutant polymerases functioning at about 55 degrees C. maintain at least 99%, 98%, 95%, 90%, 85%, or at least 80% of the optimal activity of a nearest wild-type enzyme. In some instances, mutant polymerases functioning at about 60 degrees C. maintain at least 99%, 98%, 95%, 90%, 85%, or at least 80% of the optimal activity of a nearest wild-type enzyme. In some instances, mutant polymerases functioning at least at 50 degrees C. maintain at least 99%, 98%, 95%, 90%, 85%, or at least 80% of the optimal activity of a nearest wild-type enzyme. In some instances, mutant polymerases functioning at least at 60 degrees C. maintain at least 99%, 98%, 95%, 90%, 85%, or at least 80% of the optimal activity of a nearest wild-type enzyme. In some instances, mutant polymerases functioning at 37-95 degrees C. maintain at least 99%, 98%, 95%, 90%, 85%, or at least 80% of the optimal activity of a nearest wild-type enzyme. In some instances, mutant polymerases functioning at 37-95, 37-60, 37-55, 37-42, 40-60, 50-80, 42-55, 55-60, 55-95, 60-95, or 40-80 degrees C. maintain at least 99%, 98%, 95%, 90%, 85%, or at least 80% of the optimal activity of a nearest wild-type enzyme. In some instances, mutant polymerases functioning at 42-95 degrees C. maintain at least 99%, 98%, 95%, 90%, 85%, or at least 80% of the optimal activity of a nearest wild-type enzyme. In some instances, mutant polymerases functioning at 40-80 degrees C. maintain at least 99%, 98%, 95%, 90%, 85%, or at least 80% of the optimal activity of a nearest wild-type enzyme. In some instances, mutant polymerases functioning at 37-55 degrees C. maintain at least 99%, 98%, 95%, 90%, 85%, or at least 80% of the optimal activity of a nearest wild-type enzyme. In some instances, mutant polymerases functioning at 50-95 degrees C. maintain at least 99%, 98%, 95%, 90%, 85%, or at least 80% of the optimal activity of a nearest wild-type enzyme. In some instances, Mutant polymerases functioning at 60-95 degrees C. maintain at least 99%, 98%, 95%, 90%, 85%, or at least 80% of the optimal activity of a nearest wild-type enzyme. In some cases a mutant polymerase has an increased $k_{cat}$ relative to a nearest related wild-type sequence functioning at a temperature of at least 37 degrees C. In some cases a mutant polymerase has an increased $k_{cat}$ relative to a nearest related wild-type sequence functioning at a temperature of at least 42 degrees C. In some cases a mutant polymerase has an increased $k_{cat}$ relative to a nearest related wild-type sequence functioning at a temperature of at least 55 degrees C. In some cases a mutant polymerase has an increased $k_{cat}$ relative to a nearest related wild-type sequence functioning at a temperature of at least 60 degrees C. In some cases a mutant polymerase has an increased $k_{cat}$ relative to a nearest related wild-type sequence functioning at a temperature of at least 80 degrees C. In some cases a mutant polymerase has an increased $k_{cat}$ relative to a nearest related wild-type sequence functioning at a temperature of at least 90 degrees C. In some cases a mutant polymerase has an increased $k_{cat}$ relative to a nearest related wild-type sequence functioning at a temperature of 37-95, 37-60, 37-55, 37-42, 40-60, 50-80, 42-55, 55-60, 55-95, 60-95, or 40-80 degrees C. In some cases a mutant polymerase has an increased $k_{cat}$ relative to a nearest related wild-type sequence functioning at a temperature of 37-55 degrees C. In some cases a mutant polymerase has an increased $k_{cat}$ relative to a nearest related wild-type sequence functioning at a temperature of 35-80 degrees C.

Provided herein are compositions and methods comprising mutant polypeptides relating to enzymes exhibiting increased incorporation of 3' modified nucleotides. Mutations in the polymerases described herein variously comprise one or more changes to amino acid residues present in the polypeptide. Additions, substitutions, or deletions are all examples of mutations that are used to generate mutant polypeptides. Substitutions in some instances comprise the exchange of one amino acid for an alternative amino acid, and such alternative amino acids differ from the original amino acid with regard to size, shape, conformation, or chemical structure. Mutations in some instances are conservative or non-conservative. Conservative mutations comprise the substitution of an amino acid with an amino acid that possesses similar chemical properties. Additions often comprise the insertion of one or more amino acids at the N-terminal, C-terminal, or internal positions of the polypeptide. In some cases, additions comprise fusion polypeptides, wherein one or more additional polypeptides is connected to the polypeptide. Such additional polypeptides in some instances comprise domains with additional activity, or sequences with additional function (e.g., improve expression, aid purification, improve solubility, attach to a solid support, or other function). Often a polypeptide described herein comprises one or more non-amino acid groups. Fusion polypeptides optionally comprise an amino acid or other chemical linker that connects the one or more proteins. Any number of mutations is introduced into a polypeptide or portion of a polypeptide described herein, such as 1, 2, 3, 4, 5, 6, 7, 8, 9, 10, 20, 50, or more than 50 mutations.

In some cases, entire domains (portions of the polypeptide with a defined function) are added, deleted or substituted with domains from other polypeptides. Exemplary domains include DNA/RNA binding domains, nucleotide binding domains, nuclease domains, subcellular localization domains such as nuclear localization domains, or other domains. In some embodiments, the methods and compositions of the present disclosure comprise the attachment of a domain serving as a spacer or label, and/or providing for the attachment of a linker such as a SNAP tag, an avidin moiety, a streptavidin moiety, an epitope tag, a fluorescent protein, an affinity tag, a metal binding (i.e., a His6 or polyhistidine tag) or the like. In some instances, one or more mutations are present in a catalytic site or binding domain. For example, a polypeptide comprises a reverse transcriptase-like binding domain comprising SEQ ID NO:14 or a functional equivalent thereof. A domain in some cases comprises a DNA/RNA binding site, for example comprising residues at positions 63, 64, 97, 112-115, 118, 119, and 190 of SEQ ID NO: 14. Such sites are optionally found in analogous positions after alignment of other sequences to SEQ ID NO: 14. In other instances, a domain comprises an RNase (ribonuclease) domain comprising residues at SEQ ID NO: 15, or functional equivalent thereof. In some cases, a polypeptide comprises an active site. The active site of a polypeptide may comprise, for example, residues 149-154, 190, 191, 221, 223, 224, 168, and 169 of SEQ ID NO: 14. Such sites are often found at analogous positions in other domains (identified by aligning the two or more sequences for comparison), and polypeptides that comprise such domains are consistent with methods and compositions described herein.

As used herein, the term "surrounding" an amino acid residue or sequence position has its ordinary meaning in the art, including and incorporating modifications such as substitutions, deletions, insertions, or post-translational modifications at residues from 1, 2, 3, 4, 5, 6, 7, 8, 9, 10, 11, or 12 or more residues distant from the named residue, i.e., N-terminal or C-terminal from the named residue. In some contexts, a residue greater than 12 residues or sequence positions N or C terminal from the named residue can be considered "surrounding" a named residue based on the sequence or structural (i.e., 3-dimensional) context as would be understood by one of ordinary skill in the art.

It is understood that substitutions or modifications of the residues described herein also may incorporate or may include nonstandard amino acids as are known in the art, including but not limited to hydroxyproline, N-formylmethionine, selenomethionine, selenocysteine, phosphotyrosine, phosphohistidine, and the like. The mutations, modifications, truncations, substitutions and the like as described herein may be made by any method as is known in the art, particularly the art of molecular biology and/or protein engineering. Such methods may include site directed mutagenesis using mutagenic and/or partially degenerate primers, in vitro gene assembly, gene editing (such as by CRISPR or related methods) and the like. The mutant or engineered proteins described herein may additionally be expressed, isolated, and/or purified by any such means as is known in the art. Relevant methods are described in: Green, M. and Sambrook, J., Molecular Cloning: A Laboratory Manual (Fourth Edition) which is hereby incorporated by reference in its entirety and especially with respect to its disclosure of methods for modifying, transferring, and expressing, recombinant, modified, and engineered gene sequences as well as extracting, isolating, and/or purifying engineered proteins.

In some embodiments, the compositions and methods of the present disclosure comprise one or more mutations that may affect thermal stability of the enzyme. In some embodiments, said mutation or mutations may comprise one or more substitutions, deletions, or insertions at, or at a position or location surrounding, positions 47, 86, 95, 117, 178, 280, 291, 308, 432, 502, 581, and/or 585 of SEQ ID NO 19, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue E47 of SEQ ID NO: 19 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E47 with aspartic acid, lysine, glutamine, arginine, histidine, valine, or alanine. In some embodiments, said mutation or mutations may comprise substitution of residue E47 with proline or glycine. In some embodiments, said mutation or mutations may comprise the substitution E47K. In some embodiments, said mutation or mutations may comprise the deletion of residue E47.

In some embodiments, said mutation or mutations may comprise substitution of residue D86 of SEQ ID NO: 19 with any of the 19 other natural amino acids (i.e., W, I, M, P, F, G, A, V, L, H, E, R, K, N, Y, C, S, T, or Q) or with non-natural amino acids as are known to those of skill in the art. In some embodiments, said mutation or mutations may comprise substitution of residue D86 with glutamic acid, asparagine, glutamine, valine, alanine, serine, or threonine. In some embodiments, said mutation or mutations may comprise substitution of residue D86 with proline or glycine. In some embodiments, said mutation or mutations may comprise the substitution D86A. In some embodiments, said mutation or mutations may comprise the deletion of residue D86.

In some embodiments, said mutation or mutations may comprise substitution of residue E95 of SEQ ID NO: 19 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E95 with aspartic acid, asparagine, glutamine, valine, alanine, serine, or threonine. In some embodiments, said mutation or mutations may comprise substitution of residue E95 with proline or glycine. In some embodiments, said mutation or mutations may comprise the substitution E95A. In some embodiments, said mutation or mutations may comprise the deletion of residue E95.

In some embodiments, said mutation or mutations may comprise substitution of residue L117 of SEQ ID NO: 19 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue L117 with proline, glycine, alanine, serine, valine, or threonine. In some embodiments, said mutation or mutations may comprise substitution of residue L117 with proline or glycine. In some embodiments, said mutation or mutations may comprise the substitution L117P. In some embodiments, said mutation or mutations may comprise the deletion of residue L117.

In some embodiments, said mutation or mutations may comprise substitution of residue D178 of SEQ ID NO: 19 with any of the 19 other natural amino acids (i.e., W, I, M, P, F, G, A, V, L, H, E, R, K, N, Y, C, S, T, or Q) or with non-natural amino acids as are known to those of skill in the art. In some embodiments, said mutation or mutations may comprise substitution of residue D178 with asparagine, glutamic acid, glutamine, serine, threonine, or valine. In some embodiments, said mutation or mutations may comprise substitution of residue D178 with proline or glycine. In some embodiments, said mutation or mutations may comprise the substitution D178N. In some embodiments, said mutation or mutations may comprise the deletion of residue D178.

In some embodiments, said mutation or mutations may comprise substitution of residue E280 of SEQ ID NO: 19 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E280 with aspartic acid, lysine, arginine, glutamine, histidine, valine, or alanine. In some embodiments, said mutation or mutations may comprise substitution of residue E280 with proline or glycine. In some embodiments, said mutation or mutations may comprise the substitution E280K. In some embodiments, said mutation or mutations may comprise the substitution E280R. In some embodiments, said mutation or mutations may comprise the deletion of residue E280.

In some embodiments, said mutation or mutations may comprise substitution of residue W291 of SEQ ID NO: 19 with any of the 19 other natural amino acids (i.e., I, M, P, F, G, A, V, L, H, E, R, K, D, N, Y, C, S, T, or Q) or with non-natural amino acids as are known to those of skill in the art. In some embodiments, said mutation or mutations may comprise substitution of residue W291 with phenylalanine, tyrosine, histidine, leucine, isoleucine, methionine, or valine. In some embodiments, said mutation or mutations may comprise substitution of residue W291 with proline or glycine. In some embodiments, said mutation or mutations may comprise the substitution W291F. In some embodiments, said mutation or mutations may comprise the deletion of residue W291.

In some embodiments, said mutation or mutations may comprise substitution of residue T308 of SEQ ID NO: 19 with any of the 19 other natural amino acids (i.e., W, I, M, P, F, G, A, V, L, H, E, R, K, D, N, Y, C, S, or Q) or with non-natural amino acids as are known to those of skill in the art. In some embodiments, said mutation or mutations may comprise substitution of residue T308 with proline, glycine, alanine, serine, valine, or threonine. In some embodiments, said mutation or mutations may comprise substitution of residue T308 with proline or glycine. In some embodiments, said mutation or mutations may comprise the substitution T308P. In some embodiments, said mutation or mutations may comprise the deletion of residue T308.

In some embodiments, said mutation or mutations may comprise substitution of residue N432 of SEQ ID NO: 19 with any of the 19 other natural amino acids (i.e., W, I, M, P, F, G, A, V, L, H, E, R, K, D, Y, C, S, T, or Q) or with non-natural amino acids as are known to those of skill in the art. In some embodiments, said mutation or mutations may comprise substitution of residue N432 with aspartic acid, lysine, arginine, glutamic acid, glutamine, histidine, valine, or alanine. In some embodiments, said mutation or mutations may comprise substitution of residue N432 with proline or glycine. In some embodiments, said mutation or mutations may comprise the substitution N432K. In some embodiments, said mutation or mutations may comprise the deletion of residue N432.

In some embodiments, said mutation or mutations may comprise substitution of residue D502 of SEQ ID NO: 19 with any of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said mutation or mutations may comprise substitution of residue D502 with glutamic acid, asparagine, glutamine, valine, alanine, serine, or threonine. In some embodiments, said mutation or mutations may comprise substitution of residue D502 with proline or glycine. In some embodiments, said mutation or mutations may comprise the substitution D502A. In some embodiments, said mutation or mutations may comprise the deletion of residue D502.

In some embodiments, said mutation or mutations may comprise substitution of residue L581 of SEQ ID NO: 19 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue L581 with phenylalanine, tyrosine, histidine, tryptophan, isoleucine, methionine, or valine. In some embodiments, said mutation or mutations may comprise substitution of residue L581 with proline or glycine. In some embodiments, said mutation or mutations may comprise the substitution L581W. In some embodiments, said mutation or mutations may comprise the deletion of residue L581.

In some embodiments, said mutation or mutations may comprise substitution of residue E585 of SEQ ID NO: 19 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E585 with aspartic acid, lysine, arginine, glutamine, histidine, valine, or alanine. In some embodiments, said mutation or mutations may comprise substitution of residue E585 with proline or glycine. In some embodiments, said mutation or mutations may comprise the substitution E585K. In some embodiments, said mutation or mutations may comprise the deletion of residue E585 of SEQ ID NO: 19.

In some embodiments, the mutation or mutations according to the methods and compositions of the present disclosure may comprise any 1, 2, 3, 4, 5, 6, 7, 8, 9, 10, 11, or 12 of E47K, D86A, E95A, L117P, D178N, E280K, E280R, W291F, T308P, N432K, D502A, L581W, and/or E585K, of SEQ ID NO: 19 or any subset or combination thereof, or any homolog or ortholog thereof.

In some embodiments, said mutation or mutations may comprise one or more substitutions, deletions, or insertions at, or at a position or location surrounding, positions 42, 77, 78, 86, 108, 162, 264, 285, 291, 292, 408, and/or 409 of SEQ ID NO: 20, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue E42 of SEQ ID NO: 20 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E47 with aspartic acid, lysine, glutamine, arginine, histidine, valine, or alanine. In some embodiments, said mutation or mutations may comprise substitution of residue E47 with proline or glycine. In some embodiments, said mutation or mutations may comprise the substitution E47K. In some embodiments, said mutation or mutations may comprise the deletion of residue E47.

In some embodiments, said mutation or mutations may comprise substitution of residue D77 of SEQ ID NO: 20 with any of the 19 other natural amino acids (i.e., W, I, M, P, F, G, A, V, L, H, E, R, K, N, Y, C, S, T, or Q) or with non-natural amino acids as are known to those of skill in the art. In some embodiments, said mutation or mutations may comprise substitution of residue D77 with glutamic acid, asparagine, glutamine, valine, alanine, serine, or threonine. In some embodiments, said mutation or mutations may comprise substitution of residue D77 with proline or glycine. In some embodiments, said mutation or mutations may comprise the substitution D77A. In some embodiments, said mutation or mutations may comprise the deletion of residue D77.

In some embodiments, said mutation or mutations may comprise substitution of residue Y78 of SEQ ID NO: 20 with any of the 19 other natural amino acids (i.e., W, I, M, P, F, G, A, V, L, H, E, R, K, D, N, C, S, T, or Q) or with non-natural amino acids as are known to those of skill in the art. In some embodiments, said mutation or mutations may comprise substitution of residue Y78 with glutamic acid, asparagine, glutamine, valine, alanine, serine, or threonine. In some embodiments, said mutation or mutations may comprise substitution of residue Y78 with proline or glycine. In some embodiments, said mutation or mutations may comprise the substitution Y78A. In some embodiments, said mutation or mutations may comprise the deletion of residue Y78.

In some embodiments, said mutation or mutations may comprise insertion of one or more residues between residues D77 and Y78 of SEQ ID NO: 20 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of glutamic acid, asparagine, glutamine, valine, alanine, serine, and/or threonine. In some embodiments, said mutation or mutations may comprise insertion of proline or glycine. In some embodiments, said mutation or mutations may comprise insertion of an alanine between residues D77 and Y78.

In some embodiments, said mutation or mutations may comprise substitution of residue E86 of SEQ ID NO: 20 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E86 with aspartic acid, asparagine, glutamine, valine, alanine, serine, or threonine. In some embodiments, said mutation or mutations may comprise substitution of residue E86 with proline or glycine. In some embodiments, said mutation or mutations may comprise the substitution E86A. In some embodiments, said mutation or mutations may comprise the deletion of residue E86.

In some embodiments, said mutation or mutations may comprise substitution of residue L108 of SEQ ID NO: 20 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue L108 with proline, glycine, alanine, serine, valine, or threonine. In some embodiments, said mutation or mutations may comprise substitution of residue L108 with proline or glycine. In some embodiments, said mutation or mutations may comprise the substitution L108P. In some embodiments, said mutation or mutations may comprise the deletion of residue L108.

In some embodiments, said mutation or mutations may comprise substitution of residue D162 of SEQ ID NO: 20 with any of the 19 other natural amino acids (i.e., W, I, M, P, F, G, A, V, L, H, E, R, K, N, Y, C, S, T, or Q) or with non-natural amino acids as are known to those of skill in the art. In some embodiments, said mutation or mutations may comprise substitution of residue D162 with asparagine, glutamic acid, glutamine, serine, threonine, or valine. In some embodiments, said mutation or mutations may comprise substitution of residue D162 with proline or glycine. In some embodiments, said mutation or mutations may comprise the substitution D162N. In some embodiments, said mutation or mutations may comprise the deletion of residue D162.

In some embodiments, said mutation or mutations may comprise substitution of residue E264 of SEQ ID NO: 20 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E264 with aspartic acid, lysine, arginine, glutamine, histidine, valine, or alanine. In some embodiments, said mutation or mutations may comprise substitution of residue E264 with proline or glycine. In some embodiments, said mutation or mutations may comprise the substitution E264K. In some embodiments, said mutation or mutations may comprise the substitution E264R. In some embodiments, said mutation or mutations may comprise the deletion of residue E264.

In some embodiments, said mutation or mutations may comprise substitution of residue W285 of SEQ ID NO: 20 with any of the 19 other natural amino acids (i.e., I, M, P, F, G, A, V, L, H, E, R, K, D, N, Y, C, S, T, or Q) or with non-natural amino acids as are known to those of skill in the art. In some embodiments, said mutation or mutations may comprise substitution of residue W285 with phenylalanine, tyrosine, histidine, leucine, isoleucine, methionine, or valine. In some embodiments, said mutation or mutations may comprise substitution of residue W285 with proline or glycine. In some embodiments, said mutation or mutations may comprise the substitution W285F. In some embodiments, said mutation or mutations may comprise the deletion of residue W285.

In some embodiments, said mutation or mutations may comprise substitution of residue K291 of SEQ ID NO: 20 with any of the 19 other natural amino acids (i.e., W, I, M, P, F, G, A, V, L, H, E, R, D, N, Y, C, S, T, or Q) or with non-natural amino acids as are known to those of skill in the art. In some embodiments, said mutation or mutations may comprise substitution of residue K291 with proline, glycine, alanine, serine, valine, or threonine. In some embodiments, said mutation or mutations may comprise substitution of residue K291 with proline or glycine. In some embodiments, said mutation or mutations may comprise the substitution K291P. In some embodiments, said mutation or mutations may comprise the deletion of residue K291.

In some embodiments, said mutation or mutations may comprise substitution of residue T292 of SEQ ID NO: 20 with any of the 19 other natural amino acids (i.e., W, I, M, P, F, G, A, V, L, H, E, R, K, D, N, Y, C, S, or Q) or with non-natural amino acids as are known to those of skill in the art. In some embodiments, said mutation or mutations may comprise substitution of residue T292 with proline, glycine, alanine, serine, valine, or threonine. In some embodiments, said mutation or mutations may comprise substitution of residue T292 with proline or glycine. In some embodiments, said mutation or mutations may comprise the substitution T292P. In some embodiments, said mutation or mutations may comprise the deletion of residue T292.

In some embodiments, said mutation or mutations may comprise insertion of one or more residues between residues K291 and T292 of SEQ ID NO: 20 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of proline, glycine, alanine, serine, valine, glutamic acid, aspartic acid, and/or threonine. In some embodiments, said mutation or mutations may comprise insertion of proline or glycine. In some embodiments, said mutation or mutations may comprise insertion of a proline between residues K291 and T292.

In some embodiments, said mutation or mutations may comprise substitution of residue P408 of SEQ ID NO: 20 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P408 with aspartic acid, lysine, arginine, glutamic acid, glutamine, histidine, valine, or alanine. In some embodiments, said mutation or mutations may comprise substitution of residue P408 with proline or glycine. In some embodiments, said mutation or mutations may comprise the substitution P408K. In some embodiments, said mutation or mutations may comprise the deletion of residue P408.

In some embodiments, said mutation or mutations may comprise substitution of residue A409 of SEQ ID NO: 20 with any of the 19 other natural amino acids (i.e., W, I, M, P, F, G, V, L, H, E, R, K, D, N, Y, C, S, T, or Q) or with non-natural amino acids as are known to those of skill in the art. In some embodiments, said mutation or mutations may comprise substitution of residue A409 with aspartic acid, lysine, arginine, glutamic acid, glutamine, histidine, valine, or alanine. In some embodiments, said mutation or mutations may comprise substitution of residue A409 with proline or glycine. In some embodiments, said mutation or mutations may comprise the substitution A409K. In some embodiments, said mutation or mutations may comprise the deletion of residue A409.

In some embodiments, said mutation or mutations may comprise insertion of one or more residues between residues P408 and A409 of SEQ ID NO: 20 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of aspartic acid, lysine, arginine, glutamic acid, glutamine, histidine, tryptophan, leucine, valine, and/or alanine. In some embodiments, said mutation or mutations may comprise insertion of proline or glycine. In some embodiments, said mutation or mutations may comprise insertion of a lysine between residues P408 and A409 of SEQ ID NO: 20.

In some embodiments, the mutation or mutations according to the methods and compositions of the present disclosure may comprise any 1, 2, 3, 4, 5, 6, 7, 8, 9, 10, 11, or 12 of E42K, D77A, Y78A, E86A, L108P, D162N, E264K, E264R, W285F, K291P, T292P, P408K, and/or P409K, of SEQ ID NO: 20 or any subset or combination thereof, or any homolog or ortholog thereof.

In some embodiments, said mutation or mutations may comprise one or more substitutions, deletions, or insertions at, or at a position or location surrounding, positions 47, 83, 84, 92, 114, 175, 277, 288, 324, 325, 421, and/or 422 of SEQ ID NO: 21, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue E47 of SEQ ID NO: 21 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E47 with aspartic acid, lysine, glutamine, arginine, histidine, valine, or alanine. In some embodiments, said mutation or mutations may comprise substitution of residue E47 with proline or glycine. In some embodiments, said mutation or mutations may comprise the substitution E47K. In some embodiments, said mutation or mutations may comprise the deletion of residue E47.

In some embodiments, said mutation or mutations may comprise substitution of residue D83 of SEQ ID NO: 21 with any of the 19 other natural amino acids (i.e., W, I, M, P, F, G, A, V, L, H, E, R, K, N, Y, C, S, T, or Q) or with non-natural amino acids as are known to those of skill in the art. In some embodiments, said mutation or mutations may comprise substitution of residue D83 with glutamic acid, asparagine, glutamine, valine, alanine, serine, or threonine. In some embodiments, said mutation or mutations may comprise substitution of residue D83 with proline or glycine. In some embodiments, said mutation or mutations may comprise the substitution D83A. In some embodiments, said mutation or mutations may comprise the deletion of residue D83.

In some embodiments, said mutation or mutations may comprise substitution of residue Y84 of SEQ ID NO: 21 with any of the 19 other natural amino acids (i.e., W, I, M, P, F, G, A, V, L, H, E, R, K, D, N, C, S, T, or Q) or with non-natural amino acids as are known to those of skill in the art. In some embodiments, said mutation or mutations may comprise substitution of residue Y84 with glutamic acid, asparagine, glutamine, valine, alanine, serine, or threonine. In some embodiments, said mutation or mutations may comprise substitution of residue Y84 with proline or glycine. In some embodiments, said mutation or mutations may comprise the substitution Y84A. In some embodiments, said mutation or mutations may comprise the deletion of residue Y84.

In some embodiments, said mutation or mutations may comprise insertion of one or more residues between residues D83 and Y84 of SEQ ID NO: 21 with any of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of glutamic acid, asparagine, glutamine, valine, alanine, serine, and/or threonine. In some embodiments, said mutation or mutations may comprise insertion of proline or glycine. In some embodiments, said mutation or mutations may comprise insertion of an alanine between residues D83 and Y84.

In some embodiments, said mutation or mutations may comprise substitution of residue E92 of SEQ ID NO: 21 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E92 with aspartic acid, asparagine, glutamine, valine, alanine, serine, or threonine. In some embodiments, said mutation or mutations may comprise substitution of residue E92 with proline or glycine. In some embodiments, said mutation or mutations may comprise the substitution E92A. In some embodiments, said mutation or mutations may comprise the deletion of residue E92.

In some embodiments, said mutation or mutations may comprise substitution of residue L114 of SEQ ID NO: 21 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue L114 with proline, glycine, alanine, serine, valine, or threonine. In some embodiments, said mutation or mutations may comprise substitution of residue L114 with proline or glycine. In some embodiments, said mutation or mutations may comprise the substitution L114P. In some embodiments, said mutation or mutations may comprise the deletion of residue L114.

In some embodiments, said mutation or mutations may comprise substitution of residue D175 of SEQ ID NO: 21 with any of the 19 other natural amino acids (i.e., W, I, M, P, F, G, A, V, L, H, E, R, K, N, Y, C, S, T, or Q) or with non-natural amino acids as are known to those of skill in the art. In some embodiments, said mutation or mutations may comprise substitution of residue D175 with asparagine, glutamic acid, glutamine, serine, threonine, or valine. In some embodiments, said mutation or mutations may comprise substitution of residue D175 with proline or glycine. In some embodiments, said mutation or mutations may comprise the substitution D175N. In some embodiments, said mutation or mutations may comprise the deletion of residue D175.

In some embodiments, said mutation or mutations may comprise substitution of residue E277 of SEQ ID NO: 21 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E277 with aspartic acid, lysine, arginine, glutamine, histidine, valine, or alanine. In some embodiments, said mutation or mutations may comprise substitution of residue E277 with proline or glycine. In some embodiments, said mutation or mutations may comprise the substitution E277K. In some embodiments, said mutation or mutations may comprise the substitution E277R. In some embodiments, said mutation or mutations may comprise the deletion of residue E277.

In some embodiments, said mutation or mutations may comprise substitution of residue W288 of SEQ ID NO: 21 with any of the 19 other natural amino acids (i.e., I, M, P, F, G, A, V, L, H, E, R, K, D, N, Y, C, S, T, or Q) or with non-natural amino acids as are known to those of skill in the art. In some embodiments, said mutation or mutations may comprise substitution of residue W288 with phenylalanine, tyrosine, histidine, leucine, isoleucine, methionine, or valine. In some embodiments, said mutation or mutations may comprise substitution of residue W288 with proline or glycine. In some embodiments, said mutation or mutations may comprise the substitution W288F. In some embodiments, said mutation or mutations may comprise the deletion of residue W288.

In some embodiments, said mutation or mutations may comprise substitution of residue K324 of SEQ ID NO: 21 with any of the 19 other natural amino acids (i.e., W, I, M, P, F, G, A, V, L, H, E, R, D, N, Y, C, S, T, or Q) or with non-natural amino acids as are known to those of skill in the art. In some embodiments, said mutation or mutations may comprise substitution of residue K324 with proline, glycine, alanine, serine, valine, or threonine. In some embodiments, said mutation or mutations may comprise substitution of residue K324 with proline or glycine. In some embodiments, said mutation or mutations may comprise the substitution K324P. In some embodiments, said mutation or mutations may comprise the deletion of residue K324.

In some embodiments, said mutation or mutations may comprise substitution of residue T325 of SEQ ID NO: 21 with any of the 19 other natural amino acids (i.e., W, I, M, P, F, G, A, V, L, H, E, R, K, D, N, Y, C, S, or Q) or with non-natural amino acids as are known to those of skill in the art. In some embodiments, said mutation or mutations may comprise substitution of residue T325 with proline, glycine, alanine, serine, valine, or threonine. In some embodiments, said mutation or mutations may comprise substitution of residue T325 with proline or glycine. In some embodiments, said mutation or mutations may comprise the substitution T325P. In some embodiments, said mutation or mutations may comprise the deletion of residue T325.

In some embodiments, said mutation or mutations may comprise insertion of one or more residues between residues K324 and T325 of SEQ ID NO: 21 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of proline, glycine, alanine, serine, valine, glutamic acid, aspartic acid, and/or threonine. In some embodiments, said mutation or mutations may comprise insertion of proline or glycine. In some embodiments, said mutation or mutations may comprise insertion of a proline between residues K324 and T325.

In some embodiments, said mutation or mutations may comprise substitution of residue P421 of SEQ ID NO: 21 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P421 with aspartic acid, lysine, arginine, glutamic acid, glutamine, histidine, valine, or alanine. In some embodiments, said mutation or mutations may comprise substitution of residue P421 with glycine. In some embodiments, said mutation or mutations may comprise the substitution P421K. In some embodiments, said mutation or mutations may comprise the deletion of residue P421.

In some embodiments, said mutation or mutations may comprise substitution of residue A422 of SEQ ID NO: 21 with any of the 19 other natural amino acids (i.e., W, I, M, P, F, G, V, L, H, E, R, K, D, N, Y, C, S, T, or Q) or with non-natural amino acids as are known to those of skill in the art. In some embodiments, said mutation or mutations may comprise substitution of residue A422 with aspartic acid, lysine, arginine, glutamic acid, glutamine, histidine, valine, or alanine. In some embodiments, said mutation or mutations may comprise substitution of residue A422 with proline or glycine. In some embodiments, said mutation or mutations may comprise the substitution A422K. In some embodiments, said mutation or mutations may comprise the deletion of residue A422.

In some embodiments, said mutation or mutations may comprise insertion of one or more residues between residues P421 and A422 of SEQ ID NO: 21 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of aspartic acid, lysine, arginine, glutamic acid, glutamine, histidine, tryptophan, leucine, valine, and/or alanine. In some embodiments, said mutation or mutations may comprise insertion of proline or glycine. In some embodiments, said mutation or mutations may comprise insertion of a lysine between residues P421 and A422 of SEQ ID NO: 21.

In some embodiments, the mutation or mutations according to the methods and compositions of the present disclosure may comprise any 1, 2, 3, 4, 5, 6, 7, 8, 9, 10, 11, 12, or 13 of E47K, D83A, Y84A, E92A, L114P, D175N, E277K, E277R, W288F, K324P, T325P, P421K, and/or A422K, of SEQ ID NO: 21 or any subset or combination thereof, or any homolog or ortholog thereof.

In some embodiments, said mutation or mutations may comprise one or more substitutions, deletions, or insertions at, or at a position or location surrounding, positions 10, 50, 59, 78 139, 296, 390, 391, 418, 701, 702, 791, 866, 868, and/or 870 of SEQ ID NO: 22, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue E10 of SEQ ID NO: 22 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E10 with aspartic acid, lysine, glutamine, arginine, histidine, valine, or alanine. In some embodiments, said mutation or mutations may comprise substitution of residue E10 with proline or glycine. In some embodiments, said mutation or mutations may comprise the substitution E10K. In some embodiments, said mutation or mutations may comprise the deletion of residue E10.

In some embodiments, said mutation or mutations may comprise substitution of residue K50 of SEQ ID NO: 22 with any of the 19 other natural amino acids (i.e., W, I, M, P, F, G, A, V, L, H, E, R, D, N, Y, C, S, T, or Q) or with non-natural amino acids as are known to those of skill in the art. In some embodiments, said mutation or mutations may comprise substitution of residue K50 with glutamic acid, asparagine, glutamine, valine, alanine, serine, or threonine. In some embodiments, said mutation or mutations may comprise substitution of residue K50 with proline or glycine. In some embodiments, said mutation or mutations may comprise the substitution K50A. In some embodiments, said mutation or mutations may comprise the deletion of residue K50.

In some embodiments, said mutation or mutations may comprise substitution of residue E59 of SEQ ID NO: 22 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E59 with aspartic acid, asparagine, glutamine, valine, alanine, serine, or threonine. In some embodiments, said mutation or mutations may comprise substitution of residue E59 with proline or glycine. In some embodiments, said mutation or mutations may comprise the substitution E59A. In some embodiments, said mutation or mutations may comprise the deletion of residue E59.

In some embodiments, said mutation or mutations may comprise substitution of residue L78 of SEQ ID NO: 22 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue L78 with proline, glycine, alanine, serine, valine, or threonine. In some embodiments, said mutation or mutations may comprise substitution of residue L78 with proline or glycine. In some embodiments, said mutation or mutations may comprise the substitution L78P. In some embodiments, said mutation or mutations may comprise the deletion of residue L78.

In some embodiments, said mutation or mutations may comprise substitution of residue Q139 of SEQ ID NO: 22 with any of the 19 other natural amino acids (i.e., W, I, M, P, F, G, A, V, L, H, E, R, K, N, Y, C, S, T, or D) or with non-natural amino acids as are known to those of skill in the art. In some embodiments, said mutation or mutations may comprise substitution of residue Q139 with asparagine, glutamic acid, glutamine, serine, threonine, or valine. In some embodiments, said mutation or mutations may comprise substitution of residue Q139 with proline or glycine. In some embodiments, said mutation or mutations may comprise the substitution Q139N. In some embodiments, said mutation or mutations may comprise the deletion of residue Q139.

In some embodiments, said mutation or mutations may comprise substitution of residue Y296 of SEQ ID NO: 22 with any of the 19 other natural amino acids (i.e., W, I, M, P, F, G, A, V, L, H, E, R, K, D, N, C, S, T, or Q) or with non-natural amino acids as are known to those of skill in the art. In some embodiments, said mutation or mutations may comprise substitution of residue Y296 with aspartic acid, lysine, arginine, glutamine, histidine, valine, or alanine. In some embodiments, said mutation or mutations may comprise substitution of residue Y296 with proline or glycine. In some embodiments, said mutation or mutations may comprise the substitution Y296K. In some embodiments, said mutation or mutations may comprise the substitution Y296R. In some embodiments, said mutation or mutations may comprise the deletion of residue Y296.

In some embodiments, said mutation or mutations may comprise substitution of residue P390 of SEQ ID NO: 22 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P390 with phenylalanine, tyrosine, histidine, leucine, isoleucine, methionine, or valine. In some embodiments, said mutation or mutations may comprise substitution of residue P390 with glycine. In some embodiments, said mutation or mutations may comprise the substitution P390F. In some embodiments, said mutation or mutations may comprise the deletion of residue P390.

In some embodiments, said mutation or mutations may comprise substitution of residue P391 of SEQ ID NO: 22 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P391 with phenylalanine, tyrosine, histidine, leucine, isoleucine, methionine, or valine. In some embodiments, said mutation or mutations may comprise substitution of residue P391 with glycine. In some embodiments, said mutation or mutations may comprise the substitution P391F. In some embodiments, said mutation or mutations may comprise the deletion of residue P391.

In some embodiments, said mutation or mutations may comprise insertion of one or more residues between residues P390 and P391 of SEQ ID NO: 22 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of tryptophan, phenylalanine, tyrosine, histidine, leucine, isoleucine, serine, asparagine, methionine, and/or valine. In some embodiments, said mutation or mutations may comprise insertion of proline or glycine. In some embodiments, said mutation or mutations may comprise insertion of a phenylalanine between residues P390 and P391. In some embodiments, said mutation or mutations may comprise insertion of a tryptophan between residues P390 and P391.

In some embodiments, said mutation or mutations may comprise substitution of residue A418 of SEQ ID NO: 22 with any of the 19 other natural amino acids (i.e., W, I, M, P, F, G, V, L, H, E, R, K, D, N, Y, C, S, T, or Q) or with non-natural amino acids as are known to those of skill in the art. In some embodiments, said mutation or mutations may comprise substitution of residue A418 with proline, glycine, alanine, serine, valine, or threonine. In some embodiments, said mutation or mutations may comprise substitution of residue A418 with proline or glycine. In some embodiments, said mutation or mutations may comprise the substitution A418P. In some embodiments, said mutation or mutations may comprise the deletion of residue A418.

In some embodiments, said mutation or mutations may comprise substitution of residue L701 of SEQ ID NO: 22 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue L701 with aspartic acid, lysine, arginine, glutamic acid, glutamine, histidine, valine, or alanine. In some embodiments, said mutation or mutations may comprise substitution of residue L701 with proline or glycine. In some embodiments, said mutation or mutations may comprise the substitution L701K. In some embodiments, said mutation or mutations may comprise the deletion of residue L701.

In some embodiments, said mutation or mutations may comprise substitution of residue D702 of SEQ ID NO: 22 with any of the 19 other natural amino acids (i.e., W, I, M, P, F, G, A, V, H, E, R, K, L, N, Y, C, S, T, or Q) or with non-natural amino acids as are known to those of skill in the art. In some embodiments, said mutation or mutations may comprise substitution of residue D702 with lysine, arginine, glutamic acid, glutamine, histidine, valine, or alanine. In some embodiments, said mutation or mutations may comprise substitution of residue D702 with proline or glycine. In some embodiments, said mutation or mutations may comprise the substitution D702K. In some embodiments, said mutation or mutations may comprise the deletion of residue D702.

In some embodiments, said mutation or mutations may comprise insertion of one or more residues between residues L701 and D702 of SEQ ID NO: 22 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of tryptophan, phenylalanine, tyrosine, histidine, leucine, isoleucine, serine, asparagine, methionine, and/or valine. In some embodiments, said mutation or mutations may comprise insertion of proline or glycine. In some embodiments, said mutation or mutations may comprise insertion of a lysine between residues L701 and D702.

In some embodiments, said mutation or mutations may comprise substitution of residue N791 of SEQ ID NO: 22 with any of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said mutation or mutations may comprise substitution of residue N791 with glutamic acid, asparagine, glutamine, valine, alanine, serine, or threonine. In some embodiments, said mutation or mutations may comprise substitution of residue N791 with proline or glycine. In some embodiments, said mutation or mutations may comprise the substitution N791A. In some embodiments, said mutation or mutations may comprise the deletion of residue N791.

In some embodiments, said mutation or mutations may comprise substitution of residue K866 of SEQ ID NO: 22 with any of the 19 other natural amino acids (i.e., W, I, M, P, F, G, A, V, H, E, R, L, D, N, Y, C, S, T, or Q) or with non-natural amino acids as are known to those of skill in the art. In some embodiments, said mutation or mutations may comprise substitution of residue K866 with phenylalanine, tyrosine, histidine, tryptophan, isoleucine, methionine, or valine. In some embodiments, said mutation or mutations may comprise substitution of residue K866 with proline or glycine. In some embodiments, said mutation or mutations may comprise the substitution K866W. In some embodiments, said mutation or mutations may comprise the deletion of residue K866.

In some embodiments, said mutation or mutations may comprise substitution of residue E868 of SEQ ID NO: 22 with any of the 19 other natural amino acids (i.e., W, I, M, P, F, G, A, V, H, L, R, K, D, N, Y, C, S, T, or Q) or with non-natural amino acids as are known to those of skill in the art. In some embodiments, said mutation or mutations may comprise substitution of residue E868 with phenylalanine, tyrosine, histidine, tryptophan, isoleucine, methionine, or valine. In some embodiments, said mutation or mutations may comprise substitution of residue E868 with proline or glycine. In some embodiments, said mutation or mutations may comprise the substitution E868W. In some embodiments, said mutation or mutations may comprise the deletion of residue E868.

In some embodiments, said mutation or mutations may comprise substitution of residue T870 of SEQ ID NO: 22 with any of the 19 other natural amino acids (i.e., W, I, M, P, F, G, A, V, L, H, R, K, D, N, Y, C, S, E, or Q) or with non-natural amino acids as are known to those of skill in the art. In some embodiments, said mutation or mutations may comprise substitution of residue T870 with aspartic acid, lysine, arginine, glutamine, histidine, valine, or alanine. In some embodiments, said mutation or mutations may comprise substitution of residue T870 with proline or glycine. In some embodiments, said mutation or mutations may comprise the substitution T870K. In some embodiments, said mutation or mutations may comprise the deletion of residue T870 of SEQ ID NO: 22.

In some embodiments, the mutation or mutations according to the methods and compositions of the present disclosure may comprise any 1, 2, 3, 4, 5, 6, 7, 8, 9, 10, 11, 12, 13, 14, 15, or 16 of E10K, K50A, E59A, L87P, Q139N, Y296K, Y296R, P390F, P391F, A418P, L701K, D702K, N791A, K866W, E868W and/or T870K, of SEQ ID NO: 22 or any subset or combination thereof, or any homolog or ortholog thereof.

In some embodiments, said mutation or mutations may comprise one or more substitutions, deletions, or insertions at, or at a position or location surrounding, positions 27, 65, 66, 73, 94, 146, 303, 392, 419, 704, 705, 795, 868, and/or 872 of SEQ ID NO: 23, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue E27 of SEQ ID NO: 23 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E27 with aspartic acid, lysine, glutamine, arginine, histidine, valine, or alanine. In some embodiments, said mutation or mutations may comprise substitution of residue E27 with proline or glycine. In some embodiments, said mutation or mutations may comprise the substitution E27K. In some embodiments, said mutation or mutations may comprise the deletion of residue E27.

In some embodiments, said mutation or mutations may comprise substitution of residue D65 of SEQ ID NO: 23 with any of the 19 other natural amino acids (i.e., W, I, M, P, F, G, A, V, L, H, E, R, K, N, Y, C, S, T, or Q) or with non-natural amino acids as are known to those of skill in the art. In some embodiments, said mutation or mutations may comprise substitution of residue D65 with glutamic acid, asparagine, glutamine, valine, alanine, serine, or threonine. In some embodiments, said mutation or mutations may comprise substitution of residue D65 with proline or glycine. In some embodiments, said mutation or mutations may comprise the substitution D65A. In some embodiments, said mutation or mutations may comprise the deletion of residue D65.

In some embodiments, said mutation or mutations may comprise substitution of residue R66 of SEQ ID NO: 23 with any of the 19 other natural amino acids (i.e., W, I, M, P, F, G, A, V, L, H, E, K, D, N, Y, C, S, T, or Q) or with non-natural amino acids as are known to those of skill in the art. In some embodiments, said mutation or mutations may comprise substitution of residue R66 with glutamic acid, asparagine, glutamine, valine, alanine, serine, or threonine. In some embodiments, said mutation or mutations may comprise substitution of residue R66 with proline or glycine. In some embodiments, said mutation or mutations may comprise the substitution R66A. In some embodiments, said mutation or mutations may comprise the deletion of residue R66.

In some embodiments, said mutation or mutations may comprise insertion of one or more residues between residues D65 and R66 of SEQ ID NO: 23 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of lysine, arginine, tryptophan, glutamic acid, asparagine, glutamine, valine, alanine, serine, and/or threonine. In some embodiments, said mutation or mutations may comprise insertion of proline or glycine. In some embodiments, said mutation or mutations may comprise insertion of an alanine between residues D65 and R66.

In some embodiments, said mutation or mutations may comprise substitution of residue E73 of SEQ ID NO: 23 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E73 with aspartic acid, asparagine, glutamine, valine, alanine, serine, or threonine. In some embodiments, said mutation or mutations may comprise substitution of residue E73 with proline or glycine. In some embodiments, said mutation or mutations may comprise the substitution E73A. In some embodiments, said mutation or mutations may comprise the deletion of residue E73.

In some embodiments, said mutation or mutations may comprise substitution of residue L94 of SEQ ID NO: 23 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue L94 with proline, glycine, alanine, serine, valine, or threonine. In some embodiments, said mutation or mutations may comprise substitution of residue L94 with proline or glycine. In some embodiments, said mutation or mutations may comprise the substitution L94P. In some embodiments, said mutation or mutations may comprise the deletion of residue L94.

In some embodiments, said mutation or mutations may comprise substitution of residue Q146 of SEQ ID NO: 23 with any of the 19 other natural amino acids (i.e., W, I, M, P, F, G, A, V, L, H, E, R, K, N, Y, C, S, T, or D) or with non-natural amino acids as are known to those of skill in the art. In some embodiments, said mutation or mutations may comprise substitution of residue Q146 with asparagine, glutamic acid, glutamine, serine, threonine, or valine. In some embodiments, said mutation or mutations may comprise substitution of residue Q146 with proline or glycine. In some embodiments, said mutation or mutations may comprise the substitution Q146N. In some embodiments, said mutation or mutations may comprise the deletion of residue Q146.

In some embodiments, said mutation or mutations may comprise substitution of residue Y303 of SEQ ID NO: 23 with any of the 19 other natural amino acids (i.e., W, I, M, P, F, G, A, V, L, H, R, K, D, N, E, C, S, T, or Q) or with non-natural amino acids as are known to those of skill in the art. In some embodiments, said mutation or mutations may comprise substitution of residue Y303 with aspartic acid, lysine, arginine, glutamine, histidine, valine, or alanine. In some embodiments, said mutation or mutations may comprise substitution of residue Y303 with proline or glycine. In some embodiments, said mutation or mutations may comprise the substitution Y303K. In some embodiments, said mutation or mutations may comprise the substitution Y303R. In some embodiments, said mutation or mutations may comprise the deletion of residue Y303.

In some embodiments, said mutation or mutations may comprise substitution of residue W392 of SEQ ID NO: 23 with any of the 19 other natural amino acids (i.e., I, M, P, F, G, A, V, L, H, E, R, K, D, N, Y, C, S, T, or Q) or with non-natural amino acids as are known to those of skill in the art. In some embodiments, said mutation or mutations may comprise substitution of residue W392 with phenylalanine, tyrosine, histidine, leucine, isoleucine, methionine, or valine. In some embodiments, said mutation or mutations may comprise substitution of residue W392 with proline or glycine. In some embodiments, said mutation or mutations may comprise the substitution W392F. In some embodiments, said mutation or mutations may comprise the deletion of residue W392.

In some embodiments, said mutation or mutations may comprise substitution of residue A419 of SEQ ID NO: 23 with any of the 19 other natural amino acids (i.e., W, I, M, P, F, G, T, V, L, H, E, R, K, D, N, Y, C, S, or Q) or with non-natural amino acids as are known to those of skill in the art. In some embodiments, said mutation or mutations may comprise substitution of residue A419 with proline, glycine, serine, valine, or threonine. In some embodiments, said mutation or mutations may comprise substitution of residue A419 with proline or glycine. In some embodiments, said mutation or mutations may comprise the substitution A419P. In some embodiments, said mutation or mutations may comprise the deletion of residue A419.

In some embodiments, said mutation or mutations may comprise substitution of residue V704 of SEQ ID NO: 23 with any of the 19 other natural amino acids (i.e., W, I, M, P, F, G, A, L, H, E, R, K, D, Y, C, S, T, or Q) or with non-natural amino acids as are known to those of skill in the art. In some embodiments, said mutation or mutations may comprise substitution of residue V704 with aspartic acid, lysine, arginine, glutamic acid, glutamine, histidine, valine, or alanine. In some embodiments, said mutation or mutations may comprise substitution of residue V704 with proline or glycine. In some embodiments, said mutation or mutations may comprise the substitution V704K. In some embodiments, said mutation or mutations may comprise the deletion of residue V704.

In some embodiments, said mutation or mutations may comprise substitution of residue I705 of SEQ ID NO: 23 with any of the 19 other natural amino acids (i.e., W, I, M, P, F, G, A, V, L, H, E, R, K, D, Y, C, S, T, or Q) or with non-natural amino acids as are known to those of skill in the art. In some embodiments, said mutation or mutations may comprise substitution of residue I705 with aspartic acid, lysine, arginine, glutamic acid, glutamine, histidine, valine, or alanine. In some embodiments, said mutation or mutations may comprise substitution of residue I705 with proline or glycine. In some embodiments, said mutation or mutations may comprise the substitution I705K. In some embodiments, said mutation or mutations may comprise the deletion of residue I705.

In some embodiments, said mutation or mutations may comprise insertion of one or more residues between residues V704 and I705 of SEQ ID NO: 23 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of tryptophan, leucine, serine, aspartic acid, lysine, arginine, glutamic acid, glutamine, histidine, valine, and/or alanine. In some embodiments, said mutation or mutations may comprise insertion of proline or glycine. In some embodiments, said mutation or mutations may comprise insertion of an alanine between residues V704 and I705.

In some embodiments, said mutation or mutations may comprise substitution of residue K795 of SEQ ID NO: 23 with any of the 19 other natural amino acids (i.e., W, I, M, P, F, G, A, V, L, H, E, R, D, D, N, Y, C, S, T, or Q) or with non-natural amino acids as are known to those of skill in the art. In some embodiments, said mutation or mutations may comprise substitution of residue K795 with glutamic acid, asparagine, glutamine, valine, alanine, serine, or threonine. In some embodiments, said mutation or mutations may comprise substitution of residue K795 with proline or glycine. In some embodiments, said mutation or mutations may comprise the substitution K795A. In some embodiments, said mutation or mutations may comprise the deletion of residue K795.

In some embodiments, said mutation or mutations may comprise substitution of residue T868 of SEQ ID NO: 23 with any of the 19 other natural amino acids (i.e., W, I, M, P, F, G, A, V, H, E, R, K, D, N, Y, C, S, L, or Q) or with non-natural amino acids as are known to those of skill in the art. In some embodiments, said mutation or mutations may comprise substitution of residue T868 with phenylalanine, tyrosine, histidine, tryptophan, isoleucine, methionine, or valine. In some embodiments, said mutation or mutations may comprise substitution of residue T868 with proline or glycine. In some embodiments, said mutation or mutations may comprise the substitution T868W. In some embodiments, said mutation or mutations may comprise the deletion of residue T868.

In some embodiments, said mutation or mutations may comprise substitution of residue E872 of SEQ ID NO: 23 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E872 with aspartic acid, lysine, arginine, glutamine, histidine, valine, or alanine. In some embodiments, said mutation or mutations may comprise substitution of residue E872 with proline or glycine. In some embodiments, said mutation or mutations may comprise the substitution E872K. In some embodiments, said mutation or mutations may comprise the deletion of residue E872 of SEQ ID NO: 23.

In some embodiments, the mutation or mutations according to the methods and compositions of the present disclosure may comprise any 1, 2, 3, 4, 5, 6, 7, 8, 9, 10, 11, 12, 13, 14, or 15 of E27K, D65A, R66A, E73A, L94P, Q146N, Y303K, Y303R, W392F, A419P, V704K, I705K, K795A, T868W, and/or E872K of SEQ ID NO: 23 or any subset or combination thereof, or any homolog or ortholog thereof.

In some embodiments, said mutation or mutations may comprise one or more substitutions, deletions, or insertions at, or at a position or location surrounding, positions 29, 70, 79, 100, 161, 318, 410, 443, 437, and/or 478 of SEQ ID NO: 24, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue E29 of SEQ ID NO: 24 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E29 with aspartic acid, lysine, glutamine, arginine, histidine, valine, or alanine. In some embodiments, said mutation or mutations may comprise substitution of residue E29 with proline or glycine. In some embodiments, said mutation or mutations may comprise the substitution E29K. In some embodiments, said mutation or mutations may comprise the deletion of residue E29.

In some embodiments, said mutation or mutations may comprise substitution of residue K70 of SEQ ID NO: 24 with any of the 19 other natural amino acids (i.e., W, I, M, P, F, G, A, V, L, H, E, R, D, N, Y, C, S, T, or Q) or with non-natural amino acids as are known to those of skill in the art. In some embodiments, said mutation or mutations may comprise substitution of residue K70 with glutamic acid, asparagine, glutamine, valine, alanine, serine, or threonine. In some embodiments, said mutation or mutations may comprise substitution of residue K70 with proline or glycine. In some embodiments, said mutation or mutations may comprise the substitution K70A. In some embodiments, said mutation or mutations may comprise the deletion of residue K70.

In some embodiments, said mutation or mutations may comprise substitution of residue E79 of SEQ ID NO: 24 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E79 with aspartic acid, asparagine, glutamine, valine, alanine, serine, or threonine. In some embodiments, said mutation or mutations may comprise substitution of residue E79 with proline or glycine. In some embodiments, said mutation or mutations may comprise the substitution E79A. In some embodiments, said mutation or mutations may comprise the deletion of residue E79.

In some embodiments, said mutation or mutations may comprise substitution of residue L100 of SEQ ID NO: 24 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue L100 with proline, glycine, alanine, serine, valine, or threonine. In some embodiments, said mutation or mutations may comprise substitution of residue L100 with proline or glycine. In some embodiments, said mutation or mutations may comprise the substitution L100P. In some embodiments, said mutation or mutations may comprise the deletion of residue L100.

In some embodiments, said mutation or mutations may comprise substitution of residue Q161 of SEQ ID NO: 24 with any of the 19 other natural amino acids (i.e., W, I, M, P, F, G, A, V, L, H, E, R, K, N, Y, C, S, T, or D) or with non-natural amino acids as are known to those of skill in the art. In some embodiments, said mutation or mutations may comprise substitution of residue Q161 with asparagine, glutamic acid, glutamine, serine, threonine, or valine. In some embodiments, said mutation or mutations may comprise substitution of residue Q161 with proline or glycine. In some embodiments, said mutation or mutations may comprise the substitution Q161N. In some embodiments, said mutation or mutations may comprise the deletion of residue Q161.

In some embodiments, said mutation or mutations may comprise substitution of residue Y318 of SEQ ID NO: 24 with any of the 19 other natural amino acids (i.e., W, I, M, P, F, G, A, V, L, H, R, K, D, N, E C, S, T, or Q) or with non-natural amino acids as are known to those of skill in the art. In some embodiments, said mutation or mutations may comprise substitution of residue Y318 with aspartic acid, lysine, arginine, glutamine, histidine, valine, or alanine. In some embodiments, said mutation or mutations may comprise substitution of residue Y318 with proline or glycine. In some embodiments, said mutation or mutations may comprise the substitution Y318K. In some embodiments, said mutation or mutations may comprise the substitution Y318R. In some embodiments, said mutation or mutations may comprise the deletion of residue Y318.

In some embodiments, said mutation or mutations may comprise substitution of residue W410 of SEQ ID NO: 24 with any of the 19 other natural amino acids (i.e., I, M, P, F, G, A, V, L, H, E, R, K, D, N, Y, C, S, T, or Q) or with non-natural amino acids as are known to those of skill in the art. In some embodiments, said mutation or mutations may comprise substitution of residue W410 with phenylalanine, tyrosine, histidine, leucine, isoleucine, methionine, or valine. In some embodiments, said mutation or mutations may comprise substitution of residue W410 with proline or glycine. In some embodiments, said mutation or mutations may comprise the substitution W410F. In some embodiments, said mutation or mutations may comprise the deletion of residue W410.

In some embodiments, said mutation or mutations may comprise substitution of residue A437 of SEQ ID NO: 24 with any of the 19 other natural amino acids (i.e., W, I, M, P, F, G, A, V, L, H, E, R, K, D, N, Y, C, S, or Q) or with non-natural amino acids as are known to those of skill in the art. In some embodiments, said mutation or mutations may comprise substitution of residue A437 with proline, glycine, alanine, serine, valine, or threonine. In some embodiments, said mutation or mutations may comprise substitution of residue A437 with proline or glycine. In some embodiments, said mutation or mutations may comprise the substitution A437P. In some embodiments, said mutation or mutations may comprise the deletion of residue A437.

In some embodiments, said mutation or mutations may comprise substitution of any of residues 355-361 of SEQ ID NO: 24 with any of the 19 other natural amino acids (i.e., W, I, M, P, F, G, A, V, L, H, E, R, K, D, Y, C, S, T, or Q) or with non-natural amino acids as are known to those of skill in the art.

In some embodiments, said mutation or mutations may comprise substitution of residue K65 of SEQ ID NO: 24 with any of the 19 other natural amino acids (i.e., W, I, M, P, F, G, A, V, L, H, E, R, D, N, Y, C, S, T, or Q) or with non-natural amino acids as are known to those of skill in the art. In some embodiments, said mutation or mutations may comprise substitution of residue K65 with aspartic acid, lysine, arginine, glutamine, histidine, valine, or alanine. In some embodiments, said mutation or mutations may comprise substitution of residue K65 with proline or glycine. In some embodiments, said mutation or mutations may comprise the substitution K65R. In some embodiments, said mutation or mutations may comprise the deletion of residue K65.

In some embodiments, said mutation or mutations may comprise substitution of residue V75 of SEQ ID NO: 24 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue V75 with phenylalanine, tryptophan, tyrosine, histidine, leucine, isoleucine, methionine, or valine. In some embodiments, said mutation or mutations may comprise substitution of residue V75 with proline or glycine. In some embodiments, said mutation or mutations may comprise the substitution V75I. In some embodiments, said mutation or mutations may comprise the deletion of residue V75. In some embodiments, said mutation or mutations comprise the combination of K65R and V75I.

In some embodiments, said mutation or mutations may comprise substitution of residue D443 of SEQ ID NO: 24 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue D443 with aspartic acid, asparagine, glutamic acid, glutamine, serine, threonine, or valine. In some embodiments, said mutation or mutations may comprise substitution of residue D443 with proline or glycine. In some embodiments, said mutation or mutations may comprise the substitution D443N. In some embodiments, said mutation or mutations may comprise the deletion of residue D443.

In some embodiments, said mutation or mutations may comprise substitution of residue E478 of SEQ ID NO: 24 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E478 with aspartic acid, asparagine, glutamic acid, glutamine, serine, threonine, or valine. In some embodiments, said mutation or mutations may comprise substitution of residue E478 with proline or glycine. In some embodiments, said mutation or mutations may comprise the substitution E478Q. In some embodiments, said mutation or mutations may comprise the deletion of residue E478 of SEQ ID NO: 24.

In some embodiments, the mutation or mutations according to the methods and compositions of the present disclosure may comprise any 1, 2, 3, 4, 5, 6, 7, 8, or 9 of E29K, K70A, E79A, L100P, Q161N, Y318K, Y318R, W410F, A437P, D443N, and/or E478Q of SEQ ID NO: 24 or any subset or combination thereof, or any homolog or ortholog thereof.

In some embodiments, said mutation or mutations may comprise one or more substitutions, deletions, or insertions at, or at a position or location surrounding, positions 31, 72, 81, 102, 163, 320, 412, 439, 730, 731, 828, 829, 832, 834, 900, and/or 904 of SEQ ID NO: 25, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue E31 of SEQ ID NO: 25 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E31 with aspartic acid, lysine, glutamine, arginine, histidine, valine, or alanine. In some embodiments, said mutation or mutations may comprise substitution of residue E31 with proline or glycine. In some embodiments, said mutation or mutations may comprise the substitution E31K. In some embodiments, said mutation or mutations may comprise the deletion of residue E31.

In some embodiments, said mutation or mutations may comprise substitution of residue K72 of SEQ ID NO: 25 with any of the 19 other natural amino acids (i.e., W, I, M, P, F, G, A, V, L, H, E, R, D, N, Y, C, S, T, or Q) or with non-natural amino acids as are known to those of skill in the art. In some embodiments, said mutation or mutations may comprise substitution of residue K72 with glutamic acid, asparagine, glutamine, valine, alanine, serine, or threonine. In some embodiments, said mutation or mutations may comprise substitution of residue K72 with proline or glycine. In some embodiments, said mutation or mutations may comprise the substitution K72A. In some embodiments, said mutation or mutations may comprise the deletion of residue K72.

In some embodiments, said mutation or mutations may comprise substitution of residue E81 of SEQ ID NO: 25 with any of the 19 other natural amino acids (i.e., W, I, M, P, F, G, A, V, L, H, R, K, D, N, Y, C, S, T, or Q) or with non-natural amino acids as are known to those of skill in the art. In some embodiments, said mutation or mutations may comprise substitution of residue E81 with aspartic acid, asparagine, glutamine, valine, alanine, serine, or threonine. In some embodiments, said mutation or mutations may comprise substitution of residue E81 with proline or glycine. In some embodiments, said mutation or mutations may comprise the substitution E81A. In some embodiments, said mutation or mutations may comprise the deletion of residue E81.

In some embodiments, said mutation or mutations may comprise substitution of residue L102 of SEQ ID NO: 25 with any of the 19 other natural amino acids (i.e., W, I, M, P, F, G, A, V, H, E, R, K, D, N, Y, C, S, T, or Q) or with non-natural amino acids as are known to those of skill in the art. In some embodiments, said mutation or mutations may comprise substitution of residue L102 with proline, glycine, alanine, serine, valine, or threonine. In some embodiments, said mutation or mutations may comprise substitution of residue L102 with proline or glycine. In some embodiments, said mutation or mutations may comprise the substitution L102P. In some embodiments, said mutation or mutations may comprise the deletion of residue L102.

In some embodiments, said mutation or mutations may comprise substitution of residue Q163 of SEQ ID NO: 25 with any of the 19 other natural amino acids (i.e., W, I, M, P, F, G, A, V, L, H, E, R, K, N, Y, C, S, T, or D) or with non-natural amino acids as are known to those of skill in the art. In some embodiments, said mutation or mutations may comprise substitution of residue Q163 with asparagine, aspartic acid, glutamine, serine, threonine, or valine. In some embodiments, said mutation or mutations may comprise substitution of residue Q163 with proline or glycine. In some embodiments, said mutation or mutations may comprise the substitution Q163N. In some embodiments, said mutation or mutations may comprise the deletion of residue Q163.

In some embodiments, said mutation or mutations may comprise substitution of residue Y320 of SEQ ID NO: 25 with any of the 19 other natural amino acids (i.e., W, I, M, P, F, G, A, V, L, H, R, K, D, N, E, C, S, T, or Q) or with non-natural amino acids as are known to those of skill in the art. In some embodiments, said mutation or mutations may comprise substitution of residue Y320 with aspartic acid, lysine, arginine, glutamine, histidine, valine, or alanine. In some embodiments, said mutation or mutations may comprise substitution of residue Y320 with proline or glycine. In some embodiments, said mutation or mutations may comprise the substitution Y320K. In some embodiments, said mutation or mutations may comprise the substitution Y320R. In some embodiments, said mutation or mutations may comprise the deletion of residue Y320.

In some embodiments, said mutation or mutations may comprise substitution of residue W412 of SEQ ID NO: 25 with any of the 19 other natural amino acids (i.e., I, M, P, F, G, A, V, L, H, E, R, K, D, N, Y, C, S, T, or Q) or with non-natural amino acids as are known to those of skill in the art. In some embodiments, said mutation or mutations may comprise substitution of residue W412 with phenylalanine, tyrosine, histidine, leucine, isoleucine, methionine, or valine. In some embodiments, said mutation or mutations may comprise substitution of residue W412 with proline or glycine. In some embodiments, said mutation or mutations may comprise the substitution W412F. In some embodiments, said mutation or mutations may comprise the deletion of residue W412.

In some embodiments, said mutation or mutations may comprise substitution of residue A439 of SEQ ID NO: 25 with any of the 19 other natural amino acids (i.e., W, I, M, P, F, G, T, V, L, H, E, R, K, D, N, Y, C, S, or Q) or with non-natural amino acids as are known to those of skill in the art. In some embodiments, said mutation or mutations may comprise substitution of residue A439 with proline, glycine, alanine, serine, valine, or threonine. In some embodiments, said mutation or mutations may comprise substitution of residue A439 with proline or glycine. In some embodiments, said mutation or mutations may comprise the substitution A439P. In some embodiments, said mutation or mutations may comprise the deletion of residue A439.

In some embodiments, said mutation or mutations may comprise substitution of residue D730 of SEQ ID NO: 25 with any of the 19 other natural amino acids (i.e., W, I, M, P, F, G, A, V, L, H, E, R, K, N, Y, C, S, T, or Q) or with non-natural amino acids as are known to those of skill in the art. In some embodiments, said mutation or mutations may comprise substitution of residue D730 with aspartic acid, lysine, arginine, glutamic acid, glutamine, histidine, valine, or alanine. In some embodiments, said mutation or mutations may comprise substitution of residue D730 with proline or glycine. In some embodiments, said mutation or mutations may comprise the substitution D730K. In some embodiments, said mutation or mutations may comprise the deletion of residue D730.

In some embodiments, said mutation or mutations may comprise substitution of residue I731 of SEQ ID NO: 25 with any of the 19 other natural amino acids (i.e., W, D, M, P, F, G, A, V, L, H, E, R, K, N, Y, C, S, T, or Q) or with non-natural amino acids as are known to those of skill in the art. In some embodiments, said mutation or mutations may comprise substitution of residue I731 with aspartic acid, lysine, arginine, glutamic acid, glutamine, histidine, valine, or alanine. In some embodiments, said mutation or mutations may comprise substitution of residue I731 with proline or glycine. In some embodiments, said mutation or mutations may comprise the substitution I731K. In some embodiments, said mutation or mutations may comprise the deletion of residue I731.

In some embodiments, said mutation or mutations may comprise insertion of one or more residues between residues D730 and I731 of SEQ ID NO: 25 with any one or more of the 19 other natural amino acids (i.e., W, I, M, P, F, G, A, V, L, H, E, R, K, D, N, Y, C, S, T, or Q) or with non-natural amino acids as are known to those of skill in the art. In some embodiments, said insertion may comprise 1, 2, 3, 4, 5, 6, 7, 8, 9, 10, 11, or 12 residues. In some embodiments, said insertion comprises the insertion of more than 12 residues. In some embodiments, said mutation or mutations may comprise insertion of one or more of lysine, tryptophan, leucine, glutamic acid, asparagine, glutamine, valine, alanine, serine, and/or threonine. In some embodiments, said mutation or mutations may comprise insertion of proline or glycine. In some embodiments, said mutation or mutations may comprise insertion of a lysine between residues D730 and I731.

In some embodiments, said mutation or mutations may comprise substitution of residue T828 of SEQ ID NO: 25 with any of the 19 other natural amino acids (i.e., W, I, M, P, F, G, A, V, L, H, E, R, K, D, N, Y, C, S, or Q) or with non-natural amino acids as are known to those of skill in the art. In some embodiments, said mutation or mutations may comprise substitution of residue T828 with glutamic acid, asparagine, glutamine, valine, alanine, serine, or threonine. In some embodiments, said mutation or mutations may comprise substitution of residue T828 with proline or glycine. In some embodiments, said mutation or mutations may comprise the substitution T828A. In some embodiments, said mutation or mutations may comprise the deletion of residue T828.

In some embodiments, said mutation or mutations may comprise substitution of residue K829 of SEQ ID NO: 25 with any of the 19 other natural amino acids (i.e., W, I, M, P, F, G, A, V, L, H, E, R, T, D, N, Y, C, S, or Q) or with non-natural amino acids as are known to those of skill in the art. In some embodiments, said mutation or mutations may comprise substitution of residue K829 with glutamic acid, asparagine, glutamine, valine, alanine, serine, or threonine. In some embodiments, said mutation or mutations may comprise substitution of residue K829 with proline or glycine. In some embodiments, said mutation or mutations may comprise the substitution K829A. In some embodiments, said mutation or mutations may comprise the deletion of residue K829.

In some embodiments, said mutation or mutations may comprise substitution of residue T832 of SEQ ID NO: 25 with any of the 19 other natural amino acids (i.e., W, I, M, P, F, G, A, V, L, H, E, R, K, D, N, Y, C, S, or Q) or with non-natural amino acids as are known to those of skill in the art. In some embodiments, said mutation or mutations may comprise substitution of residue T832 with glutamic acid, asparagine, glutamine, valine, alanine, serine, or threonine. In some embodiments, said mutation or mutations may comprise substitution of residue T832 with proline or glycine. In some embodiments, said mutation or mutations may comprise the substitution T832A. In some embodiments, said mutation or mutations may comprise the deletion of residue T832.

In some embodiments, said mutation or mutations may comprise substitution of residue V834 of SEQ ID NO: 25 with any of the 19 other natural amino acids (i.e., W, I, M, P, F, G, A, T, L, H, E, R, K, D, N, Y, C, S, or Q) or with non-natural amino acids as are known to those of skill in the art. In some embodiments, said mutation or mutations may comprise substitution of residue V834 with glutamic acid, asparagine, glutamine, valine, alanine, serine, or threonine. In some embodiments, said mutation or mutations may comprise substitution of residue V834 with proline or glycine. In some embodiments, said mutation or mutations may comprise the substitution V834A. In some embodiments, said mutation or mutations may comprise the deletion of residue V834.

In some embodiments, said mutation or mutations may comprise substitution of residue A900 of SEQ ID NO: 25 with any of the 19 other natural amino acids (i.e., W, I, M, P, F, G, L, V, H, E, R, K, D, N, Y, C, S, T, or Q) or with non-natural amino acids as are known to those of skill in the art. In some embodiments, said mutation or mutations may comprise substitution of residue A900 with phenylalanine, tyrosine, histidine, tryptophan, isoleucine, methionine, or valine. In some embodiments, said mutation or mutations may comprise substitution of residue A900 with proline or glycine. In some embodiments, said mutation or mutations may comprise the substitution A900W. In some embodiments, said mutation or mutations may comprise the deletion of residue A900.

In some embodiments, said mutation or mutations may comprise substitution of residue D904 of SEQ ID NO: 25 with any of the 19 other natural amino acids (i.e., W, I, M, P, F, G, A, V, L, H, R, K, E, N, Y, C, S, T, or Q) or with non-natural amino acids as are known to those of skill in the art. In some embodiments, said mutation or mutations may comprise substitution of residue D904 with aspartic acid, lysine, arginine, glutamine, histidine, valine, or alanine. In some embodiments, said mutation or mutations may comprise substitution of residue D904 with proline or glycine. In some embodiments, said mutation or mutations may comprise the substitution D904K. In some embodiments, said mutation or mutations may comprise the deletion of residue D904 of SEQ ID NO: 25.

In some embodiments, the mutation or mutations according to the methods and compositions of the present disclosure may comprise any 1, 2, 3, 4, 5, 6, 7, 8, 9, 10, 11, 12, 13, 14, 15, 16, or 17 of E31K, K72A, E81A, L102P, Q163N, Y320K, Y320R, W412F, A439P, P730K, I731K, T828A, K829A, T832A, V832A, A900W, and/or D904K of SEQ ID NO: 25 or any subset or combination thereof, or any homolog or ortholog thereof.

In some embodiments, the compositions and methods of the present disclosure comprise one or more mutations that may affect the ability of the enzyme to bind, interact with, or catalyze reactions involving, modified substrate molecules as described elsewhere herein, especially 3'-modified nucleotides, such as 3'-O-methyl, 3'-O-azido, and/or 3'-O-azidomethyl modified nucleotides. Binding, interaction, or catalysis may be measured according to various parameters as are known in the art for the characterization of enzyme-substrate interactions and catalysis, e.g., improvements in Kcat, Km, Kd, Ka, or other such parameters. In some embodiments, said mutation or mutations may comprise one or more substitutions, deletions, or insertions at, or at a position or location surrounding, positions 94, 105, 108, 130, 131, 166, 168, 200, 236, and/or 247 of SEQ ID NO: 19, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue R94 of SEQ ID NO: 19 with any of the 19 other natural amino acids (i.e., W, I, M, P, F, G, A, V, L, H, E, K, D, N, Y, C, S, T, or Q) or with non-natural amino acids as are known to those of skill in the art. In some embodiments, said mutation or mutations may comprise substitution of residue R94 with glycine, alanine, valine, cysteine, methionine, serine, threonine, leucine, phenylalanine, tyrosine or histidine. In some embodiments, said mutation or mutations may comprise substitution of residue R94 with alanine, proline or glycine. In some embodiments, said mutation or mutations may comprise any of the substitutions R94G, R94A, R94V. R94C, R94S, or R94F. In some embodiments, said mutation or mutations may comprise the deletion of residue R94.

In some embodiments, said mutation or mutations may comprise substitution of residue P105 of SEQ ID NO: 19 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P105 with lysine, arginine, histidine, threonine, serine, glutamic acid, glutamine, aspartic acid, asparagine, alanine, valine, or glycine. In some embodiments, said mutation or mutations may comprise substitution of residue P105 with alanine or glycine. In some embodiments, said mutation or mutations may comprise any of the substitutions P105K, P105T, P105R, P105E, P105A, or P105G. In some embodiments, said mutation or mutations may comprise the deletion of residue P105.

In some embodiments, said mutation or mutations may comprise substitution of residue P108 of SEQ ID NO: 19 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P108 with lysine, arginine, histidine, threonine, serine, glutamic acid, glutamine, aspartic acid, asparagine, alanine, residue P108 with alanine, proline or glycine. In some embodiments, said mutation or mutations may comprise any of the substitutions P108R, P108S, P108K, P108N, P108T, P108E, P108D, P108A, or P108G. In some embodiments, said mutation or mutations may comprise the deletion of residue P108.

In some embodiments, said mutation or mutations may comprise substitution of residue K130 of SEQ ID NO: 19 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K130 with threonine, serine, isoleucine, glutamic acid, glutamine, aspartic acid, asparagine, alanine, valine, or glycine. In some embodiments, said mutation or mutations may comprise substitution of residue K130 with alanine, proline or glycine. In some embodiments, said mutation or mutations may comprise any of the substitutions K130S, K130T, K130I, K130G, K130A, or K130V. In some embodiments, said mutation or mutations may comprise the deletion of residue K130.

In some embodiments, said mutation or mutations may comprise substitution of residue D131 of SEQ ID NO: 19 with any of the 19 other natural amino acids (i.e., W, I, M, F, G, A, V, L, H, E, R, P, N, Y, C, S, T, or Q) or with non-natural amino acids as are known to those of skill in the art. In some embodiments, said mutation or mutations may comprise substitution of residue D131 with arginine, lysine, threonine, serine, isoleucine, glutamic acid, glutamine, \asparagine, alanine, methionine, cysteine, valine, or glycine. In some embodiments, said mutation or mutations may comprise substitution of residue D131 with alanine, proline or glycine. In some embodiments, said mutation or mutations may comprise any of the substitutions D131R, D131T, D131I, D131M, D131G, D131A, or D131V. In some embodiments, said mutation or mutations may comprise the deletion of residue D131. In some embodiments, said mutation or mutations may comprise the truncation of SEQ ID NO: 19 N-terminal to residue D131, i.e., said mutation or mutations may comprise an alternative start codon for translation of SEQ ID NO: 19.

In some embodiments, mutations are present at positions 130 and 131. Exemplary combinations of mutations may comprise any of substitutions K130S, K130T, K130I, K130G, K130A, or K130V with any of substitutions D131R, D131T, D131I, D131M, D131G, D131A, or D131V.

In some embodiments, said mutation or mutations may comprise substitution of residue L166 of SEQ ID NO: 19 with any of the 19 other natural amino acids (i.e., W, I, M, F, G, A, V, H, E, R, P, D, N, Y, C, S, T, or Q) or with non-natural amino acids as are known to those of skill in the art. In some embodiments, said mutation or mutations may comprise substitution of residue L166 with arginine, lysine, threonine, serine, tyrosine, tryptophan, phenylalanine, histidine, isoleucine, glutamic acid, glutamine, aspartic acid, asparagine, alanine, methionine, cysteine, valine, proline, or glycine. In some embodiments, said mutation or mutations may comprise substitution of residue L166 with alanine, proline or glycine. In some embodiments, said mutation or mutations may comprise any of the substitutions L166W, L166I, L166M, L166P, L166F, L166G, L166A, L166V, L166H, L166E, L166R, L166K, L166D, L166N, L166Y, L166C, L166S, L166T, or L166Q. In some embodiments, said mutation or mutations may comprise the deletion of residue L166. In some embodiments, said mutation or mutations may comprise the truncation of SEQ ID NO: 19 N-terminal to residue L166, i.e., said mutation or mutations may comprise an alternative start codon for translation of SEQ ID NO: 19. In some embodiments, said mutation or mutations may comprise the truncation of SEQ ID NO: 19 C-terminal to residue L165, i.e., said mutation or mutations may comprise a stop codon terminating translation of SEQ ID NO: 19.

In some embodiments, said mutation or mutations may comprise substitution of residue Q168 of SEQ ID NO: 19 with any of the 19 other natural amino acids (i.e., W, I, M, F, G, A, V, L, H, E, R, P, D, N, Y, C, S, or T) or with non-natural amino acids as are known to those of skill in the art. In some embodiments, said mutation or mutations may comprise substitution of residue Q168 with lysine, arginine, glutamic acid, aspartic acid, asparagine, valine, alanine, serine, glycine, or threonine. In some embodiments, said mutation or mutations may comprise substitution of residue Q168 with alanine, proline or glycine. In some embodiments, said mutation or mutations may comprise any of the substitutions Q168K, Q168T, Q168R, Q168E, Q168A, or Q168G. In some embodiments, said mutation or mutations may comprise the deletion of residue Q168.

In some embodiments, said mutation or mutations may comprise substitution of residue Y200 of SEQ ID NO: 19 with any of the 19 other natural amino acids (i.e., W, I, M, F, G, A, V, L, H, E, R, P, D, N, C, S, T, or Q) or with non-natural amino acids as are known to those of skill in the art. In some embodiments, said mutation or mutations may comprise substitution of residue Y200 with lysine, arginine, glutamic acid, aspartic acid, asparagine, glutamine, valine, alanine, serine, proline, glycine, or threonine. In some embodiments, said mutation or mutations may comprise substitution of residue Y200 with alanine, proline or glycine. In some embodiments, said mutation or mutations may comprise any of the substitutions Y200K, Y200T, Y200R, Y200Q, Y200P, Y200E, Y200A, or Y200G. In some embodiments, said mutation or mutations may comprise the deletion of residue Y200.

In some embodiments, said mutation or mutations may comprise substitution of residue K236 of SEQ ID NO: 19 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K236 with arginine, glutamic acid, aspartic acid, asparagine, glutamine, valine, alanine, serine, proline, glycine, or threonine. In some embodiments, said mutation or mutations may comprise substitution of residue K236 with alanine, proline or glycine. In some embodiments, said mutation or mutations may comprise any of the substitutions K236E, K236A, K236G, K236Q, K236P, or K236R. In some embodiments, said mutation or mutations may comprise the deletion of residue K236.

In some embodiments, said mutation or mutations may comprise substitution of residue L247 of SEQ ID NO: 19 with any of the 19 other natural amino acids (i.e., W, I, M, F, G, A, V, H, E, R, P, D, N, Y, C, S, T, or Q) or with non-natural amino acids as are known to those of skill in the art. In some embodiments, said mutation or mutations may comprise substitution of residue L247 with lysine, arginine, glutamic acid, aspartic acid, asparagine, glutamine, valine, alanine, serine, proline, glycine, or threonine. In some embodiments, said mutation or mutations may comprise substitution of residue L247 with alanine, proline or glycine. In some embodiments, said mutation or mutations may comprise any of the substitutions L247S, L247R, L247T, L247P, L247G, or L247A. In some embodiments, said mutation or mutations may comprise the deletion of residue L247 of SEQ ID NO: 19.

In some embodiments, mutations are present at positions 130 and 131. Exemplary combinations of mutations may comprise any of substitutions K130S, K130T, K130I, K130G, K130A, or K130V with any of substitutions D131R, D131T, D131I, D131M, D131G, D131A, or D131V. In some embodiments, said mutations may comprise substitutions at positions K130, D131, and/or L166 of SEQ ID NO: 19 or any combination thereof. In some embodiments, said mutations may optionally comprise any of substitutions K130S, K130T, K130I, K130G, K130A, or K130V, optionally in combination with any of substitutions D131R, D131T, D131I, D131M, D131G, D131A, or D131V and/or any of substitutions L166W, L166I, L166M, L166P, L166F, L166G, L166A, L166V, L166H, L166E, L166R, L166K, L166D, L166N, L166Y, L166C, L166S, L166T, or L166Q. In some embodiments, said mutation or mutations may comprise a combination of mutations at positions 130 and 131 of SEQ ID NO: 19 with the truncation of SEQ ID NO: 19 C-terminal to residue L165, i.e., said mutation or mutations may further comprise a stop codon terminating translation of SEQ ID NO: 19.

In some embodiments, mutations are present at positions 105, 236, and/or 247 of SEQ ID NO: 19. In some embodiments, said mutations may optionally comprise any of substitutions P105K, P105T, P105R, P105E, P105A, or P105G, optionally in combination with any of substitutions K236E, K236A, K236G, K236Q, K236P, or K236R and/or any of substitutions L247S, L247R, L247T, L247P, L247G, or L247A of SEQ ID NO: 19. In some embodiments, said mutations may optionally comprise any of substitutions K236E, K236A, K236G, K236Q, K236P, or K236R, optionally in combination with any of substitutions P105K, P105T, P105R, P105E, P105A, or P105G and/or any of substitutions L247S, L247R, L247T, L247P, L247G, or L247A of SEQ ID NO: 19. In some embodiments, said mutations may optionally comprise any of substitutions L247S, L247R, L247T, L247P, L247G, or L247A, optionally in combination with any of substitutions K236E, K236A, K236G, K236Q, K236P, or K236R and/or any of substitutions P105K, P105T, P105R, P105E, P105A, or P105G of SEQ ID NO: 19.

In some embodiments, mutations are present at positions 94, 200, and/or 247 of SEQ ID NO: 19. In some embodiments, said mutations may optionally comprise any of substitutions R94G, R94A, R94V. R94C, R94S, or R94F, optionally in combination with any of substitutions Y200K, Y200T, Y200R, Y200Q, Y200P, Y200E, Y200A, or Y200G and/or any of substitutions L247S, L247R, L247T, L247P, L247G, or L247A of SEQ ID NO: 19. In some embodiments, said mutations may optionally comprise any of substitutions Y200K, Y200T, Y200R, Y200Q, Y200P, Y200E, Y200A, or Y200G, optionally in combination with any of substitutions R94G, R94A, R94V. R94C, R94S, or R94F, and/or any of substitutions L247S, L247R, L247T, L247P, L247G, or L247A of SEQ ID NO: 19. In some embodiments, said mutations may optionally comprise any of substitutions L247S, L247R, L247T, L247P, L247G, or L247A, optionally in combination with any of substitutions R94G, R94A, R94V. R94C, R94S, or R94F, and/or any of substitutions L247S, L247R, L247T, L247P, L247G, or L247A, of SEQ ID NO: 19.

In some embodiments, mutations are present at positions 94, 108, and/or 168 of SEQ ID NO: 19. In some embodiments, said mutations may optionally comprise any of substitutions R94G, R94A, R94V. R94C, R94S, or R94F, optionally in combination with any of substitutions P108R, P108S, P108K, P108N, P108T, P108E, P108D, P108A, or P108G and/or any of substitutions Q168K, Q168T, Q168R, Q168E, Q168A, or Q168G of SEQ ID NO: 19. In some embodiments, said mutations may optionally comprise any of substitutions P108R, P108S, P108K, P108N, P108T, P108E, P108D, P108A, or P108G, optionally in combination with any of substitutions R94G, R94A, R94V. R94C, R94S, or R94F and/or any of substitutions Q168K, Q168T, Q168R, Q168E, Q168A, or Q168G of SEQ ID NO: 19. In some embodiments, said mutations may optionally comprise any of substitutions Q168K, Q168T, Q168R, Q168E, Q168A, or Q168G, optionally in combination with any of substitutions P108R, P108S, P108K, P108N, P108T, P108E, P108D, P108A, or P108G and/or any of substitutions R94G, R94A, R94V. R94C, R94S, or R94F of SEQ ID NO: 19.

In some embodiments, mutations are present at positions 168, 200, and/or 236 of SEQ ID NO: 19. In some embodiments, said mutations may optionally comprise any of substitutions K236E, K236A, K236G, K236Q, K236P, or K236R, optionally in combination with any of substitutions Y200V, Y200C, Y200F, Y200L, Y200S, Y200P, Y200K, Y200T, Y200R, Y200Q, Y200P, Y200E, Y200A, or Y200G and/or any of substitutions Q168K, Q168T, Q168R, Q168E, Q168A, or Q168G of SEQ ID NO: 19. In some embodiments, said mutations may optionally comprise any of substitutions Y200V, Y200C, Y200F, Y200L, Y200S, Y200P, Y200K, Y200T, Y200R, Y200Q, Y200P, Y200E, Y200A, or Y200G, optionally in combination with any of substitutions K236E, K236A, K236G, K236Q, K236P, or K236R, and/or any of substitutions Q168K, Q168T, Q168R, Q168E, Q168A, or Q168G of SEQ ID NO: 19. In some embodiments, said mutations may optionally comprise any of substitutions Q168K, Q168T, Q168R, Q168E, Q168A, or Q168G, optionally in combination with any of substitutions Y200K, Y200T, Y200R, Y200Q, Y200P, Y200E, Y200A, or Y200G and/or any of substitutions K236E, K236A, K236G, K236Q, K236P, or K236R, of SEQ ID NO: 19.

In some embodiments, the mutation or mutations according to the methods and compositions of the present disclosure may comprise any 1, 2, 3, 4, 5, 6, 7, 8, 9, or 10 of R94G, R94A, R94V. R94C, R94S, R94F, P105K, P105T, P105R, P105E, P105A, P105G, P108R, P108S, P108K, P108N, P108T, P108E, P108D, P108A, P108G, K130S, K130T, K130I, K130G, K130A, K130V, D131R, D131T, D131I, D131M, D131G, D131A, D131V, L166W, L166I, L166M, L166P, L166F, L166G, L166A, L166V, L166H, L166E, L166R, L166K, L166D, L166N, L166Y, L166C, L166S, L166T, L166Q, Q168K, Q168T, Q168R, Q168E, Q168A, Q168G, Y200V, Y200C, Y200F, Y200L, Y200S, Y200P, Y200K, Y200T, Y200R, Y200Q, Y200P, Y200E, Y200A, Y200G, K236E, K236A, K236G, K236Q, K236P, K236R, L247S, L247R, L247T, L247P, L247G, or L247A of SEQ ID NO: 19 or any subset or combination thereof, or any homolog or ortholog thereof.

In some embodiments, said mutation or mutations may comprise one or more substitutions, deletions, or insertions at, or at a position or location surrounding, positions 85, 96, 99, 121, 122, 150, 152, 184, 220, and/or 231 of SEQ ID NO: 20, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue R85 of SEQ ID NO: 20 with any of the 19 other natural amino acids (i.e., W, I, M, P, F, G, A, V, L, H, E, K, D, N, Y, C, S, T, or Q) or with non-natural amino acids as are known to those of skill in the art. In some embodiments, said mutation or mutations may comprise substitution of residue R85 with glycine, alanine, lysine, arginine, valine, cysteine, methionine, serine, threonine, leucine, phenylalanine, tyrosine or histidine. In some embodiments, said mutation or mutations may comprise substitution of residue R85 with alanine, proline or glycine. In some embodiments, said mutation or mutations may comprise any of the substitutions R85G, R85A, R85V. R85C, R85S, or R85F. In some embodiments, said mutation or mutations may comprise the deletion of residue R85.

In some embodiments, said mutation or mutations may comprise substitution of residue P96 of SEQ ID NO: 20 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P96 with lysine, arginine, histidine, threonine, serine, glutamic acid, glutamine, aspartic acid, asparagine, alanine, valine, or glycine. In some embodiments, said mutation or mutations may comprise substitution of residue P96 with alanine or glycine. In some embodiments, said mutation or mutations may comprise any of the substitutions P96K, P96T, P96R, P96E, P96A, or P96G. In some embodiments, said mutation or mutations may comprise the deletion of residue P96.

In some embodiments, said mutation or mutations may comprise substitution of residue P99 of SEQ ID NO: 20 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P96 with lysine, arginine, histidine, threonine, serine, glutamic acid, glutamine, aspartic acid, asparagine, alanine, residue P99 with alanine or glycine. In some embodiments, said mutation or mutations may comprise any of the substitutions P99R, P99S, P99K, P99N, P99T, P99E, P99D, P99A, or P99G. In some embodiments, said mutation or mutations may comprise the deletion of residue P99.

In some embodiments, said mutation or mutations may comprise substitution of residue K121 of SEQ ID NO: 20 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K121 with threonine, serine, isoleucine, glutamic acid, glutamine, aspartic acid, asparagine, alanine, valine, or glycine. In some embodiments, said mutation or mutations may comprise substitution of residue K121 with alanine, proline or glycine. In some embodiments, said mutation or mutations may comprise any of the substitutions K121S, K121T, K121I, K121G, K121A, or K121V. In some embodiments, said mutation or mutations may comprise the deletion of residue K121.

In some embodiments, said mutation or mutations may comprise substitution of residue D122 of SEQ ID NO: 20 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue D122 with arginine, lysine, threonine, serine, isoleucine, glutamic acid, glutamine, asparagine, alanine, methionine, cysteine, valine, or glycine. In some embodiments, said mutation or mutations may comprise substitution of residue D122 with alanine, proline or glycine. In some embodiments, said mutation or mutations may comprise any of the substitutions D122R, D122T, D122I, D122M, D122G, D122A, or D122V. In some embodiments, said mutation or mutations may comprise the deletion of residue D122. In some embodiments, said mutation or mutations may comprise the truncation of SEQ ID NO: 20 N-terminal to residue D122, i.e., said mutation or mutations may comprise an alternative start codon for translation of SEQ ID NO: 20.

In some embodiments, mutations are present at positions 121 and 122. Exemplary combinations of mutations may comprise any of substitutions K121S, K121T, K121I, K121G, K121A, or K121V with any of substitutions D122R, D122T, D122I, D122M, D122G, D122A, or D122V.

In some embodiments, said mutation or mutations may comprise substitution of residue L150 of SEQ ID NO: 20 with any of the 19 other natural amino acids (i.e., W, I, M, F, G, A, V, H, E, R, P, D, N, Y, C, S, T, or Q) or with non-natural amino acids as are known to those of skill in the art. In some embodiments, said mutation or mutations may comprise substitution of residue L150 with arginine, lysine, threonine, serine, tyrosine, tryptophan, phenylalanine, histidine, isoleucine, glutamic acid, glutamine, aspartic acid, asparagine, alanine, methionine, cysteine, valine, proline, or glycine. In some embodiments, said mutation or mutations may comprise substitution of residue L150 with alanine, proline or glycine. In some embodiments, said mutation or mutations may comprise any of the substitutions L150W, L150I, L150M, L150P, L150F, L150G, L150A, L150V, L150H, L150E, L150R, L150K, L150D, L150N, L150Y, L150C, L150S, L150T, or L150Q. In some embodiments, said mutation or mutations may comprise the deletion of residue L150. In some embodiments, said mutation or mutations may comprise the truncation of SEQ ID NO: 20 N-terminal to residue L150, i.e., said mutation or mutations may comprise an alternative start codon for translation of SEQ ID NO: 20. In some embodiments, said mutation or mutations may comprise the truncation of SEQ ID NO: 20 C-terminal to residue L149, i.e., said mutation or mutations may comprise a stop codon terminating translation of SEQ ID NO: 20.

In some embodiments, said mutation or mutations may comprise substitution of residue Q152 of SEQ ID NO: 20 with any of the 19 other natural amino acids (i.e., W, I, M, F, G, A, V, L, H, E, R, P, D, N, Y, C, S, or T) or with non-natural amino acids as are known to those of skill in the art. In some embodiments, said mutation or mutations may comprise substitution of residue Q152 with lysine, arginine, glutamic acid, aspartic acid, asparagine, valine, alanine, serine, glycine, or threonine. In some embodiments, said mutation or mutations may comprise substitution of residue Q152 with alanine, proline or glycine. In some embodiments, said mutation or mutations may comprise any of the substitutions Q152K, Q152T, Q152R, Q152E, Q152A, or Q152G. In some embodiments, said mutation or mutations may comprise the deletion of residue Q152.

In some embodiments, said mutation or mutations may comprise substitution of residue Y184 of SEQ ID NO: 20 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Y184 with lysine, arginine, glutamic acid, aspartic acid, asparagine, glutamine, valine, alanine, serine, proline, glycine, or threonine. In some embodiments, said mutation or mutations may comprise substitution of residue Y184 with alanine, proline or glycine. In some embodiments, said mutation or mutations may comprise any of the substitutions Y184K, Y184T, Y184R, Y184Q, Y184P, Y184E, Y184A, or Y184G. In some embodiments, said mutation or mutations may comprise the deletion of residue Y184.

In some embodiments, said mutation or mutations may comprise substitution of residue K220 of SEQ ID NO: 20 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K220 with arginine, glutamic acid, aspartic acid, asparagine, glutamine, valine, alanine, serine, proline, glycine, or threonine. In some embodiments, said mutation or mutations may comprise substitution of residue K220 with alanine, proline or glycine. In some embodiments, said mutation or mutations may comprise any of the substitutions K220E, K220A, K220G, K220Q, K220P, or K220R. In some embodiments, said mutation or mutations may comprise the deletion of residue K220.

In some embodiments, said mutation or mutations may comprise substitution of residue L231 of SEQ ID NO: 20 with any of the 19 other natural amino acids (i.e., W, I, M, F, G, A, V, H, E, R, P, D, N, Y, C, S, T, or Q) or with non-natural amino acids as are known to those of skill in the art. In some embodiments, said mutation or mutations may comprise substitution of residue L231 with lysine, arginine, glutamic acid, aspartic acid, asparagine, glutamine, valine, alanine, serine, proline, glycine, or threonine. In some embodiments, said mutation or mutations may comprise substitution of residue L231 with alanine, proline or glycine. In some embodiments, said mutation or mutations may comprise any of the substitutions L231S, L231R, L231T, L231P, L231G, or L231A. In some embodiments, said mutation or mutations may comprise the deletion of residue L231 of SEQ ID NO: 20.

In some embodiments, mutations are present at positions 121 and 122. Exemplary combinations of mutations may comprise any of substitutions K121S, K121T, K121I, K121G, K121A, or K121V with any of substitutions D122R, D122T, D122I, D122M, D122G, D122A, or D122V. In some embodiments, said mutations may comprise substitutions at positions K121, D122, and/or L150 of SEQ ID NO: 20 or any combination thereof. In some embodiments, said mutations may optionally comprise any of substitutions K121S, K121T, K121I, K121G, K121A, or K121V, optionally in combination with any of substitutions D122R, D122T, D122I, D122M, D122G, D122A, or D122V and/or any of substitutions L150W, L150I, L150M, L150P, L150F, L150G, L150A, L150V, L150H, L150E, L150R, L150K, L150D, L150N, L150Y, L150C, L150S, L150T, or L150Q. In some embodiments, said mutation or mutations may comprise a combination of mutations at positions 121 and 122 of SEQ ID NO: 20 with the truncation of SEQ ID NO: 20 C-terminal to residue L165, i.e., said mutation or mutations may further comprise a stop codon terminating translation of SEQ ID NO: 20.

In some embodiments, mutations are present at positions 96, 220, and/or 231 of SEQ ID NO: 20. In some embodiments, said mutations may optionally comprise any of substitutions P96K, P96T, P96R, P96E, P96A, or P96G, optionally in combination with any of substitutions K220E, K220A, K220G, K220Q, K220P, or K220R and/or any of substitutions L231S, L231R, L231T, L231P, L231G, or L231A of SEQ ID NO: 20. In some embodiments, said mutations may optionally comprise any of substitutions K220E, K220A, K220G, K220Q, K220P, or K220R, optionally in combination with any of substitutions 105K, P96T, P96R, P96E, P96A, or P96G and/or any of substitutions L231S, L231R, L231T, L231P, L231G, or L231A of SEQ ID NO: 20. In some embodiments, said mutations may optionally comprise any of substitutions L231S, L231R, L231T, L231P, L231G, or L231A, optionally in combination with any of substitutions K220E, K220A, K220G, K220Q, K220P, or K220R and/or any of substitutions P96K, P96T, P96R, P96E, P96A, or P96G of SEQ ID NO: 20.

In some embodiments, mutations are present at positions 85, 184, and/or 231 of SEQ ID NO: 20. In some embodiments, said mutations may optionally comprise any of substitutions R85G, R85A, R85V. R85C, R85S, or R85F, optionally in combination with any of substitutions Y184K, Y184T, Y184R, Y184Q, Y184P, Y184E, Y184A, or Y184G and/or any of substitutions L231S, L231R, L231T, L231P, L231G, or L231A of SEQ ID NO: 20. In some embodiments, said mutations may optionally comprise any of substitutions Y184K, Y184T, Y184R, Y184Q, Y184P, Y184E, Y184A, or Y184G, optionally in combination with any of substitutions R85G, R85A, R85V. R85C, R85S, or R85F, and/or any of substitutions L231S, L231R, L231T, L231P, L231G, or L231A of SEQ ID NO: 20. In some embodiments, said mutations may optionally comprise any of substitutions L231S, L231R, L231T, L231P, L231G, or L231A, optionally in combination with any of substitutions R85G, R85A, R85V. R85C, R85S, or R85F, and/or any of substitutions L231S, L231R, L231T, L231P, L231G, or L231A, of SEQ ID NO: 20.

In some embodiments, mutations are present at positions 85, 99, and/or 152 of SEQ ID NO: 20. In some embodiments, said mutations may optionally comprise any of substitutions R85G, R85A, R85V. R85C, R85S, or R85F, optionally in combination with any of substitutions P99R, P99S, P99K, P99N, P99T, P99E, P99D, P99A, or P99G and/or any of substitutions Q152K, Q152T, Q152R, Q152E, Q152A, or Q152G of SEQ ID NO: 20. In some embodiments, said mutations may optionally comprise any of substitutions P99R, P99S, P99K, P99N, P99T, P99E, P99D, P99A, or P99G, optionally in combination with any of substitutions R85G, R85A, R85V. R85C, R85S, or R85F and/or any of substitutions Q152K, Q152T, Q152R, Q152E, Q152A, or Q152G of SEQ ID NO: 20. In some embodiments, said mutations may optionally comprise any of substitutions Q152K, Q152T, Q152R, Q152E, Q152A, or Q152G, optionally in combination with any of substitutions P99R, P99S, P99K, P99N, P99T, P99E, P99D, P99A, or P99G and/or any of substitutions R85G, R85A, R85V. R85C, R85S, or R85F of SEQ ID NO: 20.

In some embodiments, mutations are present at positions 152, 184, and/or 220 of SEQ ID NO: 20. In some embodiments, said mutations may optionally comprise any of substitutions K220E, K220A, K220G, K220Q, K220P, or K220R, optionally in combination with any of substitutions Y184K, Y184T, Y184R, Y184Q, Y184P, Y184E, Y184A, or Y184G and/or any of substitutions Q152K, Q152T, Q152R, Q152E, Q152A, or Q152G of SEQ ID NO: 20. In some embodiments, said mutations may optionally comprise any of substitutions Y184K, Y184T, Y184R, Y184Q, Y184P, Y184E, Y184A, or Y184G, optionally in combination with any of substitutions K220E, K220A, K220G, K220Q, K220P, or K220R, and/or any of substitutions Q152K, Q152T, Q152R, Q152E, Q152A, or Q152G of SEQ ID NO: 20. In some embodiments, said mutations may optionally comprise any of substitutions Q152K, Q152T, Q152R, Q152E, Q152A, or Q152G, optionally in combination with any of substitutions Y184K, Y184T, Y184R, Y184Q, Y184P, Y184E, Y184A, or Y184G and/or any of substitutions K220E, K220A, K220G, K220Q, K220P, or K220R, of SEQ ID NO: 20.

In some embodiments, the mutation or mutations according to the methods and compositions of the present disclosure may comprise any 1, 2, 3, 4, 5, 6, 7, 8, 9, or 10 of R85G, R85A, R85V. R85C, R85S, R85F, P96K, P96T, P96R, P96E, P96A, P96G, P99R, P99S, P99K, P99N, P99T, P99E, P99D, P99A, P99G, K121S, K121T, K121I, K121G, K121A, K121V, D122R, D122T, D122I, D122M, D122G, D122A, D122V, L150W, L150I, L150M, L150P, L150F, L150G, L150A, L150V, L150H, L150E, L150R, L150K, L150D, L150N, L150Y, L150C, L150S, L150T, L150Q, Q152K, Q152T, Q152R, Q152E, Q152A, Q152G, Y184K, Y184T, Y184R, Y184Q, Y184P, Y184E, Y184A, Y184G, K220E, K220A, K220G, K220Q, K220P, K220R, L231S, L231R, L231T, L231P, L231G, or L231A of SEQ ID NO: 20 or any subset or combination thereof, or any homolog or ortholog thereof.

In some embodiments, said mutation or mutations may comprise one or more substitutions, deletions, or insertions at, or at a position or location surrounding, positions 91, 102, 105, 127, 128, 163, 165, 197, 233, and/or 244 of SEQ ID NO: 21, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue R91 of SEQ ID NO: 21 with any of the 19 other natural amino acids (i.e., W, I, M, P, F, G, A, V, L, H, E, K, D, N, Y, C, S, T, or Q) or with non-natural amino acids as are known to those of skill in the art. In some embodiments, said mutation or mutations may comprise substitution of residue R91 with glycine, lysine, arginine, alanine, valine, cysteine, methionine, serine, threonine, leucine, phenylalanine, tyrosine or histidine. In some embodiments, said mutation or mutations may comprise substitution of residue R91 with alanine, proline or glycine. In some embodiments, said mutation or mutations may comprise any of the substitutions R91G, R91A, R91V. R91C, R91S, or R91F. In some embodiments, said mutation or mutations may comprise the deletion of residue R91.

In some embodiments, said mutation or mutations may comprise substitution of residue P102 of SEQ ID NO: 21 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P102 with lysine, arginine, histidine, threonine, serine, glutamic acid, glutamine, aspartic acid, asparagine, alanine, valine, or glycine. In some embodiments, said mutation or mutations may comprise substitution of residue P102 with alanine or glycine. In some embodiments, said mutation or mutations may comprise any of the substitutions P102K, P102T, P102R, P102E, P102A, or P102G. In some embodiments, said mutation or mutations may comprise the deletion of residue P102.

In some embodiments, said mutation or mutations may comprise substitution of residue P105 of SEQ ID NO: 2121 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P102 with lysine, arginine, histidine, threonine, serine, glutamic acid, glutamine, aspartic acid, asparagine, alanine, valine, or glycine. In some embodiments, said mutation or mutations may comprise substitution of residue P105 with alanine or glycine. In some embodiments, said mutation or mutations may comprise any of the substitutions P105R, P105S, P105K, P105N, P105T, P105E, P105D, P105A, or P105G. In some embodiments, said mutation or mutations may comprise the deletion of residue P105.

In some embodiments, said mutation or mutations may comprise substitution of residue K127 of SEQ ID NO: 2121 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K127 with threonine, lysine, arginine, serine, isoleucine, glutamic acid, glutamine, aspartic acid, asparagine, alanine, valine, or glycine. In some embodiments, said mutation or mutations may comprise substitution of residue K127 with alanine, proline or glycine. In some embodiments, said mutation or mutations may comprise any of the substitutions K127S, K127T, K127I, K127G, K127A, or K127V. In some embodiments, said mutation or mutations may comprise the deletion of residue K127.

In some embodiments, said mutation or mutations may comprise substitution of residue D128 of SEQ ID NO: 2121 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue D128 with arginine, lysine, threonine, serine, isoleucine, glutamic acid, glutamine, asparagine, alanine, methionine, cysteine, valine, or glycine. In some embodiments, said mutation or mutations may comprise substitution of residue D128 with alanine, proline or glycine. In some embodiments, said mutation or mutations may comprise any of the substitutions D128R, D128T, D128I, D128M, D128G, D128A, or D128V. In some embodiments, said mutation or mutations may comprise the deletion of residue D128. In some embodiments, said mutation or mutations may comprise the truncation of SEQ ID NO: 2121 N-terminal to residue D128, i.e., said mutation or mutations may comprise an alternative start codon for translation of SEQ ID NO: 2121.

In some embodiments, mutations are present at positions 127 and 128. Exemplary combinations of mutations may comprise any of substitutions K127S, K127T, K127I, K127G, K127A, or K127V with any of substitutions D128R, D128T, D128I, D128M, D128G, D128A, or D128V.

In some embodiments, said mutation or mutations may comprise substitution of residue L163 of SEQ ID NO: 2121 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue L163 with arginine, lysine, threonine, serine, tyrosine, tryptophan, phenylalanine, histidine, isoleucine, glutamic acid, glutamine, aspartic acid, asparagine, alanine, methionine, cysteine, valine, proline, or glycine. In some embodiments, said mutation or mutations may comprise substitution of residue L163 with alanine, proline or glycine. In some embodiments, said mutation or mutations may comprise any of the substitutions L163W, L163I, L163M, L163P, L163F, L163G, L163A, L163V, L163H, L163E, L163R, L163K, L163D, L163N, L163Y, L163C, L163S, L163T, or L163Q. In some embodiments, said mutation or mutations may comprise the deletion of residue L163. In some embodiments, said mutation or mutations may comprise the truncation of SEQ ID NO: 2121 N-terminal to residue L163, i.e., said mutation or mutations may comprise an alternative start codon for translation of SEQ ID NO: 2121. In some embodiments, said mutation or mutations may comprise the truncation of SEQ ID NO: 21 C-terminal to residue L165, i.e., said mutation or mutations may comprise a stop codon terminating translation of SEQ ID NO: 21.

In some embodiments, said mutation or mutations may comprise substitution of residue Q165 of SEQ ID NO: 21 with any of the 19 other natural amino acids (i.e., W, I, M, F, G, A, V, L, H, E, R, P, D, N, Y, C, S, or T) or with non-natural amino acids as are known to those of skill in the art. In some embodiments, said mutation or mutations may comprise substitution of residue Q165 with lysine, arginine, glutamic acid, aspartic acid, asparagine, valine, alanine, serine, glycine, or threonine. In some embodiments, said mutation or mutations may comprise substitution of residue Q165 with alanine, proline or glycine. In some embodiments, said mutation or mutations may comprise any of the substitutions Q165K, Q165T, Q165R, Q165E, Q165A, or Q165G. In some embodiments, said mutation or mutations may comprise the deletion of residue Q165.

In some embodiments, said mutation or mutations may comprise substitution of residue Y197 of SEQ ID NO: 21 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Y197 with lysine, arginine, glutamic acid, aspartic acid, asparagine, glutamine, valine, alanine, serine, proline, glycine, or threonine. In some embodiments, said mutation or mutations may comprise substitution of residue Y197 with alanine, proline or glycine. In some embodiments, said mutation or mutations may comprise any of the substitutions Y197K, Y197T, Y197R, Y197Q, Y197P, Y197E, Y197A, or Y197G. In some embodiments, said mutation or mutations may comprise the deletion of residue Y197.

In some embodiments, said mutation or mutations may comprise substitution of residue K233 of SEQ ID NO: 21 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K233 with arginine, glutamic acid, aspartic acid, asparagine, glutamine, valine, alanine, serine, proline, glycine, or threonine. In some embodiments, said mutation or mutations may comprise substitution of residue K233 with alanine, proline or glycine. In some embodiments, said mutation or mutations may comprise any of the substitutions K233E, K233A, K233G, K233Q, K233P, or K233R. In some embodiments, said mutation or mutations may comprise the deletion of residue K233.

In some embodiments, said mutation or mutations may comprise substitution of residue L244 of SEQ ID NO: 21 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue L244 with lysine, arginine, glutamic acid, aspartic acid, asparagine, glutamine, valine, alanine, serine, proline, glycine, or threonine. In some embodiments, said mutation or mutations may comprise substitution of residue L244 with alanine, proline or glycine. In some embodiments, said mutation or mutations may comprise any of the substitutions L244S, L244R, L244T, L244P, L244G, or L244A. In some embodiments, said mutation or mutations may comprise the deletion of residue L244 of SEQ ID NO: 21.

In some embodiments, mutations are present at positions 127 and 128. Exemplary combinations of mutations may comprise any of substitutions K127S, K127T, K127I, K127G, K127A, or K127V with any of substitutions D128R, D128T, D128I, D128M, D128G, D128A, or D128V. In some embodiments, said mutations may comprise substitutions at positions K127, D128, and/or L163 of SEQ ID NO: 21 or any combination thereof. In some embodiments, said mutations may optionally comprise any of substitutions K127S, K127T, K127I, K127G, K127A, or K127V, optionally in combination with any of substitutions D128R, D128T, D128I, D128M, D128G, D128A, or D128V and/or any of substitutions L163W, L163I, L163M, L163P, L163F, L163G, L163A, L163V, L163H, L163E, L163R, L163K, L163D, L163N, L163Y, L163C, L163S, L163T, or L163Q. In some embodiments, said mutation or mutations may comprise a combination of mutations at positions 127 and 128 of SEQ ID NO: 21 with the truncation of SEQ ID NO: 21 C-terminal to residue L162, i.e., said mutation or mutations may further comprise a stop codon terminating translation of SEQ ID NO: 21.

In some embodiments, mutations are present at positions 102, 233, and/or 244 of SEQ ID NO: 21. In some embodiments, said mutations may optionally comprise any of substitutions P102K, P102T, P102R, P102E, P102A, or P102G, optionally in combination with any of substitutions K233E, K233A, K233G, K233Q, K233P, or K233R and/or any of substitutions L244S, L244R, L244T, L244P, L244G, or L244A of SEQ ID NO: 21. In some embodiments, said mutations may optionally comprise any of substitutions K233E, K233A, K233G, K233Q, K233P, or K233R, optionally in combination with any of substitutions 105K, P102T, P102R, P102E, P102A, or P102G and/or any of substitutions L244S, L244R, L244T, L244P, L244G, or L244A of SEQ ID NO: 21. In some embodiments, said mutations may optionally comprise any of substitutions L244S, L244R, L244T, L244P, L244G, or L244A, optionally in combination with any of substitutions K233E, K233A, K233G, K233Q, K233P, or K233R and/or any of substitutions P102K, P102T, P102R, P102E, P102A, or P102G of SEQ ID NO: 21.

In some embodiments, mutations are present at positions 91, 197, and/or 244 of SEQ ID NO: 21. In some embodiments, said mutations may optionally comprise any of substitutions R91G, R91A, R91V. R91C, R91S, or R91F, optionally in combination with any of substitutions Y197K, Y197T, Y197R, Y197Q, Y197P, Y197E, Y197A, or Y197G and/or any of substitutions L244S, L244R, L244T, L244P, L244G, or L244A of SEQ ID NO: 21. In some embodiments, said mutations may optionally comprise any of substitutions Y197K, Y197T, Y197R, Y197Q, Y197P, Y197E, Y197A, or Y197G, optionally in combination with any of substitutions R91G, R91A, R91V. R91C, R91S, or R91F, and/or any of substitutions L244S, L244R, L244T, L244P, L244G, or L244A of SEQ ID NO: 21. In some embodiments, said mutations may optionally comprise any of substitutions L244S, L244R, L244T, L244P, L244G, or L244A, optionally in combination with any of substitutions R91G, R91A, R91V. R91C, R91S, or R91F, and/or any of substitutions L244S, L244R, L244T, L244P, L244G, or L244A, of SEQ ID NO: 21.

In some embodiments, mutations are present at positions 91, 105, and/or 165 of SEQ ID NO: 21. In some embodiments, said mutations may optionally comprise any of substitutions R91G, R91A, R91V. R91C, R91S, or R91F, optionally in combination with any of substitutions P105R, P105S, P105K, P105N, P105T, P105E, P105D, P105A, or P105G and/or any of substitutions Q165K, Q165T, Q165R, Q165E, Q165A, or Q165G of SEQ ID NO: 21. In some embodiments, said mutations may optionally comprise any of substitutions P105R, P105S, P105K, P105N, P105T, P105E, P105D, P105A, or P105G, optionally in combination with any of substitutions R91G, R91A, R91V. R91C, R91S, or R91F and/or any of substitutions Q165K, Q165T, Q165R, Q165E, Q165A, or Q165G of SEQ ID NO: 21. In some embodiments, said mutations may optionally comprise any of substitutions Q165K, Q165T, Q165R, Q165E, Q165A, or Q165G, optionally in combination with any of substitutions P105R, P105S, P105K, P105N, P105T, P105E, P105D, P105A, or P105G and/or any of substitutions R91G, R91A, R91V. R91C, R91S, or R91F of SEQ ID NO: 21.

In some embodiments, mutations are present at positions 165, 197, and/or 233 of SEQ ID NO: 21. In some embodiments, said mutations may optionally comprise any of substitutions K233E, K233A, K233G, K233Q, K233P, or K233R, optionally in combination with any of substitutions Y197K, Y197T, Y197R, Y197Q, Y197P, Y197E, Y197A, or Y197G and/or any of substitutions Q165K, Q165T, Q165R, Q165E, Q165A, or Q165G of SEQ ID NO: 21. In some embodiments, said mutations may optionally comprise any of substitutions Y197K, Y197T, Y197R, Y197Q, Y197P, Y197E, Y197A, or Y197G, optionally in combination with any of substitutions K233E, K233A, K233G, K233Q, K233P, or K233R, and/or any of substitutions Q165K, Q165T, Q165R, Q165E, Q165A, or Q165G of SEQ ID NO: 21. In some embodiments, said mutations may optionally comprise any of substitutions Q165K, Q165T, Q165R, Q165E, Q165A, or Q165G, optionally in combination with any of substitutions Y197K, Y197T, Y197R, Y197Q, Y197P, Y197E, Y197A, or Y197G and/or any of substitutions K233E, K233A, K233G, K233Q, K233P, or K233R, of SEQ ID NO: 21.

In some embodiments, the mutation or mutations according to the methods and compositions of the present disclosure may comprise any 1, 2, 3, 4, 5, 6, 7, 8, 9, or 10 of R91G, R91A, R91V. R91C, R91S, R91F, P102K, P102T, P102R, P102E, P102A, P102G, P105R, P105S, P105K, P105N, P105T, P105E, P105D, P105A, P105G, K127S, K127T, K127I, K127G, K127A, K127V, D128R, D128T, D128I, D128M, D128G, D128A, D128V, L163W, L163I, L163M, L163P, L163F, L163G, L163A, L163V, L163H, L163E, L163R, L163K, L163D, L163N, L163Y, L163C, L163S, L163T, L163Q, Q165K, Q165T, Q165R, Q165E, Q165A, Q165G, Y197K, Y197T, Y197R, Y197Q, Y197P, Y197E, Y197A, Y197G, K236E, K233E, K233A, K233G, K233Q, K233P, K233R, L244S, L244R, L244T, L244P, L244G, or L244A of SEQ ID NO: 21 or any subset or combination thereof, or any homolog or ortholog thereof.

In some embodiments, said mutation or mutations may comprise one or more substitutions, deletions, or insertions at, or at a position or location surrounding, positions 58, 70, 73, 90, 91, 127, 129, 161, 198, and/or 208 of SEQ ID NO: 22, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue R58 of SEQ ID NO: 22 with any of the 19 other natural amino acids (i.e., W, I, M, P, F, G, A, V, L, H, E, K, D, N, Y, C, S, T, or Q) or with non-natural amino acids as are known to those of skill in the art. In some embodiments, said mutation or mutations may comprise substitution of residue R58 with glycine, alanine, valine, cysteine, methionine, serine, threonine, leucine, phenylalanine, tyrosine or histidine. In some embodiments, said mutation or mutations may comprise substitution of residue R58 with alanine, proline or glycine. In some embodiments, said mutation or mutations may comprise any of the substitutions R58G, R58A, R58V. R58C, R58S, or R58F. In some embodiments, said mutation or mutations may comprise the deletion of residue R58.

In some embodiments, said mutation or mutations may comprise substitution of residue P70 of SEQ ID NO: 22 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P70 with lysine, arginine, histidine, threonine, serine, glutamic acid, glutamine, aspartic acid, asparagine, alanine, valine, or glycine. In some embodiments, said mutation or mutations may comprise substitution of residue P70 with alanine, proline or glycine. In some embodiments, said mutation or mutations may comprise any of the substitutions P70K, P70T, P70R, P70E, P70A, or P70G. In some embodiments, said mutation or mutations may comprise the deletion of residue P70.

In some embodiments, said mutation or mutations may comprise substitution of residue P73 of SEQ ID NO: 22 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P70 with lysine, arginine, histidine, threonine, serine, glutamic acid, glutamine, aspartic acid, asparagine, alanine, valine, or glycine. In some embodiments, said mutation or mutations may comprise substitution of residue P73 with alanine, proline or glycine. In some embodiments, said mutation or mutations may comprise any of the substitutions P73R, P73S, P73K, P73N, P73T, P73E, P73D, P73A, or P73G. In some embodiments, said mutation or mutations may comprise the deletion of residue P73.

In some embodiments, said mutation or mutations may comprise substitution of residue G90 of SEQ ID NO: 22 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue G90 with threonine, serine, isoleucine, glutamic acid, glutamine, aspartic acid, asparagine, alanine, valine, or glycine. In some embodiments, said mutation or mutations may comprise substitution of residue G90 with alanine, proline or glycine. In some embodiments, said mutation or mutations may comprise any of the substitutions G90S, G90T, G90I, G90K, G90A, or G90V. In some embodiments, said mutation or mutations may comprise the deletion of residue G90.

In some embodiments, said mutation or mutations may comprise substitution of residue D91 of SEQ ID NO: 22 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue D91 with arginine, lysine, threonine, serine, isoleucine, glutamic acid, glutamine, aspartic acid, asparagine, alanine, methionine, cysteine, valine, or glycine. In some embodiments, said mutation or mutations may comprise substitution of residue D91 with alanine, proline or glycine. In some embodiments, said mutation or mutations may comprise any of the substitutions D91R, D91T, D91I, D91M, D91G, D91A, or D91V. In some embodiments, said mutation or mutations may comprise the deletion of residue D91. In some embodiments, said mutation or mutations may comprise the truncation of SEQ ID NO: 22 N-terminal to residue D91, i.e., said mutation or mutations may comprise an alternative start codon for translation of SEQ ID NO: 22.

In some embodiments, mutations are present at positions 90 and 91. Exemplary combinations of mutations may comprise any of substitutions K90S, K90T, K90I, K90G, K90A, or K90V with any of substitutions D91R, D91T, D91I, D91M, D91G, D91A, or D91V.

In some embodiments, said mutation or mutations may comprise substitution of residue L127 of SEQ ID NO: 22 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue L127 with arginine, lysine, threonine, serine, tyrosine, tryptophan, phenylalanine, histidine, leucine, isoleucine, glutamic acid, glutamine, aspartic acid, asparagine, alanine, methionine, cysteine, valine, proline, or glycine. In some embodiments, said mutation or mutations may comprise substitution of residue L127 with alanine, proline or glycine. In some embodiments, said mutation or mutations may comprise any of the substitutions L127W, L127I, L127M, L127P, L127F, L127G, L127A, L127V, L127H, L127E, L127R, L127K, L127D, L127N, L127Y, L127C, L127S, L127T, or L127Q. In some embodiments, said mutation or mutations may comprise the deletion of residue L127. In some embodiments, said mutation or mutations may comprise the truncation of SEQ ID NO: 22 N-terminal to residue L127, i.e., said mutation or mutations may comprise an alternative start codon for translation of SEQ ID NO: 22. In some embodiments, said mutation or mutations may comprise the truncation of SEQ ID NO: 22 C-terminal to residue L129, i.e., said mutation or mutations may comprise a stop codon terminating translation of SEQ ID NO: 22.

In some embodiments, said mutation or mutations may comprise substitution of residue Q129 of SEQ ID NO: 22 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Q129 with lysine, arginine, glutamic acid, aspartic acid, asparagine, glutamine, valine, alanine, serine, glycine, or threonine. In some embodiments, said mutation or mutations may comprise substitution of residue Q129 with alanine, proline or glycine. In some embodiments, said mutation or mutations may comprise any of the substitutions Q129K, Q129T, Q129R, Q129E, Q129A, or Q129G. In some embodiments, said mutation or mutations may comprise the deletion of residue Q129.

In some embodiments, said mutation or mutations may comprise substitution of residue Y161 of SEQ ID NO: 22 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Y161 with lysine, arginine, glutamic acid, aspartic acid, asparagine, glutamine, valine, alanine, serine, proline, glycine, or threonine. In some embodiments, said mutation or mutations may comprise substitution of residue Y161 with alanine, proline or glycine. In some embodiments, said mutation or mutations may comprise any of the substitutions Y161K, Y161T, Y161R, Y161Q, Y161P, Y161E, Y161A, or Y161G. In some embodiments, said mutation or mutations may comprise the deletion of residue Y161.

In some embodiments, said mutation or mutations may comprise substitution of residue K198 of SEQ ID NO: 22 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K198 with arginine, glutamic acid, aspartic acid, asparagine, glutamine, valine, alanine, serine, proline, glycine, or threonine. In some embodiments, said mutation or mutations may comprise substitution of residue K198 with alanine, proline or glycine. In some embodiments, said mutation or mutations may comprise any of the substitutions K198E, K198A, K198G, K198Q, K198P, or K198R. In some embodiments, said mutation or mutations may comprise the deletion of residue K198.

In some embodiments, said mutation or mutations may comprise substitution of residue M208 of SEQ ID NO: 22 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue M208 with lysine, arginine, glutamic acid, aspartic acid, asparagine, glutamine, valine, alanine, serine, proline, glycine, or threonine. In some embodiments, said mutation or mutations may comprise substitution of residue M208 with alanine, proline or glycine. In some embodiments, said mutation or mutations may comprise any of the substitutions M208S, M208R, M208T, M208P, M208G, or M208A. In some embodiments, said mutation or mutations may comprise the deletion of residue M208 of SEQ ID NO: 22.

In some embodiments, mutations are present at positions 90 and 91. Exemplary combinations of mutations may comprise any of substitutions G90S, G90T, G90I, G90K, G90A, or G90V with any of substitutions D91R, D91T, D91I, D91M, D91G, D91A, or D91V. In some embodiments, said mutations may comprise substitutions at positions G90, D91, and/or L127 of SEQ ID NO: 22 or any combination thereof. In some embodiments, said mutations may optionally comprise any of substitutions G90S, G90T, G90I, G90G, G90A, or G90V, optionally in combination with any of substitutions D91R, D91T, D91I, D91M, D91G, D91A, or D91V and/or any of substitutions L127W, L127I, L127M, L127P, L127F, L127G, L127A, L127V, L127H, L127E, L127R, L127K, L127D, L127N, L127Y, L127C, L127S, L127T, or L127Q. In some embodiments, said mutation or mutations may comprise a combination of mutations at positions 90 and 91 of SEQ ID NO: 22 with the truncation of SEQ ID NO: 22 C-terminal to residue L126, i.e., said mutation or mutations may further comprise a stop codon terminating translation of SEQ ID NO: 22.

In some embodiments, mutations are present at positions 70, 198, and/or 208 of SEQ ID NO: 22. In some embodiments, said mutations may optionally comprise any of substitutions P70K, P70T, P70R, P70E, P70A, or P70G, optionally in combination with any of substitutions K198E, K198A, K198G, K198Q, K198P, or K198R and/or any of substitutions M208S, M208R, M208T, M208P, M208G, or M208A of SEQ ID NO: 22. In some embodiments, said mutations may optionally comprise any of substitutions K198E, K198A, K198G, K198Q, K198P, or K198R, optionally in combination with any of substitutions 73K, P70T, P70R, P70E, P70A, or P70G and/or any of substitutions M208S, M208R, M208T, M208P, M208G, or M208A of SEQ ID NO: 22. In some embodiments, said mutations may optionally comprise any of substitutions M208S, M208R, M208T, M208P, M208G, or M208A, optionally in combination with any of substitutions K198E, K198A, K198G, K198Q, K198P, or K198R and/or any of substitutions P70K, P70T, P70R, P70E, P70A, or P70G of SEQ ID NO: 22.

In some embodiments, mutations are present at positions 58, 161, and/or 208 of SEQ ID NO: 22. In some embodiments, said mutations may optionally comprise any of substitutions R58G, R58A, R58V. R58C, R58S, or R58F, optionally in combination with any of substitutions Y161K, Y161T, Y161R, Y161Q, Y161P, Y161E, Y161A, or Y161G and/or any of substitutions M208S, M208R, M208T, M208P, M208G, or M208A of SEQ ID NO: 22. In some embodiments, said mutations may optionally comprise any of substitutions Y161K, Y161T, Y161R, Y161Q, Y161P, Y161E, Y161A, or Y161G, optionally in combination with any of substitutions R58G, R58A, R58V. R58C, R58S, or R58F, and/or any of substitutions M208S, M208R, M208T, M208P, M208G, or M208A of SEQ ID NO: 22. In some embodiments, said mutations may optionally comprise any of substitutions M208S, M208R, M208T, M208P, M208G, or M208A, optionally in combination with any of substitutions R58G, R58A, R58V. R58C, R58S, or R58F, and/or any of substitutions M208S, M208R, M208T, M208P, M208G, or M208A, of SEQ ID NO: 22.

In some embodiments, mutations are present at positions 58, 73, and/or 129 of SEQ ID NO: 22. In some embodiments, said mutations may optionally comprise any of substitutions R58G, R58A, R58V. R58C, R58S, or R58F, optionally in combination with any of substitutions P73R, P73S, P73K, P73N, P73T, P73E, P73D, P73A, or P73G and/or any of substitutions Q129K, Q129T, Q129R, Q129E, Q129A, or Q129G of SEQ ID NO: 22. In some embodiments, said mutations may optionally comprise any of substitutions P73R, P73S, P73K, P73N, P73T, P73E, P73D, P73A, or P73G, optionally in combination with any of substitutions R58G, R58A, R58V. R58C, R58S, or R58F and/or any of substitutions Q129K, Q129T, Q129R, Q129E, Q129A, or Q129G of SEQ ID NO: 22. In some embodiments, said mutations may optionally comprise any of substitutions Q129K, Q129T, Q129R, Q129E, Q129A, or Q129G, optionally in combination with any of substitutions P73R, P73S, P73K, P73N, P73T, P73E, P73D, P73A, or P73G and/or any of substitutions R58G, R58A, R58V. R58C, R58S, or R58F of SEQ ID NO: 22.

In some embodiments, mutations are present at positions 129, 161, and/or 198 of SEQ ID NO: 22. In some embodiments, said mutations may optionally comprise any of substitutions K198E, K198A, K198G, K198Q, K198P, or K198R, optionally in combination with any of substitutions Y161K, Y161T, Y161R, Y161Q, Y161P, Y161E, Y161A, or Y161G and/or any of substitutions Q129K, Q129T, Q129R, Q129E, Q129A, or Q129G of SEQ ID NO: 22. In some embodiments, said mutations may optionally comprise any of substitutions Y161K, Y161T, Y161R, Y161Q, Y161P, Y161E, Y161A, or Y161G, optionally in combination with any of substitutions K198E, K198A, K198G, K198Q, K198P, or K198R, and/or any of substitutions Q129K, Q129T, Q129R, Q129E, Q129A, or Q129G of SEQ ID NO: 22. In some embodiments, said mutations may optionally comprise any of substitutions Q129K, Q129T, Q129R, Q129E, Q129A, or Q129G, optionally in combination with any of substitutions Y161K, Y161T, Y16IR, Y161Q, Y161P, Y161E, Y161A, or Y161G and/or any of substitutions K198E, K198A, K198G, K198Q, K198P, or K198R, of SEQ ID NO: 22.

In some embodiments, the mutation or mutations according to the methods and compositions of the present disclosure may comprise any 1, 2, 3, 4, 5, 6, 7, 8, 9, or 10 of R58G, R58A, R58V. R58C, R58S, R58F, P70K, P70T, P70R, P70E, P70A, P70G, P73R, P73S, P73K, P73N, P73T, P73E, P73D, P73A, P73G, G90S, G90T, G90I, G90G, G90A, G90V, D91R, D91T, D91I, D91M, D91G, D91A, D91V, L127W, L127I, L127M, L127P, L127F, L127G, L127A, L127V, L127H, L127E, L127R, L127K, L127D, L127N, L127Y, L127C, L127S, L127T, L127Q, Q129K, Q129T, Q129R, Q129E, Q129A, Q129G, Y161K, Y161T, Y161R, Y161Q, Y161P, Y161E, Y161A, Y161G, K198E, K198A, K198G, K198Q, K198P, K198R, M208S, M208R, M208T, M208P, M208G, or M208A of SEQ ID NO: 22 or any subset or combination thereof, or any homolog or ortholog thereof.

In some embodiments, said mutation or mutations may comprise one or more substitutions, deletions, or insertions at, or at a position or location surrounding, positions 72, 86, 89, 106, 107, 134, 136, 168, 205, and/or 215 of SEQ ID NO: 23, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue R72 of SEQ ID NO: 23 with any of the 19 other natural amino acids (i.e., W, I, M, P, F, G, A, V, L, H, E, K, D, N, Y, C, S, T, or Q) or with non-natural amino acids as are known to those of skill in the art. In some embodiments, said mutation or mutations may comprise substitution of residue R72 with glycine, alanine, valine, cysteine, methionine, serine, threonine, leucine, phenylalanine, tyrosine or histidine. In some embodiments, said mutation or mutations may comprise substitution of residue R72 with alanine, proline or glycine. In some embodiments, said mutation or mutations may comprise any of the substitutions R72G, R72A, R72V. R72C, R72S, or R72F. In some embodiments, said mutation or mutations may comprise the deletion of residue R72.

In some embodiments, said mutation or mutations may comprise substitution of residue P86 of SEQ ID NO: 23 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P86 with lysine, arginine, histidine, threonine, serine, glutamic acid, glutamine, aspartic acid, asparagine, alanine, valine, or glycine. In some embodiments, said mutation or mutations may comprise substitution of residue P86 with alanine, proline or glycine. In some embodiments, said mutation or mutations may comprise any of the substitutions P86K, P86T, P86R, P86E, P86A, or P86G. In some embodiments, said mutation or mutations may comprise the deletion of residue P86.

In some embodiments, said mutation or mutations may comprise substitution of residue P89 of SEQ ID NO: 23 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P86 with lysine, arginine, histidine, threonine, serine, glutamic acid, glutamine, aspartic acid, asparagine, alanine, valine, or glycine. In some embodiments, said mutation or mutations may comprise substitution of residue P89 with alanine, proline or glycine. In some embodiments, said mutation or mutations may comprise any of the substitutions P89R, P89S, P89K, P89N, P89T, P89E, P89D, P89A, or P89G. In some embodiments, said mutation or mutations may comprise the deletion of residue P89.

In some embodiments, said mutation or mutations may comprise substitution of residue G106 of SEQ ID NO: 23 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue G106 with threonine, serine, isoleucine, glutamic acid, glutamine, aspartic acid, asparagine, alanine, valine, or glycine. In some embodiments, said mutation or mutations may comprise substitution of residue G106 with alanine, proline or glycine. In some embodiments, said mutation or mutations may comprise any of the substitutions G106S, G106T, G106I, G106K, G106A, or G106V. In some embodiments, said mutation or mutations may comprise the deletion of residue G106.

In some embodiments, said mutation or mutations may comprise substitution of residue D107 of SEQ ID NO: 23 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue D107 with arginine, lysine, threonine, serine, isoleucine, glutamic acid, glutamine, aspartic acid, asparagine, alanine, methionine, cysteine, valine, or glycine. In some embodiments, said mutation or mutations may comprise substitution of residue D107 with alanine, proline or glycine. In some embodiments, said mutation or mutations may comprise any of the substitutions D107R, D107T, D107I, D107M, D107G, D107A, or D107V. In some embodiments, said mutation or mutations may comprise the deletion of residue D107. In some embodiments, said mutation or mutations may comprise the truncation of SEQ ID NO: 23 N-terminal to residue D107, i.e., said mutation or mutations may comprise an alternative start codon for translation of SEQ ID NO: 23.

In some embodiments, mutations are present at positions 106 and 107. Exemplary combinations of mutations may comprise any of substitutions K106S, K106T, K106I, K106G, K106A, or K106V with any of substitutions D107R, D107T, D107I, D107M, D107G, D107A, or D107V.

In some embodiments, said mutation or mutations may comprise substitution of residue L134 of SEQ ID NO: 23 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue L134 with arginine, lysine, threonine, serine, tyrosine, tryptophan, phenylalanine, histidine, leucine, isoleucine, glutamic acid, glutamine, aspartic acid, asparagine, alanine, methionine, cysteine, valine, proline, or glycine. In some embodiments, said mutation or mutations may comprise substitution of residue L134 with alanine, proline or glycine. In some embodiments, said mutation or mutations may comprise any of the substitutions L134W, L134I, L134M, L134P, L134F, L134G, L134A, L134V, L134H, L134E, L134R, L134K, L134D, L134N, L134Y, L134C, L134S, L134T, or L134Q. In some embodiments, said mutation or mutations may comprise the deletion of residue L134. In some embodiments, said mutation or mutations may comprise the truncation of SEQ ID NO: 23 N-terminal to residue L134, i.e., said mutation or mutations may comprise an alternative start codon for translation of SEQ ID NO: 23. In some embodiments, said mutation or mutations may comprise the truncation of SEQ ID NO: 23 C-terminal to residue L133, i.e., said mutation or mutations may comprise a stop codon terminating translation of SEQ ID NO: 23.

In some embodiments, said mutation or mutations may comprise substitution of residue Q136 of SEQ ID NO: 23 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Q136 with lysine, arginine, glutamic acid, aspartic acid, asparagine, glutamine, valine, alanine, serine, glycine, or threonine. In some embodiments, said mutation or mutations may comprise substitution of residue Q136 with alanine, proline or glycine. In some embodiments, said mutation or mutations may comprise any of the substitutions Q136K, Q136T, Q136R, Q136E, Q136A, or Q136G. In some embodiments, said mutation or mutations may comprise the deletion of residue Q136.

In some embodiments, said mutation or mutations may comprise substitution of residue Y168 of SEQ ID NO: 23 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Y168 with lysine, arginine, glutamic acid, aspartic acid, asparagine, glutamine, valine, alanine, serine, proline, glycine, or threonine. In some embodiments, said mutation or mutations may comprise substitution of residue Y168 with alanine, proline or glycine. In some embodiments, said mutation or mutations may comprise any of the substitutions Y168K, Y168T, Y168R, Y168Q, Y168P, Y168E, Y168A, or Y168G. In some embodiments, said mutation or mutations may comprise the deletion of residue Y168.

In some embodiments, said mutation or mutations may comprise substitution of residue K205 of SEQ ID NO: 23 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K205 with lysine, arginine, glutamic acid, aspartic acid, asparagine, glutamine, valine, alanine, serine, proline, glycine, or threonine. In some embodiments, said mutation or mutations may comprise substitution of residue K205 with alanine, proline or glycine. In some embodiments, said mutation or mutations may comprise any of the substitutions K205E, K205A, K205G, K205Q, K205P, or K205R. In some embodiments, said mutation or mutations may comprise the deletion of residue K205.

In some embodiments, said mutation or mutations may comprise substitution of residue M215 of SEQ ID NO: 23 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue M215 with lysine, arginine, glutamic acid, aspartic acid, asparagine, glutamine, valine, alanine, serine, proline, glycine, or threonine. In some embodiments, said mutation or mutations may comprise substitution of residue M215 with alanine, proline or glycine. In some embodiments, said mutation or mutations may comprise any of the substitutions M215S, M215R, M215T, M215P, M215G, or M215A. In some embodiments, said mutation or mutations may comprise the deletion of residue M215 of SEQ ID NO: 23.

In some embodiments, mutations are present at positions 106 and 107. Exemplary combinations of mutations may comprise any of substitutions G106S, G106T, G106I, G106K, G106A, or K106V with any of substitutions D107R, D107T, D107I, D107M, D107G, D107A, or D107V. In some embodiments, said mutations may comprise substitutions at positions K106, D107, and/or L134 of SEQ ID NO: 23 or any combination thereof. In some embodiments, said mutations may optionally comprise any of substitutions G106S, G106T, G106I, G106K, G106A, or G106V, optionally in combination with any of substitutions D107R, D107T, D107I, D107M, D107G, D107A, or D107V and/or any of substitutions L134W, L134I, L134M, L134P, L134F, L134G, L134A, L134V, L134H, L134E, L134R, L134K, L134D, L134N, L134Y, L134C, L134S, L134T, or L134Q. In some embodiments, said mutation or mutations may comprise a combination of mutations at positions 106 and 107 of SEQ ID NO: 23 with the truncation of SEQ ID NO: 23 C-terminal to residue L133, i.e., said mutation or mutations may further comprise a stop codon terminating translation of SEQ ID NO: 23.

In some embodiments, mutations are present at positions 86, 205, and/or 215 of SEQ ID NO: 23. In some embodiments, said mutations may optionally comprise any of substitutions 86K, P86T, P86R, P86E, P86A, or P86G, optionally in combination with any of substitutions K205E, K205A, K205G, K205Q, K205P, or K205R and/or any of substitutions M215S, M215R, M215T, M215P, M215G, or M215A of SEQ ID NO: 23. In some embodiments, said mutations may optionally comprise any of substitutions K205E, K205A, K205G, K205Q, K205P, or K205R, optionally in combination with any of substitutions 86K, P86T, P86R, P86E, P86A, or P86G and/or any of substitutions M215S, M215R, M215T, M215P, M215G, or M215A of SEQ ID NO: 23. In some embodiments, said mutations may optionally comprise any of substitutions M215S, M215R, M215T, M215P, M215G, or M215A, optionally in combination with any of substitutions K205E, K205A, K205G, K205Q, K205P, or K205R and/or any of substitutions 86K, P86T, P86R, P86E, P86A, or P86G of SEQ ID NO: 23.

In some embodiments, mutations are present at positions 72, 168, and/or 215 of SEQ ID NO: 23. In some embodiments, said mutations may optionally comprise any of substitutions R72G, R72A, R72V. R72C, R72S, or R72F, optionally in combination with any of substitutions Y168K, Y168T, Y168R, Y168Q, Y168P, Y168E, Y168A, or Y168G and/or any of substitutions M215S, M215R, M215T, M215P, M215G, or M215A of SEQ ID NO: 23. In some embodiments, said mutations may optionally comprise any of substitutions Y168K, Y168T, Y168R, Y168Q, Y168P, Y168E, Y168A, or Y168G, optionally in combination with any of substitutions R72G, R72A, R72V. R72C, R72S, or R72F, and/or any of substitutions M215S, M215R, M215T, M215P, M215G, or M215A of SEQ ID NO: 23. In some embodiments, said mutations may optionally comprise any of substitutions M215S, M215R, M215T, M215P, M215G, or M215A, optionally in combination with any of substitutions R72G, R72A, R72V. R72C, R72S, or R72F, and/or any of substitutions M215S, M215R, M215T, M215P, M215G, or M215A, of SEQ ID NO: 23.

In some embodiments, mutations are present at positions 72, 89, and/or 136 of SEQ ID NO: 23. In some embodiments, said mutations may optionally comprise any of substitutions R72G, R72A, R72V. R72C, R72S, or R72F, optionally in combination with any of substitutions P89R, P89S, P89K, P89N, P89T, P89E, P89D, P89A, or P89G and/or any of substitutions Q136K, Q136T, Q136R, Q136E, Q136A, or Q136G of SEQ ID NO: 23. In some embodiments, said mutations may optionally comprise any of substitutions P89R, P89S, P89K, P89N, P89T, P89E, P89D, P89A, or P89G, optionally in combination with any of substitutions R72G, R72A, R72V. R72C, R72S, or R72F and/or any of substitutions Q136K, Q136T, Q136R, Q136E, Q136A, or Q136G of SEQ ID NO: 23. In some embodiments, said mutations may optionally comprise any of substitutions Q136K, Q136T, Q136R, Q136E, Q136A, or Q136G, optionally in combination with any of substitutions P89R, P89S, P89K, P89N, P89T, P89E, P89D, P89A, or P89G and/or any of substitutions R72G, R72A, R72V. R72C, R72S, or R72F of SEQ ID NO: 23.

In some embodiments, mutations are present at positions 136, 168, and/or 205 of SEQ ID NO: 23. In some embodiments, said mutations may optionally comprise any of substitutions K205E, K205A, K205G, K205Q, K205P, or K205R, optionally in combination with any of substitutions Y168K, Y168T, Y168R, Y168Q, Y168P, Y168E, Y168A, or Y168G and/or any of substitutions Q136K, Q136T, Q136R, Q136E, Q136A, or Q136G of SEQ ID NO: 23. In some embodiments, said mutations may optionally comprise any of substitutions Y168K, Y168T, Y168R, Y168Q, Y168P, Y168E, Y168A, or Y168G, optionally in combination with any of substitutions K205E, K205A, K205G, K205Q, K205P, or K205R, and/or any of substitutions Q136K, Q136T, Q136R, Q136E, Q136A, or Q136G of SEQ ID NO: 23. In some embodiments, said mutations may optionally comprise any of substitutions Q136K, Q136T, Q136R, Q136E, Q136A, or Q136G, optionally in combination with any of substitutions Y168K, Y168T, Y168R, Y168Q, Y168P, Y168E, Y168A, or Y168G and/or any of substitutions K205E, K205A, K205G, K205Q, K205P, or K205R, of SEQ ID NO: 23.

In some embodiments, the mutation or mutations according to the methods and compositions of the present disclosure may comprise any 1, 2, 3, 4, 5, 6, 7, 8, 9, or 10 of R72G, R72A, R72V. R72C, R72S, R72F, P86K, P86T, P86R, P86E, P86A, P86G, P89R, P89S, P89K, P89N, P89T, P89E, P89D, P89A, P89G, G106S, G106T, G106I, G106K, G106A, G106V, D107R, D107T, D107I, D107M, D107G, D107A, D107V, L134W, L134I, L134M, L134P, L134F, L134G, L134A, L134V, L134H, L134E, L134R, L134K, L134D, L134N, L134Y, L134C, L134S, L134T, L134Q, Q136K, Q136T, Q136R, Q136E, Q136A, Q136G, Y168K, Y168T, Y168R, Y168Q, Y168P, Y168E, Y168A, Y168G, K205E, K205A, K205G, K205Q, K205P, K205R, M215S, M215R, M215T, M215P, M215G, or M215A of SEQ ID NO: 23 or any subset or combination thereof, or any homolog or ortholog thereof.

In some embodiments, said mutation or mutations may comprise one or more substitutions, deletions, or insertions at, or at a position or location surrounding, positions 78, 92, 95, 112, 113, 149, 151, 183, 220, and/or 230 of SEQ ID NO: 24, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue R78 of SEQ ID NO: 24 with any of the 19 other natural amino acids (i.e., W, I, M, P, F, G, A, V, L, H, E, K, D, N, Y, C, S, T, or Q) or with non-natural amino acids as are known to those of skill in the art. In some embodiments, said mutation or mutations may comprise substitution of residue R78 with glycine, alanine, valine, cysteine, methionine, serine, threonine, leucine, phenylalanine, tyrosine or histidine. In some embodiments, said mutation or mutations may comprise substitution of residue R78 with alanine, proline or glycine. In some embodiments, said mutation or mutations may comprise any of the substitutions R78G, R78A, R78V. R78C, R78S, or R78F. In some embodiments, said mutation or mutations may comprise the deletion of residue R78.

In some embodiments, said mutation or mutations may comprise substitution of residue L92 of SEQ ID NO: 24 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue L92 with lysine, arginine, histidine, threonine, serine, glutamic acid, glutamine, aspartic acid, asparagine, alanine, valine, or glycine. In some embodiments, said mutation or mutations may comprise substitution of residue L92 with alanine, proline or glycine. In some embodiments, said mutation or mutations may comprise any of the substitutions L92K, L92T, L92R, L92E, L92A, or L92G. In some embodiments, said mutation or mutations may comprise the deletion of residue L92.

In some embodiments, said mutation or mutations may comprise substitution of residue P95 of SEQ ID NO: 24 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue L92 with lysine, arginine, histidine, threonine, serine, glutamic acid, glutamine, aspartic acid, asparagine, alanine, valine, or glycine. In some embodiments, said mutation or mutations may comprise substitution of residue P95 with alanine, proline or glycine. In some embodiments, said mutation or mutations may comprise any of the substitutions P95R, P95S, P95K, P95N, P95T, P95E, P95D, P95A, or P95G. In some embodiments, said mutation or mutations may comprise the deletion of residue P95.

In some embodiments, said mutation or mutations may comprise substitution of residue G112 of SEQ ID NO: 24 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue G112 with threonine, serine, isoleucine, glutamic acid, glutamine, aspartic acid, asparagine, alanine, valine, or glycine. In some embodiments, said mutation or mutations may comprise substitution of residue G112 with alanine, proline or glycine. In some embodiments, said mutation or mutations may comprise any of the substitutions G112S, G112T, G112I, G112K, G112A, or G112V. In some embodiments, said mutation or mutations may comprise the deletion of residue G112.

In some embodiments, said mutation or mutations may comprise substitution of residue D113 of SEQ ID NO: 24 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue D113 with arginine, lysine, threonine, serine, isoleucine, glutamic acid, glutamine, aspartic acid, asparagine, alanine, methionine, cysteine, valine, or glycine. In some embodiments, said mutation or mutations may comprise substitution of residue D113 with alanine, proline or glycine. In some embodiments, said mutation or mutations may comprise any of the substitutions D113R, D113T, D113I, D113M, D113G, D113A, or D113V. In some embodiments, said mutation or mutations may comprise the deletion of residue D113. In some embodiments, said mutation or mutations may comprise the truncation of SEQ ID NO: 24 N-terminal to residue D113, i.e., said mutation or mutations may comprise an alternative start codon for translation of SEQ ID NO: 24.

In some embodiments, mutations are present at positions 112 and 113. Exemplary combinations of mutations may comprise any of substitutions G112S, G112T, G112I, G112K, G112A, or G112V with any of substitutions D113R, D113T, D113I, D113M, D113G, D113A, or D113V.

In some embodiments, said mutation or mutations may comprise substitution of residue L149 of SEQ ID NO: 24 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue L149 with arginine, lysine, threonine, serine, tyrosine, tryptophan, phenylalanine, histidine, leucine, isoleucine, glutamic acid, glutamine, aspartic acid, asparagine, alanine, methionine, cysteine, valine, proline, or glycine. In some embodiments, said mutation or mutations may comprise substitution of residue L149 with alanine, proline or glycine. In some embodiments, said mutation or mutations may comprise any of the substitutions L149W, L149I, L149M, L149P, L149F, L149G, L149A, L149V, L149H, L149E, L149R, L149K, L149D, L149N, L149Y, L149C, L149S, L149T, or L149Q. In some embodiments, said mutation or mutations may comprise the deletion of residue L149. In some embodiments, said mutation or mutations may comprise the truncation of SEQ ID NO: 24 N-terminal to residue L149, i.e., said mutation or mutations may comprise an alternative start codon for translation of SEQ ID NO: 24. In some embodiments, said mutation or mutations may comprise the truncation of SEQ ID NO: 24 C-terminal to residue L151, i.e., said mutation or mutations may comprise a stop codon terminating translation of SEQ ID NO: 24.

In some embodiments, said mutation or mutations may comprise substitution of residue Q151 of SEQ ID NO: 24 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Q151 with lysine, arginine, glutamic acid, aspartic acid, asparagine, glutamine, valine, alanine, serine, glycine, or threonine. In some embodiments, said mutation or mutations may comprise substitution of residue Q151 with alanine, proline or glycine. In some embodiments, said mutation or mutations may comprise any of the substitutions Q151K, Q151T, Q151R, Q151E, Q151A, or Q151G. In some embodiments, said mutation or mutations may comprise the deletion of residue Q151.

In some embodiments, said mutation or mutations may comprise substitution of residue Y183 of SEQ ID NO: 24 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Y183 with lysine, arginine, glutamic acid, aspartic acid, asparagine, glutamine, valine, alanine, serine, proline, glycine, or threonine. In some embodiments, said mutation or mutations may comprise substitution of residue Y183 with alanine, proline or glycine. In some embodiments, said mutation or mutations may comprise any of the substitutions Y183K, Y183T, Y183R, Y183Q, Y183P, Y183E, Y183A, or Y183G. In some embodiments, said mutation or mutations may comprise the deletion of residue Y183.

In some embodiments, said mutation or mutations may comprise substitution of residue K220 of SEQ ID NO: 24 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K220 with lysine, arginine, glutamic acid, aspartic acid, asparagine, glutamine, valine, alanine, serine, proline, glycine, or threonine. In some embodiments, said mutation or mutations may comprise substitution of residue K236 with alanine, proline or glycine. In some embodiments, said mutation or mutations may comprise any of the substitutions K220E, K220A, K220G, K220Q, K220P, or K220R. In some embodiments, said mutation or mutations may comprise the deletion of residue K220.

In some embodiments, said mutation or mutations may comprise substitution of residue M230 of SEQ ID NO: 24 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue M230 with lysine, arginine, glutamic acid, aspartic acid, asparagine, glutamine, valine, alanine, serine, proline, glycine, or threonine. In some embodiments, said mutation or mutations may comprise substitution of residue M230 with alanine, proline or glycine. In some embodiments, said mutation or mutations may comprise any of the substitutions M230S, M230R, M230T, M230P, M230G, or M230A. In some embodiments, said mutation or mutations may comprise the deletion of residue M230 of SEQ ID NO: 24.

In some embodiments, mutations are present at positions 112 and 113. Exemplary combinations of mutations may comprise any of substitutions G112S, G112T, G112I, G112K, G112A, or G112V with any of substitutions D113R, D113T, D113I, D113M, D113G, D113A, or D113V. In some embodiments, said mutations may comprise substitutions at positions G112, D113, and/or L149 of SEQ ID NO: 24 or any combination thereof. In some embodiments, said mutations may optionally comprise any of substitutions G112S, G112T, G112I, G112K, G112A, or G112V, optionally in combination with any of substitutions D113R, D113T, D113I, D113M, D113G, D113A, or D113V and/or any of substitutions L149W, L149I, L149M, L149P, L149F, L149G, L149A, L149V, L149H, L149E, L149R, L149K, L149D, L149N, L149Y, L149C, L149S, L149T, or L149Q. In some embodiments, said mutation or mutations may comprise a combination of mutations at positions 112 and 113 of SEQ ID NO: 24 with the truncation of SEQ ID NO: 24 C-terminal to residue L148, i.e., said mutation or mutations may further comprise a stop codon terminating translation of SEQ ID NO: 24. Further exemplary combinations may comprise any of substitutions G112W, G112I, G112M, G112P, G112F, G112A, G112V, G112L, G112F, G112N, G112Y, G112C, G112S, G112T, G112Q, G112H, G112E, G112R, G112K, or G112D, optionally in combination with any of substitutions D113W, D113I, D113M, D113P, D113F, D113G, D113A, D113V, D113L, D113F, D113N, D113Y, D113C, D113S, D113T, D113Q, D113H, D113E, D113R, or D113K, and/or any of substitutions L149W, L149I, L149M, L149P, L149F, L149G, L149A, L149V, L149F, L149N, L149Y, L149C, L149S, L149T, L149Q, L149H, L149E, L149R, L149K, or L149D.

In some embodiments, mutations are present at positions 92, 220, and/or 230 of SEQ ID NO: 24. In some embodiments, said mutations may optionally comprise any of substitutions L92K, L92T, L92R, L92E, L92A, or L92G, optionally in combination with any of substitutions K236E, K236A, K236G, K236Q, K236P, or K236R and/or any of substitutions M230S, M230R, M230T, M230P, M230G, or M230A of SEQ ID NO: 24. In some embodiments, said mutations may optionally comprise any of substitutions K220E, K220A, K220G, K220Q, K220P, or K220R, optionally in combination with any of substitutions 95K, L92T, L92R, L92E, L92A, or L92G and/or any of substitutions M230S, M230R, M230T, M230P, M230G, or M230A of SEQ ID NO: 24. In some embodiments, said mutations may optionally comprise any of substitutions M230S, M230R, M230T, M230P, M230G, or M230A, optionally in combination with any of substitutions K236E, K236A, K236G, K236Q, K236P, or K236R and/or any of substitutions L92K, L92T, L92R, L92E, L92A, or L92G of SEQ ID NO: 24. Further exemplary combinations may comprise any of substitutions L92W, L92I, L92M, L92F, L92G, L92A, L92V, L92L, L92F, L92N, L92Y, L92C, L92S, L92T, L92Q, L92H, L92E, L92R, L92K, or L92D optionally in combination with any of substitutions K220W, K220I, K220M, K220P, K220F, K220G, K220A, K220V, K220L, K220F, K220N, K220Y, K220C, K220S, K220T, K220Q, K220H, K220E, K220R, or K220D, and/or optionally in combination with any of substitutions M230W, M230I, M230P, M230F, M230G, M230A, M230V, M230L, M230F, M230N, M230Y, M230C, M230S, M230T, M230Q, M230H, M230E, M230R, M230K, or M230D.

In some embodiments, mutations are present at positions 78, 183, and/or 230 of SEQ ID NO: 24. In some embodiments, said mutations may optionally comprise any of substitutions R78G, R78A, R78V. R78C, R78S, or R78F, optionally in combination with any of substitutions Y183K, Y183T, Y183R, Y183Q, Y183P, Y183E, Y183A, or Y183G and/or any of substitutions M230S, M230R, M230T, M230P, M230G, or M230A of SEQ ID NO: 24. In some embodiments, said mutations may optionally comprise any of substitutions Y183K, Y183T, Y183R, Y183Q, Y183P, Y183E, Y183A, or Y183G, optionally in combination with any of substitutions R78G, R78A, R78V. R78C, R78S, or R78F, and/or any of substitutions M230S, M230R, M230T, M230P, M230G, or M230A of SEQ ID NO: 24. In some embodiments, said mutations may optionally comprise any of substitutions M230S, M230R, M230T, M230P, M230G, or M230A, optionally in combination with any of substitutions R78G, R78A, R78V. R78C, R78S, or R78F, and/or any of substitutions M230S, M230R, M230T, M230P, M230G, or M230A, of SEQ ID NO: 24. Further exemplary combinations may comprise any of substitutions R78W, R78I, R78M, R78P, R78F, R78G, R78A, R78V, R78L, R78F, R78N, R78Y, R78C, R78S, R78T, R78Q, R78H, R78E, R78K, or R78D, optionally in combination with any of substitutions M230W, M230I, M230P, M230F, M230G, M230A, M230V, M230L, M230F, M230N, M230Y, M230C, M230S, M230T, M230Q, M230H, M230E, M230R, M230K, or M230D, and/or optionally in combination with any of substitutions Y183W, Y183I, Y183M, Y183P, Y183F, Y183G, Y183A, Y183V, Y183L, Y183F, Y183N, Y183C, Y183S, Y183T, Y183Q, Y183H, Y183E, Y183R, Y183K, or Y183D.

In some embodiments, mutations are present at positions 78, 95, and/or 151 of SEQ ID NO: 24. In some embodiments, said mutations may optionally comprise any of substitutions R78G, R78A, R78V. R78C, R78S, or R78F, optionally in combination with any of substitutions P95R, P95S, P95K, P95N, P95T, P95E, P95D, P95A, or P95G and/or any of substitutions Q151K, Q151T, Q151R, Q151E, Q151A, or Q151G of SEQ ID NO: 24. In some embodiments, said mutations may optionally comprise any of substitutions P95R, P95S, P95K, P95N, P95T, P95E, P95D, P95A, or P95G, optionally in combination with any of substitutions R78G, R78A, R78V. R78C, R78S, or R78F and/or any of substitutions Q151K, Q151T, Q151R, Q151E, Q151A, or Q151G of SEQ ID NO: 24. In some embodiments, said mutations may optionally comprise any of substitutions Q151K, Q151T, Q151R, Q151E, Q151A, or Q151G, optionally in combination with any of substitutions P95R, P95S, P95K, P95N, P95T, P95E, P95D, P95A, or P95G and/or any of substitutions R78G, R78A, R78V. R78C, R78S, or R78F of SEQ ID NO: 24. Further exemplary combinations may comprise any of substitutions R78W, R78I, R78M, R78P, R78F, R78G, R78A, R78V, R78L, R78F, R78N, R78Y, R78C, R78S, R78T, R78Q, R78H, R78E, R78K, or R78D, and/or optionally in combination with any of substitutions P95W, P95I, P95M, P95F, P95G, P95A, P95V, P95L, P95F, P95N, P95Y, P95C, P95S, P95T, P95Q, P95H, P95E, P95R, P95K, or P95D, and/or optionally in combination with any of substitutions Q151W, Q151I, Q151M, Q151P, Q151F, Q151G, Q151A, Q151V, Q151L, Q151F, Q151N, Q151Y, Q151C, Q151S, Q151T, Q151H, Q151E, Q151R, Q151K, or Q151D.

In some embodiments, mutations are present at positions 151, 183, and/or 220 of SEQ ID NO: 24. In some embodiments, said mutations may optionally comprise any of substitutions K220E, K220A, K220G, K220Q, K220P, or K220R, optionally in combination with any of substitutions Y183K, Y183T, Y183R, Y183Q, Y183P, Y183E, Y183A, or Y183G and/or any of substitutions Q151K, Q151T, Q151R, Q151E, Q151A, or Q151G of SEQ ID NO: 24. In some embodiments, said mutations may optionally comprise any of substitutions Y183K, Y183T, Y183R, Y183Q, Y183P, Y183E, Y183A, or Y183G, optionally in combination with any of substitutions K236E, K236A, K236G, K236Q, K236P, or K236R, and/or any of substitutions Q151K, Q151T, Q151R, Q151E, Q151A, or Q151G of SEQ ID NO: 24. In some embodiments, said mutations may optionally comprise any of substitutions Q151K, Q151T, Q151R, Q151E, Q151A, or Q151G, optionally in combination with any of substitutions Y183K, Y183T, Y183R, Y183Q, Y183P, Y183E, Y183A, or Y183G and/or any of substitutions K220E, K220A, K220G, K220Q, K220P, or K220R, of SEQ ID NO: 24. Further exemplary combinations may comprise any of substitutions Q151W, Q151I, Q151M, Q151P, Q151F, Q151G, Q151A, Q151V, Q151L, Q151F, Q151N, Q151Y, Q151C, Q151S, Q151T, Q151H, Q151E, Q151R, Q151K, or Q151D, and/or optionally in combination with any of substitutions Y183W, Y183I, Y183M, Y183P, Y183F, Y183G, Y183A, Y183V, Y183L, Y183F, Y183N, Y183C, Y183S, Y183T, Y183Q, Y183H, Y183E, Y183R, Y183K, or Y183D, and/or optionally in combination with any of substitutions K220W, K220I, K220M, K220P, K220F, K220G, K220A, K220V, K220L, K220F, K220N, K220Y, K220C, K220S, K220T, K220Q, K220H, K220E, K220R, or K220D.

In some embodiments, the mutation or mutations according to the methods and compositions of the present disclosure may comprise any 1, 2, 3, 4, 5, 6, 7, 8, 9, or 10 of R78G, R78A, R78V. R78C, R78S, R78F, L92K, L92T, L92R, L92E, L92A, L92G, P95R, P95S, P95K, P95N, P95T, P95E, P95D, P95A, P95G, G112S, G112T, G112I, G112K, G112A, G112V, D113R, D113T, D113I, D113M, D113G, D113A, D113V, L149W, L149I, L149M, L149P, L149F, L149G, L149A, L149V, L149H, L149E, L149R, L149K, L149D, L149N, L149Y, L149C, L149S, L149T, L149Q, Q151K, Q151T, Q151R, Q151E, Q151A, Q151G, Y183K, Y183T, Y183R, Y183Q, Y183P, Y183E, Y183A, Y183G, K220E, K220A, K220G, K220Q, K220P, K220R, M230S, M230R, M230T, M230P, M230G, or M230A of SEQ ID NO: 24 or any subset or combination thereof, or any homolog or ortholog thereof. In some embodiments, the mutation or mutations according to the methods and compositions of the present disclosure may comprise any 1, 2, 3, 4, 5, 6, 7, 8, 9, or 10 of R78W, R78I, R78M, R78P, R78F, R78G, R78A, R78V, R78L, R78F, R78N, R78Y, R78C, R78S, R78T, R78Q, R78H, R78E, R78K, R78D, L92W, L92I, L92M, L92F, L92G, L92A, L92V, L92L, L92F, L92N, L92Y, L92C, L92S, L92T, L92Q, L92H, L92E, L92R, L92K, L92D, P95W, P95I, P95M, P95F, P95G, P95A, P95V, P95L, P95F, P95N, P95Y, P95C, P95S, P95T, P95Q, P95H, P95E, P95R, P95K, P95D, G112W, G112I, G112M, G112P, G112F, G112A, G112V, G112L, G112F, G112N, G112Y, G112C, G112S, G112T, G112Q, G112H, G112E, G112R, G112K, G112D, D113W, D113I, D113M, D113P, D113F, D113G, D113A, D113V, D113L, D113F, D113N, D113Y, D113C, D113S, D113T, D113Q, D113H, D113E, D113R, D113K, L149W, L149I, L149M, L149P, L149F, L149G, L149A, L149V, L149F, L149N, L149Y, L149C, L149S, L149T, L149Q, L149H, L149E, L149R, L149K, L149D, Q151W, Q151I, Q151M, Q151P, Q151F, Q151G, Q151A, Q151V, Q151L, Q151F, Q151N, Q151Y, Q151C, Q151S, Q151T, Q151H, Q151E, Q151R, Q151K, Q151D, Y183W, Y183I, Y183M, Y183P, Y183F, Y183G, Y183A, Y183V, Y183L, Y183F, Y183N, Y183C, Y183S, Y183T, Y183Q, Y183H, Y183E, Y183R, Y183K, Y183D, M230W, M230I, M230P, M230F, M230G, M230A, M230V, M230L, M230F, M230N, M230Y, M230C, M230S, M230T, M230Q, M230H, M230E, M230R, M230K, M230D, K220W, K220I, K220M, K220P, K220F, K220G, K220A, K220V, K220L, K220F, K220N, K220Y, K220C, K220S, K220T, K220Q, K220H, K220E, K220R, or K220D of SEQ ID NO: 24 or any subset or combination thereof, or any homolog or ortholog thereof.

In some embodiments, said mutation or mutations may comprise one or more substitutions, deletions, or insertions at, or at a position or location surrounding, positions 80, 94, 97, 114, 115, 151, 153, 185, 222, and/or 232 of SEQ ID NO: 25, or any combination thereof, or homologs or orthologs thereof. In some embodiments, said mutation or mutations may comprise substitution of said residues with any of the 19 other natural amino acids (i.e., W, I, M, P, F, G, A, V, L, H, R, K, D, N, Y, C, S, T, or Q) or with non-natural amino acids as are known to those of skill in the art.

In some embodiments, said mutation or mutations may comprise substitution of residue R80 of SEQ ID NO: 25 with any of the 19 other natural amino acids (i.e., W, I, M, P, F, G, A, V, L, H, E, K, D, N, Y, C, S, T, or Q) or with non-natural amino acids as are known to those of skill in the art. In some embodiments, said mutation or mutations may comprise substitution of residue R80 with glycine, alanine, valine, cysteine, methionine, serine, threonine, leucine, phenylalanine, tyrosine or histidine. In some embodiments, said mutation or mutations may comprise substitution of residue R80 with alanine, proline or glycine. In some embodiments, said mutation or mutations may comprise any of the substitutions R80G, R80A, R80V. R80C, R80S, or R80F. In some embodiments, said mutation or mutations may comprise the deletion of residue R80.

In some embodiments, said mutation or mutations may comprise substitution of residue P94 of SEQ ID NO: 25 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P94 with lysine, arginine, histidine, threonine, serine, glutamic acid, glutamine, aspartic acid, asparagine, alanine, valine, or glycine. In some embodiments, said mutation or mutations may comprise substitution of residue P94 with alanine, proline or glycine. In some embodiments, said mutation or mutations may comprise any of the substitutions P94K, P94T, P94R, P94E, P94A, or P94G. In some embodiments, said mutation or mutations may comprise the deletion of residue P94.

In some embodiments, said mutation or mutations may comprise substitution of residue P97 of SEQ ID NO: 25 with any of the 19 other natural amino acids (i.e., W, I, M, F, G, A, V, L, H, E, R, K, D, N, Y, C, S, T, or Q) or with non-natural amino acids as are known to those of skill in the art. In some embodiments, said mutation or mutations may comprise substitution of residue P94 with lysine, arginine, histidine, threonine, serine, glutamic acid, glutamine, aspartic acid, asparagine, alanine, residue P97 with alanine, proline or glycine. In some embodiments, said mutation or mutations may comprise any of the substitutions P97R, P97S, P97K, P97N, P97T, P97E, P97D, P97A, or P97G. In some embodiments, said mutation or mutations may comprise the deletion of residue P97.

In some embodiments, said mutation or mutations may comprise substitution of residue G114 of SEQ ID NO: 25 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue G114 with threonine, serine, isoleucine, glutamic acid, glutamine, aspartic acid, asparagine, alanine, valine, or glycine. In some embodiments, said mutation or mutations may comprise substitution of residue G114 with alanine, proline or glycine. In some embodiments, said mutation or mutations may comprise any of the substitutions G114S, G114T, G114I, G114K, G114A, or G114V. In some embodiments, said mutation or mutations may comprise the deletion of residue G114.

In some embodiments, said mutation or mutations may comprise substitution of residue D115 of SEQ ID NO: 25 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue D115 with arginine, lysine, threonine, serine, isoleucine, glutamic acid, glutamine, aspartic acid, asparagine, alanine, methionine, cysteine, valine, or glycine. In some embodiments, said mutation or mutations may comprise substitution of residue D115 with alanine, proline or glycine. In some embodiments, said mutation or mutations may comprise any of the substitutions D115R, D115T, D115I, D115M, D115G, D115A, or D115V. In some embodiments, said mutation or mutations may comprise the deletion of residue D115. In some embodiments, said mutation or mutations may comprise the truncation of SEQ ID NO: 25 N-terminal to residue D115, i.e., said mutation or mutations may comprise an alternative start codon for translation of SEQ ID NO: 25.

In some embodiments, mutations are present at positions 114 and 115. Exemplary combinations of mutations may comprise any of substitutions G114S, G114T, G114I, G114K, G114A, or G114V with any of substitutions D115R, D115T, D115I, D115M, D115G, D115A, or D115V.

In some embodiments, said mutation or mutations may comprise substitution of residue L151 of SEQ ID NO: 25 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue L151 with arginine, lysine, threonine, serine, tyrosine, tryptophan, phenylalanine, histidine, leucine, isoleucine, glutamic acid, glutamine, aspartic acid, asparagine, alanine, methionine, cysteine, valine, proline, or glycine. In some embodiments, said mutation or mutations may comprise substitution of residue L151 with alanine, proline or glycine. In some embodiments, said mutation or mutations may comprise any of the substitutions L151W, L151I, L151M, L151P, L151F, L151G, L151A, L151V, L151H, L151E, L151R, L151K, L151D, L151N, L151Y, L151C, L151S, L151T, or L151Q. In some embodiments, said mutation or mutations may comprise the deletion of residue L151. In some embodiments, said mutation or mutations may comprise the truncation of SEQ ID NO: 25

N-terminal to residue L151, i.e., said mutation or mutations may comprise an alternative start codon for translation of SEQ ID NO: 25. In some embodiments, said mutation or mutations may comprise the truncation of SEQ ID NO: 25 C-terminal to residue L151, i.e., said mutation or mutations may comprise a stop codon terminating translation of SEQ ID NO: 25.

In some embodiments, said mutation or mutations may comprise substitution of residue Q153 of SEQ ID NO: 25 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Q153 with lysine, arginine, glutamic acid, aspartic acid, asparagine, glutamine, valine, alanine, serine, glycine, or threonine. In some embodiments, said mutation or mutations may comprise substitution of residue Q153 with alanine, proline or glycine. In some embodiments, said mutation or mutations may comprise any of the substitutions Q153K, Q153T, Q153R, Q153E, Q153A, or Q153G. In some embodiments, said mutation or mutations may comprise the deletion of residue Q153.

In some embodiments, said mutation or mutations may comprise substitution of residue Y185 of SEQ ID NO: 25 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue Y185 with lysine, arginine, glutamic acid, aspartic acid, asparagine, glutamine, valine, alanine, serine, proline, glycine, or threonine. In some embodiments, said mutation or mutations may comprise substitution of residue Y185 with alanine, proline or glycine. In some embodiments, said mutation or mutations may comprise any of the substitutions Y185K, Y185T, Y185R, Y185Q, Y185P, Y185E, Y185A, or Y185G. In some embodiments, said mutation or mutations may comprise the deletion of residue Y185.

In some embodiments, said mutation or mutations may comprise substitution of residue K222 of SEQ ID NO: 25 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue K222 with lysine, arginine, glutamic acid, aspartic acid, asparagine, glutamine, valine, alanine, serine, proline, glycine, or threonine. In some embodiments, said mutation or mutations may comprise substitution of residue K222 with alanine, proline or glycine. In some embodiments, said mutation or mutations may comprise any of the substitutions K222E, K222A, K222G, K222Q, K222P, or K222R. In some embodiments, said mutation or mutations may comprise the deletion of residue K222.

In some embodiments, said mutation or mutations may comprise substitution of residue M232 of SEQ ID NO: 25 with any of the 19 other natural amino acids (i.e., W, I, M, F, G, A, V, L, H, E, R, P, D, N, Y, C, S, T, or Q) or with non-natural amino acids as are known to those of skill in the art. In some embodiments, said mutation or mutations may comprise substitution of residue M232 with lysine, arginine, glutamic acid, aspartic acid, asparagine, glutamine, valine, alanine, serine, proline, glycine, or threonine. In some embodiments, said mutation or mutations may comprise substitution of residue M232 with alanine, proline or glycine. In some embodiments, said mutation or mutations may comprise any of the substitutions M232S, M232R, M232T, M232P, M232G, or M232A. In some embodiments, said mutation or mutations may comprise the deletion of residue M232 of SEQ ID NO: 25.

In some embodiments, mutations are present at positions 114 and 115. Exemplary combinations of mutations may comprise any of substitutions G114S, G114T, G114I, G114K, G114A, or G114V with any of substitutions D115R, D115T, D115I, D115M, D115G, D115A, or D115V. In some embodiments, said mutations may comprise substitutions at positions G114, D115, and/or L151 of SEQ ID NO: 25 or any combination thereof. In some embodiments, said mutations may optionally comprise any of substitutions G114S, G114T, G114I, G114K, G114A, or G114V, optionally in combination with any of substitutions D115R, D115T, D115I, D115M, D115G, D115A, or D115V and/or any of substitutions L151W, L151I, L151M, L151P, L151F, L151G, L151A, L151V, L151H, L151E, L151R, L151K, L151D, L151N, L151Y, L151C, L151S, L151T, or L151Q. In some embodiments, said mutation or mutations may comprise a combination of mutations at positions 114 and 115 of SEQ ID NO: 25 with the truncation of SEQ ID NO: 25 C-terminal to residue L150, i.e., said mutation or mutations may further comprise a stop codon terminating translation of SEQ ID NO: 25.

In some embodiments, mutations are present at positions 94, 222, and/or 232 of SEQ ID NO: 25. In some embodiments, said mutations may optionally comprise any of substitutions P94K, P94T, P94R, P94E, P94A, or P94G, optionally in combination with any of substitutions K222E, K222A, K222G, K222Q, K222P, or K222R and/or any of substitutions M232S, M232R, M232T, M232P, M232G, or M232A of SEQ ID NO: 25. In some embodiments, said mutations may optionally comprise any of substitutions K222E, K222A, K222G, K222Q, K222P, or K222R, optionally in combination with any of substitutions P94K, P94T, P94R, P94E, P94A, or P94G and/or any of substitutions M232S, M232R, M232T, M232P, M232G, or M232A of SEQ ID NO: 25. In some embodiments, said mutations may optionally comprise any of substitutions M232S, M232R, M232T, M232P, M232G, or M232A, optionally in combination with any of substitutions K222E, K222A, K222G, K222Q, K222P, or K222R and/or any of substitutions P94K, P94T, P94R, P94E, P94A, or P94G of SEQ ID NO: 25.

In some embodiments, mutations are present at positions 80, 185, and/or 232 of SEQ ID NO: 25. In some embodiments, said mutations may optionally comprise any of substitutions R80G, R80A, R80V. R80C, R80S, or R80F, optionally in combination with any of substitutions Y185K, Y185T, Y185R, Y185Q, Y185P, Y185E, Y185A, or Y185G and/or any of substitutions M232S, M232R, M232T, M232P, M232G, or M232A of SEQ ID NO: 25. In some embodiments, said mutations may optionally comprise any of substitutions Y185K, Y185T, Y185R, Y185Q, Y185P, Y185E, Y185A, or Y185G, optionally in combination with any of substitutions R80G, R80A, R80V. R80C, R80S, or R80F, and/or any of substitutions M232S, M232R, M232T, M232P, M232G, or M232A of SEQ ID NO: 25. In some embodiments, said mutations may optionally comprise any of substitutions M232S, M232R, M232T, M232P, M232G, or M232A, optionally in combination with any of substitutions R80G, R80A, R80V. R80C, R80S, or R80F, and/or any of substitutions M232S, M232R, M232T, M232P, M232G, or M232A, of SEQ ID NO: 25.

In some embodiments, mutations are present at positions 80, 97, and/or 153 of SEQ ID NO: 25. In some embodiments, said mutations may optionally comprise any of substitutions R80G, R80A, R80V. R80C, R80S, or R80F, optionally in combination with any of substitutions P97R, P97S, P97K, P97N, P97T, P97E, P97D, P97A, or P97G and/or any of substitutions Q153K, Q153T, Q153R, Q153E, Q153A, or Q153G of SEQ ID NO: 25. In some embodiments, said mutations may optionally comprise any of substitutions P97R, P97S, P97K, P97N, P97T, P97E, P97D, P97A, or P97G, optionally in combination with any of substitutions R80G, R80A, R80V. R80C, R80S, or R80F and/or any of substitutions Q153K, Q153T, Q153R, Q153E, Q153A, or Q153G of SEQ ID NO: 25. In some embodiments, said mutations may optionally comprise any of substitutions Q153K, Q153T, Q153R, Q153E, Q153A, or Q153G, optionally in combination with any of substitutions P97R, P97S, P97K, P97N, P97T, P97E, P97D, P97A, or P97G and/or any of substitutions R80G, R80A, R80V. R80C, R80S, or R80F of SEQ ID NO: 25.

In some embodiments, mutations are present at positions 153, 185, and/or 222 of SEQ ID NO: 25. In some embodiments, said mutations may optionally comprise any of substitutions K222E, K222A, K222G, K222Q, K222P, or K222R, optionally in combination with any of substitutions Y185K, Y185T, Y185R, Y185Q, Y185P, Y185E, Y185A, or Y185G and/or any of substitutions Q153K, Q153T, Q153R, Q153E, Q153A, or Q153G of SEQ ID NO: 25. In some embodiments, said mutations may optionally comprise any of substitutions Y185K, Y185T, Y185R, Y185Q, Y185P, Y185E, Y185A, or Y185G, optionally in combination with any of substitutions K222E, K222A, K222G, K222Q, K222P, or K222R, and/or any of substitutions Q153K, Q153T, Q153R, Q153E, Q153A, or Q153G of SEQ ID NO: 25. In some embodiments, said mutations may optionally comprise any of substitutions Q153K, Q153T, Q153R, Q153E, Q153A, or Q153G, optionally in combination with any of substitutions Y185K, Y185T, Y185R, Y185Q, Y185P, Y185E, Y185A, or Y185G and/or any of substitutions K222E, K222A, K222G, K222Q, K222P, or K222R, of SEQ ID NO: 25.

In some embodiments, the mutation or mutations according to the methods and compositions of the present disclosure may comprise any 1, 2, 3, 4, 5, 6, 7, 8, 9, or 10 of R80G, R80A, R80V. R80C, R80S, R80F, P94K, P94T, P94R, P94E, P94A, P94G, P97R, P97S, P97K, P97N, P97T, P97E, P97D, P97A, P97G, G114S, G114T, G114I, G114K, G114A, G114V, D115R, D115T, D115I, D115M, D115G, D115A, D115V, L151W, L151I, L151M, L151P, L151F, L151G, L151A, L151V, L151H, L151E, L151R, L151K, L151D, L151N, L151Y, L151C, L151S, L151T, L151Q, Q153K, Q153T, Q153R, Q153E, Q153A, Q153G, Y185K, Y185T, Y185R, Y185Q, Y185P, Y185E, Y185A, Y185G, K222E, K222A, K222G, K222Q, K222P, K222R, M232S, M232R, M232T, M232P, M232G, or M232A of SEQ ID NO: 25 or any subset or combination thereof, or any homolog or ortholog thereof.

One of ordinary skill in the art will readily recognize that the methods and compositions of the present disclosure will further include such improvements, modifications, and reasonable equivalents as may be identified by one of ordinary skill. The methods and compositions of the present disclosure may be further illustrated by reference to the following non-limiting examples.

Further provided herein are polypeptides that comprise nucleic acid extension activity. For example, mutant polypeptides possess increased extension activity when provided modified nucleotides relative to a nearest wild-type polypeptide or to a polypeptide that is wild-type for the mutations listed. Increased extension activity variously refers to an increase in reaction kinetics (increased $k_{cat}$), increased $K_D$, decreased $K_m$, increased $k_{cat}/K_m$ ratio, faster turnover rate, higher turnover number, or other metric that is beneficial to the use of the polypeptide for nucleic acid extension with modified nucleotides. The polypeptides described herein often incorporate at least 30% more modified nucleotides than the nearest wild-type polypeptide in total or in a given duration of time. The polypeptides described herein often incorporate at least 10%, 20%, 30%, 50%, 75%, 100%, 125%, 150%, 200%, 500%, more modified nucleotides than the nearest wild-type polypeptide for a fixed amount of time and modified nucleotide concentration. In some cases, the polypeptides described herein incorporate modified nucleotides at least 1.5, 2, 2.5, 5, 10, 15, 20, 25, or at least 50 times faster than the nearest wild-type polypeptide for a fixed amount of time. Such measurements are often measured under conditions such as a set period of time, such as at least, at most, or exactly 1, 2, 3, 5, 8, 10, 15, 20, or more than 20 minutes. Such measurements are often measured under conditions such as a set nucleotide concentration, such as less than 10 uM, 10 uM, 20 uM, 50 uM, 100 uM, 200 uM, 300 uM, 500 uM, or more than 500 uM, or any concentration within the range identified by the previous list.

Different modified nucleotides are compatible with the compositions and methods described herein. Modified nucleotides in some instances comprise modifications to naturally occurring nucleotides, such as modified bases, sugars, phosphates, or other chemical modification. An exemplary modification is a 3'OH blocking group on the sugar. Such blocking groups allow for iterative coupling of individual nucleotides to a growing chain. Examples of blocking groups comprise azido, aminoxy, disulfide, nitrate, or other group that prevents further extension reactions at the 3' OH group. Such groups are often reversible, and are removed to allow subsequent extension reactions. Additional nucleotide modifications include modified bases in some cases. Modified bases comprise additional linking groups, or detectable moieties in some instances. Detectable moieties variously comprise fluorescent tags, mass tags, capture moieties (e.g., biotin, maltose, folate, or other capture moiety), or other chemical moiety that can be detected. Such modifications optionally allow the detection and identification of the base in a sequencing workflow.

Sequencing by Synthesis Process with Mutant Polypeptides

Systems, methods and compositions disclosed herein are optionally employed in a number of sequencing approaches, such as single molecule sequencing, long read sequencing, or sequencing by synthesis (SBS) workflows. A typical workflow in some instances comprises at least one step up to all of the steps comprising (1) sample acquisition, (2) library preparation, (3) sequencing, and (4) data analysis. The arrangement and presence or absence of steps or substeps in the methods vary in some instances consistent with various embodiments of the disclosure herein.

Samples comprising polynucleotides are acquired from any number of sources, such as human, animal, plant, fungal, virus, bacterial, or other biological source. In some cases, samples are from a purely synthetic origin. Samples are often obtained from tissues, fluids, or any other source comprising polynucleotides to be sequenced. Any source comprising polynucleotides is often a suitable source for polynucleotides to be sequenced.

Library preparation generally comprises one or more of the following steps: (1) sample digestion, (2) polyadenylation, (3) adapter ligation, (4) library amplification, (5) target capture/purification, and (6) amplification. Polynucleotide samples are first digested either enzymatically or mechanically to generate small fragments. These fragments are extended using a kinase, a polymerase, ATP, and/or klenow enzyme to add one or more adenines to the ends of the fragments. The fragments are then ligated to adapter sequences that in some instances comprise universal primer sequences, graft sequences, and/or index sequences using enzymes such as a ligase. The library of adapter tagged polynucleotides is then optionally amplified using universal primers and a polymerase. In some embodiments capture probes are used to selectively bind and purify desired sequences from the library. After capture, washing, and release of the enriched polynucleotides, the enriched library is optionally amplified. The library is then loaded onto a surface, such as a flow cell for sequencing by synthesis.

Single strands of the library polynucleotides (target polynucleotides) are often hybridized to complementary grafting regions covalently attached to the synthesis surface, such as by annealing to complementary grafting sequences present on the adapters. These strands often serve as template polynucleotides for sequencing by synthesis. Solid phase amplification is commonly employed in which the non-surface bound end of the single strands hybridize to neighboring graft sequences, and extension generates reverse complement "copies" of the original single strand at sites in close physical proximity to the original strand ("bridging"). This process is often referred to as cluster or clonal generation, which results in clusters of surface-bound polynucleotide sequences corresponding to the reverse complement of the original strand. Denaturation of bridging strands results in clusters of single stranded polynucleotides (original sequence strands and reverse complement strands). In some instances, this process is repeated to increase cluster density. Generally, each cluster represents a polynucleotide (fragment) that is optionally reassembled into the original sequence after sequencing. In some aspects sequencing primers that bind to the target polynucleotide strands are then added, along with four chain terminating fluorescently labeled dNTPs and a polypeptide with polymerase activity described herein. These matching, complementary labeled dNTPs are added to the growing primer chain, and the surface is imaged to establish the identity of the added nucleotide at each cluster. Cleavage of the fluorescent label and deprotection of the 3' sugar OH allows a subsequent cycle to commence; the process is optionally repeated until the entire target polynucleotide has been sequenced. Optionally, the complement strand is also used as a template by utilizing a reverse primer to generate a reverse read. The base call data obtained from the forward read and reverse reads is in some aspects a paired-end read. Images collected at each cycle of synthesis are in some aspects analyzed to make base calls, and the sequence of each fragment is identified. In some instances, multiple fragments are sequenced in such a manner and aligned to generate complete sequences of the original target polynucleotides.

In some cases, data analysis comprises evaluation of base calls for polynucleotides that have been sequenced. In some aspects, sequenced polynucleotide (fragments) are reassembled into larger sequences during data analysis. Data analysis optionally comprises any number of steps for processing or interpreting data acquired using the methods and compositions described herein.

The methods and compositions described herein often result in a decreased analysis time. In some cases the analysis time for a single cycle (includes imaging, wherein all base calls generated for a single nucleotide position) is no more than 8 minutes, no more than 7.5, 7, 6.5, 6, 5.5, 5, 4.5, 4, 3.5, 3, 2.5, or no more than 2.5 minutes. In some cases the analysis time for a single cycle is at least 8 minutes, at least 7.5, 7, 6.5, 6, 5.5, 5, 4.5, 4, 3.5, 3, 2.5, or at least 2.5 minutes. In some cases the analysis time for a single cycle is about 8 minutes, about 7.5, 7, 6.5, 6, 5.5, 5, 4.5, 4, 3.5, 3, 2.5, or about 2.5 minutes. In some cases the analysis time for a single cycle is about 2 minutes to about 10 minutes, about 2 minutes to about 8 minutes, about 2 minutes to about 6 minutes, about 3 minutes to about 8 minutes, about 3 minutes to about 6 minutes, about 4 minutes to about 7 minutes, about 3 minutes to about 8 minutes or about 4 minutes to about 10 minutes.

The methods and compositions described herein often allow for longer average read lengths (including forward and reverse reads). In some cases the average read length is at least 100 base pairs, at least 125, 150, 175, 200, 225, 250, 275, 300, 325, 350, 375, 400, 425, 450, 475, 500, 550, 600, 650, or at least 700 base pairs. In some cases the average read length is no more than 100 base pairs, no more than 125, 150, 175, 200, 225, 250, 275, 300, 325, 350, 375, 400, 425, 450, 475, 500, 550, 600, 650, or no more than 700 base pairs. In some cases the average read length is about 100 base pairs, about 125, 150, 175, 200, 225, 250, 275, 300, 325, 350, 375, 400, 425, 450, 475, 500, 550, 600, 650, or about 700 base pairs. In some cases the average read length is about 100 to 700 base pairs, about 100 to 600 base pairs, about 100 to 500 base pairs, about 150 to 400 base pairs, about 200 to 350 base pairs, about 250 to 400 base pairs, about 300 to 500 base pairs, about 400 to 650 base pairs, or about 500 to 700 base pairs.

Discussion of the Accompanying Figures

FIG. 1 illustrates the concentration of product (nM) on the Y-axis as a function of time (see) on the X-axis for the wild-type MMLVRT. The X axis is labeled from 0 to 60 at 20 second intervals, and the Y-axis is labeled from 0 to 200 at 50 nM intervals. The legend on the right side of the graph shows various concentrations of 3' methylazido dUTP tested: 25 uM, 50 uM, 75 uM, 100 uM, 200 uM, 300 uM, and 500 uM.

Figure 2:
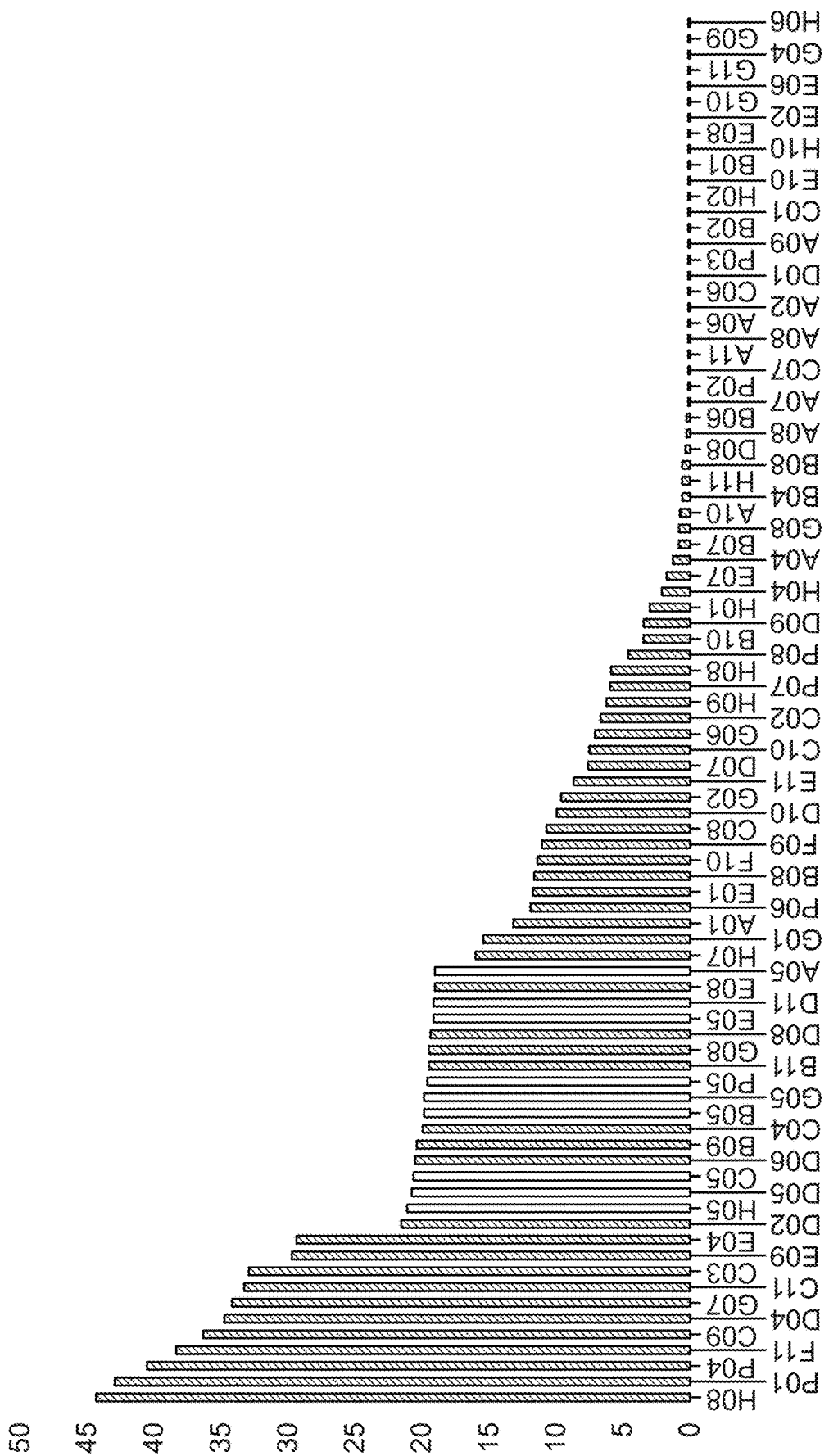
FIG. 2 illustrates a plot comparing extension product formation of wild-type and mutant reverse transcriptases in the presence of 3'methylazido dUTP.

FIG. 2 illustrates the concentration of product (nM) on the Y axis as a function of various transcriptases on the X-axis for the wild-type MML VRT (light grey bars) and MML VRT mutant (dark grey bars) transcriptases described herein. The X-axis is labeled with 96 well plate locations used to identify the transcriptases, and the Y-axis is labeled from 0 to 50 at 5 nM intervals.

FIG. 3 illustrates an exemplary annotated sequence of MMLV, with a retro-transcriptase-like domain underlined, a DNA binding domain in lower case, a reverse transcriptase domain in italics, the putative active site doubleunderlined, the putative NTP binding site in bold, the RNase exonuclease site highlighted in grey, and the DNA/RNA hybrid binding site in bold underline. Residues replaced by mutations as described herein are marked with large font, and are, in order, K152, D153, A154, F155, F156, and Q190.

FIG. 4A illustrates an exemplary sequence alignment between SEQ ID NOs:1-4, 17, and 18 (top to bottom) for residues 1-384 (SEQ ID NO: 1 reference numbering). Residues showing 100% conservation across sequences are shown in red. Residues replaced by mutations as described herein are marked above with an asterisk (*), and are, in order, K152, D153, A154, F155, F156, and Q190. Marking of these residues makes clear that their homologous position in related proteins is readily identified, both for the proteins aligned herein and for other proteins readily identified by one of skill in the art using standard sequence search capabilities such as a BLAST search, available at the NCBI website affiliated with the National Institutes of Health and the National Library of Medicine (ncbi.nlm.nih.gov). Residues showing 100% conservation across sequences are shown in red.

FIG. 4B illustrates an exemplary sequence alignment between SEQ ID NOs:1-4, 17, and 18 (top to bottom) for residues 385-672 (SEQ ID NO: 1 reference numbering). Residues showing 100% conservation across sequences are shown in red.

Definitions

As used herein and in the appended claims, the singular forms "a," "and," and "the" include plural referents unless the context clearly dictates otherwise. Thus, for example, reference to "polynucleotide" includes a plurality of such polynucleotides and reference to "detecting a nucleotide base" includes reference to one or more methods for detecting nucleotide bases and equivalents thereof known to those skilled in the art, and so forth.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "sequencing read" as used herein, refers to a polynucleotide fragment in which the sequence has been determined. The identity of individual bases in the fragment are determined by the process of "base calling".

The term "nucleotide" as used herein, refers to a molecule comprising an aromatic base, a sugar, and a phosphate. Canonical or non-canonical nucleotides are consistent with use of the term. The phosphate in some instances comprises a monophosphate, diphosphate, or triphosphate, or corresponding phosphate analog. Occasionally, "nucleotide" is used informally to refer to a base in a nucleic acid molecule.

The term "amino acid" as used herein, refers to a molecule comprising an amine, a side chain, and a carboxylic acid or analogue thereof. Canonical or non-canonical amino acids are consistent with use of the term. The amino acid in some instances is part of a larger protein, connected through an amide, ester, thioester, alkyl, amide isostere, or other type of chemical linkage.

The term "polypeptide" as used herein, refers to a molecule comprising two or more amino acids that are chemically linked through an amide bond or equivalent.

"About," as used herein in reference to a number refers to that number +/−10% of that number. As used in reference to a range, 'about' refers to a range having a lower limit 10% less than the indicated lower limit of the range and an upper limit that is 10% greater than the indicated upper limit of the range.

The term "percent identity" refers to a comparison between two nucleic acid or amino acid sequences. Such comparisons are measured using any number of alignment methods known in the art, including but not limited to global (e.g., Needleman-Wunsch algorithm) or local alignments (e.g., Smith-Waterman, Sellers, or other algorithm). Percent identity often refers to the percentage of matching positions of two sequences for a contiguous section of positions, wherein the two sequences are aligned in such a way to maximize matching positions and minimize gaps of non-matching positions. In some instances, alignments are conducted wherein there are no gaps between the two sequences. In some instances, the alignment results in less than 5% gaps, less than 3% gaps, or less than 1% gaps. Additional methods of sequence comparison or alignment are also consistent with the disclosure.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

The following illustrative examples are representative of embodiments of compositions and methods described herein and are not meant to be limiting in any way.

EXAMPLES

Example 1: Synthesis and Evaluation of MMLV Library with a 3' Blocked Nucleotide A vector comprising an expression cassette (promoter, wild-type MMLVRT gene, and terminator) was transformed into E. coli (DE3) cells, plated, and individual colonies picked for expression in liquid cultures as follows. pJ404-MMLV-RT plasmid was codon optimized and synthesized by ATUM and transformed into NEB 5-alpha competent E. coli (C2987H) using manufacturer's protocol. 52 overlapping oligonucleotides were designed based on the optimized DNA sequence to assemble the MMLV-RT gene. Equal volumes of Q5A Hot Start High-Fidelity 2× Master Mix (New England Biolabs) and oligonucleotide mixture containing 50 nM of each oligonucleotide were PCR amplified for 25 cycles. 0.25 µL of the amplified DNA was then reamplified without purification for 32 cycles using only 100 nM terminal primers to generate the oligonucleotide assembled wild type MMLVRT gene. Individual mutagenic oligonucleotides were substituted for the corresponding native oligonucleotide and PCR amplified using the same protocol to generate mutant MMLVRT. Amplified genes were then assembled into pJ404 plasmid using NEBuilder HiFi DNA Assembly Master Mix (New England Biolabs) and transformed into NEB 5-alpha competent E. coli. A 10 µL aliquot of transformants were serially diluted and plated on LB plates supplemented with carbenicillin to check library diversity. Plates were grown at 37° C. for 16 hours, scraped into 10 mL of LB, and miniprepped without amplification to reduce growth bias. Library DNA was stored at −20° C. for transformation into selection cell line.

After transformation, overnight cultures of individual colonies were diluted, grown to O.D. 0.6, induced with IPTG, and grown overnight to express wild-type MMLVRT. Cultures were then centrifuged to remove media, lysed, and the wild-type MMLVRT protein isolated.

Isolated enzyme was placed in buffer and assayed for activity by its ability to incorporate 3' blocked methylazido dUTP nucleotide into a primer template. Various concentrations of nucleotide and reaction times were evaluated. Quenching buffer was then added after a set period of time to stop the reactions. Extension rates for various concentrations of wild-type MMLVRT were measured and are shown in FIG. 1. Reaction rates for the wild-type enzyme are too slow under conditions suitable for nucleotide extension in a nucleic acid sequencing workflow (>300 uM 3' blocked methylazido dUTP required).

Example 2: Synthesis and Evaluation of an MMLV Library

Mutant libraries comprising MMLV genes, each comprising point mutations were generated using standard mutagenesis protocols, and these genes were cloned into vector-based expression cassettes. Vectors were transformed into *E. coli* (DE3) cells, plated, and individual colonies picked for expression in liquid cultures following the general procedure of Example 1. Overnight cultures of individual colonies were diluted, grown to O.D. 0.6, induced with IPTG, and grown overnight to express mutant reverse transcriptases. Cultures were then centrifuged to remove media, lysed, and the reverse transcriptases isolated.

Isolated reverse transcriptases were placed in buffer and assayed for activity by their ability to incorporate 3' blocked methylazido dUTP nucleotide into a primer template. Methylazido dUTP was added at 10 uM, and reactions were quenched with quenching buffer after 20 minutes. Extension products were purified on a 15% acrylamide gel, and the percent extended product measured, as shown in FIG. 2. Ratios were also obtained as an average of measurements relative to the rate of the wild-type enzyme at different time intervals and nucleotide concentrations. Data for an exemplary mutant F134N (SEQ ID NO: 1 numbering) is shown in Table 3, showing the ratios of extended product for the F134N mutant vs. the wild type F134 polymerase.

TABLE 3

| Time (sec) | 25 uM | 50 uM | 75 uM | 100 uM | 200 uM | 300 uM | 500 uM |
| --- | --- | --- | --- | --- | --- | --- | --- |
| 10 | 0.25 | 0.27 | 0.29 | 0.35 | 0.36 | 0.40 | 0.44 |
| 20 | 0.61 | 0.54 | 0.52 | 0.54 | 0.54 | 0.58 | 0.64 |
| 30 | 0.80 | 0.68 | 0.65 | 0.66 | 0.64 | 0.69 | 0.73 |
| 45 | 0.90 | 0.82 | 0.76 | 0.75 | 0.71 | 0.75 | 0.78 |
| 60 | 1.04 | 0.95 | 0.86 | 0.86 | 0.78 | 0.81 | 0.83 |
| 90 | 1.09 | 1.03 | 0.97 | 0.96 | 0.86 | 0.87 | 0.89 |
| 120 | 1.19 | 1.08 | 1.03 | 1.00 | 0.90 | 0.91 | 0.92 |
| 180 | 1.19 | 1.13 | 1.05 | 1.04 | 0.94 | 0.90 | 0.94 |
| 300 | 1.29 | 1.16 | 1.07 | 1.06 | 0.98 | 0.97 | 0.97 |

Mutant polymerases were identified with rates suitable for a nucleic acid sequencing workflow.

Example 3: Sequencing by Synthesis

A researcher wishes to sequence a polynucleotide sample using standard sequencing by synthesis methodologies, with modification. The polymerase is replaced with a mutant reverse transcriptase comprising at least 85% identity with SEQ ID NO: 2 and the mutation F134N. After sequencing, the researcher is able to ascertain both the identity of all bases in all polynucleotides (fragments) in the sample, as well as correctly reassemble the plurality of polynucleotide fragments in the sample.

Example 4: Modification of a Homologous RT Domain

A protein having RT activity is identified and aligned to a protein of FIGS. 4A-4B. Residues at positions homologous to positions K152, D153, A154, F155, F156, and Q190 indicated in FIG. 4A are identified, and a mutation is introduced in at least one of these residues. The resultant protein is assessed for its incorporation of 3' modified nucleotides in an assay such as the assay described in FIG. 2, and is observed to have increased incorporation.

Example 5

Figure 5:
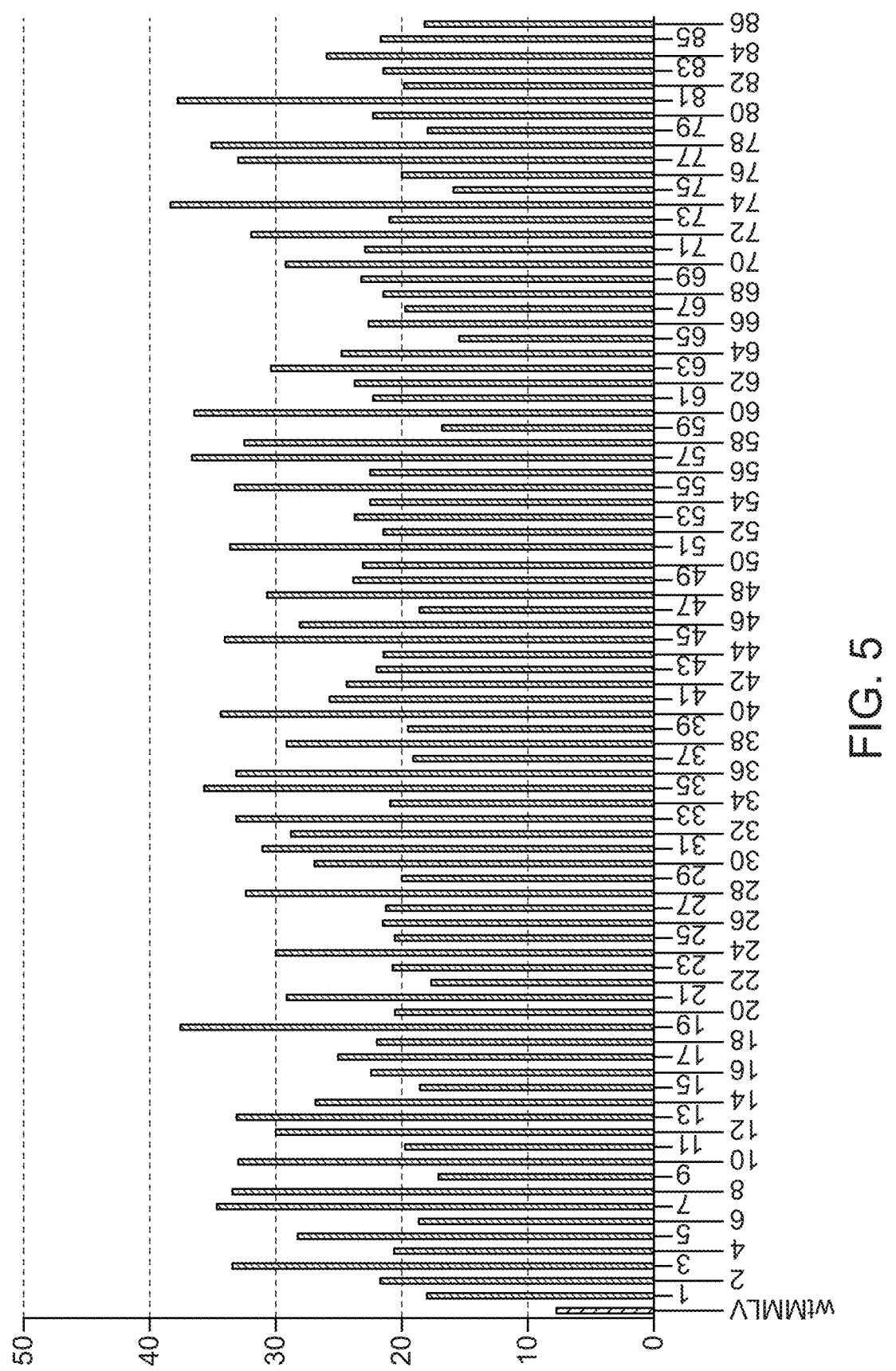
FIG. 5 illustrates relative activity of further additional variants of MMLV in incorporation of 3'methylazido nucleotides at the N+1 position of an extending polynucleotide chain at 42° C. Variants are present in cleared lysates from expression strains. Leftmost bar: WT-MMLV-RT. Mutants 1-86 are listed along the X axis.
Figure 6:
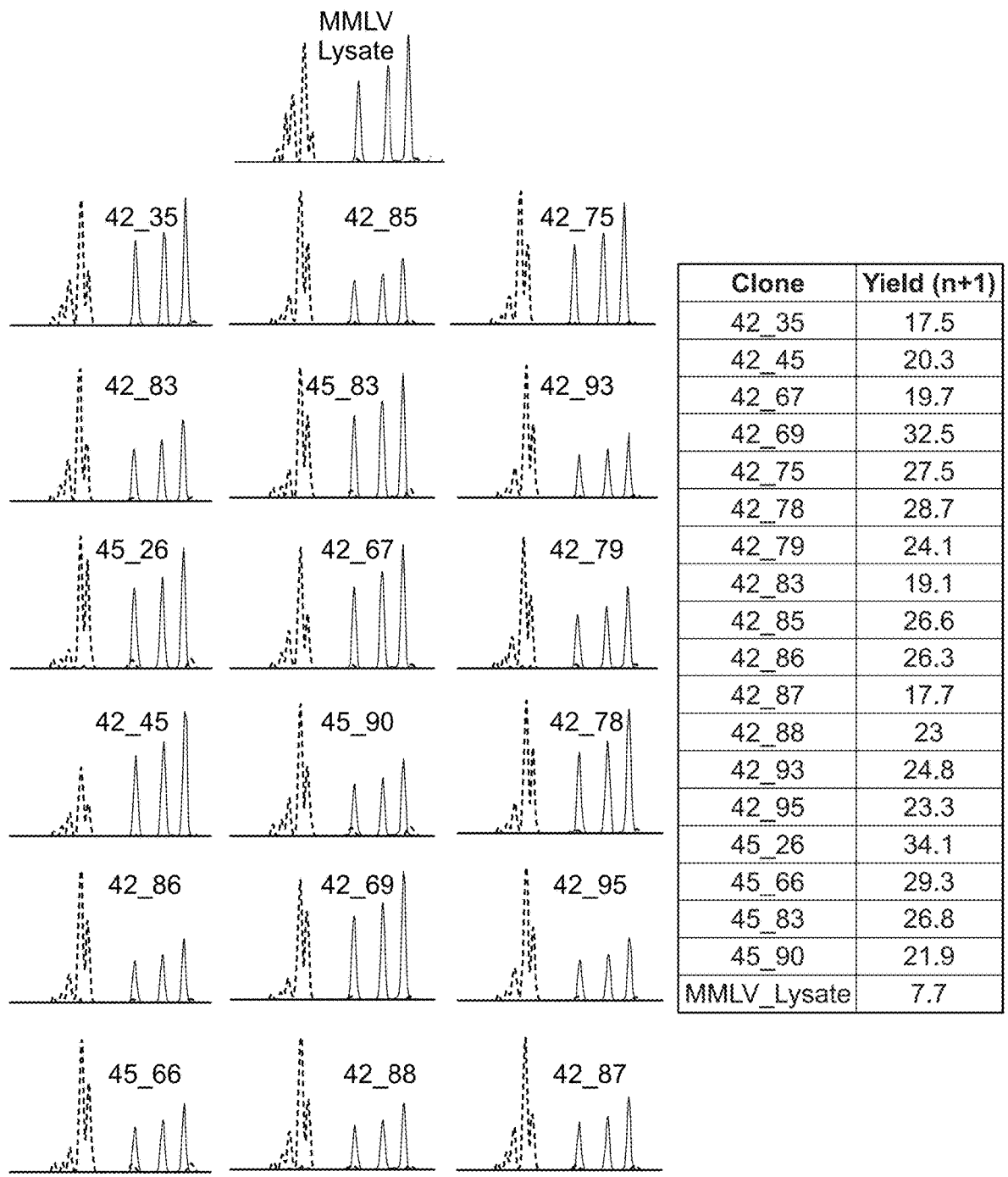
FIG. 6 shows fluorescence traces and fluorescence quantification of clarified lysates showing the activity of variants of MMLV in incorporation of 3'methylazido nucleotides at the N+1 position of an extending polynucleotide chain at 42° C. Mutations are listed in Table 4.

Positions 47, 86, 94, 95, 105, 108, 117, 130, 131, 166, 168, 178, 200, 236, 247, 280, 291, 308, 432, 502, 581, and 585 of SEQ ID NO: 19 were separately mutated to all possible residues by PCR-based site directed mutagenesis using oligonucleotide primers encoding all possible codons at the relevant codon position (FIG. 5 and FIG. 6). The Y-axis represents the percent yield of n+1 extended product for each mutant along the X-axis.

TABLE 4

| Clone | Mutations |
| --- | --- |
| 42_35 | R94N, Y200P, L247R |
| 42_45 | R94H, Y200G, L247G |
| 42_62 | K236L, L247T |
| 42_67 | K130S, D131H, L166E |
| 42_69 | D131Y, L166T |
| 42_75 | D131R, L166Q |
| 42_78 | K130Q, D131H, L166Y |
| 42_79 | D131H, L166S |
| 42_85 | L166V, Y200L, K236S |
| 42_86 | Q168A, Y200G, K236S |
| 42_93 | L166R, Q168G, Y200A, L247R |
| 45_26 | R94A, P108E, Q168A |
| 45_66 | L166S, D203N, E297K, E350K, A355P |
| 45_83 | L166N, K236R, L247P |
| 45_90 | Q168E, Y200C, K236S |
| 2_15 | R94T, P108T, Q168K |
| 2_21 | R94H, P108T, Q168A |
| 3_7 | R94H, Y200A, L251 |

Figure 7:
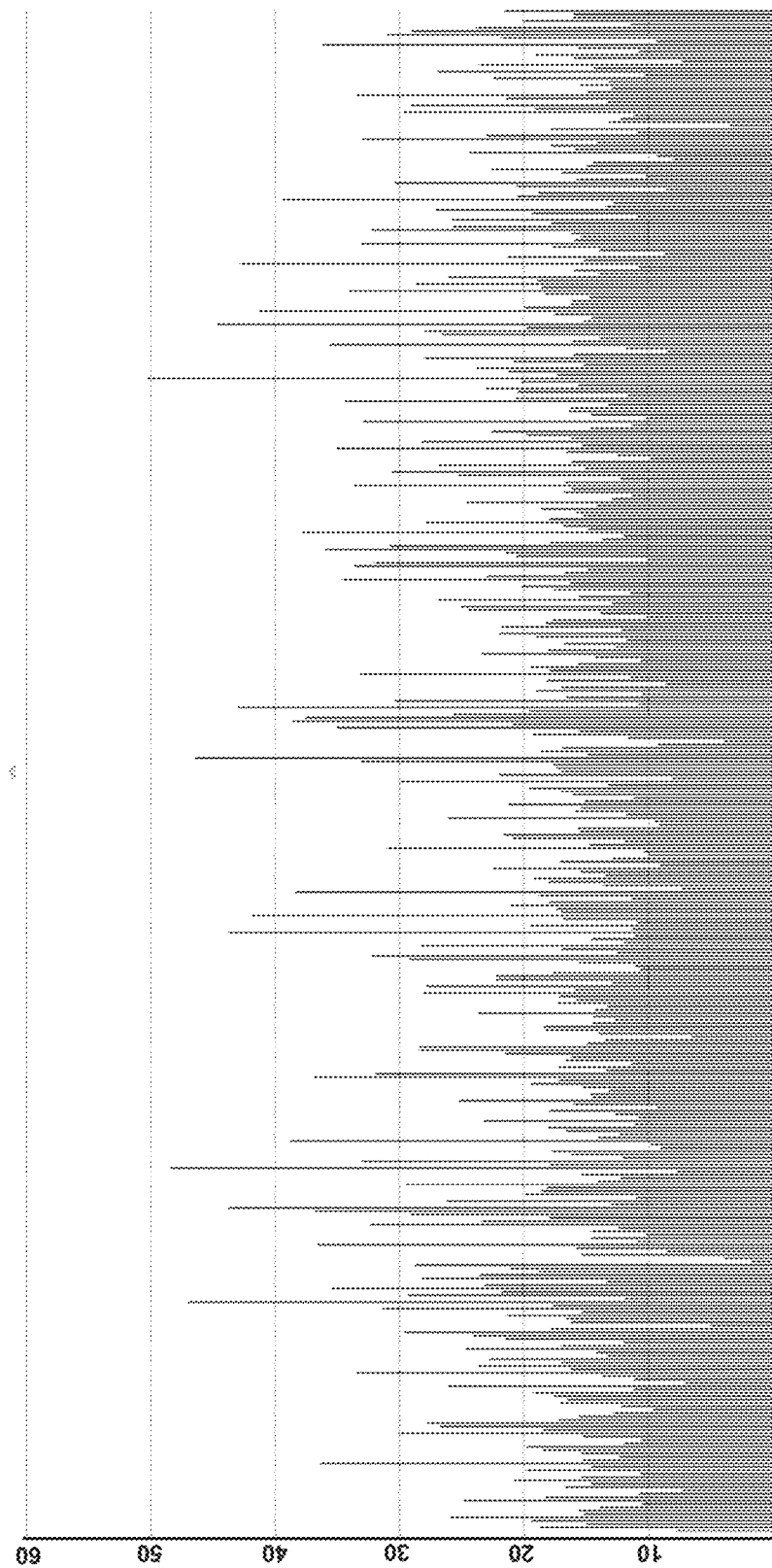
FIG. 7 illustrates relative activity of additional variants of MMLV in incorporation of 3'methylazido nucleotides at the N+1 position of an extending polynucleotide chain at 42° C. Variants are present in cleared lysates from expression strains. Leftmost bar: WT-MMLV-RT. Variants shown are, from left to right, Wild-Type, 1_41, 2_2, 4_40, 42_57, 1_28, 1_8, L18_3, 45_93, 1_25, 2_33, 2_28, 3_46, 1_15, 2_90, 2_34, 4_19, 2_20, 1_67, 1_48, L61_2, 3_19, 4_28, 2_72, 5_13, L05_1, 1_44, 2_46, 45_95, 42_27, 3_96, 42_2, 42_33, 42_34, L53_1, L69_1, 45_65, 5_68, L26, 4_1, 4_26, 4_44, 2_8, 45_29, L71_4, 4_10, 3_44, 4_12, 2_36, 2_29, L38_2, L64_3, 3_7, 42_25, 45_97, 3_91, 5_14, 2_41, 4_38, 4_7, 1_16, 2_55, 45_96, 45_80, 2_81, 45_75, 4_32, 2_96, 4_93, 1_94, L07, 2_48, 1_1, L88_1, 2_1, 1_2, 1_18, 2_42, 2_31, L10, L89_1, 3_14, 4_16, 42_59, 42_22, 3_6, 3_24, 3_40, 2_87, 1_87, 1_34, 2_10, 4_11, 42_9, L24_5, L27_3, 1_24, L72_1, 2_63, 2_88, 42_88, 3_1, L32_4, L81_5, 42_26, 4_31, 4_91, 1_51, 45_16, L62_2, 4_9, 3_12, 2_30, 2_38, 3_39, 2_32, L08, L86_5, L20_4, L45_4, L63, 1_10, 1_29, 1_40, L34, L59, 2_17, 3_18, 4_47, 2_23, 45_72, 2_27, 1_6, 45_17, 45_33, 45_91, L48_4, L44_1, L52, 2_25, 1_19, 1_27, 2_4, 2_24, 42_98, 42_80, 42_61, 45_5, 45_6, 45_76, L04_3, 4_33, 1_35, 1_23, 2_7, 42_93, L47_4, 3_23, 2_85, 45_31, 1_31, L78_2, 2_54, 1_54, L02_2, L60, 3_27, 2_43, 3_15, L28_5, L51, 45_51, 42_51, L80_5, 45_82, L85_2, 45_38, H13_4, L13_4, 42_37, 42_23, 42_31, L68_4, 1_17, 4_35, 4_4, 3_38, 45_66, 3_48, 42_42, 42_54, L43_2, 4_36, 2_45, 4_39, 2_47, 42_1, 42_70, 42_74, 3_10, 45_68, L03_5, L46_3, L95_3, 1_13, 1_22, 2_6, 42_48, 45_89, 42_36, 1_45, 3_56, 5_95, L54_5, 3_33, 4_41, _3_4, 3_47, L33_3, 3_8, 5_46, 5_35, 45_85, 45_27, 5_45, 42_16, 45_52, 1_14, 1_46, L06_4, 3_3, 5_75, 2_75, 2_35, 2_15, 42_91, 45_1, 45_2, 4_42, 1_20, 4_20, 1_39, 2_39, 42_15, 42_66, 42_4, 42_62, 42_47, 2_22, 45_77, 4_8, L23_4, 5_90, 5_34, L15_3, 1_9, 4_3, 4_43, L83_1, 1_37, 42_86, 45_81, 3_25, 3_41, 3_11, L87, 3_32, 42_75, L82_2, L30, L41_2, 3_28, 4_6, 5_92, 5_87, L79_4, 3_26, 45_60, 45_7, L29_2, 4_25, 3_34, 3_35, 4_23, 2_18, 2_19, L19_1, 1_33, 3_42, 4_34, 5_23, 5_69, L09, L49_5, 45_69, 5_88, 5_65, 42_39, 3_22, 4_24, 42_58, L17_5, 45_12, 42_41, 42_81, 42_69, 5_44, 5_15, 3_9, 1_26, 2_26, 1_30, 1_47, 42_87, 1_11, 2_37, 42_19, 42_52, 5_12, 5_83, 42_95, _2_5, 2_16, 45_83, L77_3, 42_76, 4_22, 1_4, 42_40, 4_2, 4_14, 45_73, 45_61, 45_63, 42_10, 42_94, 42_46, 45_37, 4_46, 42_55, 42_43, 45_41, 45_57, 45_94, 42_28, L90_3, L92_2, 45_34, 45_19, 42_89, 45_25, 45_49, 45_62, 42_85, 42_20, 3_2, 42_82, 1_42, 2_14, 4_17, 4_27, 1_21, 4_30, 5_96, 5_24, 42_90, 5_78, 5_16, 5_26, L57, 42_72, 42_96, 45_47, 5_93, 5_43, L75_3, 42_6, 45_39, 45_43, L21_1, L22_5, L76, 3_17, L36_4, 2_13, 45_10, 3_36, L25_1, 45_24, L96, L93, L67_5, 1_7, 45_14, L35, 45_78, 42_68, 45_59, 42_92, L50_3, 2_3, 45_11, 42_38, L12, 45_90, 42_30, 45_54, 45_20, 42_78, 45_74, 45_18, 45_86, 45_45, 1_5, 45_26, 45_30, 45_56, 2_12, 42_83, 2_21, L16_4, 4_13, 45_42, L65_3, L74, 5_28, 45_28, 42_79, 1_3, 45_50, 42_67, 45_35, L11_2, 5_98, L73, 42_45, 45_71, L31, 5_48, 45_48, L55, 3_20, 3_31, L91_5, 45_23, 45_36, 3_30, 42_63, 42_84, 45_44, 45_55, 1_12, and 5_18.

Alternatively, positions 47, 86, 94, 95, 105, 108, 117, 130, 131, 166, 168, 178, 200, 236, 247, 280, 291, 308, 432, 502, 581, and 585 of SEQ ID NO: 19 were mutated in combination by the use of oligonucleotides encoding all possible codons at the relevant codon positions during the assembly of the gene encoding SEQ ID NO. 19. Plasmids encoding mutants were transformed into *E. coli* cells as described in Example 1, and subjected to screening to identify binding to 3'-blocked nucleotides. Several variants, including mutants shown in Table 4 were shown to have enhanced thermostability and binding of 3'-blocked nucleotides relative to proteins encoded by SEQ ID NO: 19. (FIG. 7). The Y-axis represents the yield of extended n+1 product for each mutant along the X-axis.

Example 6

Positions 29, 70, 78, 79, 92, 95, 100, 112, 113, 149, 151, 161, 183, 220, 230, 318, 410, and 437 of SEQ ID NO: 24 were separately mutated to all possible residues by PCR-based site directed mutagenesis using oligonucleotide primers encoding all possible codons at the relevant codon position. Alternatively, positions 29, 70, 78, 79, 92, 95, 100, 112, 113, 149, 151, 161, 183, 220, 229, 230 318, 328, 410, and 437 of SEQ ID NO: 24 were mutated in combination by the use of oligonucleotides encoding all possible codons at the relevant codon positions during the assembly of the gene encoding SEQ ID NO. 24. Plasmids encoding mutants were transformed into *E. coli* cells as described for MMLV-RT in Example 1, and subjected to screening to identify binding to 3'-blocked nucleotides. Several variants, including mutants shown in Table 5 were shown to have enhanced thermostability and binding of 3'-blocked nucleotides relative to proteins encoded by SEQ ID NO: 24.

TABLE 5

| Clone | HIV-RT Mutation |
|---|---|
| 5 | Y318I, A437P |
| 6 | R78A, E79Y, Y183D, K220A, W229F, Y318I, W410E, A437P |
| 11 | L92A, P95R, P170R, R172V, K220A, W229F, Y318W |
| 13 | G112V, D113Q, W229P, Y318K, A437E |
| 15 | R78V, E79W, L92N, P95V |
| 16 | R78E, E79Y, L92P, P95N, L149T, Q151V, Y183S, K220G, W229Y |
| 17 | L92Y, P95I |
| 20 | R78W, E79W, L92K, P95N, L100V, L149T, Q15IF, W229P |
| 25 | E79S |
| 26 | R78W, E79F, L92N, P95L, Y183W, K220L, W229D, Y328F |
| 28 | Q161P, Y318G |
| 29 | E29R, L149S, Q161L, K220T, W229V, Y319T |
| 30 | Q151L, Y183T, K220R, W229G, Y319W |
| 31 | R78W, E79W, L92K, L100V, L149T, Q151F, Y183D, K220T, W229P |
| 32 | E29L, R78R, E79P, L92L, P95T, L100N, L149L, Q151D, Q161A, Y183C, W229R |

Example 7

Cell Lysate Preparation:

Colonies were inoculated into 1.5 mL of LB-carbenicillin media with Overnight Express Autoinduction System 1 (Novagen) and grown for 24 hours. Cells were pelleted by centrifuging at 3,500 RCF for 15 min and then resuspended with 200 L of Bugbuster (MilliporeSigma) with 1 μL of lysonase (MilliporeSigma) diluted to 1/64 of the stock concentration. Cells were allowed to lyse for 15 min at room temperature.

Blocked-Nucleotide Incorporation Reactions:

Single stranded FAM labeled primer was annealed to unlabeled template containing a 7 nucleotide extension by gradient cooling in annealing buffer (10 mM Tris-HCl pH 7.5, 50 mM NaCl, 1 mM EDTA) from 95° C. to 4° C. The first base to be incorporated on the template determines the blocked nucleotide to be added, i.e. a G on the template would incorporate a C-blocked nucleotide. A reaction master mix comprising 20 nM annealed DNA template and 50 UM d-CTP-azido (Jena Bioscience) or other blocked nucleotide in enzyme dependent buffer was prepared. Individual lysates were diluted 10 fold in the master mix and the reaction was allowed to proceed at 37° C. for 15 min then quenched with 50 mM EDTA in formamide. The quenched reactions were diluted to 500 pM DNA in a standard master mix containing LIZ120 (ThermoFisher Scientific) in formamide for analysis on Applied Biosystems 3500 genetic analyzer. Incorporation of the blocked nucleotide was monitored by using a standard curve generated using single stranded Fam labeled DNA at length 17-27. Purified enzymes were analyzed similarly. Misincorporation was analyzed similarly by using a HEX labeled template with a mismatch first base i.e. a T, C, or A with a blocked-C nucleotide.

Reaction kinetics were monitored by running incorporation reactions and removing 5 μL aliquots into quench buffer in a time series from 0-60 min at varying concentrations of purified enzyme, DNA template, and blocked-nucleotide substrate.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for nucleotide extension, the method comprising:
   a) contacting a plurality of template nucleotides having hybridized thereto a plurality of nucleotide primers with a plurality of nucleotide analogues and a plurality of mutant reverse transcriptase enzymes under conditions suitable for extending the plurality of nucleotide primers by the reverse transcriptase enzyme, wherein the plurality of mutant reverse transcriptase enzymes has the amino acid sequence comprising SEQ ID NO:19 and at most 22 amino acid substitutions, wherein the at most 22 amino acid substitutions include Asp131Tyr and Leu166Thr; and
   b) extending the plurality of nucleotide primers in (a) by incorporating a nucleotide analogue of the plurality of nucleotide analogues into the plurality of nucleotide primers by the plurality of mutant reverse transcriptase enzymes.

2. The method of claim 1, wherein at least one of the plurality of nucleotide analogues comprises:
   a) a nucleobase comprising a detectable moiety attached thereto;
   b) a 3' OH sugar with a blocking group comprising an azido, aminooxy, disulfide or nitrate group attached thereto;
   c) a 3' OH sugar with a blocking group comprising a methyl group attached thereto;
   d) a 3' OH sugar with a blocking group comprising an azido or azidomethyl group attached thereto; or
   e) any combination of (a) to (d).

3. The method of claim 1, wherein the plurality of nucleotide analogues comprises dATP, dGTP, dCTP, dTTP or dUTP.

4. The method of claim 1, wherein the plurality of nucleotide analogues comprises a mixture of dATP, dGTP, dCTP and dTTP.

5. The method of claim 1, wherein the plurality of nucleotide analogues comprises a mixture of dATP, dGTP, dCTP, dTTP and dUTP.

6. The method of claim 1, wherein the plurality of nucleotide analogues comprises 3' methyl azido-dUTP.

7. The method of claim 1, wherein the plurality of template nucleotides comprises:
   a) ribonucleic acid (RNA);
   b) an RNA analogue; or
   c) a derivative of (a) or (b).

8. The method of claim 1, wherein the plurality of nucleotide analogues comprises deoxyribonucleic acid (DNA) analogues or derivatives thereof.

9. The method of claim 1, wherein the plurality of nucleotide primers comprises:
   a) deoxyribonucleic acid (DNA);
   b) complementary DNA (cDNA);
   c) a DNA or cDNA analogue; or
   d) a derivative of (a) or (b).

10. The method of claim 1, wherein the plurality of template nucleotides is acquired from humans, animals, plants, fungi, viruses, bacteria, or any combination thereof.

11. The method of claim 1, wherein the mutant reverse transcriptase enzyme is more thermostable as compared with the reverse transcriptase that has the amino acid sequence comprising SEQ ID NO: 19 that does not have the at most 22 amino acid substitutions that includes Asp131 Tyr and Leu166Thr.

12. The method of claim 1, wherein the extending in (b) is performed by the mutant reverse transcriptase enzyme under isothermal conditions.

13. The method of claim 1, wherein extending in (b) is performed under conditions comprising a temperature that is between about 37 degrees C. to about 95 degrees C.

14. The method of claim 1, further comprising:
   c) generating a second plurality of template nucleotides from the plurality of primers extended in (b); and
   d) determining an identity of a nucleotide of the second plurality of template nucleotides in a nucleotide binding reaction.

15. The method of claim 14, wherein determining the identity of the nucleotide of the second plurality of template nucleotides in (d) is performed by detecting binding between the nucleotide analog and the nucleotide of the second plurality of template nucleotides, wherein the nucleotide analog comprises a detectable moiety.

16. The method of claim 1, wherein the plurality of template nucleotides is single stranded.

17. The method of claim 1, wherein the plurality of template nucleotides comprises a nucleic acid sequence comprising at least one mutation in an RNA or DNA binding site relative to an otherwise identical reference sequence.

* * * * *